United States Patent [19]
Baker et al.

[11] Patent Number: 5,854,268
[45] Date of Patent: Dec. 29, 1998

[54] AZETIDINE, PYRROLIDINE AND PIPERIDINE DERIVATIVES

[75] Inventors: Raymond Baker, Uley; Sylvie Bourrain; Jose Luis Castro Pineiro, both of Harlow; Mark Stuart Chambers, Puckeridge; Alexander Richard Guiblin, Harlow; Sarah Christine Hobbs, Great Dunmow; Richard Alexander Jelley; Andrew Madin, both of Sawbridgeworth, all of United Kingdom; Victor Giulio Matassa, Rome, Italy; Austin John Reeve, Great Dunmow, United Kingdom; Michael Geoffrey Russell; Graham Andrew Showell, both of Welwyn Garden City, United Kingdom; Francine Sternfeld, London, United Kingdom; Leslie Joseph Street, Harlow, United Kingdom; Monique Bodil Van Niel, Welwyn Garden City, United Kingdom

[73] Assignee: Merck Sharp & Dohme, Ltd., Hoddesdon, England

[21] Appl. No.: 776,024

[22] PCT Filed: Aug. 1, 1995

[86] PCT No.: PCT/GB95/01819

§ 371 Date: Jan. 22, 1997

§ 102(e) Date: Jan. 22, 1997

[87] PCT Pub. No.: WO96/04274

PCT Pub. Date: Feb. 15, 1996

[30] Foreign Application Priority Data

Aug. 2, 1994 [GB] United Kingdom .................. 9415552
Aug. 2, 1994 [GB] United Kingdom .................. 9415579
Dec. 21, 1994 [GB] United Kingdom .................. 9426375

[51] Int. Cl.$^6$ ...................... C07D 403/14; C07D 401/14; C07D 405/14; A61K 31/41
[52] U.S. Cl. ...................... 514/383; 548/255; 548/262.2; 548/262.8; 548/263.8; 548/264.4; 548/311.1; 548/314.7; 546/184; 546/192; 546/207; 546/208; 546/152; 546/164; 514/396; 514/397; 514/398; 514/383; 514/381; 514/385; 514/315; 514/317; 514/326; 514/311
[58] Field of Search ............... 548/311.1, 314.7, 548/262.2, 254, 266.4, 312.1, 255, 262.8, 263.8; 546/207, 208, 152, 164; 514/398, 381, 311, 385, 315, 317, 326

[56] References Cited

U.S. PATENT DOCUMENTS

| | | | |
|---|---|---|---|
| 3,644,403 | 2/1972 | Cauas-Rodriguez | 260/326.11 |
| 3,801,594 | 4/1974 | Poletto et al. | 260/326.15 |
| 4,453,001 | 6/1984 | Brand et al. | 548/466 |
| 4,839,377 | 6/1989 | Bays et al. | 514/415 |
| 4,851,406 | 7/1989 | Mertens et al. | 514/212 |
| 4,870,085 | 9/1989 | Glaser et al. | 514/323 |
| 5,037,845 | 8/1991 | Oxford | 514/415 |
| 5,298,520 | 3/1994 | Baker et al. | 514/383 |

FOREIGN PATENT DOCUMENTS

| | | | |
|---|---|---|---|
| 0 497 512 A2 | 8/1992 | European Pat. Off. | C07D 403/06 |
| 0 497 512 A3 | 8/1992 | European Pat. Off. | |
| 0 581 538 A1 | 2/1994 | European Pat. Off. | C07D 403/14 |
| WO 93/18029 | 9/1993 | WIPO | C07D 403/14 |
| WO 94/02477 | 2/1994 | WIPO | C07D 403/14 |

*Primary Examiner*—Jose' G. Dees
*Assistant Examiner*—Sabiha N. Qazi
*Attorney, Agent, or Firm*—Philippe L. Durette; Melvin Winokur

[57] ABSTRACT

A class of substituted azetidine, pyrrolidine and piperidine derivatives are selective agonists of 5-HT$_1$-like receptors, being potent agonists of the human 5-HT$_{1D\alpha}$ receptor subtype whilst possessing at least a 10-fold selective affinity for the 5-HT$_{1D\alpha}$ receptor subtype relative to the 5-HT$_{1D\beta}$ subtype; they are therefore useful in the treatment and/or prevention of clinical conditions, in particular migraine and associated disorders, for which a subtype-selective agonist of 5-HT$_{1D}$ receptors is indicated, whilst eliciting fewer side-effects, notably adverse cardiovascular events, than those associated with non-subtype-selective 5-HT$_{1D}$ receptor agonists.

10 Claims, No Drawings

AZETIDINE, PYRROLIDINE AND PIPERIDINE DERIVATIVES

This application has been filed under 35 USC 371 as a national stage application of PCT/GB 95/0189 filed Aug. 1, 1995.

The present invention relates to a class of substituted azetidine, pyrrolidine and piperidine derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

It has been known for some time that 5-HT$_1$-like receptor agonists which exhibit selective vasoconstrictor activity are of use in the treatment of migraine (see, for example, A. Doenicke et al., *The Lancet*, 1988, Vol. 1, 1309–11; and W. Feniuk and P. P. A. Humphrey, *Drug Development Research*, 1992, 26, 235–240).

The human 5-HT$_1$-like or 5-HT$_{1D}$ receptor has recently been shown by molecular cloning techniques to exist in two distinct subtypes. These subtypes have been termed 5-HT$_{1D\alpha}$ (or 5-HT$_{1D-1}$) and 5-HT$_{1D\beta}$ (or 5-HT$_{1D-2}$), and their amino acid sequences are disclosed and claimed in WO-A-91/17174.

The 5-HT$_{1D\alpha}$ receptor subtype in humans is believed to reside on sensory terminals in the dura mater. Stimulation of the 5-HT$_{1D\alpha}$ subtype inhibits the release of inflammatory neuropeptides which are thought to contribute to the headache pain of migraine. The human 5-HT$_{1D\beta}$ receptor subtype, meanwhile, is located predominantly on the blood vessels and in the brain, and hence may play a part in mediating constriction of cerebral and coronary arteries, as well as CNS effects.

Administration of the prototypical 5-HT$_{1D}$ agonist sumatriptan (GR43175) to humans is known to give rise at therapeutic doses to certain adverse cardiovascular events (see, for example, F. Willett et al., *Br. Med. J.*, 1992, 304, 1415; J. P. Ottervanger et al., *The Lancet*, 1993, 341, 861–2; and D. N. Bateman, *The Lancet*, 1993, 341, 221–4). Since sumatriptan barely discriminates between the human 5-HT$_{1D\alpha}$ and 5-HT$_{D\beta}$ receptor subtypes (cf. WO-A-91/17174, Table 1), and since it is the blood vessels with which the 5-HT$_{1D\beta}$ subtype is most closely associated, it is believed that the cardiovascular side-effects observed with sumatriptan can be attributed to stimulation of the 5-HT$_{1D\beta}$ receptor subtype. It is accordingly considered (cf. G. W. Rebeck et al., *Proc. Natl. Acad. Sci. USA*, 1994, 91, 3666–9) that compounds which can interact selectively with the 5-HT$_{1D\alpha}$ receptor subtype, whilst having a less pronounced action at the 5-HT$_{1D\beta}$ subtype, might be free from, or at any rate less prone to, the undesirable cardiovascular and other side-effects associated with non-subtype-selective 5-HT$_{1D}$ receptor agonists, whilst at the same time maintaining a beneficial level of anti-migraine activity.

The compounds of the present invention, being selective 5-HT$_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human 5-HT$_{1D\alpha}$ receptor subtype. Moreover, the compounds in accordance with this invention have been found to possess at least a 10-fold selective affinity for the 5-HT$_{1D\alpha}$ receptor subtype relative to the 5-HT$_{1D\beta}$ subtype, and they can therefore be expected to manifest fewer side-effects than those associated with non-subtype-selective 5-HT$_{1D}$ receptor agonists.

Several distinct classes of substituted five-membered heteroaromatic compounds are described in published European patent applications 0438230, 0494774 and 0497512, and published International patent applications 93/18029, 94/02477 and 94/03446. The compounds described therein are stated to be agonists of 5-HT$_1$-like receptors, and accordingly to be of particular use in the treatment of migraine and associated conditions. None of these publications, however, discloses nor even suggests the substituted azetidine, pyrrolidine and piperidine derivatives provided by the present invention.

Moreover, nowhere in the prior art available to date is there any disclosure of a subtype-selective 5-HT$_{1D}$ receptor agonist having a 5-HT$_{1D\alpha}$ receptor binding affinity (IC$_{50}$) below 50 nM and at least a 10-fold selective affinity for the 5-HT$_{1D\alpha}$ receptor subtype relative to the 5-HT$_{1D\beta}$ subtype.

The compounds according to the present invention are subtype-selective 5-HT$_{1D}$ receptor agonists having a human 5-HT$_{1D\alpha}$ receptor binding affinity (IC$_{50}$) below 50 nM, typically below 10 nM and preferably below 1 nM; and at least a 10-fold selective affinity, typically at least a 50-fold selective affinity and preferably at least a 100-fold selective affinity, for the human 5-HT$_{1D\alpha}$ receptor subtype relative to the 5-HT$_{1D\beta}$ subtype.

The present invention provides a compound of formula I, or a salt or prodrug thereof:

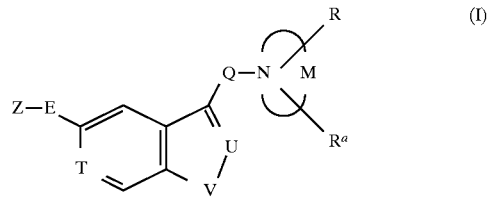

wherein

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

E represents a chemical bond or a straight or branched alkylene chain containing from 1 to 4 carbon atoms;

Q represents a straight or branched alkylene chain containing from 1 to 4 carbon atoms, optionally substituted in any position by a hydroxy group;

T represents nitrogen or CH;

U represents nitrogen or C—R$^2$;

V represents oxygen, sulphur or N—R$^3$;

R$^2$ and R$^3$ independently represent hydrogen or C$_{1-6}$ alkyl;

M represents the residue of an azetidine, pyrrolidine or piperidine ring;

R represents a group of formula —W—R$^1$;

W represents a chemical bond or a straight or branched alkylene chain containing from 1 to 4 carbon atoms, optionally substituted in any position by a hydroxy group;

R$^1$ represents —OR$^x$, —SR$^x$, —SOR$^x$, —SO$_2$R$^x$ or —NR$^x$R$^y$;

R$^x$ and R$^y$ independently represent hydrogen, hydrocarbon or a heterocyclic group; or R$^x$ and R$^y$ together represent a C$_{2-6}$ alkylene group, which alkylene group may be optionally substituted by one or more substituents selected from C$_{1-6}$ alkyl, aryl and hydroxy, or fused with a phenyl ring; and $R^a$ represents hydrogen, hydroxy, hydrocarbon or a heterocyclic group.

The present invention also provides compounds of formula I above wherein T represents CH; W represents a chemical bond or a straight or branched alkylene chain containing from 1 to 4 carbon atoms; $R^1$ represents —$OR^x$, —$SR^x$ or —$NR^xR^y$; $R^x$ and $R^y$ independently represent hydrogen, hydrocarbon or a heterocyclic group, or $R^x$ and $R^y$ together represent a $C_{2-6}$ alkylene group; and Z, E, Q, U, V, M and $R^a$ are as defined above.

The present invention further provides compounds of formula I above wherein Q represents a straight or branched alkylene chain containing from 1 to 4 carbon atoms; T represents CH; W represents a chemical bond or a straight or branched alkylene chain containing from 1 to 4 carbon atoms; $R^1$ represents —$OR^x$, —$SR^x$ or —$NR^xR^y$; $R^x$ and $R^y$ independently represent hydrogen, hydrocarbon or a heterocyclic group, or $R^x$ and $R^y$ together represent a $C_{2-6}$ alkylene group; $R^a$ represents hydrogen; and Z, E, U, V and M are as defined above.

The present invention still further provides compounds of formula I above wherein Q represents a straight or branched alkylene chain containing from 1 to 4 carbon atoms; T represents nitrogen; U represents C—$R^2$; V represents N—$R^3$; W represents a chemical bond or a straight or branched alkylene chain containing from 1 to 4 carbon atoms; $R^1$ represents —$OR^x$, —$SR^x$ or —$NR^xR^y$; $R^x$ and $R^y$ independently represent hydrogen, hydrocarbon or a heterocyclic group, or $R^x$ and $R^y$ together represent a $C_{2-6}$ alkylene group; $R^a$ represents hydrogen; and Z, E, $R^2$, $R^3$ and M are as defined above.

The five-membered heteroaromatic ring Z in the compounds of formula I above may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z. Examples of suitable substituents on the five-membered heteroaromatic ring Z include $C_{1-6}$ alkyl, $C_{2-6}$ alkenyl, $C_{2-6}$ alkynyl, $C_{3-7}$ cycloalkyl, aryl, aryl($C_{1-6}$)alkyl, $C_{3-7}$ heterocydoalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$) alkylamino, halogen, cyano or trifluoromethyl.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, indanyl, aryl and aryl($C_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl and heteroaryl($C_{1-6}$)alkyl groups.

Suitable alkyl groups include straight-chained and branched alkyl groups containing from 1 to 6 carbon atoms. Typical examples include methyl and ethyl groups, and straight-chained or branched propyl, butyl and pentyl groups. Particular alkyl groups are methyl, ethyl, n-propyl, isopropyl, isobutyl, t-butyl and 2,2-dimethylpropyl.

Suitable alkenyl groups include straight-chained and branched alkenyl groups containing from 2 to 6 carbon atoms. Typical examples include vinyl, allyl and dimethylallyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Typical examples of $C_{3-7}$ cycloalkyl($C_{1-6}$)alkyl groups include cyclopropylmethyl, cyclohexylmethyl and cyclohexylethyl.

Particular indanyl groups include indan-1-yl and indan-2-yl.

Particular aryl groups include phenyl and naphthyl.

Particular aryl($C_{1-6}$)alkyl groups include benzyl, phenylethyl, phenylpropyl and naphthylmethyl.

Suitable heterocycloalkyl groups include azetidinyl, pyrrolidyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridylmethyl, pyridylethyl, pyrimidinylmethyl, pyrazinylmethyl, quinolylmethyl and isoquinolylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, aminocarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —$NR^vR^w$, —$NR^vCOR^w$, —$NR^vCO_2R^w$, —$NR^vSO_2R^w$, —$CH_2NR^vSO_2R^w$, —$NHCONR^vR^w$, —$CONR^vR^w$, —$SO_2NR^vR^w$ and —$CH_2SO_2NR^vR^w$, in which $R^v$ and $R^w$ independently represent hydrogen, $C_{1-6}$ alkyl, aryl or aryl($C_{1-6}$)alkyl, or $R^v$ and $R^w$ together represent a $C_{2-6}$ alkylene group.

When $R^x$ and $R^y$, or $R^v$ and $R^w$, together represent a $C_{2-6}$ alkylene group, this group may be an ethylene, propylene, butylene, pentamethylene or hexamethylene group, preferably butylene or pentamethylene.

When $R^x$ and $R^y$ together represent a $C_{2-6}$ alkylene group, this group may be unsubstituted or substituted by one or more substituents selected from $C_{1-6}$ alkyl, aryl and hydroxy. Typical substituents include methyl, phenyl and hydroxy.

Furthermore, when $R^x$ and $R^y$ together represent a $C_{2-6}$ alkylene group, this group may optionally be fused with a phenyl ring. In this context, a typical group of formula —$NR^xR^y$ as defined for the substituent $R^1$ is 1,2,3,4-tetrahydroisoquinolinyl.

The term "halogen" as used herein includes fluorine, chlorine, bromine and iodine, especially fluorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In particular, where M represents the residue of a pyrrolidine ring, and the substituent R is attached to the 2-position thereof, then the absolute stereochemical configuration of the carbon atom at the point of attachment of the moiety R is preferably as depicted in structure IA as follows:

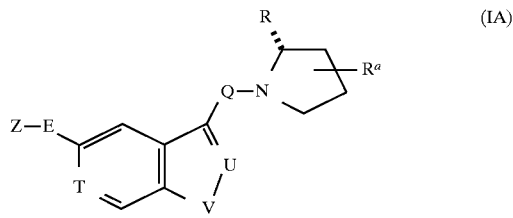

(IA)

wherein Z, E, Q, T, U, V, R and $R^a$ are as defined above.

Moreover, where M represents the residue of a pyrrolidine ring, and the substituent R is attached to the 3-position thereof, then the absolute stereochemical configuration of the carbon atom at the point of attachment of the moiety R is preferably as depicted in structure IB as follows:

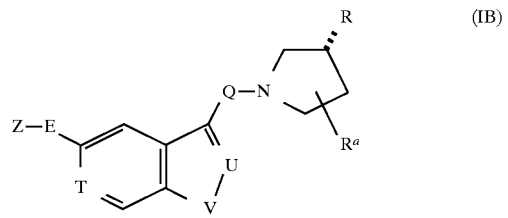

(IB)

wherein Z, E, Q, T, U, V, R and $R^a$ are as defined above.

The optionally substituted five-membered heteroaromatic ring Z in formula I is suitably a 1,3-oxazole, 1,3-thiazole, imidazole, 1,2,4-oxadiazole, 1,3,4-oxadiazole, 1,2,4-thiadiazole, 1,3,4-thiadiazole, 1,2,3-triazole, 1,2,4-triazole or tetrazole ring. Preferably, the ring is a 1,3-oxazole, 1,3-thiazole, imidazole, 1,2,4-oxadiazole, 1,2,4-thiadiazole or 1,2,4-triazole ring, in particular an imidazol-1-yl, 1,2,4-triazol-1-yl or 1,2,4-triazol-4-yl moiety.

Suitably, the five-membered heteroaromatic ring Z is unsubstituted. Examples of optional substituents which may typically be attached to the moiety Z include methyl, ethyl, benzyl and amino.

Where E, Q and W, which may be the same or different, represent straight or branched alkylene chains, these may be, for example, methylene, ethylene, 1-methylethylene, propylene, 2-methylpropylene or butylene. In addition, Q and W may be substituted in any position by a hydroxy group giving rise, for example, to a hydroxymethylmethylene, 2-hydroxypropylene or 2-hydroxymethylpropylene linkage. Moreover, E and W may each independently represent a chemical bond. Where E represents a chemical bond, the moiety Z is attached directly to the central fused bicyclic heteroaromatic ring system containing the variables T, U and V. Similarly, where W represents a chemical bond, the substituent $R^1$ is attached directly to the azetidine, pyrrolidine or piperidine ring of which M is the residue.

Suitably, E represents a chemical bond or a methylene linkage.

Suitably, Q represents an ethylene or propylene linkage.

The compound of formula I in accordance with the present invention is suitably an indole, benzofuran or benzthiophene derivative of formula IC, an indazole derivative of formula ID, or a pyrrolo[2,3-c]-pyridine derivative of formula IE:

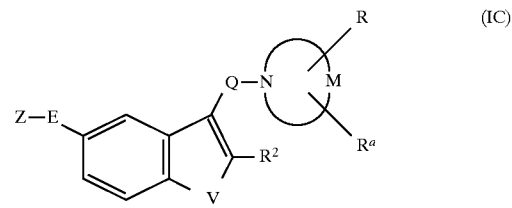

(IC)

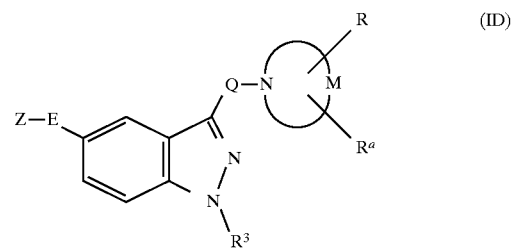

(ID)

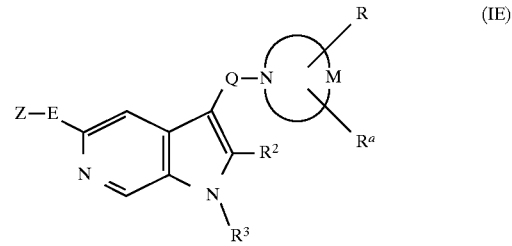

(IE)

wherein Z, E, Q, V, M, R, $R^a$, $R^2$ and $R^3$ are as defined above. Preferably, the compounds according to the invention are indole or pyrrolo[2,3-c]-pyridine derivatives of formula IF:

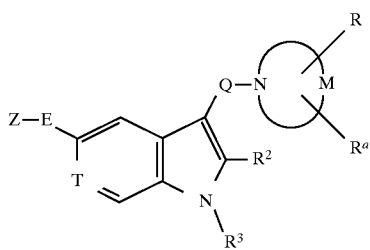

wherein Z, E, Q, T, M, R, $R^a$, $R^2$ and $R^3$ are as defined above, in particular wherein $R^2$ and $R^3$ are both hydrogen.

Suitably, W represents a chemical bond or a methylene or hydroxymethyl-methylene linkage, in particular a chemical bond or a methylene linkage.

Suitably, $R^x$ and $R^y$ independently represent hydrogen, $C_{1-6}$ alkyl, $C_{2-6}$ alkenyl, $C_{3-7}$ cycloalkyl($C_{1-6}$)alkyl, indanyl, aryl, aryl($C_{1-6}$)alkyl, heteroaryl or heteroaryl($C_{1-6}$)alkyl, any of which groups may be optionally substituted by one or more substituents selected typically from $C_{1-6}$ alkyl, halogen, hydroxy, C1-6 alkoxy, aminocarbonyloxy, amino, $C_{2-6}$ alkylcarbonylamino, $C_{1-6}$ alkylsulphonylamino and $C_{1-6}$ alkylaminosulphonylmethyl. Particular values of $R^x$ and $R^y$ include hydrogen, methyl, hydroxyethyl, isobutyl, 2,2-dimethylpropyl, allyl, dimethylallyl, 1-cyclohexylethyl, 2-cyclohexylethyl, indanyl, hydroxy-indanyl, phenyl, benzyl, methyl-benzyl, fluorobenzyl, methoxy-benzyl, acetylamino-benzyl, 1-phenylethyl, 2-phenylethyl, 2-hydroxy-1-phenylethyl, 2-methoxy-1-phenylethyl, 2-aminocarbonyloxy-1-phenylethyl, 1-(fluorophenyl)ethyl, 1-(fluorophenyl)-2-hydroxyethyl, 1-(fluorophenyl)-2-methoxyethyl, 1-(acetylamino-phenyl)ethyl, 2-(acetylamino-phenyl)ethyl, 2-hydroxy-1-phenylprop-1-yl, 1-phenylprop-2-yl, 2-phenylprop-2-yl, 1-hydroxy-1-phenylprop-2-yl, 1-hydroxy-2-phenylprop-2-yl, 1-hydroxy-3-phenylprop-2-yl, furylmethyl, thienylmethyl and pyridylmethyl.

In addition, where $R^x$ and $R^y$ together represent an optionally substituted or phenyl ring-fused $C_{2-6}$ alkylene group, the substituent —$NR^xR^y$ as defined for $R^1$ may suitably represent 3,3-dimethylpiperidinyl, 2-phenylpiperidinyl, 3-hydroxy-2-phenylpiperidinyl or 1,2,3,4-tetrahydroisoquinolin-2-yl.

Suitable values for the substituent $R^1$ include hydroxy, benzyloxy, methoxy-benzyloxy, pyridylmethoxy, benzylthio, fluorobenzyl-thio, phenylsulphinyl, benzylsulphinyl, fluorobenzyl-sulphinyl, fluorobenzyl-sulphonyl, amino, methylamino, indanylamino, hydroxyindanyl-amino, benzylamino, N-(methylbenzyl)-amino, N-(acetylamino-benzyl)-amino, N-(1-phenylethyl)-amino, N-(2-phenylethyl)-amino, N-(2-hydroxy-1-phenylethyl)-amino, N-(2-methoxy-1-phenylethyl)-amino, N-(2-aminocarbonyloxy-1-phenylethyl)-amino, N-[1-(fluorophenyl)ethyl]-amino, N-[1-(fluorophenyl)-2-hydroxyethyl]-amino, N-[1-(fluorophenyl)-2-methoxyethyl]-amino, N-[1-(acetylamino-phenyl)ethyl]-amino, N-[2-(acetylamino-phenyl)ethyl]-amino, N-(2-hydroxy-1-phenylprop-1-yl)-amino, N-(1-phenylprop-2-yl)-amino, N-(2-phenylprop-2-yl)-amino, N-(1-hydroxy-1-phenylprop-2-yl)-amino, N-(1-hydroxy-2-phenylprop-2-yl)-amino, N-(1-hydroxy-3-phenylprop-2-yl)-amino, N-(furylmethyl)-amino, N-(pyridylmethyl)-amino, dimethylamino, N-isobutyl-N-methylamino, N-(2,2-dimethylpropyl)-N-methylamino, N-allyl-N-methylamino, N-(3,3-dimethylprop-2-en-1-yl)-N-methylamino, N-(1-cyclohexylethyl)-N-methylamino, N-benzyl-N-methylamino, N-methyl-N-(methylbenzyl)-amino, N-(fluorobenzyl)-N-methylamino, N-(acetylamino-benzyl)-N-methylamino, N-methyl-N-(1-phenylethyl)-amino, N-methyl-N-(2-phenylethyl)-amino, N-(2-hydroxy-1-phenylethyl)-N-methylamino, N-(2-methoxy-1-phenylethyl)-N-methylamino, N-[2-(acetylamino-phenyl)ethyl]-N-methylamino, N-(furylmethyl)-N-methylamino, N-methyl-N-(thienylmethyl)-amino, N-benzyl-N-(2-hydroxyethyl)-amino, N,N-bis(furylmethyl)-amino, 3,3-dimethylpiperidinyl, 2-phenylpiperidinyl, 3-hydroxy-2-phenylpiperidinyl and 1,2,3,4-tetrahydroisoquinolin-2-yl.

Particular values of the group R include hydroxy, benzyloxy, benzyloxymethyl, methoxy-benzyloxy, pyridylmethoxy, benzylthio-methyl, fluorobenzylthio-methyl, phenylsulphinylmethyl, benzylsulphinylmethyl, fluorobenzyl-sulphinyl, fluorobenzyl-sulphinylmethyl, fluorobenzyl-sulphonylmethyl, indanylamino, indanylaminomethyl, hydroxyindanyl-amino, benzylamino, benzylaminomethyl, 1-(N-benzylamino)-2-hydroxyethyl, N-(methylbenzyl)-aminomethyl, N-(acetylamino-benzyl)-amino, N-(acetylamino-benzyl)-aminomethyl, N-(1-phenylethyl)-amino, N-(1-phenylethyl)-aminomethyl, N-(2-phenylethyl)-aminomethyl, N-(2-hydroxy-1-phenylethyl)-amino, N-(2-hydroxy-1-phenylethyl)-aminomethyl, N-(2-methoxy-1-phenylethyl)-amino, N-(2-aminocarbonyloxy-1-phenylethyl)-amino, N-[1-(fluorophenyl)ethyl]-amino, N-[1-(fluorophenyl)-2-hydroxyethyl]-amino, N-[1-(fluorophenyl)-2-methoxyethyl]-amino, N-[1-(acetylamino-phenyl)ethyl]-amino, N-[1-(acetylamino-phenyl)ethyl]-aminomethyl, N-[2-(acetylamino-phenyl)ethyl]-amino, N-(2-hydroxy-1-phenylprop-1-yl)-amino, N-(1-phenylprop-2-yl)-amino, N-(2-phenylprop-2-yl)-aminomethyl, N-(1-hydroxy-1-phenylprop-2-yl)-amino, N-(1-hydroxy-2-phenylprop-2-yl)-amino, N-(1-hydroxy-3-phenylprop-2-yl)-amino, N-(furylmethyl)-amino, N-(furylmethyl)-aminomethyl, N-(pyridylmethyl)-aminomethyl, N-isobutyl-N-methyl-aminomethyl, N-(2,2-dimethylpropyl)-N-methyl-aminomethyl, N-allyl-N-methylamino, N-(3,3-dimethylprop-2-en-1-yl)-N-methylamino, N-(1-cyclohexylethyl)-N-methyl-aminomethyl, N-benzyl-N-methylamino, N-benzyl-N-methyl-aminomethyl, N-methyl-N-(methylbenzyl)-aminomethyl, N-(fluorobenzyl)-N-methylamino, N-(acetylamino-benzyl)-N-methyl-aminomethyl, N-methyl-N-(1-phenylethyl)-aminomethyl, N-methyl-N-(2-phenylethyl)-aminomethyl, N-(2-hydroxy-1-phenylethyl)-N-methylamnino, N-(2-hydroxy-1-phenylethyl)-N-methyl-aminomethyl, N-(2-methoxy-1-phenylethyl)-N-methylamino, N-[2-(acetylamino-phenyl) ethyl]-N-methylamino, N-(furylmethyl)-N-methylamino, N-methyl-N-(thienylmethyl)-amino, N-benzyl-N-(2-hydroxyethyl-aminomethyl, N,N-bis(furylmethyl)-amino, 3,3-dimethylpiperidinylmethyl, 2-phenylpiperidinyl, 2-phenylpiperidinylmethyl, 3-hydroxy-2-phenylpiperidinylmethyl and 1,2,3,4-tetrahydroisoquinolin-2-yl.

Suitable values of $R^a$ include hydrogen, hydroxy and benzyl, especially hydrogen.

Suitably, $R^2$ and $R^3$ independently represent hydrogen or methyl, especially hydrogen.

A particular sub-class of compounds according to the invention is represented by the compounds of formula IIA, and salts and prodrugs thereof:

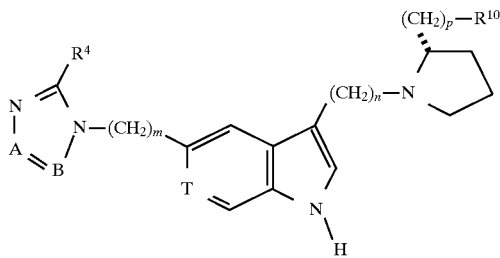

(IIA)

wherein
  m is zero, 1, 2 or 3, preferably zero or 1;
  n is 2, 3 or 4, preferably 2 or 3;
  p is zero, 1 or 2;
  T represents nitrogen or CH;
  A represents nitrogen or CH;
  B represents nitrogen or C—$R^5$;
  $R^4$ and $R^5$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl; and
  $R^{10}$ represents —X—$R^{11}$ or a group of formula (a) or (b):

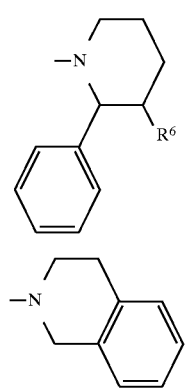

in which
  $R^6$ represents hydrogen or hydroxy;
  X represents oxygen, sulphur, —SO—, —$SO_2$— or N—$R^{12}$; and
  $R^{11}$ and $R^{12}$ independently represent hydrogen, $C_{1-6}$ alkyl, $C_{2-6}$ alkenyl, $C_{3-7}$ cycloalkyl($C_{1-6}$)alkyl, indanyl, aryl, aryl($C_{1-6}$)alkyl, heteroaryl or heteroaryl($C_{1-6}$) alkyl, any of which groups may be optionally substituted.

Examples of suitable optional substituents on the groups $R^{11}$ and $R^{12}$ include $C_{1-6}$ alkyl, halogen, cyano, trifluoromethyl, hydroxy, $C_{1-6}$ alkoxy, aminocarbonyloxy, $C_{2-6}$ alkylcarbonyl, amino, $C_{1-6}$ alkylamino, di($C_{1-6}$) alkylamino, $C_{2-6}$ alkylcarbonylamino, $C_{1-6}$ alkylsulphonylamino and $C_{1-6}$ alkylaminosulphonylmethyl.

Particular values of $R^4$ and $R^5$ include hydrogen, methyl, ethyl, benzyl and amino, especially hydrogen.

Particular values of $R^{11}$ and $R^{12}$ include hydrogen, methyl, hydroxyethyl, isobutyl, 2,2-dimethylpropyl, allyl, dimethylallyl, 1-cyclohexylethyl, 2-cyclohexylethyl, indanyl, hydroxy-indanyl, phenyl, benzyl, methyl-benzyl, fluorobenzyl, methoxy-benzyl, acetylamino-benzyl, 1-phenylethyl, 2-phenylethyl, 2-hydroxy-1-phenylethyl, 2-methoxy-1-phenylethyl, 2-aminocarbonyloxy-1-phenylethyl, 1-(fluorophenyl)ethyl, 1-(fluorophenyl)-2-hydroxyethyl, 1-(fluorophenyl)-2-methoxyethyl, 1-(acetylamino-phenyl)ethyl, 2-(acetylamino-phenyl)ethyl, 2-hydroxy-1-phenylprop-1-yl, 1-phenylprop-2-yl, 2-phenylprop-2-yl, 1-hydroxy-1-phenylprop-2-yl, 1-hydroxy-2-phenylprop-2-yl, 1-hydroxy-3-phenylprop-2-yl, furylmethyl, thienylmethyl and pyridylmethyl.

In relation to formula IIA, the variable p is preferably 1.

Another sub-class of compounds according to the invention is represented by the compounds of formula IIB, and salts and prodrugs thereof:

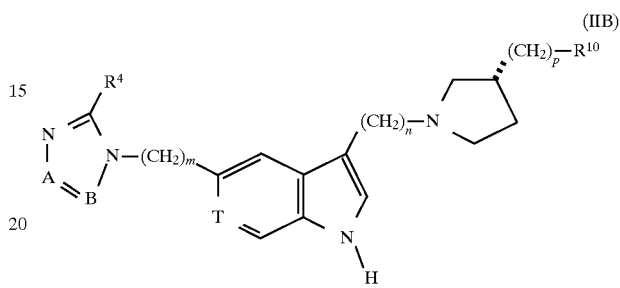

(IIB)

wherein m, n, p, T, A, B, $R^4$ and $R^{10}$ are as defined with reference to formula IIA above.

In relation to formula IIB, the variable p is suitably zero or 1.

A further sub-class of compounds according to the invention is represented by the compounds of formula IIC, and salts and prodrugs thereof:

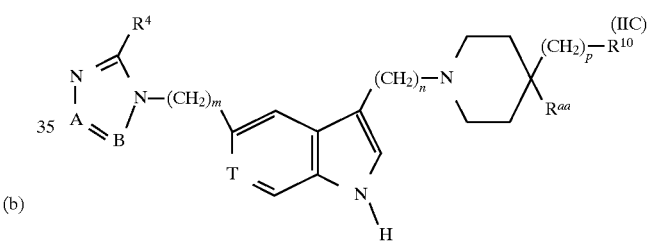

(IIC)

wherein
  $R^{aa}$ represents hydrogen, hydroxy or aryl($C_{1-6}$)alkyl; and
  m, n, p, T, A, B, $R^4$ and $R^{10}$ are as defined with reference to formula IIA above.

Suitable values of $R^{aa}$ include hydrogen, hydroxy and benzyl, especially hydrogen.

In relation to formula IIC, the variable p is suitably zero or 1.

In one subset of the compounds of formula IIC above, $R^{aa}$ is hydrogen.

A still further sub-class of compounds according to the invention is represented by the compounds of formula IID, and salts and prodrugs thereof:

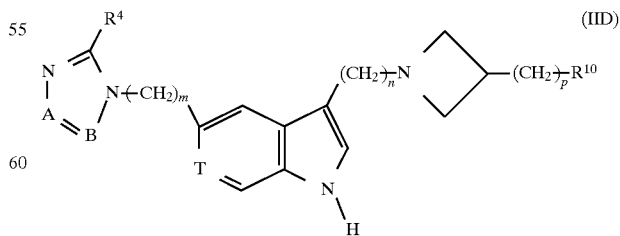

(IID)

wherein m, n, p, T, A, B, $R^4$ and $R^{10}$ are as defined with reference to formula IIA above.

In relation to formula IID, the variable p is suitably zero or 1.

The present invention also provides compounds of formula IIA, IIB, IIC and IID as defined above wherein T represents CH; $R^{10}$ represents —X—$R^{11}$; X represents oxygen, sulphur or N—$R^{12}$; $R^{11}$ and $R^{12}$ independently represent hydrogen, $C_{1-6}$ alkyl, aryl, aryl($C_{1-6}$)alkyl, heteroaryl or heteroaryl($C_{1-6}$)alkyl, any of which groups may be optionally substituted; and m, n, p, A, B and $R^4$ are as defined above.

The present invention further provides compounds of formula IIA, IIB and IIC as defined above wherein T represents nitrogen; $R^{10}$ represents —X—$R^{11}$; X represents oxygen, sulphur or N—$R^{12}$; $R^{11}$ and $R^{12}$ independently represent hydrogen, $C_{1-6}$ alkyl, aryl, aryl($C_{1-6}$)alkyl, heteroaryl or heteroaryl($C_{1-6}$)alkyl, any of which groups may be optionally substituted; $R^{aa}$ represents hydrogen; and m, n, p, A, B and $R^4$ are as defined above.

Specific compounds within the scope of the present invention include:

(3R)-3-benzyloxy-1-[2-(5-(1,2,4-triazol-4-yl)-1H-indol-3-yl)ethyl]pyrrolidine;
(3R)-3-(4-methoxyphenyl)methoxy-1-[2-(5-(1,2,4-triazol-4-yl)-1H-indol-3-yl)ethyl]pyrrolidine;
(3R)-3-(pyridin-3-yl)methoxy-1-[2-(5-(1,2,4-triazol-4-yl)-1H-indol-3-yl)ethyl]pyrrolidine;
(3R)-3-benzyloxymethyl-1-[2-(5-(1,2,4-triazol-4-yl)-1H-indol-3-yl)ethyl]pyrrolidine;
(3S)-3-(N-benzyl-N-methyl)aminomethyl-1-[2-(5-(1,2,4-triazol-4-yl)-1H-indol-3-yl)ethyl]pyrrolidine;
(2S)-2-(N-benzyl-N-methyl)aminomethyl-1-[2-(5-(1,2,4-triazol-4-yl)-1H-indol-3-yl)ethyl]pyrrolidine;
(3S)-3-(N-benzyl)aminomethyl-1-[2-(5-(1,2,4-triazol-4-yl)-1H-indol-3-yl)ethyl]pyrrolidine;
4-(4-acetylaminophenyl)methylamino-1-[3-(5-(1,2,4-triazol-4-yl)-1H-indol-3-yl)propyl]piperidine;
4-benzylamino-1-[3-(5-(1,2,4-triazol-4-yl)-1H-indol-3-yl)propyl]piperidine;
4-(N-benzyl-N-methyl)amino-1-[3-(5-(1,2,4-triazol-4-yl)-1H-indol-3-yl)propyl]piperidine;
4-(N-benzyl)aminomethyl-1-[3-(5-(1,2,4-triazol-4-yl)-1H-indol-3-yl)propyl]piperidine;
(2S)-2-(N-benzyl-N-methylaminomethyl)-1-[2-(5-(1,2,4-triazol-1-yl)-1H-pyrrolo[2,3-c]pyridin-3-yl)ethyl]pyrrolidine;
4-(N-benzyl-N-methyl)aminomethyl-1-[3-(5-(1,2,4-triazol-4-yl)-1H-indol-3-yl)propyl]piperidine;
1-[3-(5-(1,2,4-triazol-4-yl)-1H-indol-3-yl)propyl]-4-[(R)-α-(methyl)benzylamino]piperidine;
1-[3-(5-(1,2,4-triazol-4-yl)-1H-indol-3-yl)propyl]-4-[(S)-α-(methyl)benzylamino]piperidine;
1-[3-(5-(1,2,4-triazol-4-yl)-1H-indol-3-yl)propyl]-4-[(S)-α-(hydroxymethyl)benzylamino]piperidine;
1-[3-(5-(1,2,4-triazol-4-yl)-1H-indol-3-yl)propyl]-4-[(R)-α-(hydroxymethyl)benzylamino]piperidine;
1-[3-(5-(1,2,4-triazol-4-yl)-1H-indol-3-yl)propyl]-4-[(S)-(1-hydroxymethyl-2-phenyl)ethylamino]piperidine;
1-[3-(5-(1,2,4-triazol-4-yl)-1H-indol-3-yl)propyl]-4-[(1R,2S)-(2-hydroxy-1-methyl-2-phenyl)ethylamino]piperidine; 1-[3-(5-(1,2,4-triazol-4-yl)-1H-indol-3-yl)propyl]-4-[(1S,2R)-(2-hydroxy-1-methyl-2-phenyl)ethylamino]piperidine;
1-[3-(5-(1,2,4-triazol-4-yl)-1H-indol-3-yl)propyl]-4-[(1R,2R)-(2-hydroxy-1-methyl-2-phenyl)ethylamino]piperidine;
1-[3-(5-(1,2,4-triazol-4-yl)-1H-indol-3-yl)propyl]-4-[2-(4-acetylaminophenyl)ethylamino]piperidine;
1-[3-(5-(1,2,4-triazol-4-yl)-1H-indol-3-yl)propyl]-4-[(R)-α-(methyl)benzylamino]methylpiperidine;
1-[3-(5-(1,2,4-triazol-4-yl)-1H-indol-3-yl)propyl]-4-[(S)-α-(methyl)benzylamino]methylpiperidine;
1-[3-(5-(1,2,4-triazol-4-yl)-1H-indol-3-yl)propyl]-4-[(S)-1-(4-acetylaminophenyl)ethylamino]methylpiperidine;
1-[3-(5-(1,2,4-triazol-4-yl)-1H-indol-3-yl)propyl]-4-[(R)-1-(4-acetylaminophenyl)ethylamino]methylpiperidine;
1-[3-(5-(1,2,4-triazol-4-yl)-1H-indol-3-yl)propyl]-4-[N-[(R)-α-(hydroxymethyl)benzyl]-N-methylamino]piperidine;
1-[3-(5-(1,2,4-triazol-4-yl)-1H-indol-3-yl)propyl]-4-[N-[(S)-α-(hydroxymethyl)benzyl]-N-methylamino]piperidine;
1-[3-(5-(1,2,4-triazol-4-yl)-1H-indol-3-yl)propyl]-4-[N-(2-(4-acetylaminophenyl)ethyl)-N-methylamino]piperidine;
1-[3-(5-(1,2,4-triazol-4-yl)-1H-indol-3-yl)propyl]-4-[N-(4-acetylaminobenzyl)-N-methylamino]methylpiperidine;
1-[3-(5-(1,2,4-triazol-4-yl)-1H-indol-3-yl)propyl]-4-[N-(thien-2-yl)methyl-N-methylamino]piperidine;
1-[3-(5-(1,2,4-triazol-4-yl)-1H-indol-3-yl)propyl]-4-[(R)-α-(hydroxymethyl)benzylamino]methylpiperidine;
(3S)-3-(4-acetylaminobenzyl)aminomethyl-1-[2-(5-(1,2,4-triazol-4-yl)-1H-indol-3-yl)ethyl]pyrrolidine;
(3R)-3-(N-benzyl)aminomethyl-1-[2-(5-(1,2,4-triazol-4-yl)-1H-indol-3-yl)ethyl]pyrrolidine;
(3S)-3-(pyridin-4-ylmethyl)aminomethyl-1-[2-(5-(1,2,4-triazol-4-yl)-1H-indol-3-yl)ethyl]pyrrolidine;
3-(N-benzyl)aminomethyl-1-[2-(5-(1,2,4-triazol-4-yl)-1H-indol-3-yl)ethyl]azetidine;
4-benzyl-4-hydroxy-1-[3-(5-(1,2,4-triazol-4-yl)-1H-indol-3-yl)propyl]piperidine;
3-(N-benzyl)aminomethyl-1-[3-(5-(1,2,4-triazol-4-yl)-1H-indol-3-yl)propyl]azetidine;
4-(N-benzyl)aminomethyl-4-hydroxy-1-[3-(5-(1,2,4-triazol-4-yl)-1H-indol-3-yl)propyl]piperidine;
4-(N-benzyl-N-methyl)aminomethyl-4-hydroxy-1-[3-(5-(1,2,4-triazol-4-yl)-1H-indol-3-yl)propyl]piperidine;
3-(N-benzyl-N-methyl)aminomethyl-1-[2-(5-(1,2,4-triazol-4-yl)-1H-indol-3-yl)ethyl]azetidine;
(3S)-3-[N-(R)-α-(methyl)benzyl]aminomethyl-1-[2-(5-(1,2,4-triazol-4-yl)-1H-indol-3-yl)ethyl]pyrrolidine;
(3S)-3-[N-(S)-α-(methyl)benzyl]aminomethyl-1-[2-(5-(1,2,4-triazol-4-yl)-1H-indol-3-yl)ethyl]pyrrolidine;
(3S)-3-[N-(furan-3-ylmethyl)amino]methyl-1-[2-(5-(1,2,4-triazol-4-yl)-1H-indol-3-yl)ethyl]pyrrolidine;
(3S)-3-[N-(furan-2-ylmethyl)amino]methyl-1-[2-(5-(1,2,4-triazol-4-yl)-1H-indol-3-yl)ethyl]pyrrolidine;
(3S)-3-[N-(R)-α-(hydroxymethyl)benzyl]ainomethyl-1-[2-(5-(1,2,4-triazol-4-yl)-1H-indol-3-yl)ethyl]pyrrolidine;
(3S)-3-[N-(S)-α-(hydroxymethyl)benzyl]aminomethyl-1-[2-(5-(1,2,4-triazol-4-yl)-1H-indol-3-yl)ethyl]pyrrolidine;
(3S)-3-[N-benzyl-N-(2-hydroxy)ethyl]aminomethyl-1-[2-(5-(1,2,4-triazol-4-yl)-1H-indol-3-yl)ethyl]pyrrolidine;
(3S)-3-[N-(2-phenylethyl)amino]methyl-1-[2-(5-(1,2,4-triazol-4-yl)-1H-indol-3-yl)ethyl]pyrrolidine; (3S)-3-[N-(2-phenylethyl)-N-methylnmino]methyl-1-[2-(5-(1,2,4-triazol-4-yl)-1H-indol-3-yl)ethyl]pyrrolidine;
(3S)-3-(N-α-dimethylbenzyl)aminomethyl-1-[2-(5-(1,2,4-triazol-4-yl)-1H-indol-3-yl)ethyl]pyrrolidine;
(3S)-3-[N-(S)-α-methylbenzyl]aminomethyl-1-[2-(5-(1,2,4-triazol-1-yl)-1H-indol-3-yl)ethyl]pyrrolidine;
(3S)-3-[N-(R)-α-(hydroxymethyl)benzyl]aminomethyl-1-[2-(5-(1,2,4-triazol-1-yl)-1H-indol-3-yl)ethyl]pyrrolidine;
(3S)-3-(N-benzyl)aminomethyl-1-[2-(5-(1,2,4-triazol-1-ylmethyl)-1H-indol-3-yl)ethyl]pyrrolidine;
(3S)-3-[N-(S)-α-methylbenzyl]aminomethyl-1-[2-(5-(1,2,4-triazol-1-ylmethyl)-1H-indol-3-yl)ethyl]pyrrolidine;

(3S)-3-[N-(R)-α-(hydroxymethyl)benzyl]aminomethyl-1-[2-(5-(1,2,4-triazol-1-ylmethyl)-1H-indol-3-yl)ethyl]pyrrolidine;
(3S)-3-(N-benzyl-N-methyl)aminomethyl-1-[2-(5-(imidazol-1-yl)-1H-indol-3-yl)ethyl]pyrrolidine;
(3S)-3-(N-benzyl-N-methyl)aminomethyl-1-[2-(5-(1,2,4-triazol-1-ylmethyl)-1H-indol-3-yl)ethyl]pyrrolidine;
(3R)-3-[N-methyl-N-(S)-α-methylbenzyl]aminomethyl-1-[2-(5-(1,2,4-triazol-1-ylmethyl)-1H-indol-3-yl)ethyl]pyrrolidine;
(3R)-3-[N-methyl-N-(R)-α-hydroxymethylbenzyl]aminomethyl-1-[2-(5-(1,2,4-triazol-1-ylmethyl)-1H-indol-3-yl)ethyl]pyrrolidine;
(3R)-3-[N-methyl-N-(S)-α-methylcyclohexylmethyl]aminomethyl-1-[2-(5-(1,2,4-triazol-1-ylmethyl)-1H-indol-3-yl)ethyl]pyrrolidine;
(3R)-3-[3-(R)-hydroxy-2-(R)-phenylpiperidin-1-yl]methyl-1-[2-(5-(1,2,4-triazol-1-ylmethyl)-1H-indol-3-yl)ethyl]pyrrolidine;
(3R)-3-[3-(R)-hydroxy-2-(R)-phenylpiperidin-1-yl]methyl-1-[2-(5-(1,2,4-triazol-1-yl)-1H-indol-3-yl)ethyl]pyrrolidine;
4-hydroxy-4-(phenylsulfinyl)methyl-1-[3-(5-(1,2,4-triazol-4-yl)-1H-indol-3-yl)propyl]piperidine;
(3R)-3-[2-(R,S)-phenylpiperidin-1-yl]methyl-1-[2-(5-(1,2,4-triazol-1ylmethyl)-1H-indol-3-yl)ethyl]pyrrolidine;
4-(3,3-dimethylpiperidin-1-yl)methyl-4-hydroxy-1-[3-(5-(1,2,4-triazol-4-yl)-1H-indol-3-yl)propyl]piperidine;
4-hydroxy-4-(1,2,3,4-tetrahydroisoquinolin-2-yl)methyl-1-[3-(5-(1,2,4-triazol-4-yl)-1H-indol-3-yl)propyl]piperidine;
4-hydroxy-4-(N-isobutyl-N-methyl)aminomethyl-1-[3-(5-(1,2,4-triazol-4-yl)-1H-indol-3-yl)propyl]piperidine;
4-[N-benzyl-N-(2-hydroxyethyl)amino]methyl-4-hydroxy-1-[3-(5-(1,2,4-triazol-4-yl)-1H-indol-3-yl)propyl]piperidine;
4-[N-(2,2-dimethylpropyl)-N-methylamino]methyl-4-hydroxy-1-[3-(5-(1,2,4-triazol-4-yl)-1H-indol-3-yl)propyl]piperidine;
4-[N-(R)-α-hydroxymethylbenzyl-N-methylamino]methyl-4-hydroxy-1-[3-(5-(1,2,4-triazol-4-yl)-1H-indol-3-yl)propyl]piperidine;
4-hydroxy-4-(2-pyridylmethyl)aminomethyl-1-[3-(5-(1,2,4-triazol-4-yl)-1H-indol-3-yl)propyl]piperidine;
4-hydroxy-4-(2-methylphenylmethyl)aminomethyl-1-[3-(5-(1,2,4-triazol-4-yl)-1H-indol-3-yl)propyl]piperidine;
4-hydroxy-4-[N-(2-methylphenylmethyl)-N-methylamino]methyl-1-[3-(5-(1,2,4-triazol-4-yl)-1H-indol-3-yl)propyl]piperidine;
3-(benzylamino)methyl-3-hydroxy-1-[3-(5-(1,2,4-triazol-4-yl)-1H-indol-3-yl)propyl]pyrrolidine;
3-(benzylamnino)methyl-3-hydroxy-1-[2-(5-(1,2,4-triazol-4-yl)-1H-indol-3-yl)ethyl]pyrrolidine;
1-[3-(5-(1,2,4-triazol-4-yl)-1H-indol-3-yl)propyl]-4-[(R)-α-(carbamoyl-oxymethyl)benzylamino]piperidine;
1-[3-(5-(1,2,4-triazol-4-yl)-1H-indol-3-yl)propyl]-4-[(1R,2S)-2-hydroxy-1-phenylpropylamino]piperidine;
1-[3-(5-(1,2,4-triazol-4-yl)-1H-indol-3-yl)propyl]-4-[(1R,2R)-2-hydroxy-1-phenylpropylamino]piperidine;
1-[3-(5-(1,2,4-triazol-4-yl)-1H-indol-3-yl)propyl]-4-[(R,S)-1-hydroxy-2-phenylprop-2-ylamino]piperidine;
1-[3-(5-(1,2,4-triazol-4-yl)-1H-indol-3-yl)propyl]-4-[(R)-2-hydroxy-1-(4-fluorophenyl)ethylamino]piperidine;
1-[3-(5-(1,2,4-triazol-4-yl)-1H-indol-3-yl)propyl]-4-[(1R,2R)-2-hydroxyindan-1-ylamino)piperidine;
1-[3-(5-(1,2,4-triazol-4-yl)-1H-indol-3-yl)propyl]-4-[(R,S)-indan-1-ylamino]piperidine;
1-[3-(5-(1,2,4-triazol-4-yl)-1H-indol-3-yl)propyl]-4-[(R,S)-1-(4-fluorophenyl)ethylamino]piperidine;
1-[3-(5-(1,2,4-triazol-4-yl)-1H-indol-3-yl)propyl]-4-[(R)-1-phenylprop-2-ylamino]piperidine;
1-[3-(5-(1,2,4-triazol-4-yl)-1H-indol-3-yl)propyl]-4-[N-(thien-3-ylmethyl)-N-methylamino]piperidine;
1-[3-(5-(1,2,4-triazol-4-yl)-1H-indol-3-yl)propyl]-4-[N-(furan-3-ylmethyl)-N-methylamino]piperidine;
1-[3-(5-(1,2,4-triazol-4-yl)-1H-indol-3-yl)propyl]-4-(furan-3-ylmethyl)aminopiperidine;
1-[3-(5-(1,2,4-triazol-4-yl)-1H-indol-3-yl)propyl]-4-[N,N-di-(furan-3-ylmethyl)amino]piperidine;
1-[3-(5-(1,2,4-triazol-4-yl)-1H-indol-3-yl)propyl]-4-[N-(3,3-dimethylallyl)-N-methylamino]piperidine;
1-[3-(5-(1,2,4-triazol-4-yl)-1H-indol-3-yl)propyl]-4-(N-allyl-N-methylamino)piperidine;
1-[3-(5-(1,2,4-triazol-4-yl)-1H-indol-3-yl)propyl]-4-(indan-1-ylaminomethyl)piperidine;
1-[3-(5-(1,2,4-triazol-4-yl) -1H-indol-3-yl)propyl]-4-[N-(R)-α-(hydroxymethyl)benzyl-N-methylaminomethyl]piperidine;
(3R)-3-(benzylthio)methyl-1-[2-(5-(1,2,4-triazol-4-yl)-1H-indol-3-yl)ethyl]pyrrolidine;
(±)-1-[3-(5-(1,2,4-triazol-4-yl)-1H-indol-3-yl)propyl]-4-(1-benzylamino-2-hydroxyethyl)piperidine;
1-[3-(5-(1,2,4-triazol-1-yl)-1H-indol-3-yl)propyl]-4-[(R)-α-(hydroxymethyl)benzylamino]piperidine;
1-[3-(5-(imidazol-1-yl)-1H-indol-3-yl)propyl]-4-[(R)-α-(methyl)benzylamino]piperidine;
1-[3-(5-(imidazol-1-yl)-1H-indol-3-yl)propyl]-4-[(R)-α-(hydroxymethyl)benzylamino]piperidine;
1-[3-(5-(1,2,4-triazol-1-ylmethyl)-1H-indol-3-yl)propyl]-4-[(R)-α-(hydroxymethyl)benzylamino]piperidine;
1-[3-(5-(1,2,4-triazol-4-yl)-1H-indol-3-yl)propyl]-4-[(R)-α-(methoxymethyl)benzylamino]piperidine;
1-[3-(5-(1,2,4-triazol-4-yl)-1H-indol-3-yl)propyl]-4-[N-(R)-α-(methoxymethyl)benzyl-N-methylamino]piperidine;
1-[3-(5-(imidazol-1-yl)-1H-indol-3-yl)propyl]-4-[(R)-α-(methoxymethyl)benzylamino]piperidine;
1-[3-(5-(1,2,4-triazol-1-ylmethyl)-1H-indol-3-yl)propyl]-4-[(R)-1-(4-fluorophenyl)-2-methoxyethylamino]piperidine;
1-[3-(5-(1,2,4-triazol-1-ylmethyl)-1H-indol-3-yl)propyl]-4-[N-(4-fluorobenzyl)-N-methylamino]piperidine;
1-[3-(5-(1,2,4-triazol-4-yl)-1H-indol-3-yl)propyl]-4-(2-phenylpiperidin-1-yl)piperidine;
1-[3-(5-(1,2,4-triazol-4-yl)-1H-indol-3-yl)propyl]-4-[(R)-1-(4-fluorophenyl)-2-methoxyethylamino]piperidine;
(3R)-3-(benzylsulfinyl)methyl-1-[2-(5-(1,2,4-triazol-4-yl)-1H-indol-3-yl)ethyl]pyrrolidine;
(3R)-3-(4-fluorobenzylthio)methyl-1-[2-(5-(1,2,4-triazol-1-ylmethyl)-1H-indol-3-yl)ethyl]pyrrolidine;
(3R)-3-(4-fluorobenzylsulfinyl)methyl-1-[2-(5-(1,2,4-triazol-1-ylmethyl)-1H-indol-3-yl)ethyl]pyrrolidine;
(3R)-3-(4-fluorobenzylsulfonyl)methyl-1-[2-(5-(1,2,4-triazol-1-ylmethyl)-1H-indol-3-yl)ethyl]pyrrolidine;
4-(4-fluorobenzylsulfinyl)-1-[3-(5-(1,2,4-triazol-4-yl)-1H-indol-3-yl)propyl]piperidine;
and salts and prodrugs thereof The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention wherein T represents CH, U represents C—$R^2$ and V represents N—$R^3$, corresponding to the indole derivatives of formula IC as defined above, may be prepared by a process which comprises reacting a compound of formula III:

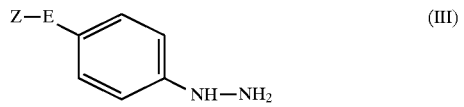

wherein Z and E are as defined above; with a compound of formula IV, or a carbonyl-protected form thereof.

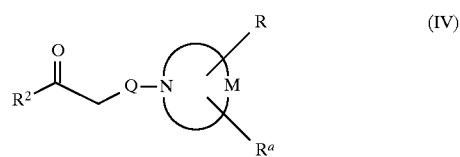

wherein $R^2$, Q, M, R and $R^a$ are as defined above; followed, where required, by N-alkylation by standard methods to introduce the moiety $R^3$.

The reaction between compounds III and IV, which is an example of the well-known Fischer indole synthesis, is suitably carried out by heating the reagents together under mildly acidic conditions, e.g. 4% sulphuric acid at reflux.

Suitable carbonyl-protected forms of the compounds of formula IV include the dimethyl acetal or ketal derivatives. Where the alkylene chain Q is substituted by a hydroxy group, this group may condense with the carbonyl moiety in compound IV whereby the carbonyl moiety is protected in the form of a cyclic hemiacetal.

The Fischer reaction between compounds III and IV may be carried out in a single step, or may proceed via an initial non-cyclising step at a lower temperature to give an intermediate of formula V:

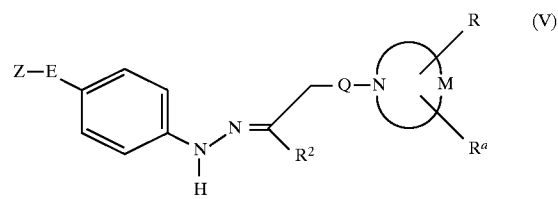

wherein Z, E, Q, $R^2$, M, and $R^a$ are as defined above; followed by cyclisation using a suitable reagent, e.g. a polyphosphate ester.

The intermediates of formula IV, or carbonyl-protected forms thereof, may be prepared by reacting a compound of formula VI, or a carbonyl-protected form thereof, with a compound of formula VII:

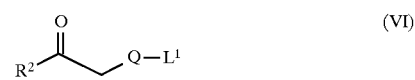

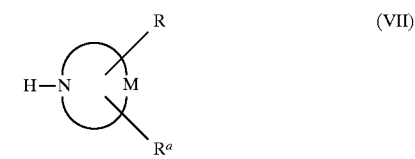

wherein Q, $R^2$, M, R and $R^a$ are as defined above, and $L^1$ represents a suitable leaving group.

The leaving group $L^1$ is suitably a halogen atom, e.g. chlorine or bromine.

Where $L^1$ represents a halogen atom, the reaction between compounds VI and VII is conveniently effected by stirring the reactants under basic conditions in a suitable solvent, for example sodium carbonate or potassium carbonate in 1,2-dimethoxyethane or N,N-dimethyl-formamide, or triethylamine in tetrahydrofuran or acetonitrile, optionally in the presence of catalytic sodium iodide.

In an alternative procedure, the compounds according to the invention may be prepared by a process which comprises reacting a compound of formula VII as defined above with a compound of formula VIII:

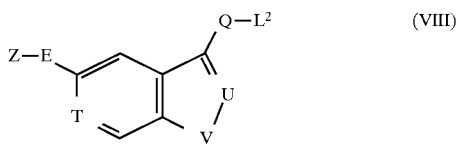

wherein Z, E, Q, T, U and V are as defined above, and $L^2$ represents a suitable leaving group.

The leaving group $L^2$ is suitablyan alkylsulphonyloxy or arylsulphonyloxy group, e.g. methanesulphonyloxy (mesyloxy) or p-toluenesulphonyloxy (tosyloxy).

Where $L^2$ represents an alkylsulphonyloxy or arylsulphonyloxy group, the reaction between compounds VII and VIII is conveniently carried out in a suitable solvent such as isopropanol or 1,2-dimethoxy-ethane, typically in the presence of a base such as sodium carbonate or potassium carbonate, optionally in the presence of sodium iodide.

In one representative approach, the compounds of formula VIII wherein T and U both represent CH, V represents NH and $L^2$ represents a mesyloxy or tosyloxy group may be prepared by the sequence of steps illustrated in the following reaction scheme (cf. Larock and Yum, *J. Am. Chem. Soc.*, 1991, 113, 6689):

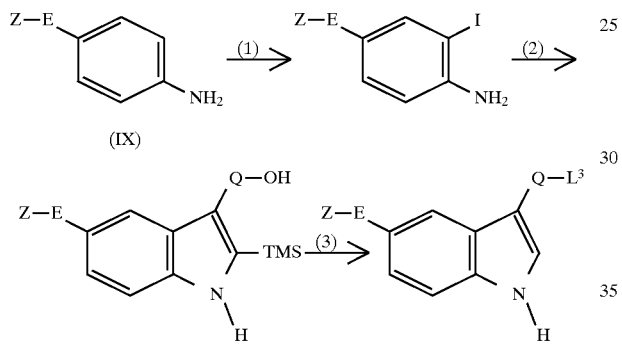

wherein Z, E and Q are as defined above, $L^3$ represents mesyloxy or tosyloxy, and TMS is an abbreviation for trimethylsilyl.

In Step 1 of the reaction scheme, the aniline derivative IX is treated with iodine monochloride, advantageously in methanol in the presence of a base such as calcium carbonate, in order to introduce an iodine atom ortho to the amine moiety. Step 2 involves a palladium-mediated coupling reaction with the protected acetylene derivative TMS—C≡C—Q—OH, typically using palladium acetate and triphenylphosphine in the presence of lithium chloride and sodium carbonate, suitably in N,N-dimethyl-formamide at an elevated temperature. This is followed in Step 3 by removal of the TMS moiety, ideally in refluxing methanolic hydrochloric acid; followed in turn by mesylation or tosylation, suitably by using mesyl chloride or tosyl chloride respectively in pyridine.

In another representative approach, the compounds of formula VIII wherein T and U both represent CH, V represents NH, Q represents a propylene chain and $L^2$ represents a mesyloxy or tosyloxy group may be prepared by reacting 3,4-dihydro-2H-pyran with a compound of formula III as defined above or a salt thereof, under a variant of the Fischer reaction conditions as described above for the reaction between compounds III and IV; followed by mesylation or tosylation of the 3-hydroxypropyl-indole derivative thereby obtained, typically by treatment with mesyl chloride or tosyl chloride under standard conditions.

The Fischer reaction with 3,4-dihydro-2H-pyran is suitably brought about by heating the hydrazine derivative III or an acid addition salt thereof, typically the hydrochloride salt, in an inert solvent such as dioxan, advantageously in the presence of a mineral acid such as hydrochloric acid or a Lewis acid such as zinc chloride, at the reflux temperature of the solvent.

In a further procedure, the compounds according to the invention wherein T represents CH, U represents nitrogen and V represents N—$R^3$, corresponding to the indazole derivatives of formula IB as defined above, may be prepared by a process which comprises cyclising a compound of formula X:

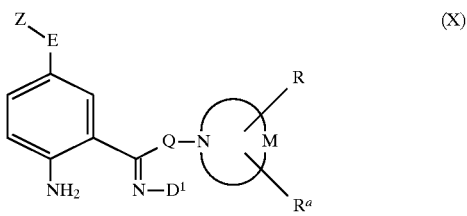

wherein Z, E, Q, M, R and $R^a$ are as defined above, and $D^1$ represents a readily displaceable group; followed, where required, by N-alkylation by standard methods to introduce the moiety $R^3$.

The cyclisation of compound X is conveniently achieved in a suitable organic solvent at an elevated temperature, for example in a mixture of m-xylene and 2,6-lutidine at a temperature in the region of 140° C.

The readily displaceable group $D^1$ in the compounds of formula X suitably represents a $C_{1-4}$ alkanoyloxy group, preferably acetoxy. Where $D^1$ represents acetoxy, the desired compound of formula X may be conveniently prepared by treating a carbonyl compound of formula XI:

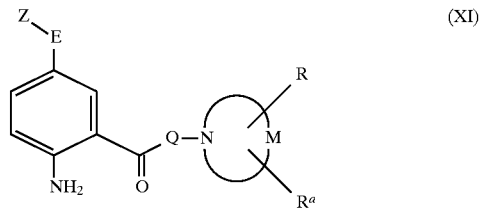

wherein Z, E, Q, M, R and $R^a$ are as defined above; or a protected derivative thereof, preferably the N-formyl protected derivative; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivatives of the intermediates of formula XI may conveniently be prepared by ozonolysis of the corresponding indole derivative of formula XII:

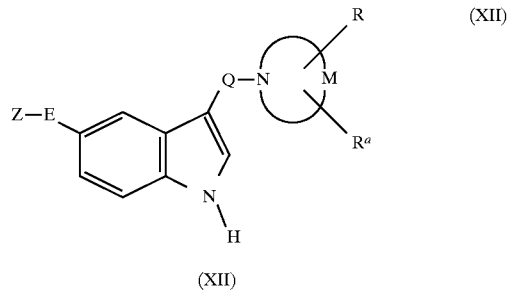

wherein Z, E, Q, M, R and $R^a$ are as defined above; followed by a reductive work-up, advantageously using dimethylsulphide.

The indole derivatives of formula XII may be prepared by methods analogous to those described in the accompanying Examples, or by procedures well known from the art.

In a still further procedure, the compounds according to the invention wherein T represents CH, U represents C—$R^2$ and V represents oxygen or sulphur, corresponding to the benzofuran or benzthiophene derivatives of formula IA wherein V is oxygen or sulphur respectively, may be prepared by a process which comprises cyclising a compound of formula XIII:

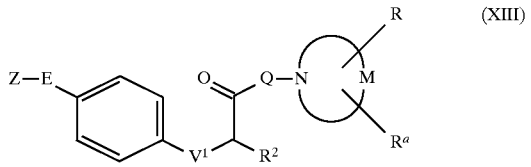

wherein Z, E, Q, $R^2$, M, R and $R^a$ are as defined above, and $V^1$ represents oxygen or sulphur.

The cyclisation of compound XIII is conveniently effected by using polyphosphoric acid or a polyphosphate ester, advantageously at an elevated temperature.

The compounds of formula XIII may be prepared by reacting a compound of formula XIV with a compound of formula XV:

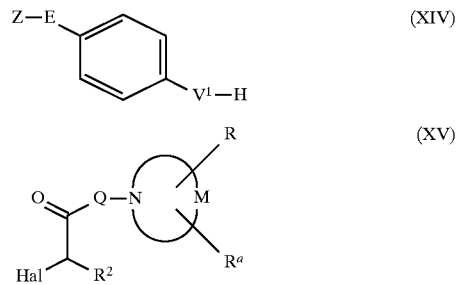

wherein Z, E, Q, $R^2$, $V^1$, M, R and $R^a$ are as defined above, and Hal represents a halogen atom.

The reaction is conveniently effected in the presence of a base such as sodium hydroxide.

The hydroxy and mercapto derivatives of formula XIV may be prepared by a variety of methods which will be readily apparent to those skilled in the art. One such method is described in EP-A-0497512.

In a yet further procedure, the compounds according to the invention may be prepared by a process which comprises reducing a compound of formula XVI:

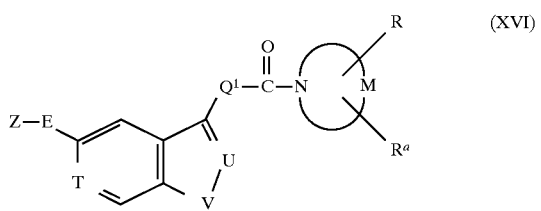

wherein Z, E, T, U, V, M, R and $R^a$ are as defined above, and —$Q^1$—$CH_2$— corresponds to the moiety Q as defined above.

The reaction is suitably carried out by treating the compound of formula XVI with a reducing agent such as lithium aluminium hydride in an appropriate solvent, e.g. diethyl ether, tetrahydrofuran or mixtures thereof.

The compounds of formula XVI above may suitably be prepared by reacting a compound of formula VII as defined above with the appropriate compound of formula XVII:

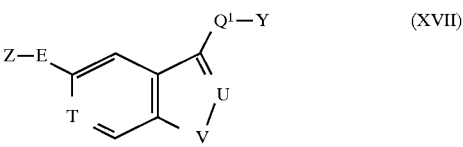

wherein Z, E, T, U, V and $Q^1$ are as defined above, and Y represents a reactive carboxylate moiety.

Suitable values for the reactive carboxylate moiety Y include esters, for example $C_{1-4}$ alkyl esters; acid anhydrides, for example mixed anhydrides with $C_{1-4}$ alkanoic acids; acid halides, for example acid chlorides; and acylimidazoles.

By way of example, the intermediates of formula XVII above wherein Y is an acid chloride moiety may be prepared by treating the corresponding carboxylic acid derivative with thionyl chloride in toluene. Similarly, the intermediates of formula XVII wherein Y is an acylimidazole moiety may be prepared by treating the corresponding carboxylic acid derivative with 1,1'-carbonyldiimidazole. Alternatively, the reactive carboxylate moiety Y may be obtained by treating the corresponding compound wherein Y is carboxy with 1-(3-dimethylaminopropyl)-3-ethylcarbodiimide hydrochloride and 1-hydroxybenzotriazole hydrate, optionally in the presence of triethylamine; the resulting activated carboxylate intermediate may then suitably be reacted in situ with the required compound of formula VII.

The hydrazine derivatives of formula III above may be prepared by methods analogous to those described in WO-A-94/02477, EP-A-0438230 and EP-A-0497512, as also may the aniline derivatives of formula IX.

Where they are not commercially available, the starting materials of formula VI, VII, XV and XVII may be prepared by the methods described in the accompanying Examples, or by analogous procedures which will be apparent to those skilled in the art.

It will be understood that any compound of formula I initially obtained from any of the above processes may, where appropriate, subsequently be elaborated into a further compound of formula I by techniques known from the art. For example, a compound of formula I wherein $R^x$ is benzyl initially obtained may be converted into a compound of formula I wherein $R^x$ is hydrogen typically by conventional catalytic hydrogenation, or by transfer hydrogenation using a hydrogenation catalyst such as palladium on charcoal in the presence of a hydrogen donor such as ammonium formate. Moreover, a compound of formula I wherein $R^1$ is hydroxy initially obtained may be converted into the corresponding carbonyl compound (aldehyde or ketone) by treatment with a conventional oxidising agent such as sulphur trioxide-pyridine complex; the resulting carbonyl compound may then be converted in turn into a compound of formula I wherein $R^1$ represents —$NHR^y$, suitably by a standard reductive amination procedure which comprises treating the carbonyl compound with the appropriate amine of formula $R^y$—$NH_2$ in the presence of a suitable reducing agent, typically sodium cyanoborohydride. Alternatively, the carbonyl compound may be converted into a compound of formula I wherein R represents —$CH_2$—$SOR^x$ and $R^a$ represents hydroxy by treatment of the carbonyl compound with the anion of $CH_3$—$SOR^x$. Furthermore, a compound of formula I wherein $R^1$ represents —$NHR^y$ initially obtained may be converted into a further compound of formula I wherein $R^1$ represents —$NR^xR^y$, in which $R^x$ corresponds to the group —$CH_2R^z$, suitably by a reductive amination procedure which comprises treating the compound of formula I wherein $R^1$ represents —$NHR^y$ with the appropriate aldehyde of formula $R^2$-CHO in the presence of a reducing agent such as sodium cyanoborohydride. In addition, a compound of formula I wherein $R^3$ is hydrogen initially obtained may be converted into a compound of formula I wherein $R^3$ represents $C_{1-6}$ alkyl by standard alkylation techniques, for example by treatment with an alkyl iodide, e.g. methyl iodide, typically under basic conditions, e.g. sodium hydride in dimethylformamide, or triethylamine in acetonitrile.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (–)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the 5-$HT_{1D\alpha}$ receptor subtype, inhibit forskolin-stimulated adenylyl cyclase activity, and stimulate [$^{35}$S]-GTPγS binding to membranes from clonal cell lines expressing human cloned receptors.

5-$HT_{1D\alpha}$/5-$HT_{1D\beta}$ Radioligand Binding

Chinese hamster ovary (CHO) clonal cell lines expressing the human 5-$HT_{1D\alpha}$ and 5-$HT_{1D\beta}$ receptors were harvested in PBS and homogenised in ice cold 50 mM Tris-HCl (pH 7.7 at room temperature) with a Kinematica polytron and centrifuged at 48,000 g at 4° C. for 11 min. The pellet was then resuspended in 50 mM Tris-HCl followed by a 10 min incubation at 37° C. Finally the tissue was recentrifuged at 48,000 g, 4° C. for 11 min and the pellet resuspended, in assay buffer (composition in mM: Tris-HCl 50, pargyline 0.01, $CaCl_2$ 4; ascorbate 0.1%; pH 7.7 at room temperature) to give the required volume immediately prior to use (0.2 mg protein/ml). Incubations were carried out for 30 min at 37° C. in the presence of 0.02–150 nM [$^3$H]-5-HT for saturation studies or 2–5 nM [$^3$H]-5-HT for displacement studies. The final assay volume was 1 ml. 5-HT (10 μM) was used to define non-specific binding. The reaction was initiated by the addition of membrane and was terminated by rapid filtration through Whatman GF/B filters (presoaked in 0.3% PEI/0.5% Triton X) followed by 2×4 ml washings with 50 mM Tris-HCl. The radioactive filters were then counted on a LKB beta or a Wallac beta plate counter. Binding parameters were determined by non-linear, least squares regression analysis using an iterative curve fitting routine, from which $IC_{50}$ (the molar concentration of compound necessary to inhibit binding by 50%) values could be calculated for each test compound. The $IC_{50}$ values for binding to the 5-$HT_{1D\alpha}$ receptor subtype obtained for the compounds of the accompanying Examples were below 50 nM in each case. Furthermore, the compounds of the accompanying Examples were all found to possess a selective affinity for the 5-$HT_{1D\alpha}$ receptor subtype of at least 10-fold relative to the 5-$HT_{1D\beta}$ subtype.

5-$HT_{1D\alpha}$/5-$HT_{1D\beta}$ Adenylyl Cyclase Assay

Studies were performed essentially as described in *J. Pharmacol. Exp. Ther.*, 1986, 238, 248. CHO clonal cell lines expressing the human cloned 5-$HT_{1D\alpha}$ and 5-$HT_{1D\beta}$ receptors were harvested in PBS and homogenised, using a motor driven teflon/glass homogeniser, in ice cold Tris HCl-EGTA buffer (composition in mM: Tris HCl 10, EGTA 1, pH 8.0 at room temperature) and incubated on ice for 30–60 min. The tissue was then centrifuged at 20,000 g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of α-[$^{33}$P]-ATP to [$^{33}$P]-cyclic AMP. A 10 μl aliquot of the membrane suspension was incubated, for 10–15 min, in a final volume of 50 μl, at 30° C., with or without forskolin (10 μM), in the presence or absence of test compound. The incubation buffer consisted of 50 mM Tris HCl (pH 7.6 at room temperature), 100 mM NaCl, 30 μM GTP, 50 μM cyclic AMP, 1 mM dithiothreitol, 1 mM ATP, 5 mM $MgCl_2$, 1 mM EGTA, 1 mM 3-isobutyl-1-methylxanthine, 3.5 mM creatinine phosphate, 0.2 mg/ml creatine phosphokinase, 0.5–1 μCi α-[$^{33}$P]-ATP and 1 nCi [$^3$H]-cyclic AMP. The incubation was initiated by the addition of membrane, following a 5 min preincubation at 30° C., and was terminated by the addition of 100 μl SDS (composition in mM: sodium lauryl sulphate 2%, ATP 45, cyclic AMP 1.3, pH 7.5 at room temperature). The ATP and cyclic AMP were separated on a double column chromatography system (*Anal. Biochem.*, 1974, 58, 541). Functional parameters were determined using a least squares curve fitting programme ALLFIT (*Am. J. Physiol.*, 1978, 235, E97) from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the 5-$HT_{1D\alpha}$ receptor obtained for the compounds of the accompanying Examples were below 500 nM in each case. Moreover, the compounds of the accompanying Examples which were tested were all found to possess at least a 10-fold selectivity for the 5-$HT_{1D\alpha}$ receptor subtype relative to the 5-$HT_{1D\beta}$ subtype.

5-$HT_{1D\alpha}$/5-$HT_{1D\beta}$ GTPγS Binding

Studies were performed essentially as described in *Br. J. Pharmacol.*, 1993, 109, 1120. CHO clonal cell lines expressing the human cloned 5-$HT_{1D\alpha}$ and 5-$HT_{1D\beta}$ receptors were harvested in PBS and homogenised using a Kinematica polytron in ice cold 20 mM HEPES containing 10 mM EDTA, pH 7.4 at room temperature. The membranes were then centrifuged at 40,000 g, 4° C. for 15 min. The pellet was then resuspended in ice cold 20 mM HEPES containing 0.1 mM EDTA, pH 7.4 at room temperature and recentrifuged at 40,000 g, 4° C. for 15–25 minutes. The membranes were then resuspended in assay buffer (composition in mM:

HEPES 20, NaCl 100, MgCl$_2$ 10, pargyline 0.01; ascorbate 0.1%; pH 7.4 at room temperature) at a concentration of 40 μg protein/ml for the 5-HT$_{1D\alpha}$ receptor transfected cells and 40–50 μg protein/ml for the 5-HT$_{1D\beta}$ receptor transfected cells. The membrane suspension was then incubated, in a volume of 1 ml, with GDP (100 μM for 5-HT$_{1D\alpha}$ receptor transfected cells, 30 μM for the 5-HT$_{1D\beta}$ receptor transfected cells) and test compound at 30° C. for 20 min and then transferred to ice for a further 15 min. [$^{35}$S]-GTPγS was then added at a final concentration of 100 pM and the samples incubated for 30 min at 30° C. The reaction was initiated by the addition of membrane and was terminated by rapid filtration through Whatman GFIB filters and washed with 5 ml water. The radioactive filters were then counted on a LKB beta counter. Functional parameters were determined by a non-linear, least squares regression analysis using an iterative curve fitting routine, from which E$_{max}$ (maxinal effect) and EC$_{50}$ (the molar concentration of compound necessary to inhibit the maximal effect by 50%) values were obtained for each test compound. Of those compounds which were tested in this assay, the EC$_{50}$ values for the 5-HT$_{1D\alpha}$ receptor obtained for the compounds of the accompanying Examples were below 500 nM in each case. Moreover, the compounds of the accompanying Examples which were tested were all found to possess at least a 10-fold selectivity for the 5-HT$_{1D\alpha}$ receptor subtype relative to the 5-HT$_{1D\beta}$ subtype.

EXAMPLE 1

(3R)-3-Benzyloxy-1-[2-(5-(1,2,4-triazol-4-yl)-1H-indol-3-yl)ethyl]pyrrolidine. Hydrogen Oxalate. Hemihydrate.

1. Intermediate 1: 4'-(1,2,4-Triazol-4-yl)phenylhydrazine
a) 4'-Aminoacetanilide A solution of 4-nitroacetanilide (5.0 g, 27.8 mmol) in EtOH/EtOAc (160 ml, 1:1), H$_2$O (15 ml) and 5N HCl (5.6 ml, 28.0 mmol) was hydrogenated over 10% Pd—C (0.50 g) at 50 psi for 0.25 h. The catalyst was removed by filtration through celite and the solvents removed under vacuum. The free base was generated by dissolving the product in H$_2$O, basifying with 2N NaOH and extracting into EtOAc. The combined extracts were dried (MgSO$_4$) and evaporated to give the title-aniline (3.75 g, 90%). δ (250 MHz, CDCl$_3$/d$_4$-MeOH) 2.10 (3H, s, Me), 6.68 (2H, d, J=8.8 Hz, Ar—H), 7.27 (2H, d, J=8.8 Hz, Ar—H).
b) 4'-(1,2,4-Triazol-4-yl)acetanilide A mixture of the preceding aniline (3.52 g, 23.4 mmol), N,N-dimethylformamide azine (3.33 g, 23.4 mmol; J. Chem Soc. (C), 1967, 1664) and p-toluenesulphonic acid monohydrate (0.223 g, 1.17 mmol), in anhydrous toluene (100 ml) was heated at reflux for 17 h. The beige coloured precipitate was filtered off and washed with toluene and CH$_2$C$_2$ and dried under vacuum to give the desired triazole (4.29 g, 91%), δ (250 MHz, d$_4$-MeOH/d$_6$-DMSO) 2.14 (3H, s, CH$_3$), 7.60 (2H, d, J=8.8 Hz, Ar—H), 7.78 (2H, d, J=8.8 Hz, Ar—H), 8.96 (2H, s, Ar—H).
c) 4'-(1,2,4-Triazol-4-yl)aniline A solution of the preceding acetamilide (4.91 g, 24.3 mmol) in 5N HCl (100 ml) was heated at 125° C. for 1.5 h. The mixture was cooled to 0° C., basified with concentrated aqueous NaOH solution and extracted with CH$_2$Cl$_2$(×5). The combined extracts were dried MgSO$_4$) and evaporated and the residue chromatographed on silica gel, eluting with CH$_2$Cl$_2$/MeOH/NH$_3$ (80:8: 1), to give the title-aniline (2.94 g, 76%), δ (250 MHz, CDCl$_3$) 3.80 (2H, s, NH$_2$), 6.71 (2H, d, J=8.8 Hz, Ar—H), 7.08 (2H, d, J=8.8 Hz, Ar—H), 8.36 (2H, s, Ar—H).

d) 4'(1,2,4-Triazol-4-yl)phenylhydrazine

To a solution of the preceding aniline (1.60 g, 9.99 mmol) in concentrated HCl/H$_2$O (23 ml and 3 ml respectively) was added, at −21° C., a solution of NaNO$_2$ (0.69 g, 9.99 mmol) in H$_2$O (8 ml), at such a rate as to maintain the temperature below −10° C. The mixture was stirred for 0.3 h and then filtered rapidly through a sinter, under vacuum. The filtrate was added to a cooled (−20° C.) solution of SnCl$_2$.2H$_2$O (9.02 g, 40.0 mmol) in concentrated HCl (17 ml). The mixture was stirred at −20° C. for 0.25 h and then at room temperature for 1.25 h. The resulting solid was filtered off, washed with Et$_2$O and dried under vacuum. The crude product was dissolved in H$_2$O, basified with concentrated aqueous NaOH and extracted with EtOAc (×5). The combined extracts were dried (MgSO$_4$) and evaporated to afford the title-product (0.95 g, 54%), δ (250 MHz, CDCl$_3$/d$_4$-MeOH) 3.98 (3H, br s, NH and NH$_2$), 6.97 (2H, d, J=12.0 Hz, Ar—H), 7.25 (2H, d, J=12.0 Hz, Ar—H), 8.48 (2H, s, Ar—H).

2. Intermediate 2: (3R)-4-(3-Benzyloxy)pyrrolidin-1-ylbutanal dimethylacetal
a) (3R)-N-tert-Butyloxycarbonylpyrrolidin-3-ol A mixture of (3R)-N-benzylpyrrolidin-3-ol (Aldrich; 5.00 g, 28.2 mmol), di-tert-butyldicarbonate (7.39 g, 33.8 mmol), Pearlmans catalyst (0.55 g), methanol (200 ml) and water (20 ml) were hydrogenated at 40 psi in a Parr apparatus for 2 h. The catalyst was removed by filtration through celite and the solvents removed under vacuum. The crude product was chromatographed on silica gel eluting with ethyl acetate/hexane (1:1) to give the title-pyrrolidinol (4.55 g, 86%), δ (250 MHz, CDCl$_3$) 1.46 (9H, s, OC(Me)$_3$), 1.87–2.03 (2H, m, CH$_2$),2.07 (1H, s, OH), 3.33–3.50 (4H, m, 2 of CH$_2$), 4.42–4.48 (1H, m,C$\underline{H}$—OH).
b) (3R)-N-tert-Butyloxycarbonyl-3-benzyloxypyrrolidine A solution of (3R)-N-tert-butyloxycarbonylpyrrolidin-3-ol (2.25 g, 12.0 mmol), in anhydrous THF (10 ml) was added portionwise to a slurry of sodium hydride (60% dispersion in oil, 0.63 g, 13.8 mmol) in THF (35 ml) and the mixture stirred for 0.3 h at 0° C. A solution of benzyl bromide (2.37 g, 13.8 mmol) in dry THF (2 ml) was added and the mixture warmed to room temperature and stirred for 18 h. Water (70 ml) was added and the mixture extracted with ethyl acetate (3×100 ml). The combined extracts were washed with brine, dried (MgSO$_4$) and evaporated. The crude product was chromatographed on silica gel eluting with CH$_2$Cl$_2$/MeOH (100:0→97:3) to give the desired product (2.53 g, 76%), δ (250 MHz, CDCl$_3$) 1.46 (9H, s, OC(Me)$_3$), 1.87–2.11 (2H, m, CH$_2$), 3.42–3.50 (4H, m, 2 of CH$_2$), 4.10–4.16 (1H, m, C$\underline{H}$—OBn), 4.53 (2H, s, OC$\underline{H}_2$Ar), 7.26–7.39 (5H, m, Ar).
c) (3R)-N-(H)-3-Benzyloxypyrrolidine A solution of the preceding N-Boc pyrrolidine (5.0 g, 18.0 mmol) in 90% formic acid (150 ml) was stirred at 0° C. for 0.3 h and then at room temperature for 2.5 h. The solvents were removed under reduced pressure and the resulting residue was neutralised by addition of saturated K$_2$CO$_3$ solution. The aqueous was extracted with n-butanol (2×40 ml), the solvent removed under vacuum and azeotroped with ethanol (×2). The product was chromatographed on silica gel eluting with CH$_2$Cl$_2$/MeOH/NH$_3$ (80:8:1) to give the title-product (2.62 g, 82%), δ (250 MHz, CDCl$_3$) 1.85–1.93 (2H, m, CH$_2$), 2.79–2.89 (2H, m, CH$_2$), 3.07–3.17 (2H, m, CH$_2$), 4.08–4.14 (1H, m, C$\underline{H}$—OBn), 4.53 (2H, s, OC$\underline{H}_2$Ar), 7.24–7.38 (5H, m, Ar—H).
d) (3R)-4-(3-Benzyloxy)pyrrolidin-1-ylbutanal dimethyl acetal A mixture of 4-chlorobutanal dimethyl acetal (J. Chem. Soc., Perkin Trans. 1, 1981, 251–255; 2.29 g, 15.0 mmol), (3R)—N—(H)-3-benzyloxypyrrolidine (2.60 g, 15.0 mmol)

and $K_2CO_3$ (2.23 g, 16.0 mmol), in dry THF (40 ml), was heated at reflux for 48 h. The mixture was cooled to room temperature, water (70 ml) added and extracted with ethyl acetate (3×70 ml). The combined extracts were dried ($MgSO_4$) and evaporated and the residue chromatographed on silica gel eluting with $MeOH/CH_2Cl_2$ (5:95) to give the title-dimethyl acetal (1.9 g, 44%), δ (250 MHz, $CDCl_3$) 1.57–1.67 (4H, m, 2 of $CH_2$), 1.84–1.96 (1H, m, CH of $CH_2$), 2.03–2.17 (1H, m, CH of $CH_2$), 2.46–2.74 (5H, m, 2 of $CH_2$ and CH of $CH_2$), 2.89 (1H, dd, J=10.3 and 6.1 Hz, CH of $CH_2$), 3.31 (6H, s, CH(OMe)$_2$), 4.10–4.18 (1H, m, C HOBn), 4.38 (1H, t, J=5.2 Hz, CH(OMe)$_2$), 4.48 (2H, ABq, J=11.9 Hz, CH$_2$OAr), 7.24–7.38 (5H, m, Ar).

3. (3R)-3-Benzyloxy-1-[2-(5-(1,2,4-triazol-4-yl)-1H-indol-3-yl)ethyl]pyrrolidine. Hydrogen Oxalate. Hemihydrate.

A solution of Intermediate 1 (1.25 g, 7.1 mmol) and Intermediate 2 (1.90 g, 6.48 mmol) in 4% $H_2SO_4$ (25 ml) was heated at reflux for 48 h. The mixture was cooled to room temperature and basified with $K_2CO_3$. The product was extracted into ethyl acetate (×3), the combined extracts dried ($MgSO_4$) and the solvent removed under vacuum. The crude product was purified by chromatography on silica gel eluting with $CH_2Cl_2/MeOH/NH_3$ (90:8:1) to give the title-indole (0.55 g, 22%). The hydrogen oxalate hemihydrate salt was prepared: mp 97°–98° C. (Found: C, 61.76, H, 5.56, N, 14.28. $C_{23}H_{25}N_5O.C_2H_2O_4.0.5\ H_2O$ requires C, 61.72, H, 5.80 N, 14.39%), m/e 388 (M+1$^+$), δ (360 MHz, $D_6$-DMSO) 1.96–2.22 (2H, m, CH$_2$), 3.02–3.28 (4H, m, 2 of CH$_2$), 4.24–4.28 (1H, m, CH—OBn), 4.50 (2H, s, CH$_2$Ar), 7.29–7.38 (7H, m, Ar—H), 7.51 (1H, d, J=8.6 Hz, Ar—H), 7.87 (1H, d, J=1.8 Hz, Ar—H), 9.02 (2H, s, Ar—H), 11.25 (1H, s, NH).

EXAMPLE 2

(3R)-3-(4-Methoxybenzyloxy)-1-[2-(5-(1,2,4-triazol-4-yl)-1H-indol-3-yl)ethyl]pyrrolidine. 1.2 Oxalate. Hemihydrate.

1. Intermediate 3: 2-[5-(1,2,4-Triazol-4-yl)-1H-indol-3-yl] ethyl alcohol a) 2-Iodo-4-(1,2,4-triazol-4-yl)phenylaniline A solution of iodine monochloride (22.3 g, 137 mmol) in methanol (300 ml) was added over 0.75 h to a stirred suspension of 4-(1,2,4-triazol-4-yl)phenylaniline (20.0 g, 125 mmol) and calcium carbonate (25.0 g, 250 mmol) in methanol (800 ml) at −30° C. under nitrogen. The mixture was allowed to warm to room temperature and stirred for 16 h before filtering through a pad of celite. The filtrate was evaporated in vacuo and the residue dissolved in EtOAc and washed with 50% w/w sodium bisulphite solution. The solid material was filtered off and the organic layer dried ($MgSO_4$), evaporated in vacuo and combined with the solid material to give the title product (23.9 g, 67%), δ (250 MHz, $d_6$-DMSO) 5.54 (2H, br s, NH$_2$), 6.84 (1H, d, J=8.7 Hz, Ar—H), 7.38 (1H, dd, J=2.6 and 8.7 Hz, Ar—H), 7.87 (1H, d, J=2.5 Hz, Ar—H), 8.92 (2H, s, Ar—H).

b) 2-[5-(1,2,4-Triazol-4-yl)-2-trimethylsilyl-1H-indol-3-yl] ethyl alcohol

A mixture of the preceding iodoaniline (23.9 g, 83.6 mmol), 4-trimethylsilyl-3-butyn-1-ol (prepared by silylation of 3-butyn-1-ol) (17.83 g, 125.3 mmol), lithium chloride (3.54 g, 83.6 mmol), sodium carbonate (44.24 g, 417.8 mmol) and triphenylphosphine (1.10 g, 4.18 mmol) in DMF (900 ml) was degassed with nitrogen for 0.5 h at room temperature. Palladium (II) acetate (0.94 g, 4.18 mmol) was added in one portion and the mixture heated at 100° C. under nitrogen for 6 h. A second portion of palladium (II) acetate (5 g, 22.2 mmol) was added and the mixture heated at 100° C. for 1 h. The solvent was evaporated in vacuo and the residue partitioned between ethyl acetate (800 ml) and water (1000 ml) and filtered through celite. The aqueous layer was separated and re-extracted with ethyl acetate (3×800 ml). The combined extracts were dried and evaporated, and the crude product chromatographed on silica gel, eluting with $CH_2Cl_2/EtOH/NH_3$ (80:8:1), to give the title product (8.5 g, 34%), δ (250 MHz, $d_6$-DMSO) 0.38 (9H, s, SiMe$_3$), 2.97 (2H, t, J=7.6 Hz, CH$_2$), 3.58 (2H, m, CH$_2$), 4.69 (1H, t, J=5.3 Hz, OH), 7.30 (1H, dd, J=2.1 and 8.6 Hz, Ar—H), 7.48 (1H, d, J=8.7 Hz, Ar—H), 7.78 (1H, d, J=2.1 Hz, Ar—H), 9.03 (2H, s, Ar—H), 10.83 (1H, br s, NH).

c) 2-[5-(1,2,4-Triazol-4-yl)-1H-indol-3-yl]ethyl alcohol

A solution of the preceding 2-trimethylsilyl-indole (8.5 g, 28.3 mmol) in methanol (68 ml) and 5N HCl (57 ml) was heated at 60° C. for 16 h. The methanol was evaporated in vacuo and the residue neutrahsed with concentrated $NH_3$ solution. The precipitate was filtered off, washed with $Et_2O$ (2×100 ml) and dried in vacuo to give the title alcohol (6.0 g, 92%), δ (250 MHz, $d_6$-DMSO), 2.88 (2H, t, J=7.2 Hz, CH$_2$), 3.68 (2H, m, CH$_2$), 4.66 (1H, br s, OH), 7.23–7.32 (2H, m, Ar—H), 7.48 (1H, d, J=8.5 Hz, Ar—H), 7.81 (1H, d, J=2.1 Hz, Ar—H), 9.03 (2H, s, Ar—H), 11.15 (1H, br s, NH).

2. Intermediate 4: (3R)-N-(H)-3-(4-Methoxybenzyloxy) pyrrolidine a) (3R)-N-tert-Butyloxycarbonyl-3-(4-methoxybenzyloxy) pyrrolidine A solution of (3R)-N-tert-butyloxycarbonylpyrrolidin-3-ol (2.00 g, 10.7 mmol) in anhydrous DMF (12 ml) was added dropwise to a stirred slurry of sodium hydride (60% dispersion in oil, 0.465 g, 11.6 mmol) in DMF (25 ml) at −10° C. under nitrogen and the mixture stirred at this temperature for 0.67 h. 4-Methoxybenzyl chloride (1.52 ml, 11.2 mmol) was added dropwise and the mixture warmed to 0° C. over 1 h and then stirred at RT for 2 h. Water was added and the mixture poured into ether and washed with water (×3). The ethereal layer was dried ($MgSO_4$), evaporated in uacuo and the crude product chromatographed on silica gel, eluting with ethyl acetate/hexane (30:70), to afford the title pyrrolidine (3.09 g, 94%),δ (250 MHz, $CDCl_3$) 1.46 (9H, br s, OC(Me)$_3$), 1.73–2.09 (2H, m, CH$_2$), 3.40–3.46 (4H, m, 2 of CH$_2$), 3.81 (3H, s, OMe), 4.12 (1H, m, CHOCH$_2$Ar), 4.45 (2H, s, OCH$_2$Ar), 6.85–6.91 (2H, m, Ar—H), 7.23–7.27 (2H, m, Ar—H).

b) (3R)-N-(H)-3-(4-Methoxybenzyloxy)-pyrrolidine

Prepared from the preceding N-Boc pyrrolidine as described for Example 1, part 2c, δ (250 MHz, $CDCl_3$) 1.85–1.93 (2H, m, CH$_2$),2.81–2.91 (2H, m, CH$_2$), 3.06–3.17 (2H, m, CH$_2$), 3.80 (3H, s, OMe), 4.10 (1H, m, C HOCH$_2$Ar), 4.41 (2H, s, OCH$_2$Ar), 6.85–6.91 (2H, m, Ar—H), 7.23–7.27 (2H, m, Ar—H).

3. (3R)-3-(4-Methoxybenzyloxy)-1-[2-(5-(1,2,4-triazol-4-yl)-1H-indol-3-yl)ethyl]pyrrolidine. 1.2 Oxalate Hemihydrate.

Methanesulphonyl chloride (0.20 ml, 2.62 mmol) was added dropwise to a stirred suspension of Intermediate 3 (400 mg, 1.75 mmol) in pyridine (10 ml) at −10° C. under nitrogen. The mixture was warmed to, and stirred at, room temperature overnight and the solvent evaporated under high vacuum. The residue was partitioned between ethyl acetate and water and the aqueous layer extracted with ethyl acetate (×4). The combined extracts were dried ($MgSO_4$) and evaporated in vacuo. The residue (335 mg) was taken with sodium carbonate (161 mg, 1.07 mmol) and sodium iodide (114 mg, 1.08 mmol) in 1,2-dimethoxyethane (8 ml) and a solution of Intermediate 4 (224 mg, 1.08 mmol) in 1,2- dimethoxyethane (2 ml) added. The mixture was heated at reflux under nitrogen for 21 h in the dark. Water was added and the mixture extracted with ethyl acetate (3×100 ml). The combined extracts were dried ($MgSO_4$) and evaporated in vacuo, and the residue chromatographed on silica gel, eluting with $CH_2Cl_2$/MeOH/$NH_3$ (90:8:1), to give the title indole (87 mg, 12%). The 1.2 oxalate hemihydrate salt was prepared. (Found: C, 59.47, H, 5.49, N, 12.99. $C_{24}H_{27}N_5O_2$.1.2($C_2H_2O_4$).0.5 $H_2O$ requires C, 59.32, H, 5.73, N, 13.10%), m/e (M+1$^+$) 418, δ (360 MHz, $d_6$-DMSO) 2.06 (1H, m, CH of $CH_2$), 2.18 (1H, m, CH of $CH_2$), 3.07–3.11 (2H, m, $CH_2$), 3.20–3.42 (6H, m, 3 of $CH_2$), 3.74 (3H, s, OMe), 4.27 (1H, m, C<u>H</u>OCH$_2$Ar), 4.43 (2H, s, CHOC<u>H</u>$_2$Ar), 6.89 (2H, d, J=8.7 Hz, 2 of Ar—H), 7.25 (2H, d, J=8.6 Hz, 2 of Ar—H), 7.31 (1H, dd, J=2.1 and 8.4 Hz, Ar—H), 7.35 (1H, s, Ar—H), 7.51 (1H, d, J=8.4 Hz, Ar—H), 7.81 (1H, d, J=2.0 Hz, Ar—H), 8.89 (2H, s, Ar—H), 11.08 (1H, br s, NH).

EXAMPLE 3

(3R)-3-(Pyridin-3-ylmethyloxy)-1-[2-(5-(1,2,4-triazol-4-yl)-1H-indol-3-yl)ethyl]pyrrolidine. Bisoxalate. 0.25 Hydrate.

a) (3R)-N-tert-Butyloxycarbonyl-3-(pyridin-3-ylmethyloxy)pyrrolidine

A suspension of 3-picolylchloride hydrochloride (1.84 g, 11.2 mmol) in DMF (50 ml) was added to a stirred slurry of sodium hydride (60% dispersion in oil, 0.45 g, 11.2 mmol) in DMF at 0° C. under nitrogen. The mixture was stirred at 0° C. for 0.25 h and then added to a mixture of (3R)-N-tert-butyloxycarbonylpyrrolidin-3-ol (2.0 g, 10.7 mmol) and sodium hydride (60% dispersion in oil, 0.45 g, 11.2 mmol) in DMF at 0° C. under nitrogen (mixture stirred for 0.2 h at 0° C. prior to the addition). The reaction mixture was stirred at room temperature for 2.5 h. Water (200 ml) was added and the mixture extracted with ethyl acetate (1×200 ml), dried ($Na_2SO_4$) and evaporated in vacuo. The crude product was chromatographed on silica gel, eluting with $Et_2O$/MeOH (95:5), to give the desired product (1.63 g, 55%), δ (250 MHz, $d_4$-MeOH), 1.46 (9H, s, OC(Me)$_3$), 1.95–2.18 (2H, m, $CH_2$), 3.34–3.51 (4H, m, 2 of $CH_2$), 4.22 (1H, m, C <u>H</u>OCH$_2$Ar), 4.59 (2H, s, OC<u>H</u>$_2$Ar), 7.43 (1H, dd, J=4.7 and 7.8 Hz, Ar—H), 7.48 (1H, d, J=7.9 Hz, Ar—H), 8.45–8.51 (2H, m, 2 of Ar—H).

b) (3R)-N-(H)-3-(pyridin-3-ylmethyloxy)pyrrolidine

Prepared from the preceding N-Boc pyrrolidine as described for Intermediate 2, part c, δ (250 MHz, $CDCl_3$) 1.86–2.01 (2H, m, $CH_2$), 2.81–2.91 (2H, m, $CH_2$), 3.07–3.18 (2H, m, $CH_2$), 4.13 (1H, m, C<u>H</u>OCH$_2$Ar), 4.50 (2H, s, OC <u>H</u>$_2$Ar), 7.28 (1H, m, Ar—H), 7.68 (1H, m, Ar—H), 8.74–8.98 (2H, m, 2 of Ar—H).

c) (3R)-3-(Pyridin-3-ylmethyloxy)-1-[2-(5-(1,2,4-triazol-4-yl)-1H-indol-3-yl)ethyl]pyrrolidine. Bisoxalate. 0.25 Hydrate.

Prepared from Intermediate 3 and the preceding N(H)-pyrrolidine using the procedure described for Example 2. The bisoxalate 0.25 hydrate salt was prepared which crystallised out containing a small amount of ether; m.p. 87°–89° C. (Found: C, 54.53, H, 5.08, N, 14.58. $C_{22}H_{24}N_6O$.2 ($C_2H_2O_4$).0.25 $H_2O$.0.04($C_4H_{10}O$) requires C, 54.55, H, 5.06, N, 14.59%). m/e 389 (M+1$^+$), δ (360 MHz, $d_6$-DMSO) 2.08–2.30 (2H, m, $CH_2$), 3.10–3.15 (2H, m, $CH_2$), 3.38–3.50 (6H, m, $CH_2$), 4.37 (1H, br s, C<u>H</u>OCH$_2$Ar), 4.57 (2H, s, OC <u>H</u>$_2$Ar), 7.34–7.41 (3H, m, 3 of Ar—H), 7.53 (1H, d, J=8.7 Hz, Ar—H), 7.78 (1H, br d, J=7.9 Hz, Ar—H), 7.88 (1H, s, Ar—H), 8.50 (1H, m, Ar—H), 8.98 (1H, s, Ar—H), 9.02 (2H, s, Ar—H), 11.30 (1H, br s, NH).

EXAMPLE 4

(3R)-3-Benzyloxymethyl-1-[2-(5-(1,2,4-triazol-4-yl)-1H-indol-3-yl) ethyl]pyrrolidine. Hydrogen Oxalate Hemihydrate.

a) (3R)-N-tert-Butyloxycarbonyl-3-hydroxymethylpyrolidine

Prepared from (3R)-N-[(R)-1-phenylethyl]-3-(hydroxymethyl) pyrrolidine (*J. Med. Chem.*, 1990, 33 (1), 71) as described for Example 1, part 2a, δ (250 MHz, $D_6$-DMSO) 1.39 (9H, s, OC(Me)$_3$), 1.31–1.64 (2H, m, $CH_2$), 1.79–1.88 (1H, m, CH), 2.19–2.31 (1H, m, CH of $CH_2$), 2.95 (1H, dd, J=10.7 and 7.0 Hz, CH of $CH_2$), 3.11–3.35 (4H, m, 2 of $CH_2$),4.67 (1H, t, J=5.3 Hz, OH).

b) (3R)-4-(3-Benzyloxymethyl)pyrrolidin-1-ylbutanal dimethyl acetal

The title compound was prepared from (3R)-N-tert-butyloxycarbonyl-3-hydroxymethylpyrrolidine as described for Example 1, parts 2b-d, δ (250 MHz, $D_6$-DMSO) 1.24–1.56 (6H, m, 3 of $CH_2$), 1.75–1.89 (1H, m, CH), 2.21–2.55 (6H, m, 3 of $CH_2$),3.20 (6H, s, CH (O<u>Me</u>)$_2$), 3.30 (2H, d, J=7.1 Hz, C<u>H</u>$_2$OBn), 4.34 (1H, t, J=5.3 Hz, C <u>H</u>(OMe)$_2$), 4.45 (2H, s, OC<u>H</u>$_2$Ar), 7.24–7.39 (5H, m, Ar—H).

c) (3R)-3-Benzyloxymethyl-1-[2-(5-(1,2,4-triazol-4-yl)-1H-indol-3-yl)ethyl]pyrrolidine. Hydrogen Oxalate. Hemihydrate.

A solution of Intermediate 1 (2.17 g, 12.36 mmol) and (3R)-4-(3-benzyloxymethyl)pyrrolidin-1-ylbutanal dimethyl acetal (3.80 g, 12.36 mmol) in 4% $H_2SO_4$ (30 ml) was heated at reflux for 60 h. The solution was cooled to room temperature and basified by addition of 4N NaOH solution and extracted with n-butanol (1×75 ml). The solvent was removed under vacuum and the crude product chromatographed on silica eluting with $CH_2Cl_2$/MeOH/$NH_3$ (80:8:1) to give the title-indole (0.45 g 10%). The hydrogen oxalate hemihydrate salt was prepared: mp 145° C. (Found: C, 62.16; H, 5.97; N, 13.76. $C_{24}H_{27}N_5O$.$C_2H_2O_4$. 0.6 $H_2O$ requires C, 62.16; H, 6.06; N, 13.94%), δ (360 MHz, $D_6$-DMSO) 1.64–1.78 (1H, m, CH of $CH_2$), 2.04–2.16 (1H, m, CH of $CH_2$), 2.60–2.72 (1H, m, CH), 3.04–3.50 (10H, m, 5 of $CH_2$), 4.49 (2H, s, OC<u>H</u>$_2$Ar), 7.27–7.40 (7H, m, Ar—H), 7.52 (1H, d, J=8.6 Hz, Ar—H), 7.90 (1H, d, J=2.0 Hz, Ar—H), 9.04 (2H, s, Ar—H), 11.30 (1H, s, NH).

EXAMPLE 5

(3S)-3-(N-Benzyl-N-methyl)aminomethyl-1-[2-(5-(1,2,4-triazol-4-yl)-1H-indol-3-yl)ethyl]pyrrolidine Sesauioxalate. 0.3 Hydrate.

a) (3R)-N-tert-Butyloxycarbonyl-3-methylsuphonyloxymethylpyrrolidine

A solution of methane sulphonyl chloride (3.37 g, 29.39 mmol) in $CH_2Cl_2$ (30 ml) was added dropwise to a solution of (3R)-N-tert-butyloxycarbonyl-3-hydroxymethylpyrrolidine (5.4 g, 26.7 mmol) and anhydrous triethylamine (2.97 g, 29.39 mmol), in $CH_2Cl_2$ (100 ml), at −15° C. The mixture was warmed to room temperature and stirred for 16 h before adding saturated $K_2CO_3$ solution (50 ml) and diluting with $CH_2Cl_2$ (100 ml). The aqueous was separated and extracted further with $CH_2Cl_2$ (2×100 ml). The combined extracts were dried ($Na_2SO_4$) and evaporated to give the title-mesylate (7.5 g, 100%), δ (250 MHz, $CDCl_3$) 1.46 (9H, s, OC(Me)$_3$), 1.62–1.84 (1H, m, CH of $CH_2$), 2.00–2.14 (1H, m, CH of $CH_2$), 2.58–2.72 (1H, m, CH), 3.04 (3H, s, Me), 3.08–3.62 (4H, m, 2 of $CH_2$), 4.11–4.33 (2H, m, C<u>H</u>$_2$OMs).

b) (3S)-N-tert-Butyloxycarbonyl-3-(N-benzyl-N-methyl) aminomethylpyrrolidine

A solution of the preceding mesylate (7.46 g, 26.72 mmol) in N-benzylmethylamine (22.7 g, 187.0 mmol) was heated at 100° C. for 4 h. The solvent was removed under vacuum, ethyl acetate (150 ml) was added to the residue and the solution washed with water (100 ml). The organic phase was dried ($Na_2SO_4$) and evaporated and the crude product chromatographed on silica gel eluting with $CH_2Cl_2$/MeOH (98:2) to give the title-N-methylbenzylamine (6.9 g, 85%), δ (250 MHz, $CDCl_3$) 1.46 (9H, s, $OC(Me)_3$), 1.50–1.72 (2H, m, $CH_2$), 1.90–2.02 (1H, m, CH), 2.21 (3H, s, NMe), 2.30–2.50 (2H, m, $CH_2$), 2.92–3.05 (1H, m, CH of $CH_2$), 3.18–3.62 (2H, m, 2 of $CH_2$ and CH of $CH_2$), 7.20–7.38 (5H, m, Ar—H).

c) (3S)-N(H)-3-(N-Benzyl-N-methyl)-aminomethylpyrrolidine

A solution of the preceding N-Boc pyrrolidine (6.9 g, 22.7 mmol) in trifluoroacetic acid (30 ml) and $CH_2Cl_2$ (100 ml) was stirred at room temperature for 16 h. The solvents were removed under vacuum and the resulting residue was chromatographed on silica gel eluting with $CH_2Cl_2$/MeOH/$NH_3$ (60:8:1) to give the title-product (4.6 g, 99%), δ (250 MHz, $D_6$-DMSO) 1.41–1.55 (1H, m, CH of $CH_2$), 1.89–2.02 (1H, m, CH of $CH_2$), 2.11 (3H, s, Me), 2.31 (2H, d, J=7.5 Hz, $CH_2NMe$), 2.38–2.52 (1H, m, CH), 2.73 (1H, dd, J=11.3 and 6.9 Hz, CH of $CH_2$), 2.95–3.23 (5H, m, 2 of $CH_2$ and CH of $CH_2$), 3.46 (2H, ABq, J=13.4 Hz, NC$\underline{H}_2$Ar), 7.19–7.36 (5H, m, Ar—H).

d) (3S)-4-(3-(N-Benzyl-N-methyl)aminomethyl)-pyrrolidin-1-ylbutanal dimethyl acetal A mixture of the preceding N(H)-pyrrolidine (3.0 g, 14.68 mmol), 4-chlorobutanal dimethyl acetal (2.24 g, 14.68 mmol), NaI (2.42 g, 16.15 mmol) and $Na_2CO_3$ (1.71 g, 16.15 mmol), in dimethoxyethane (50 ml), was heated at reflux for 16 h, in the absence of light. The solvent was removed under vacuum and ethyl acetate (100 ml), water (70 ml) and saturated $K_2CO_3$ solution (10 ml) were added to the residue. The aqueous was separated and further extracted with EtOAc (2×100 ml). The combined extracts were dried and evaporated and the residue chromatographed on silica gel eluting with $CH_2Cl_2$/iPA/$NH_3$ (80:8: 1) to give the title-acetal (2.06 g, 44%), δ (250 MHz, $D_6$-DMSO) 1.23–1.55 (5H, m, 2 of $CH_2$ and CH), 1.75–1.89 (1H, m, CH of $CH_2$), 2.09 (3H, s, Me), 2.14–2.40 (9H, m, 4 of $CH_2$ and CH), 3.20 (6H, s, $(OMe)_2$), 3.42 (2H, ABq, J=13.3 Hz NC$\underline{H}_2$Ar), 4.33 (1H, t, J=5.4 Hz, C$\underline{H}(OMe)_2$) 7.19–7.35 (5H, m, Ar—H).

e) (3S)-3-(N-Benzyl-N-methyl)aminomethyl-1-[2-(5-(1,2,4-triazol-4-yl)-1H-indol-3-yl)ethyl]pyrrolidine Sesquioxalate. 0.3 Hydrate.

Prepared from Intermediate 1 and the preceding acetal using the procedure described for Example 1. The sesquioxalate 0.3 hydrate salt was prepared; mp 116°–117° C., (Found: C, 60.57; H, 6.47; N, 14.93. $C_{25}H_{30}N_6$.1.5($C_2H_2O_4$).0.3 $H_2O$ requires C, 60.59; H, 6.10; N, 15.14%); m/e 415 (M+1$^+$). δ (250 MHz, $CDCl_3$ on free base) 1.44–1.60 (1H, m, CH of $CH_2$), 1.94–2.12 (1H, m, CH of $CH_2$), 2.20 (3H, s, Me), 2.31–3.01 (11H, m, 5 of $CH_2$ and CH), 3.48 (2H, ABq, J=13.2 Hz, NC$\underline{H}_2$Ar), 7.15 (1H, dd, J=8.6 and 2.1 Hz, Ar—H), 7.19 (1H, d, J=2.3 Hz, Ar—H), 7.19–7.26 (5H, m, Ar—H), 7.47 (1H, d, J=8.6 Hz, Ar—H), 7.57 (1H, d, J=2.1 Hz, Ar—H), 8.41 (1H, br s, NH), 8.47 (2H, s, Ar—H).

EXAMPLE 6

(2S)-2-(N-Benzyl-N-methyl)aminomethyl-1-[2-(5-(1,2,4-triazol-4-yl)-1H-indol-3-yl)ethyl]pyrrolidine. Sesquisuccinate. Sesquihydrate.

The title compound was prepared from (2S)-N-tert-butyloxycarbonyl-2-hydroxymethylpyrrolidine (L-prolinol from Aldrich) using the procedures described for the preparation of Example 5. The sesquisuccinate sesquihydrate salt was prepared, mp 70°–72° C., (Found: C, 61.45, H, 6.65, N, 13.95. $C_{25}H_{30}N_6$.1.5($C_4H_6O_4$).1.5 $H_2O$ requires C, 61.52, H, 6.75, N, 13.89%), δ (360 MHz, $D_2O$) 1.70–1.77 (1H, m, CH of $CH_2$), 1.85–1.93 (1H, m, CH of $CH_2$), 2.06–2.18 (1H, m, CH of $CH_2$), 2.22 (3H, s, Me), 2.22–2.33 (1H, m, CH of $CH_2$), 2.68–2.79 (2H, m, $CH_2$), 3.12–3.76 (9H, m, 4 of $CH_2$ and CH), 7.01–7.03 (2H, m, Ar—H), 7.15–7.21 (3H, m, Ar—H), 7.32 (1H, dd, J=8.6 and 2.1 Hz, Ar—H), 7.47 (1H, s, Ar—H), 7.64 (1H, d, J=2.1 Hz, Ar—H), 7.67 (1H, d, J=8.6 Hz, Ar—H), 8.70 (2H, s, Ar—H).

EXAMPLE 7

(3S)-3-(N-Benzyl)aminomethyl-1-[2-(5-(1,2,4-triazol-4-yl)-1H-indol-3-yl)ethyl]pyrrolidine. 2.6 Hydrogen Oxalate. 0.1 Hydrate.

a) (3S)-N(H)-3-(N-Benzyl)aminomethylpyrrolidine

Prepared from (3R)-N-tert-butyloxycarbonyl-3-methylsulphonyloxymethylpyrrolidine and benzylamine as described for Example 5, parts b and c, δ (250 MHz, $CDCl_3$) 1.38 (1H, m, CH), 1.90 (1H, m, CH), 2.24 (1H, qu, J=7.4 Hz, CH), 2.54–2.62 (3H, m, $CH_2$ and CH of $CH_2$), 2.83–2.99 (2H, m, $CH_2$), 3.08 (1H, dd, J=7.6 and 11.0 Hz, CH of $CH_2$), 3.80 (2H, s, C$\underline{H}_2$Ar), 7.21–7.36 (5H, m, Ar—H).

b) (3S)-3-(N-Benzyl)aminomethyl-1-[2-(5-(1,2,4-triazol-4-yl)-1H-indol-3-yl)ethyl]pyrrolidine. 2.6 Hydrogen Oxalate. 0.1 Hydrate.

Prepared from Intermediate 3 and the preceding N(H)-pyrrolidine using the procedure described for Example 2. The 2.6 hydrogen oxalate, 0.1 hydrate salt was prepared, mp 228°–230° C. (Found, C, 55.16, H, 5.30, N, 13.00. $C_{24}H_{28}N_6$.2.6($C_2H_2O_4$).0.1 $H_2O$ requires C, 55.20, H, 5.29, N, 13.21%); m/e 401 (M+1$^+$), δ (360 MHz, $d_6$-DMSO) 1.96 (1H, m, $CH_2$), 2.10 (1H, m, $CH_2$), 2.76 (1H, m, CH of $CH_2$), 3.00–3.24 (5H, m, $CH_2$), 3.30–3.60 (5H, m, $CH_2$), 4.14 (2H, s, C$\underline{H}_2$Ar), 7.35–7.54 (8H, m, Ar—H), 7.91 (1H, s, Ar—H), 9.04 (2H, s, Ar—H), 11.30 (1H, br s, NH).

EXAMPLE 8

1-{3-[5-(1,2,4-Triazol-4-yl)-1H-indol-3-yl]propyl}-4-[4-(acetylamino) benzylamino]piperidine. 2.85 Hydrogen Oxalate.

1. 5-Bromopentanal dimethyl acetal

To a solution of 5-bromovaleryl chloride (50 g, 0.251 mol) in anhydrous THF (500 ml), at −78° C., was added lithium tri-tert-butoxyaluminohydride (1.0M solution in tetrahydrofuran, 300 ml; 0.30 mol), keeping the temperture below 70° C. The solution was stirred at −78° C. for 5 h and then quenched by dropwise addition of 2M hydrochloric acid (350 ml). The mixture was warmed to room temperature and stirred for 16 h. Diethyl ether (500 ml) was added, the aqueous phase separated and extracted further with ether (×2). The combined extracts were washed with saturated $Na_2CO_3$ solution (×1), water (×1) and brine (×2), dried ($Na_2SO_4$) and evaporated to give 5-bromovaleraldehyde (37.5 g, 91%). A solution of 5-bromovaleraldehyde (37.5 g, 0.227 mol) in methanol (250 ml) and concentrated sulphuric acid (0.5 ml) was stirred at room temperature for 3 h. The solvent was removed under vacuum and to the residue was added $K_2CO_3$ solution (50 ml) and diethyl ether (500 ml). The aqueous layer was separated and re-extracted with ether (×2). The combined extracts were washed with water and brine, dried ($Na_2SO_4$) and evaporated. The crude product was chromatographed on silica eluting with diethyl ether/hexane (1:9) to give the title-acetal (27.5 g, 57%). δ (250

MHz, CDCl₃) 1.43–1.67 (4H, m, 2 of CH₂), 1.83–1.94 (2H, m, CH₂), 3.38 (6H, s, CH(OMe)₂), 3.42 (2H, t, J=7 Hz, CH₂Br), 4.37 (1H, t, J=7 Hz, CH(OMe)₂).

2. 5-(4-Hydroxypiperidin-1-yl)pentanal dimethyl acetal

A mixture of 5-bromopentanal dimethyl acetal (3.34 g, 15.82 mmol), anhydrous potassium carbonate (2.218 g, 15.82 mmol) and 4-hydroxypiperidine (2.0 g, 19.77 mmol) in anhydrous dimethylformamide (50 ml) was stirred at 80°–90° C. for 3 hours under nitrogen. After cooling, the mixture was diluted with water (150 ml), basified with saturated aqueous potassium carbonate and the product was extracted with ethyl acetate (3×250 ml). The combined organic solutions were dried (Na₂SO₄) and concentrated. Flash chromatography of the residue (silica gel, dichloromethane/methanol/ammonia, 90:10:1) gave 2.71 g (74%) of the title compound as a colourless oil, δ (250 MHz, d₆-DMSO) 1.06–1.56 (8H, m), 1.62–1.75 (2H, m), 1.86–2.00 (2H, m), 3.20 (6H, s), 3.34–3.47 (1H, m), 4.31 (1H, t, J=5.7 Hz), 4.53 (1H, d, J=4.2 Hz), m/e (ES) 232 (M+1⁺).

3. 1-{3-[5-(1,2,4-Triazol-4-yl)-1H-indol-3-yl]propyl}-4-hydroxypiperidine. 1.35 Hydrogen Oxalate.

A solution of the preceding dimethyl acetal (2.70 g, 11.67 mmol) and 4-(1,2,4-triazol-4-yl)phenylhydrazine (2.15 g, 12.25 mmol) in 4% sulphuric acid (100 ml) was refluxed for 9 h. After cooling to room temperature, the reaction mixture was basified with saturated aqueous potassium carbonate and products were extracted with ethyl acetate (3×250 ml) and with a mixture of ethyl acetate and n-butanol (1:1, 2×250 ml). The combined organic solutions were washed with brine (1×50 ml), dried (Na₂SO₄) and concentrated. Flash chromatography of the residue (silica gel, dichloromethane/methanol/ammonia, 85:15:1.5) gave 1.96 g (51.6%) of the title compound free base as a pale yellow foam. The oxalate salt was prepared and recrystallised from ethanol-diethyl ether, mp 102°–105° C., (Found: C, 55.76, H, 5.99, N, 15.43. $C_{18}H_{23}N_5O.1.35(C_2H_2O_4)$ requires: C, 55.63, H, 5.80: N, 15.67%), δ (360 MHz, D₂O) 7.31 (1H, dd, J=8.6 and 2.6 Hz), 7.36 (1H, d, J=2.6 Hz), 7.61 (1H, d, J=8.6 Hz), 7.75 (1H, s), 8.87 (2H, s) among other signals, m/e (ES) 326 (M+1⁺).

4. 1-{3-[5-(1,2,4-Triazol-4-yl)-1H-indol-3-yl]propyl}-4-ketopiperidine

To a stirred solution of the preceding alcohol free base (105 mg, 0.322 mmol) in a mixture of anhydrous dimethyl sulfoxide (3 ml) and anhydrous triethylamine (314 μl, 2.25 mmol) was added portionwise, under nitrogen, solid sulphur trioxide pyridine complex (185 mg, 1.16 mmol) over 7 minutes. After 55 minutes of stirring at room temperature, the mixture was diluted with water (20 ml), basified with saturated aqueous potassium carbonate and extracted with ethyl acetate (3×70 ml). The organic phases were combined, washed with brine (1×20 ml), dried (Na₂SO₄) and concentrated. Flash chromatography of the residue (silica gel, dichloromethane/methanol/ammonia, 90:10:1) afforded 72 mg (69%) of the title compound as a waxy solid, δ (250 MHz, CDCl₃) 1.96 (2H, qn, J=7.3 Hz), 2.42–2.62 (6H, m), 2.72–2.90 (6H, m), 7.13–7.19 (2H, m), 7.50 (1H, d, J=8.5 Hz), 7.57 (1H, d, J=2.0 Hz), 8.42 (1H, br s), 8.48 (2H, s), m/e (ES) 324 (M+1⁺).

5. 1-{3-[5-(1,2,4-Triazol-4-yl)-1H-indol-3-yl]propyl}-4-[4-(acetylamino)benzylamino]piperidine. 2.85 Hydrogen Oxalate.

To a stirred solution of the preceding ketone (100 mg, 0.309 mmol) and 4-(acetylamino)benzylamine hydrochloride (111.5 mg, 0.371 mmol) in methanol (7 ml) was added anhydrous triethylamine (51.7 μl, 0.371 mmol) followed by glacial acetic acid (70.7 μl, 1.236 mmol). After 15 minutes, sodium cyanoborohydride (25 mg) was added and stirring was continued at room temperature for 3.5 hours. Saturated aqueous potassium carbonate (4 ml) was added and the methanol was removed under vacuum. The aqueous residue was diluted with brine (25 ml) and products were extracted with ethyl acetate (1×50 ml), chloroform (2×50 ml) and chloroform-n-butanol (1:2; 1×150 ml). The combined organic extracts were dried (Na₂SO₄) and concentrated. Flash chromatography of the residue (silica gel, dichloromethane/methanol/ammonia, 85:15:1.5) gave 95 mg (65%) of the title compound free base. The oxalate salt was prepared and crystallised from ethanol-diethyl ether, mp 205°–210° C., (Found: C, 53.64, H, 5.26, N, 13.74. $C_{27}H_{33}N_7O.2.85(C_2H_2O_4)$ requires C, 53.94, H, 5.36, N, 13.46%), δ (360 MHz, D₂O) 1.86–2.04 (2H, m), 2.10–2.24 (2H, m), 2.17 (3H, s), 2.45 (2H, br d, J=13 Hz), 2.90 (2H, t, J=7.0 Hz), 3.04 (2H, t, J=12 Hz), 3.14–3.24 (2H, m), 3.55 (1H, br t), 3.71 (2H, br d, J=13 Hz), 4.27 (2H, s), 7.32–7.40 (2H, m), 7.46 (2H, d, J=8.6 Hz), 7.49 (2d, J=8.6 Hz), 7.64 (1H, d, J=8.7 Hz), 7.80 (1H, s), 9.02 (2H, s), m/e (ES) 472 (M+1⁺).

EXAMPLE 9

1-{3-[5-(1,2,4-Triazol-4-yl)-1H-indol-3-yl]propyl}-4-(benzylamino) pipperidine. Dihydrogen Oxalate Dihydrate The title compound was prepared from 1-{3-[5-(1,2,4-triazol-4-yl)-1H-indol-3-yl]propyl}-4-ketopiperidine and benzylamine using a similar procedure to that described for Example 8 (step 5), mp 233°–234° C., (Found: C, 55.49; H, 5.69; N, 13.26. $C_{25}H_{30}N_6.2(C_2H_2O_4).2 H_2O$ requires C, 55.23; H, 6.07; N, 13.33%). δ (360 MHz, d₆-DMSO) 1.85–2.00 (2H, m), 2.01–2.11 (2H, m), 2.19–2.22 (2H, m), 2.73–2.90 (4H, m), 2.91–3.00 (2H, m), 3.16–3.25 (1H, m), 3.4–3.5 (2H, m), 4.14 (2H, s), 7.30–7.33 (2H, m), 7.40–7.42 (3H, m), 7.48–7.51 (3H, m), 7.80–7.81 (1H, m), 9.02 (2H, s), 11.20 (1H, s), m/e (ES) 415 (M+1⁺).

EXAMPLE 10

1-{3-[5-(1,2,4-Triazol-4-yl)-1H-indol-3-yl]propyl}-4-[N-benzyl-N-methylamino]piperidine. 1.5 Hydrogen Oxalate.

To a stirred solution of the preceding amine (Example 9) (164 mg, 0.396 mmol), formaldehyde (38% wt in H₂O, 32 μL, 0.436 mmol) and glacial acetic acid (90 mg, 1.584 mmol) in methanol (10 ml) was added sodium cyanoborohydride (27 mg, 0.436 mmol). Stirring was continued for 3 h. Saturated aqueous potassium carbonate (4 ml) was added and the methanol removed under vacuum. The aqueous residue was partitioned between ethyl acetate (30 ml) and water (20 ml). The organic layer was dried (Na₂SO₄) and concentrated. Flash chromatography (silica gel, dichloromethane/methanol/ammonia, 90:10:1) gave 128 mg (76%) of the title compound free base. The oxalate salt was prepared and crystallised from methanol-diethyl ether, mp 134°–136° C.; (Found: C, 59.39; H, 6.08; N, 14.10. $C_{26}H_{32}N_6.1.5(C_2H_2O_4).1.3 H_2O$ requires, C, 59.33, H, 6.46, N, 14.31%); δ (360× MHz, d₆-DMSO) 1.74–1.88 (2H, m), 1.90–2.08 (4H, m), 2.16 (3H, s), 2.70–2.84 (5H, m), 2.92–3.02 (2H, m), 3.36–3.46 (2H, m), 3.65 (2H, s), 7.20–7.36 (7H, m), 7.50 (1H, d, 8.6 Hz), 7.80 (1H, s), 9.02 (2H, s), 11.18 (1H, s). m/e (ES⁺) 429 (M+1⁺).

EXAMPLE 11

1-{3-[5-(1,2,4-Triazol-4-yl)-1H-indol-3-yl]propyl}-4-[(benzylamino) methyl]pipperidine. 2.5 Hydrogen Oxalate.

1. 4-[(Benzylamino)methyl]pipperidine

A solution of 4-(aminomethyl)piperidine (22.8 g, 200 mmol) and benzaldehyde (21.2 g, 200 mmol) in toluene (200 ml) was refluxed for 5 h, under nitrogen, using a Dean-Stark trap. After cooling, the toluene was removed under vacuum and the residual oil was dissolved in absolute ethanol (400 ml) and cooled to 5° C. Sodium borohydride (6 g, 158.7 mmol) was added portionwise to the above solution over 40 minutes, under nitrogen, and the mixture was stirred for a further 1 hour 15 minutes before excess borohydride was destroyed by dropwise addition of 5N hydrochloric acid (150 ml) (CAUTION: hydrogen evolution). The ethanol was removed under vacuum and the aqueous residue was basified and extracted with ethyl acetate (5×500 ml). The combined organic solutions were dried ($Na_2SO_4$) and concentrated. Column chromatography (alumina, activity II-III; dichloromethane/methanol/ammonia, 95:5:0.35) of the residue afforded 19.3 g (47%) of the title compound as a pale yellow oil, δ (250 MHz, $d_6$-DMSO) 1.13 (2H, dq, J=12 and 4.0 Hz), 1.50–1.70 (1H, m), 1.78 (2H, br d, J=11 Hz), 2.47 (2H, d, J=6.6 Hz), 2.56 (2H, dt, J=12 and 2.3 Hz), 3.05 (2H, br d, J=12 Hz), 3.83 (2H, s), 7.30–7.50 (5H, m), m/e (ES) 205 ($M+1^+$).

2. 5-{4-[(Benzylamino)methyl]piperidin-1-yl}pentanal dimethyl acetal

The title compound was prepared in 58% yield from 5-bromopentanal dimethyl acetal and 4-[(benzylamino) methyl]piperidine using a similar method to that described for Example 8 (step 2). δ (250 MHz, $d_6$-DMSO) 1.26–2.14 (13H, m), 2.49 (2H, t, J=7.0 Hz), 2.63 (2H, d, J=6.6 Hz), 3.04–3.14 (2H, m), 3.49 (6H, s), 3.95 (2H, s), 4.61 (1H, t, J=5.7 Hz), 7.44–7.62 (5H, m), m/e (ES) 335 ($M+1^+$).

3. 1-{3-[5-(1,2,4-Triazol-4-yl)-1H-indol-3-yl]propyl}-4-[(benzylamino)methyl]piperidine. 2.5 Hydrogen Oxalate.

A solution of the preceding acetal (2.70 g, 8.07 mmol) and 4'-(1,2,4-triazol-4-yl)phenylhydrazine (1.50 g, 8.5 mmol) in 4% $H_2SO_4$ (100 ml) was refluxed for 20 hours. After cooling, the mixture was basified with 4N sodium hydroxide and products were extracted with ethyl acetate (3×200 ml). The combined organic solutions were washed with brine (1×50 ml), dried ($Na_2SO_4$) and concentrated. Flash chromatogrpahy of the residue (silica gel, dichloromethane/methanol/ammonia, 90:10:0.9) gave 1.63 g (47%) of the title compoun;d free base as a thick pale yellow oil. The oxalate salt was prepared and recrystallised from ethanol-methanol, mp 215°–220° C., (Found: C, 56.78; H, 5.56; N, 12.82. $C_{26}H_{32}N_6.2.5(C_2H_2O_4)$ requires: C, 56.96; H, 5.71; N, 12.86%). δ (360 MHz, $d_6$-DMSO) 1.36–1.56 (2H, m), 1.86–2.12 (5H, m), 2.70–2.94 (6H, m), 2.98–3.08 (2H, m), 3.36–3.50 (2H, m), 4.12 (2H, s), 7.30–7.54 (8H, m), 7.80 (1H, s), 9.02 (2H, s), 11.95 (1H, s), m/e (ES) 429 ($M+1^+$).

EXAMPLE 12

1-{3-[5-(1,2,4-Triazol-4-yl)-1H-indol-3-yl]propyl}-4-[(N-benzyl-N-methylamino)methyl]piperidine. 2.65 Hydrogen Oxalate.

The title compound was prepared in 73% isolated yield from the product of Example 11 using a similiar procedure to that described for Example 10. The oxalate salt was prepared and recrystallised from ethanol, mp 131°–134° C. (Found: C, 56.96; H, 5.84; N, 12.21. $C_{27}H_{34}N_6.2.56(C_2H_2O_4)$ requires: C, 56.95; H, 5.82; N, 12.34%), δ (360 MHz, DMSO-$d_6$) 2.29 (3H, s), 3.72 (2H, s), 7.40–7.24 (7H, m), 7.50 (1H, d, J=8.6 Hz), 7.81 (1H, d, J=1.9 Hz), 9.02 (2H, s), 11.19 (1H, s) among other signals; m/e (ES) 443 ($M^++1$).

Examples 13–20 were prepared from 1-{3-[5-(1,2,4-triazol-4-yl)-1H-indol-3-yl]propyl}-4-ketopiperidine and the corresponding commercially available amines using a similar method to that described for Example 8 (step 5).

EXAMPLE 13

1-{3-[5-(1,2,4-Triazol-4-yl)-1H-indol-3-yl]propyl}-4-[(R)-α-(methyl) benzylamine]piperidine. 2.7 Hydrogen Oxalate. 0.4 Hydrate.

The oxalate salt was prepared from ethanol, mp 111°–115° C. (Found: C, 55.62; H, 5.82; N, 12.04. $C_{26}H_{32}N_6.2.7(C_2H_2O_4).0.4 H_2O$ requires: C, 55.55; H, 5.67; N, 12.38%.) δ (360 MHz, DMSO-$d_6$) 1.51 (3H, d, J=6.5 Hz), 1.74–2.22 (6H, m), 2.64–2.96 (7H, m), 3.34–3.48 (2H, m), 4.42 (1H, br q, J=6.5 Hz), 7.28–7.68 (8H, m), 7.78 (1H, d, J=2.0 Hz), 9.01 (2H, s), 11.17 (1H, s); m/e (ES) 429 ($M+1)^+$; $[α]_D$+24 (c 0.52, MeOH).

EXAMPLE 14

1-{3-[5-(1,2,4-Triazol-4-yl)-1H-indol-3-yl]propyl}-4-[(S)-α-(methyl) benzylamino]piperidine. 2.7 Hydrogen Oxalate. 0.3 Hydrate.

The oxalate salt was prepared from ethanol, mp 121°–125° C. (Found: C, 56.51; H, 5.86; N, 12.57. $C_{26}H_{32}N_6.2.5(C_2H_2O_4).0.3 H_2O$ requires: C, 56.49; H, 5.75; N, 12.75%). $[α]_D$–23.9 (c 0.51, MeOH).

EXAMPLE 15

1-{3-[5-(1,2,4-Triazol-4-yl)-1H-indol-3-yl]propyl}-4-[(S)-α-(hydroxymethyl)benzylamino]piperidine. 2.6 Hydrogen Oxalate.

The oxalate salt was prepared from methanol-diethyl ether, mp 175°–180° C. (Found: C, 54.92; H, 5.49; N, 12.59. $C_{26}H_{32}N_6.2.6(C_2H_2O_4)$ requires: C, 55.22; H, 5.53; N, 12.38%). δ (360 MHz, DMSO-$d_6$) 1.62–1.84 (2H, m), 1.90–2.16 (4H, m), 2.60–2.96 (7H, m), 3.28–3.42 (2H, m), 3.63 (2H, br s), 4.19 (1H, m), 7.36–7.54 (8H, m), 7.78 (1H, d, J=2.0 Hz), 9.01 (2H, s), 11.17 (1H, s); m/e (ES) 445 ($M^++1$).

EXAMPLE 16

1-{3-[5-(1,2,4-Triazol-4-yl)-1H-indol-3-yl]propyl}-4-[(R)-α-(hydroxymethyl) benzylamino]pipieridine. 1.9 Hydrogen Oxalate. Monohydrate.

The oxalate salt was prepared from methanol-diethyl ether, mp 154°–157° C. (Found: C, 56.69; H, 6.20; N, 12.91. $C_{26}H_{32}N_6O.1.9(C_2H_2O_4).1.0 H_2O.0.15(C_4H_{10}O)$ requires: C, 56.63; H, 6.14; N, 13.03%).

EXAMPLE 17

1-{3-[5-(1,2,4-Triazol-4-yl)-1H-indol-3-yl]propyl}-4-{(S)-[1-hydroxymethyl-2-phenyl] ethylamino}piperidine. 2.0 Hydrogen Oxalate. 1.4 Hydrate.

The oxalate salt was prepared from methanol-diethyl ether, mp 180°–185° C. (Found: C, 56.14; H, 6.10; N, 12.83. $C_{27}H_{34}N_6O.2.0(C_2H_2O_4).1.4 H_2O$ requires: C, 56.08; H, 6.19; N, 12.66%). δ (360 MHz, DMSO-$d_6$) 1.68–1.86 (2H, m), 1.94–2.18 (4H, m), 2.54–3.00 (8H, m), 3.24–3.40 (5H, m), 3.53 (1H, d, J=9.5 Hz), 7.20–7.36 (7H, m), 7.49 (1H, d, J=8.6 Hz), 7.80 (1H, d, J=2.0 Hz), 9.02 (2H, s), 11.17 (1H, s); m/e (ES) 459 ($M^++1$).

EXAMPLE 18

1-{3-[5-(1,2,4-Triazol-4-yl)-1H-indol-3-yl]propyl}-4-{(1R,2S)-[2-hydroxy-1-methyl-2-phenyl]ethylamino}peridine. 2.3 Hydrogen Oxalate. Monohydrate.

The oxalate salt was prepared from methanol-diethyl ether, mp 148°–152° C. (Found: C, 55.48; H, 6.16; N, 12.23. $C_{27}H_{34}N_6O.2.3(C_2H_2O_4)$. 1.0 $H_2O.0.15(C_4H_{10}O)$ requires: C, 55.66; H, 6.12; N, 12.10%). δ (360 MHz, DMSO-$d_6$) 0.92 (3H, d, J=6.5 Hz), 1.70–1.86 (2H, m), 1.90–2.04 (2H, m), 2.08–2.30 (2H, m), 2.52–2.86 (5H, m), 3.23–3.52 (5H, m), 5.07 (1H, s), 7.22–7.44 (7H, m), 7.50 (1H, d, J=8.6 Hz), 7.80 (1H, d, J=2.0 Hz), 9.02 (2H, s), 11.17 (1H, s); m/e (ES) 459 (M$^+$+1).

EXAMPLE 19

1-{3-[5-(1,2,4-Triazol-4-yl)-1H-indol-3-yl]propyl}-4-{1S,2R)-[2-hydroxy-1-methyl-2-phenyl]ethylamino}piperidine. 2.1Hydrogen Oxalate.

The oxalate salt was prepared from methanol-diethyl ether, mp 148°–151° C. (Found: C, 56.36; H, 6.16; N, 12.58. $C_{27}H_{34}N_6O.2.1(C_2H_2O_4).0.1(C_4H_{10}O)$ requires: C, 56.39; H, 6.17; N, 12.49%). m/e (ES) 459 (M$^+$+1).

EXAMPLE 20

1-{3-[5-(1,2,4-Triazol-4-yl)-1H-indol-3-yl]propyl}-4-{1R,2R)-[2-hydroxy-1-methyl-2-phenyl]ethylamino}piperidine. 2.4 Hydrogen Oxalate. 1.1 Hydrate.

The oxalate salt was prepared from methanol-diethyl ether, mp 125°–128° C. (Found: C, 55.12; H, 6.47; N, 11.82. $C_{27}H_{34}N_6O.2.4(C_2H_2O_4).1.1$ $H_2O.0.2(C_4H_{10}O)$ requires: C, 55.20; H, 6.11; N, 11.85%). δ (360 MHz, DMSO-$d_6$) 0.94 (3H, d, J=6.6 Hz), 1.76–2.24 (6H, m), 2.70–2.84 (4H, m), 2.86–2.98 (2H, m), 3.30–3.47 (4H, m), 4.51 (1H, d, J=9.0 Hz), 7.28–7.42 (7H, m), 7.50 (1H, d, J=8.6 Hz), 7.81 (1H, d, J=2.0 Hz), 9.03 (2H, s), 11.19 (1H, s); m/e (ES) 459 (M$^+$+1).

EXAMPLE 21

1-{3-[5-(1,2,4-Triazol-4-yl)-1H-indol-3-yl]propyl}-4-{[2-(4-acetylaminophenyl)ethyl]amino}piperidine. 2.4 Hydrogen Oxalate. Monohydrate.

a) 4-(Acetylamino)phenethylamine

To a cooled (0° C.) and stirred solution of 4-aminobenzyl cyanide (2.38 g, 18.04 mmol) in anhydrous dichloromethane (30 ml) was added anhydrous triethylamine (7.54 ml, 54.12 mmol) followed by acetic anhydride (2.56 ml, 27.06 mmol) under nitrogen. The mixture was allowed to warm to room temperature and it was stirred for 18 h before it was diluted with ethyl acetate (150 ml) and-washed with 10% aqueous sodium bicarbonate (100 ml), 2M hydrochloric acid (50 ml), brine (50 ml), then dried (MgSO$_4$) and concentrated to give 4-(acetylamino)benzyl cyanide as an orange solid. The crude nitrile (2.8 g) was dissolved in absolute ethanol (200 ml) and chloroform (4 ml) and it was hydrogenated at 50 psi over platinum (IV) oxide for 16 h. The catalyst was filtered off, washed with ethanol and the filtrate was concentrated under vacuum. The residue was dissolved in 2M sodium hydroxide (30 ml) and the product was extracted with dichloromethane (4×150 ml), then dried (Na$_2$SO$_4$) and concentrated. Flash chromatography of the residue (silica gel, dichloromethane/methanol/ammonia, 85:15:1.5) gave 2.3 g (80%) of the title compound as a yellow solid. δ (360 MHz, CDCl$_3$) 2.16 (3H, s), 2.71 (2H, t, J=6.8 Hz), 2.94 (2H, t, J=6.8 Hz), 7.14 (2H, d, J=8.3 Hz), 7.26 (1H, br s), 7.41 (2H, d, J=8.3 Hz).

b) 1-{3-[5-(1,2,4-Triazol-4-yl)-1H-indol-3-yl]propyl}-4-{[2-(4-acetylaminophenyl)ethyl]amino}piperidine. 2.4 Hydrogen Oxalate. Monohydrate.

The title compound was prepared from 1-{3-[5-(1,2,4-triazol-4-yl)-1H-indol-3-yl]propyl}-4-ketopiperidine and 4-(acetylamino)phenylamine using a similar method to that described for Example 8 (step 5). Oxalate salt prepared from methanol-diethyl ether, mp 195°–202° C. (Found: C, 54.87; H, 5.68; N, 13.83. $C_{28}H_{35}N_7O.2.4(C_2H_2O_4).1.0$ $H_2O$ requires: C, 54.74; H, 5.85; N, 13.62%). δ (360 MHz, DMSO-$d_6$) 1.70–1.86 (2H, m), 2.94–2.22 (5H, m and s), 2.60–2.94 (8H, m), 3.06–3.28 (3H, m), 3.34–3.44 (1H, m), 7.18 (2H, d, J=8.4 Hz), 7.28–7.36 (2H, m), 7.46–7.56 (3H, m), 7.80 (1H, d, J=2.0 Hz), 9.02 (2H, s), 9.92 (1H, s), 11.17 (1H, s); m/e (ES) 486 M$^+$+1).

EXAMPLE 22

1-{3-[5-(1,2,4-Triazol-4-yl)-1H-indol-3-yl]propyl}-4-{[(R)-α-(methyl) benzylamino]methyl}piperidine. Hydrogen Oxalate. 2.6 Hydrate.

a) 5-[4-(Hydroxymethyl)piperidin-1-yl]pentanal dimethyl acetal

To a cooled (0° C.) and stirred suspension of isonipecotic acid (25.83 g, 200 mmol), in anhydrous THF (100 ml) was added lithium aluminium hydride (1M in THF; 200 ml), under a nitrogen atmosphere. The reaction was allowed to attain room temperature and it was stirred for 18 h, then refluxed for a further 4 h. The reaction was quenched by sequential addition of water (7.5 ml), 15% sodium hydroxide solution (7.5 ml) and water (15 ml). The reaction was filtered to remove a granular precipitate and the filtrate was concentrated under vacuum to give 11.24 g of 4-(hydroxymethyl)piperidine as a colourless oil. The title compound was prepared from 5-chloropentanal dimethyl acetal (20.4 g, 122 mmol) and 4-(hydroxymethyl)piperidine (15.7 g) using a similar method to that described for Example 8 (step 2). δ (360 MHz, DMSO-$d_6$) 1.10 (2H, m), 1.28 (2H, m), 1.39 (2H, m), 1.48 (2H, m), 1.60 (2H, br d), 1.77 (2H, t), 2.20 (2H, t), 2.80 (2H, br d), 3.21 (8H, m), 4.31 (1H, t), 4.37 (1H, t).

b) 1-{3-[5-(1,2,4-Triazol-4-yl)-1H-indol-3-yl]propyl}-4-(hydroxymethyl piperidine The title compound was prepared from the preceding dimethyl acetal (18.64 g, 76 mmol) and 4'-(1,2,4-triazol-4-yl)phenyl hydrazine (15.98 g) using a similar method to that described for Example 8 (step 3). δ (250 MHz, DMSO-$d_6$) 1.11 (2H, m), 1.30 (1H, m), 1.60 (2H, d), 1.80 (4H, m), 2.29 (2H, t), 2.70 (2H, t), 2.84 (2H, d), 3.22 (2H, t), 4.40 (1H, t), 7.26–7.31 (2H, m), 7.46 (1H, d), 7.78 (1H, d), 9.02 (2H, s), 11.08 (1H, s).

c) 1-{3-[5-(1.2 4-Triazol-4-yl)-1H-indol-3-yl]propyl}-4-{[(R)-α-(methyl)benzylamino]methyl}piperidine. Hydrogen Oxalate. 2.6 Hydrate.

To a solution of the preceding alcohol (0.5 g, 1.48 mmol) in a mixture of anhydrous dimethyl sulphoxide (20 ml) and anhydrous triethylamine (755 μl, 10.29 mmol) was added portionwise, under nitrogen, solid sulphur trioxide pyridine complex, (844 mg, 5.3 mmol). After 2 hours of stirring, the reaction was cooled to 0° C., quenched by dropwise addition of saturated aqueous potassium carbonate (5 ml) and it was partitioned between water-butanol (30 ml–70 ml). The organic phase was concentrated to 5 ml under vacuum and diluted with methanol (10 ml). Acetic acid (506 μl) and (R)-α-methylbenzylamine (209 μl, 1.62 mmol) were added followed, after 10 minutes, by sodium cyanoborohydride (102 mg). After 18 h of stirring, the reaction was quenched with saturated aqueous potassium carbonate, volatiles removed in vacuo and the residue was partitioned between water-butanol. The organic phase was concentrated and purified by flash chromatography (silica gel, dichloromethane/methanol/ammonia, 92:8:1) to give 85 mg of the title compound free base as a colourless solid. The oxalate salt was prepared and crystallised from methanol/diethyl/ether, mp 140° C. (Found: C, 59.86; H, 6.81; N, 14.37. $C_{27}H_{34}N_6 \cdot C_2H_2O_4 \cdot 2.6H_2O$ requires C, 59.90; H, 6.93; N, 14.45%). δ (360 MHz, DMSO-$d_6$) 1.20 (2H, m), 1.39 (3H, d), 1.58 (1H, m), 1.76 (2H, brt), 1.92 (2H, m), 2.27–2.30(3H, m), 2.69–2.72 (5H, m), 3.12–3.16 (2H, m), 3.97 (1H, d), 7.29–7.50 (8H, m), 7.78 (1H, d), 9.02 (2H, s), 11.16 (1H, s); m/e (ES) 443 ($M^+$+1). HPLC analysis on a Chiralpak AD column, using hexane/ethanol/diethylamine (25:75:0.1) as the mobile phase (UV detection at 280 nm; flow 1 ml/min; 40° C.) showed the compound to have a retention time of 6.4 min.

EXAMPLE 23

1-{3-[5-(1,2,4-Triazol-4-yl)-1H-indol-3-yl]propyl}-4-{[(S)-α-(methyl) benzylamino]methyl}piperidine. 1.5 Hydrogen Oxalate. Monohydrate.

The title compound was prepared using a similar procedure to that described for Example 22. The oxalate salt was prepared and recrystallised from methanol-diethyl ether, mp. 149°–150° C. (Found: C, 60.11; H, 6.92; N, 14.51. $C_{27}H_{34}N_6 \cdot 1.5(C_2H_2O_4) \cdot H_2O$ requires: C, 60.49; H, 6.60; N, 14.11%). Other spectroscopic data identical to product from Example 22. HPLC analysis retention time=8.3 min (see Example 22 for conditions).

EXAMPLE 24

1-{3-[5-(1,2,4-Triazol-4-yl)-1H-indol-3-yl]propyl}-4-{[(S)-1-(4-acetylaminonhenyl)ethylamino] methyl}piperidine. 2.0 Hydrogen Oxalate. 2.0 Hydrate.

a) N-tert-Butyloxycarbonyl-(S)-1-(4-nitrophenyl) ethylamine

To a suspension of (S)-1-(4-nitrophenyl)ethylamine hydrochloride (2.12 g, 10.4 mmol) in anhydrous dichloromethane (50 ml) was added triethylamine (1.45 ml). A solution of di-tert-butyldicarbonate (2.28 g) in anhydrous dichloromethane (50 ml) was added and the reaction allowed to stand for 18 h. The reaction was washed with water, dried (MySO₄), concentrated and purified by chromatography on silica gel using 1:1 ethyl acetate:petroleum ether as eluant. The title compound was obtained as a yellow oil which crystallised slowly.

b) N-tert-Butyloxycarbonyl-(S)-1-(4-acetamidophenyl) ethylamine

A solution of the product from above (2.96 g) in ethyl acetate (100 ml) was hydrogenolysed over PtO₂ (0.11 g) at 15 psi for 50 minutes in the presence of acetic anhydride (0.97 ml). The catalyst was removed by filtration and washed with ethanol. The filtrate was concentrated to give the title compound. δ (250 MHz, $D_6$-DMSO) 1.26 (3H, d, J=10 Hz), 1.35 (9H, s), 2.02 (3H, s), 4.54 (1H, m), 7.19 (2H, d, J=12.9 Hz), 7.30 (1H, d, J=11.6 Hz), 7.47 (2H, d, J=12.2 Hz).

c) (S)-1-(4-Acetamidophenyl)ethylamine

The product from above (1.89 g, 6.8 mmol) was dissolved in 90% formic acid (5 ml) and was stirred at room temperature, until all the starting material had reacted. The reaction was concentrated, basified with saturated potassium carbonate solution and extracted into butanol. The solvent was removed to give the title compound as a brown foam, which could be crystallised from methanol-ethyl acetate. δ (360 MHz, $D_6$-DMSO) 1.28 (3H, d, J=6.6 Hz), 2.02 (3H, s), 4.03 (1H, m), 7.29 (2H, d, J=8.6 Hz), 7.50 (2H, d, J=8.6 Hz), 8.46 (2H, br s), 10.02 (1H, s).

d) 1-{3-[5-(1,2,4-Triazol-4-yl)-1H-indol-3-yl]propyl}-4-{[(S)-1-(4-acetylaminoohenyl)ethylamino]methyl}piperidine. 2.0 Hydrogen Oxalate. 2.0 Hydrate.

The title compound was prepared from the amine described above using a similar procedure to that described in Example 22 (step 4). The oxalate salt was prepared and recrystallised from methanol-diethyl ether to give a hygroscopic solid; (Found: C, 55.41; H, 6.12; N, 13.38. $C_{29}H_{37}N_7O \cdot 2(C_2H_2O_4) \cdot 2H_2O$ requires: C, 55.37; H, 6.33; N, 13.69%). δ (360 MHz, $D_6$-DMSO) 1.2–1.4 (2H, m), 1.44 (3H, d, J=6.7 Hz), 1.8–2.0 (3H, m), 1.8–2.1 (5H, m), 2.37 (2H, m), 2.37–2.6 (2H, m), 2.7–2.9 (4H, m), 3.0–3.1 (2H, m), 3.3–3.5 (1H, m), 4.0–4.1 (1H, br s), 7.31–7.36 (4H, m,), 7.49–7.51 (1H, d, J=8.6 Hz), 7.56–7.59 (2H, m), 7.80 (1H, s), 9.07 (2H, s), 10.01 (1H, s), 11.19 (1H, s); m/e ($ES^+$) 450 $(M+1)^+$.

EXAMPLE 25

1-{3-[5-(1,2,4-Triazol-4-yl)-1H-indol-3-yl]propyl}-4-{[(R)-1-(4-acetylaminophenyl)ethyl] amino}piperidine. 3.0 Hydrogen Oxalate. 1.2 Hydrate.

The title compound was prepared from 1-{3-[5-(1,2,4-triazol-4-yl)-1H-indol-3-yl]propyl}-4-ketopiperidine and (R)-1-(4-acetamidophenyl) ethylamine using a similar method to that described for Example 8 (step 5). The oxalate salt was prepared from methanol-diethyl ether, mp 135°–140° C. (Found: C, 52.51; H, 5.79; N, 12.59. $C_{28}H_{35}N_7O \cdot 3.0(C_2H_2O_4) \cdot 1.2 H_2O \cdot 0.2(C_4H_{10}O)$ requires: C, 52.76; H, 5.78; N, 12.38%). δ (360 MHz, $D_6$-DMSO) 1.50 (3H, d, J=6.5 Hz), 1.72–1.90 (2H, m), 1.92–2.20 (7H, m and s), 2.62–2.96 (7H, m), 3.32–3.44 (2H, m), 4.34–4.42 (1H, m), 7.29 (1H, s), 7.31 (1H, d, J=8.6 Hz), 7.45 (2H, d, J=8.6 Hz), 7.48 (1H, d, J=8.6 Hz), 7.61 (2H, d, J=8.6 Hz), 7.78 (1H, d, J=2.0 Hz), 9.01 (2H, s), 10.6 (1H, s), 11.16 (1H, s); m/e (ES) 486 $(M+1)^+$.

Examples 26–28 were prepared from the products of Examples 15, 16 and 21 using a similar method to that described for Example 10.

EXAMPLE 26

1-{3-[5-(1,2,4-Triazol-4-yl)-1H-indol-3-yl]propyl}-4-{N-[(R)-α-(hydroxymethyl)benzyl]-N-methylamino}piperidine. 2.0 Hydrogen Oxalate. 1.4 Hydrate.

The oxalate salt was prepared from methanol-diethyl ether, mp 105°–110° C. (Found: C, 56.13; H, 6.24; N, 12.34. $C_{27}H_{34}N_6O \cdot 2.0(C_2H_2O_4) \cdot 1.4 H_2O \cdot 0.1(C_4H_{10}O)$ requires: C, 56.18, H, 6.28; N, 12.34% δ (360 MHz, DMSO-$d_6$) 1.78–2.08 (6H, m) 2.28 (3H, s), 2.70–3.06 (7H, m), 3.38–3.48 (2H, m), 3.72 (1H, dd, J=11.3 and 5.1 Hz), 3.85 (1H, dd, J=11.3 and 6.1 Hz), 4.01 (1H, m), 7.24–7.42 (7H, m), 7.49 (1H, d, J=8.5 Hz), 7.79 (1H, d, J=2.0 Hz), 9.01 (2H, s), 11.18 (1H, s); m/e (ES) 459 ($M^+$+1).

EXAMPLE 27

1-{3-[5-(1,2,4-Triazol-4-yl)-1H-indol-3-yl]propyl}-4-{N-[(S)-α-(hydroxymethyl)benzyl]-N-methylamino}piperidine. 2.9 Hydrogen Oxalate. Monohydrate.

The oxalate salt was prepared from methanol-diethyl ether, mp 95°–100° C. (Found: C, 53,37; H, 5.78, N, 11.49. $C_{27}H_{34}N_6O.2.9(C_2H_2O_4).0.1(C_4H_{10}O)$ requires: C, 53.52; H, 5.79; N, 11.28%). m/e (ES) 459 (M$^+$+1).

EXAMPLE 28

1-{3-[5-(1,2,4-Triazol-4-yl)-1H-indol-3-yl]propyl}-4-{N-[2-(4-acetylaminophenyl)ethyl]-N-methylamino}piperidine. 3.0 Hydrogen Oxalate. 1.1 Hydrate.

The oxalate salt was prepared from methanol-ether, mp 128°–135° C. (Found: C, 53.36; H, 6.01; N, 12.19. $C_{28}H_{35}N_7O.3.0(C_2H_2O_4)1.1\ H_2O.0.2(C_4H_{10}O)$ requires: C, 53.45; H, 5.91; N, 12.19%). δ (360 MHz, DMSO-$d_6$) 1.80–2.12 (9H, m), 2.62 (3H, s), 2.70–2.90 (6H, m), 2.91–3.01 (2H, m), 3.03–3.12 (2H, m), 3.18–3.30 (1H, m), 3.39–3.52 (2H, m), 7.16–7.22 (2H, m), 7.29–7.36 (2H, m), 7.46–7.54 (3H, m), 7.80 (1H, d, J=2.0 Hz), 9.02 (2H, s) 9.89 (1H, s), 11.18 (1H, s); m/e (ES) 500 (M$^+$+1).

EXAMPLE 29

1-{3-[5-(1,2,4-Triazol-4-yl)-1H-indol-3-yl]propyl}-4-{[N-(4-acetylaminobenzyl)-N-methylamino]methyl}piperidine. 3.7 Hydrogen Oxalate.

a) 1-{3-[5-(1,2,4-Triazol-4-yl)-1H-indol-3-yl]propyl}-4-[(N-methylamino)methyl]piperidine A solution of the product from Example 12 (free base; 730 mg) in absolute ethanol (60 ml) was hydrogenated over 20% Pearlman's catalyst (500 mg) for 24 h at 45 psi. The catalyst was filtered off, washed with ethanol (3×30 ml) and the filtrate was concentrated under vacuum to give 573 mg (99%) of the title compound as a yellow foam; m/e (ES) 353 (M$^+$+1).

b) 1-{3-[5-(1,2,4-Triazol-4-yl)-1H-indol-3-yl]propyl}-4-{[N-(4-acetylaminobenzyl)-N-methylamino]methyl}piperidine. 3.7 Hydrogen Oxalate.

The title compound was prepared from the product of the preceding step and 4-acetamidobenzaldehyde using a similar method to that described for Example 10. The oxalate salt was prepared, mp 155°–165° C. (Found: C, 52.57; H, 5.47; N, 11.78. $C_{29}H_{37}N_7O.3.7(C_2H_2O_4)$ requires: C, 52.50; H, 5.37; N, 11.77%). δ (360 MHz, DMSO-$d_6$) 1.23–1.42 (2H, m), 1.85–2.10 (8H, m and s), 2.39 (3H, s), 2.50–2.62 (2H, m), 2.72–2.96 (4H, m), 3.00–3.10 (2H, m), 3.36–3.54 (2H, m), 3.82 (2H, s), 7.28–7.36 (4H, m), 7.50 (1H, d, J=8.6 Hz), 7.58 (2H, d, J=8.4 Hz), 7.80 (1H, d, J=2.0 Hz), 9.02 (2H, s), 10.01 (1H, s), 11.19 (1H, s); m/e (ES) 500 (M$^+$+1).

EXAMPLE 30

1-{3-[5-(1,2,4-Triazol-4-yl)-1H-indol-3-yl]propyl}-4-{N-[(thiophen-2-yl)methyl]-N-methylamino}piperidine. 2.0 Hydrogen Oxalate. Monohydrate.

a) 1-Benzyl-4-(N-tert-butyloxycarbonyl-N-methylamino)piperidine

To a cooled (0° C.) and stirred solution of 1-benzyl-4-aminopiperidine (100 g, 0.53 mol) in anhydrous dichloromethane (500 ml) was added a solution of di-tert-butyldicarbonate (126 g) in anhydrous dichloromethane (500 ml). The reaction was allowed to attain room temperature and stirred overnight. Concentration and trituration with diethyl ether gave 1-benzyl-4-(N-tert-butyloxycarbonylamino)piperidine.

To a cooled (−5° C.) and stirred solution of lithium aluminium hydride (1M in THF; 258 ml) in anhydrous tetrahydrofuran (250 ml) was added a solution of the above amine (50 g, 172 mmol) in anhydrous tetrahydrofuran (750 ml) over 20 minutes under nitrogen. The reaction mixture was then refluxed for 2.5 hours, cooled to room temperature and quenched by addition of water (10 ml), 15% aqueous sodium hydroxide (15 ml) and water (30 ml). The resulting mixture was filtered to remove a granular precipitate and the filtrate was cooled to 0° C. before di-tert-butyldicarbonate (41.3 g) was added. After 2 hours at room temperature, the solvent was removed under vacuum and the residue was partitioned between 2N aqueous sodium hydroxide and dichloromethane. The organic phase was washed with brine, dried ($Na_2SO_4$) and concentrated. Flash chromatography of the residue (silica gel, dichloromethane/methanol/ammonia, 89:10:1) gave the title compound. δ (250 MHz, DMSO-$d_6$) 1.38–1.49 (12H, m and s), 1.66 (2H, m), 1.94 (2H, m), 2.65 (3H, s), 2.90 (2H, br d), 3.44 (2H, s), 7.19–7.35 (5H, m).

b) 5-[4-(N-tert-Butyloxycarbonyl-N-methylamino)piperidin-1-yl]pentanal dimethyl acetal A solution of the preceding benzylic amine (5 g, 16.4 mmol) in methanol (100 ml) was hydrogenolysed over 10% palladium hydroxide (1 g) at 50 psi for 18 hours. The catalyst was filtered off and the filtrate was concentrated to give 4-(N-tert-butyloxycarbonyl-N-methylamino) piperidine as a colourless oil.

The title compound was prepared from the above amine and 5-bromopentanal dimethyl acetal using a similar method to that described for Example 8 (Step 2). δ (360 MHz, CDCl$_3$) 1.34 (1H, m), 1.46–1.73 (19H, m and s), 1.98 (2H, m), 1.33 (2H, m), 2.73 (3H, s), 2.99 (2H, m), 3.31 (6H, s), 4.36 (1H, t).

c) 1-{3-[5-(1,2,4-Triazol-4-yl)-1H-indol-3-yl]propyl}-4-(N-methylamino)piperidine The preceding acetal was reacted in a similar manner to that described in Example 11 (Step 3) to give the title compound as a brown foam. δ (360 MHz, DMSO-$d_6$) 1.16–1.24 (3H, m), 1.73–1.90 (6H, m), 2.25 (6H, m), 2.70 (2H, t), 2.78 (2H, m), 7.28 (2H, m), 7.46 (1H, d), 7.77 (1H, d), 9.01 (2H, s), 11.08 (1H, s).

d) 1-{3-[5-(1,2,4-Triazol-4-yl)-1H-indol-3-yl]propyl}-4-{N-[(thiophen-2-yl)methyl]-N-methylamino}piperidine. 2.0 Hydrogen oxalate. Monohydrate.

To a solution of the preceding amine (390 mg, 1.15 mmol), acetic acid (0.2 ml) and thiophen-2-carboxaldehyde (0.12 ml) in anhydrous ethanol (10 ml) was added sodium cyanoborohydride (80 mg). The reaction was allowed to stir under a nitrogen atmosphere for 18 h. The reaction was quenched by addition of saturated aqueous $K_2CO_3$ solution, concentrated to remove the ethanol, and extracted with butanol. Concentration and purification of the residue by chromatography on silica gel using methanol/dichloromethane/ammonia (10:90:1) as eluant gave the title compound free base (306 mg). The oxalate salt was prepared and crystallised from methanol-diethyl ether, m.p. 132°–135° C., (Found: C, 53.31; H, 5.64; N, 12.59. $C_{24}H_{30}N_6S.2(C_2H_2O_4).H_2O.0.2(C_4H_{10}O)$ requires: C, 53.42; H, 5.91; N, 12.98%). δ (360 MHz, D$_2$O) 2.00–2.20 (4H, m), 2.18–2.50 (2H, m), 2.82 (3H, s), 2.84–2.90 (2H, m), 3.0–3.10 (2H, m), 3.10–3.20 (2H, m), 3.60–3.80 (3H, m), 4.66 (2H, s), 7.16–7.18 (1H, m), 7.30–7.36 (3H, m), 7.61–7.65 (2H, m), 7.75 (1H, s), 8.88 (2H, s); m/e (ES$^+$) 435 (M+1$^+$).

EXAMPLE 31

1-{3-[5-(1,2,4-Triazol-4-yl)-1H-indol-3-yl]propyl}-4-{[(R)-α-(hydroxymethyl) benzylamino] methyl}piperidine. 1.5 Hydrogen Oxalate. Dihydrate.

The title compound was prepared from 1-{3-[5-(1,2,4-triazol-4-yl)-1H-indol-3-yl]propyl}-4-(hydroxymethyl) piperidine and (R)-2-phenylglycinol using a similar method to that described for Example 22 (Step 4). The oxalate salt was prepared and recrystallised from methanol/diethyl ether, mp 143°–145° C. (Found: C, 56.83; H, 6.92; N, 13.49. $C_{27}H_{34}N_6O.1.5$ $(C_2H_2O_4).2.0$ $H_2O$ requires: C, 57.22; H, 6.56; N, 13.35%). δ (360 MHz, DMSO-$d_6$) 1.26 (2H, m), 1.61 (1H, m), 1.73 (1H, m), 1.88 (1H, m), 1.97 (2H, m), 2.37 (1H, m), 2.49 (1H, m), 2.60 (2H, m), 2.74 (2H, t), 2.87 (2H, m), 3.25 (2H, m), 3.41 (1H, m), 3.50 (1H, m), 3.75 (1H, m), 7.26–7.36 (7H, m), 7.49 (1H, d), 7.79 (1H, d), 9.01 (2H, s), 11.17 (1H, s); m/e (ES) 459 (M$^+$+1).

EXAMPLE 32

(3S)-3-(4-(Acetylamino)benzylamino)methyl-1-[2-(5-(1,2,4-triazol-4-yl)-1H-indol-3-yl)ethyl] pyrrolidine. 2.6 Hydrogen Oxalate. 0.1Hydrate.

a) (3S)-3-Aminomethyl-1-[2-(5-(1,2,4-triazol-4-yl)-1H-indol-3-yl)ethyl]pyrrolidine A mixture of (3S)-3-(N-benzyl)aminomethyl-1-[2-(5-(1,2,4-triazol-4-yl)-1H-indol-3-yl)ethyl]pyrrolidine (Example 7; 0.277 g, 0.639 mmol), ammonium formate (0.218 g, 3.46 mmol) and 10% Pd-C (0.28 g), in anhydrous methanol (20 ml) was stirred at 62° C. for 0.75 h. The mixture was cooled to 25° C. and the catalyst removed filtration through celite. The solvent was removed under vacuum and the residue chromatographed on silica gel eluting with $CH_2Cl_2$/MeOH/$NH_3$ (20:8:1) to give the title compound (0.145 g, 68%), δ (250 MHz, CDCl$_3$) 1.48–1.59 (1H, m, CH of CH$_2$), 2.03–2.14 (1H, m, CH of CH$_2$), 2.29–2.41 (2H, m, 2 of CH), 2.63–3.02 (9H, m, 4 of CH$_2$ and CH), 7.14 (1H, dd, J=2.1 and 8.6 Hz, Ar—H), 7.21 (1H, s, Ar—H), 7.49 (1H, d, J=8.6 Hz, Ar—H), 7.60 (1H, d, J=2.1 Hz, Ar—H), 8.54 (2H, s, Ar—H).

b) (3S)-3-(4-Acetylamino)benzylamino)methyl-1-[2-(5-(1,2,4-triazol-4-yl)-1H-indol-3-yl)ethyl]pyrrolidine. 2.6 Hydrogen Oxalate. 0.1Hydrate.

To a solution of the preceding aminomethyl pyrrolidine (0.14 g, 0.452 mmol) in ethanol (10 ml) was added p-acetamidobenzaldehyde (0.074 g, 0.452 mmol) and the mixture stirred at 25° C. for 16 h. Sodium borohydride (17 mg, 0.456 mmol) was added and the solution stirred for 1 h. The solvent was removed under vacuum and the residue was taken up into $H_2O$ and acidified with 2N HCl. The mixture was then basified with saturated $K_2CO_3$ solution and extracted with ethyl acetate (×4). The combined organic extracts were washed with brine, dried (Na$_2$SO$_4$) and evaporated. The residue was chromatographed on silica gel eluting with $CH_2Cl_2$/MeOH/NH$_3$ (70:8:1) to give the title product (73 mg, 35%). The 2.6 hydrogen oxalate 0.1 hydrate salt was prepared, mp 197°–199° C. (Found: C, 54.22, H, 5.50, N, 14.12. $C_{26}H_{31}N_7O.2.6(C_2H_2O_4).0.1$ $H_2O$ requires C, 54.04; H, 5.29; N, 14.14%), m/e 458 (M+1)$^+$. δ (250 MHz, D$_6$DMSO) 1.66–1.86 (1H, m, CH of CH$_2$), 2.05 (3H, s, NH Ac), 2.12–2.26 (1H, m, CH of CH$_2$), 2.62–3.58 (11H, m, 5 of CH$_2$ and CH), 4.06 (2H, s, CH$_2$NH), 7.34–7.42 (4H, m, Ar—H), 7.52 (1H, d, J=8.6 Hz, Ar—H), 7.61 (2H, d, J=8.4 Hz, Ar—H), 7.90 (1H, d, J=2.0 Hz, Ar—H), 9.05 (2H, s, Ar—H), 10.08 (1H, s, NH), 11.30 (1H, s, NH).

EXAMPLE 33

(3R)-3-(N-Benzyl)aminomethyl-1-[2-(5-(1,2,4-triazol-4-yl)-1H-indol-3-yl)ethyl]pyrrolidine. 2.5 Hydrogen Oxalate. 0.5 Etherate.

Prepared from (3S)-N-[(R)-1-phenethyl]-3-(hydroxymethyl)pyrrolidine (*J. Med. Chem.*, 1990, 33 (1), 71) and Intermediate 3 using the procedures described for Examples 2 and 7. The 2.5 hydrogen oxalate 0.5 etherate salt was prepared, mp 230°–232° C. (Found: C, 55.88; H, 6.02; N. 12.94. $C_{24}H_{28}N_6.2.5(C_2H_2O_4).0.5(Et_2O)$ requires C, 56.18; H, 5.78; N, 12.68%), m/e 401 (M+1)$^+$. δ (360 MHz, D$_6$-DMSO) 1.70–1.84 (1H, m, CH of CH$_2$), 2.14–2.26 (1H, m, CH of CH$_2$), 2.68–3.60 (11H, m, 5 of CH$_2$ and CH), 4.13 (2H, s, CH$_2$Bn), 7.35–7.54 (8H, m, Ar—H), 7.90 (1H, s, Ar—H), 9.04 (2H, s, Ar—H), 11.30 (1H, s, NH).

EXAMPLE 34

(3S)-3-(4-(Pyridyl)methyl)aminomethl-1-[2-(5-(1,2,4-triazol-4-yl)-1H-indol-3-yl)ethyl]pyrrolidine. 3.0 Hydrogen Oxalate. 0.7 Hydrate. 0.2 Etherate.

a) (3S)-N (H)-3-(4-(Pyridyl)methyl)aminomethyl pyrrolidine

Prepared from (3R)-N-tert-butyloxycarbonyl-3-methylsulphonyloxymethylpyrrolidine and 4-aminomethyl pyridine using the procedures described for Example 5, parts b and c. δ (250 MHz, D$_4$-MeOH) 1.33–1.46 (1H, m, CH of CH$_2$), 1.88–2.04 (1H, m, CH of CH$_2$), 2.21–3.05 (7H, m, 3 of CH$_2$ and CH), 3.83 (2H, s, CH$_2$-pyridyl), 7.42–7.45 (2H, m, Ar—H), 8.45–8.48 (2H, m, Ar—H).

b) (3S)-3-(4-(Pyridyl)methyl)aminomethyl-1-[2-(5-(1,2,4-triazol-4-yl)-1H-indol-3-yl)ethyl]pyrrolidine. 3.0 Hydrogen Oxalate. 0.7 Hydrate. 0.2 Etherate.

Prepared from Intermediate 3 and the preceding N(H)-pyrrolidine using the procedure described for Example 2. The 3.0 hydrogen oxalate 0.7 hydrate 0.2 etherate salt was prepared, mp 213°–215° C. (Found: C, 51.00; H, 5.15; N, 13.73. $C_{23}H_{27}N_7.3.0(C_2H_2O_4).0.7$ $H_2O.0.2(Et_2O)$ requires C, 51.20; H, 5.25; N, 14.03%); m/e 402 (M+1)$^+$. δ (360 MHz, D$_6$-DMSO) 1.70–1.84 (1H, m, CH of CH$_2$), 2.14–2.26 (1H, m, CH of CH$_2$), 2.66–2.80 (1H, m, CH of CH$_2$), 2.94–3.62 (10H, m, 4 of CH$_2$ and 2 of CH), 4.12 (2H, s, CH$_2$-pyridyl), 7.36 (1H, dd, J=1.8 and 8.6 Hz, Ar—H), 7.40 (1H, s, Ar—H), 7.49 (2H, d, J=5.7 Hz, Ar—H), 7.53 (1H, d, J=8.6 Hz, Ar—H), 7.90 (1H, d, J=1.8 Hz, Ar—H), 8.61 (2H, d, J=5.7 Hz, Ar—H), 9.04 (2H, s, Ar—H), 11.30 (1H, s, NH).

EXAMPLE 35

3-(N-Benzyl)aminomethyl-1-[2-(5-(1,2,4-triazol-4-yl)-1H-indol-3-yl)ethyl]azetidine. 2.0 Hydrogen Oxalate. Hemihydrate.

a) N-tert-Butyloxycarbonylazetidin-3-ol

A suspension of azetidin-3-ol hydrochloride (*J. Chem. Soc., Chem. Commun.*, 1968, 93; 18.4 g, 168.1 mmol), (Boc)$_2$O (56 g, 256.6 mmol) and NEt$_3$ (52 ml, 373 mmol), in anhydrous THF (1000 ml) was stirred at room temperature for 16 h. The solvent was removed under vacuum and the residue partitioned between EtOAc (260 ml) and H$_2$O (200 ml). The aqueous was further extracted with EtOAc (3×200 ml). The combined extracted were dried (Na$_2$SO$_4$) and evaporated and the crude product was chromatographed on silica gel eluting with CH$_2$Cl$_2$/MeOH (95:5→90:10) to give the title product (16.9 g, 58%). δ (250 MHz, CDCl$_3$) 1.43 (9H, s, (Me)$_3$), 3.28 (1H, br s, OH), 3.77–3.83 (2H, m, CH$_2$), 4.10–4.17 (2H, m, CH$_2$), 4.50–4.62 (1H, m, CH).

b) N-tert-Butyloxycarbonyl-3-cyanoazetidine

Methane sulphonyl chloride (4.7 ml, 60 mmol) was added slowly to a stirred solution of the preceding alcohol (7.0 g, 40 mmol) in dry pyridine (40 ml) at +20° C. The mixture was stirred for 4 h and the solvent then removed under vacuum. The residue was partitioned between EtOAc/H$_2$O and the aqueous was extracted with EtOAc (×2). The combined extracts were dried (Na$_2$SO$_4$) and evaporated to give the desired mesylate (10.2 g, 100%). A mixture of the mesylate (2.5 g, 10 mmol) and tetra-n-butylammonium cyanide (8.0 g, 30 mmol), in anhydrous toluene (80 ml) was heated at reflux for 64 h. The mixture was cooled to room temperature and partitioned between EtOAc/H$_2$O. The aqueous was extracted with EtOAc (×2), the combined extracts dried (Na$_2$SO$_4$) and evaporated and the residue chromatographed on silica gel eluting with 40% EtOAc/petroleum ether to give the title nitrile (1.15 g, 80%). δ (250 MHz, CDCl$_3$) 1.45 (9H, s (Me)$_3$), 3.33–3.46 (1H, m, CH), 4.11–4.25 (4H, m, 2 of CH$_2$).

c) N-tert-Butyloxycarbonyl-3-formylazetidine

Diisobutyl aluminium hydride (39.8 ml of a 1.0M solution in toluene, 39.8 mmol) was added slowly to a stirred solution of the preceding nitrile (3.63 g, 19.9 mmol), in anhydrous THF (100 ml), at 0° C. The mixture was allowed to warm to room temperature and stir for 2 h. The reaction was quenched by addition of EtOAc (40 ml) and aqueous NH$_4$Cl (40 ml) and partitioned between EtOAc/H$_2$O. The aqueous was further extracted with EtOAc (×3) and the combined extracts were dried (Na$_2$SO$_4$) and evaporated. The residue was purified by chromatography on silica gel eluting with 65% EtOAc/petroleum ether to give the desired aldehyde (1.35 g, 37%). δ (250 MHz, CDCl$_3$) 1.45 (9H, s, (Me)$_3$), 3.30–3.42 (1H, m, CH), 4.05–4.17 (4H, m, 2 of CH$_2$), 9.85 (1H, d, J=2.1 Hz, CHO).

d) N-(1H)-3-(Benzylamino)methyl azetidine

Sodium cyanoborohydride (1.15 g, 18.3 mmol) was added to a solution of benzylamine (1.04 ml, 9.5 mmol) and glacial acetic acid (2.10 ml, 36.7 mmol), in dry methanol (150 ml), at room temperature. The solution was cooled to 0° C. and a solution of the preceding aldehyde (1.35 g, 7.3 mmol), in methanol (50 ml), was added. The mixture was warmed to room temperature and stirred for 20 h. The volatiles were removed in vacuo and the residue partitioned between EtOAc/aq. K$_2$CO$_3$. The aqueous was extracted with EtOAc (×3) and the combined extracts dried and evaporated. The crude product was chromatographed on silica gel eluting with CH$_2$Cl$_2$/MeOH (95:5→92:8) to give the desired N-benzylaminoazetidine (1.5 g, 73%). A mixture of formic acid (99%, 18 ml) and H$_2$O(2 ml) was added to N-tert-butyloxycarbonyl-3-(benzylamino)methyl azetidine (1.5 g, 5.3 mmol) at 0° C. The mixture was warmed to room temperature, stirred for 16 h, and the solvent then removed under vacuum. Saturated aqueous K$_2$CO$_3$ (25 ml) was added to the residue and extracted with $^n$BuOH (5×25 ml). The combined extracts were evaporated and the residue treated with CH$_2$Cl$_2$ (50 ml) and filtered to remove inorganics. The filtrate was dried (Na$_2$SO$_4$) and evaporated to give the title compound (0.512 g, 55%). δ (360 MHz, CDCl$_3$) 2.85 (2H, s, CH$_2$Ph), 3.36–3.39 (1H, m, CH), 3.57–3.72 (4H, m, 2 of CH$_2$), 3.79 (2H, s, CH$_2$), 7.23–7.34 (5H, m, Ar—H).

e) 3-(N-Benzyl)aminomethyl-1-[2-(5-(1,2,4-triazol-4-yl)-1H-indol-3-yl)ethyl]azetidine. 2.0 Hydrogen Oxalate. Hemihydrate.

Methane sulphonyl chloride (360 μL, 4.65 mmol) was added to a stirred suspension of 2-[5-(1,2,4-triazol-4-yl)-1H-indol-3-yl]ethyl alcohol (Intermediate 3; 0.7 g, 3.07 mmol) in dry pyridine (17 ml), at −20° C. The mixture was stirred at this temperature for 0.25 h and then warmed to room temperature and stirred for 16 h. The reaction mixture was quenched by addition of H$_2$O (50 ml) and then extracted with EtOAc (50 ml) and CH$_2$Cl$_2$ (2×50 ml). The combined extracts were dried (Na$_2$SO$_4$) and evaporated and the residue purified by chromatography on silica gel eluting with CH$_2$Cl$_2$/MeOH (9:1) to give the desired mesylate (0.59 g, 63%). The mesylate (0.39 g, 1.2 mmol) was added to a stirred suspension of N-(1H)-3-(benzylamino) methylazetidine (0.269 g, 1.53 mmol), K$_2$CO$_3$ (0.49 g, 3.55 mmol) and NaI (0.18 g, 1.20 mmol), in IPA (40 ml). The mixture was heated at reflux for 18 h, cooled to room temperature and the solvent removed in vacuo. The residue was partitioned between CH$_2$Cl$_2$/H$_2$O and the aqueous further extracted with CH$_2$Cl$_2$ (×3). The combined extracts were dried Na$_2$SO$_4$) and evaporated and the residue chromatographed on silica gel eluting with CH$_2$Cl$_2$/MeOH/NH$_3$ (50:8:1) to give the title product (0.135 g, 27%). The 2.0 hydrogen oxalate hemihydrate salt was prepared, mp 156°–158° C. Found: C, 55.98; H, 5.50; N, 14.40. C$_{23}$H$_{26}$N$_6$.2(C$_2$H$_2$O$_4$) .0.5 H$_2$O requires C, 56.34; H, 5.43; N, 14.60%); m/e 387 (M+1)$^+$. δ (360 MHz, D$_6$-DMSO) 2.80–3.22 (5H, m, 2 of CH$_2$ and CH), 3.36–3.44 (2H, m, CH$_2$), 3.76–3.86 (2H, m, CH$_2$), 3.98–4.08 (4H, m, 2 of CH$_2$), 7.28–7.48 (7H, m, Ar—H), 7.52 (1H, d, J=8.7 Hz, Ar—H), 7.89 (1H, d, J=1.8 Hz, Ar—H), 9.04 (2H, s, Ar—H), 11.31 (1H, s, NH).

EXAMPLE 36

4-Benzyl-4-hydroxy-1-[3-(5-(1,2,4-triazol-4-yl)-1H-indol-3-yl)propyl]piperidine. Hydrogen Oxalate.

a) 3-[5-(1,2,4-Triazol-4-yl)-1H-indol-3-yl]propan-1-ol

A solution of 4'-(1,2,4-triazol-4-yl)phenylhydrazine (25 g, 143 mmol) in dioxan (250 ml) was treated with dihydropyran (24 g, 286 mmol) followed by 1M hydrochloric acid (150 ml) and heated at reflux for 18 h. The reaction mixture was evaporated, treated with toluene then re-evaporated. Inorganic solids were removed by treating the residue with a mixture of methanol and acetonitrile. The mother liquors were purified by column chromatography on silica using dichloromethane/methanol (9:1→4:1) as the eluant. The compound was recrystallised from acetonitrile to afford the title compound as a colourless solid (10.24 g, 30%); mp 205°–207° C. (Found: C, 64.37; H, 5.76; N, 22.83. C$_{13}$H$_{14}$N$_4$O requires C, 64.45; H, 5.82; N, 23.13%.) δ (360 MHz, d$_6$-DMSO) 1.81 (2H, q, J=7 Hz, CH$_2$), 2.75 (2H, t, J=8 Hz, CH$_2$), 3.46 (2H, dt, J$_1$=6, J$_2$=5 Hz, CH$_2$), 4.43 (1H, t, J=5 Hz, OH), 7.26 (1H, d, J=2 Hz, Ar—H), 7.29 (1H, dd, J$_1$=9, J$_2$=2 Hz, Ar—H), 7.47 (1H, d, J=9 Hz, Ar—H), 7.77 (1H, d, J=2 Hz, Ar—H), 9.01 (2H, s, triazole-H), 11.05 (1H, br s, indole NH). MS, CI$^+$, m/z=243 for (M+H)$^+$.

b) 4-Benzyl-4-hydroxy-1[3-(5-(1,2,4-triazol-4-yl)-1H-indol-3-yl)propyl]piperidine. Hydrogen Oxalate.

A fine suspension of the preceding indole (300 mg, 1.24 mmol), stirred under a nitrogen atmosphere in anhydrous tetrahydrofuran (30 ml) was treated with triethylamine (0.35 ml, 2.48 mmol) followed by methanesulphonyl chloride (0.2 ml, 2.48 mmol). The reaction mixture was stirred at ambient temperature for 1.5 h, filtered, then evaporated to dryness. The residue was partitioned between dichloromethane (40 ml) and water (30 ml). The organic layer was separated, washed with water (30 ml), then dried (sodium sulphate) and evaporated to dryness to give the mesylate as a dark yellow semi-solid. The mesylate was dissolved in propan-2-ol (70 ml) then treated with potassium carbonate (514 mg, 3.72 mmol) and 4-benzyl-4-hydroxypiperidine (712 mg, 3.72 mmol) and heated at reflux, with stirring, for 24 hours. The reaction mixture was evaporated to dryness, the residue partitioned between dichloromethane (50 ml) and water (30 ml). The organic layer was separated, washed with water (30 ml), dried (potassium carbonate) then evaporated to give an orange gum which was purified by column chromatography on silica using dichloromethane/methanol/ammonia (20:1:0.1 to 8:1:0.1) to afford the title product free base as a viscous colourless gum (302 mg, 59%). The hydrogen oxalate salt had mp 117°–119° C. (propan-2-ol/ethanol (2:1)). (Found: C, 62.05; H, 6.22; N, 12.17. $C_{25}H_{29}N_5O.1.3$ $(C_2H_2O_4).0.4(CH_3)_2CHOH$ requires C, 62.15; H, 6.30; N, 12.58%.) δ (360 MHz, $d_6$-DMSO) 1.55 (2H, d, J=12 Hz, $CH_2$), 1.74 (2H, dd, $J_1=J_2=12$ Hz, $CH_2$), 1.98–2.05 (2H, m, $CH_2$), 2.72–2.75 (4H, m, $CH_2$-indole and $CH_2$-phenyl), 2.96–3.10 (4H, m, 2×$CH_2$), 3.20–3.32 (2H, m, $CH_2$), 7.20–7.33 (7H, m, Ar—H), 7.49 (1H, d, J=8 Hz, Ar—H), 7.79 (1H, d, J=2 Hz, Ar—H), 9.01 (2H, s, triazole-H), 11.19 (1H, s, indole-NH); MS, $ES^+$, m/e=416 for $(M+H)^+$ of free base.

EXAMPLE 37

3-(N-Benzyl)aminomethyl-1-[3-(5-(1,2,4-triazol-4-yl)-1H-indol-3-yl)propyl]azetidine. 2.0 Hydrogen Oxalate. 0.1 Etherate. Monohydrate.

Prepared from 3-(5-[1,2,4-triazol-4-yl]-1H-indol-3-yl) propan-1-ol and N-(1H)-3-(benzylamino)methyl azetidine as exemplified for Example 35. The 2.0 hydrogen oxalate 0.1 etherate monohydrate salt was prepared, mp 151°–154° C. (Found: C, 56.61; H, 6.06; N, 13.57. $C_{24}H_{28}N_6.2$ $(C_2H_2O_4).0.1(Et_2O).1.0 H_2O$ requires C, 56.29; H, 5.82; N, 13.87%), m/e 401 $(M+1)^+$. δ (360 MHz, $d_6$-DMSO) 1.74–1.88 (2H, m, $CH_2$), 2.75 (2H, t, J=7.5 Hz, $CH_2$), 2.98–3.14 (5H, m, CH and 2 of $CH_2$), 3.77 (2H, t, J=7.5 Hz, $CH_2$), 3.96–4.06 (4H, m, 2 of $CH_2$), 7.31–7.44 (7H, m, Ar—H), 7.50 (1H, d, J=8.5 Hz, Ar—H), 7.80 (1H, d, J=1.6 Hz, Ar—H), 9.02 (2H, s, Ar—H), 11.18 (1H, s, NH).

EXAMPLE 38

4-(Benzylamino)methyl-4-hydroxy-1-[3-[5-(1,2,4-triazol-4-yl)-1H-indol-3-yl]propyl]piperidine a) 1-Benzyl-4-hydroxy-4-(tert-butyloxycarbonylamino) methyl piperidine To a stirred solution of 4-aminomethyl-1-benzyl-4-hydroxy piperidine (*Synth. Commun.*, 1994, 24 (10), 1483) (11 g, 50 mmol) in dichloromethane (300 ml) was added di-tert-butyldicarbonate (11 g, 50 mmol). The solution was stirred overnight at ambient temperature, and then quenched with 10% aqueous potassium carbonate (150 ml). The organic layer was decanted, dried (sodium sulphate) and evaporated under high vacuum. The residue was purified by column chromatography on silica, using dichloromethane/methanol as eluant, to afford the title compound (11.6 g, 70%), mp 109°–112° C. δ (250 MHz, $d_6$-DMSO) 1.16–1.47 (4H, m, 2 of $CH_2$), 1.27 (9H, s, $OC(Me)_3$), 2.09–2.26 (2H, m, $CH_2$), 2.29–2.44 (2H, m, $CH_2$), 2.80 (2H, d, J=6 Hz, $CH_2$), 3.25 (2H, s, $CH_2$), 4.09 (1H, s, OH), 6.49 (1H, t, J=6 Hz, NH), 7.08–7.26 (5H, m, Ar—H). MS, m/e=321 for $(M+H)^+$.

b) 4-Hydroxy-4-(tert-butyloxycarbonylamino)methyl piperidine

To a solution of the foregoing amine (12.5 g, 39 mmol) in methanol (300 ml) was added 10% palladium on carbon (2.5 g) in methanol (20 ml), and ammonium formate (7 g, 11 mmol). The suspension was stirred at ambient temperature for 3 h, then the catalyst filtered off and washed with methanol. The solvent was evaporated in vacuo and the residue triturated with dichloromethane. The resulting solid was dissolved in saturated aqueous potassium carbonate and extracted with dichloromethane (12×). The combined organics were dried (sodium sulphate) and evaporated to give the required product as a solid (7 g, 78%) mp 136°–138° C. δ (360 MHz, $d_6$-DMSO) 1.22–1.48 (4H, m, 2 of $CH_2$), 1.38 (9H, s, $OC(Me)_3$), 2.52–2.62 (2H, m, $CH_2$), 2.62–2.76 (2H, m, $CH_2$), 2.88 (2H, d, J=6 Hz, $CH_2$), 4.12 (1H, s, OH), 6.49 (1H, t, J=6 Hz, NH). MS, m/e=231 for $(M+H)^+$.

c) 4-(tert-Butyloxycarbonylamino)methyl-4-hydroxy-1-[3-(5-(1,2,4-triazol-4-yl)-1H-indol-3-yl]propyl piperidine The title compound was obtained (2.7 g, 60%) from the compounds in steps a and b, as described in Example 36; mp 86° C. (sintered). (Found: C, 60.43; H, 7.79; N, 16.95. $C_{24}H_{34}N_6O_3.H_2O.0.4(CH_3OH)$ requires C, 60.33; H, 7.81; N, 17.31%. δ (250 MHz, $d_6$-DMSO) 1.26–1.56 (4H, m, 2 of $CH_2$), 1.37 (9H, s, $OC(Me)_3$), 1.72–1.90 (2H, m, $CH_2$), 2.14–2.54 (6H, m, 3 of $CH_2$), 2.70 (2H, t, J=7 Hz, $CH_2$), 2.89 (2H, d, J=6 Hz, $CH_2$), 4.15 (1H, s, OH), 6.56 (1H, br t, NH), 7.25–7.32 (2H, m, Ar—H), 7.47 (1H, d, J=8 Hz, Ar—H), 7.77 (1H, d, J=2 Hz, Ar—H), 9.02 (2H, s, Ar—H), 11.08 (1H, s, NH); MS; m/e=455 for $(M+H)^+$.

d) 4-Aminomethyl-4-hydroxy-1-[3-[5-(1,2,4-triazol-4-yl)-1H-indol-3-yl]propyl]piperidine To a solution of the preceding product (2.5 g, 5.5 mmol) in dichloromethane (50 ml) was added trifluoroacetic acid (4.2 ml, 55 mmol). The mixture was stirred overnight at ambient temperature then further trifluoroacetic acid (4.2 ml, 55 mmol) was added and the mixture stirred 1.5 hours at 35° C. The solvent and excess reagent were evaporated in vacuo, and the residue dissolved in a minimum of methanol and washed with diethyl ether (2×10 ml). The methanol was evaporated in vacuo and the residue partitioned between 10% aqueous potassium carbonate and n-butanol. The aqueous was re-extracted with n-butanol (3×). The combined organics were evaporated to dryness and the low melting solid used crude in the next reaction. MS, m/e=355 for $(M+H)^+$. δ (250 MHz, $d_6$-DMSO) 1.32–1.50 (4H, m, 2 of $CH_2$), 1.72–1.88 (2H, m, $CH_2$), 2.17–2.36 (4H, m, 2 of $CH_2$), 2.36–2.55 (2H, m, $CH_2$), 2.34 (2H, s, $CH_2$), 2.70 (2H, t, J=7 Hz, $CH_2$), 7.24–7.32 (2H, m, Ar—H), 7.48 (1H, d, J=8 Hz, Ar—H), 7.78 (1H, d, J=2 Hz, Ar—H), 9.02 (2H, s, Ar—H), 11.21 (1H, s, NH).

e) 4-(Benzylamino)methyl-4-hydroxy-1-[3-[5-(1,2,4-triazol-4-yl)-1H-indol-3-yl]propyl]piperidine To a stirred solution of the foregoing amine (400 mg, 1.1 mmol) in methanol (10 ml) was added benzaldehyde (100 μl, 1 mmol), glacial acetic acid (100 μl, 1.7 mmol) and sodium cyanoborohydride (69 mg, 1.1 mmol). The yellow solution was stirred overnight at room temperature, then 10% aqueous potassium carbonate (5 ml) was added. The mixture was evaporated in vacuo and the residue partitioned between 10% aqueous potassium carabonate and n-butanol. The aqueous was re-extracted once with n-butanol. The combined organics were evaporated to dryness to give a foam which was purified by column chromatography on silica using dichloromethane/methanol/ammonia as eluant, to afford the title compound (200 mg, 41%); mp>60° C. (sintered). (Found: C, 67.55; H, 7.04; N, 17.75. $C_{26}H_{37}N_6O.H_2O$ requires C, 67.51; H, 7.41; N, 18.17%. δ (360 MHz, $d_6$-DMSO) 1.40–1.58 (4H, m, 2 of $CH_2$), 1.74–1.86 (2H, m, $CH_2$), 2.20–2.55 (6H, m, 3 of $CH_2$), 2.39 (2H, s, $CH_2$), 2.70 (2H, t, J=7 Hz, $CH_2$), 3.71 (2H, s, $CH_2$), 4.01 (1H, s, OH), 7.17–7.32 (7H, m, Ar—H), 7.46 (1H, d, J=8 Hz, Ar—H), 7.76 (1H, d, J=2 Hz, Ar—H), 9.00 (2H, s, Ar—H), 11.05 (1H, s, NH). MS, m/e=445 for $(M+H)^+$.

EXAMPLE 39

4-[(N-Benzyl-N-methyl)amino]methyl-4-hydroxy-1-[3-[5-(1,2,4-triazol-4-yl)-1H-indol-3-yl]proyl] piperidine. 2.0 Hydrogen Oxalate.

To a solution of 4-(benzylamino)methyl-4-hydroxy-1-[3-[5-(1,2,4-triazol-4-yl)-1H-indol-3-yl]propyl]piperidine (150 mg, 0.34 mmol) in methanol (8 ml) were added 38% in water formaldehyde (27 μl, 0.37 mmol), glacial acetic acid (85 μl, 1.48 mmol) and sodium cyanoborohydride (23 mg, 0.37 mmol). The solution was stirred overnight at room temperature, the 10% aqueous potassium carbonate (5 ml) was added. The mixture was evaporated to dryness and the residue partitioned between 10% aqueous potassium carbonate and dichloromethane. The aqueous was re-extracted with dichloromethane (3×). The combined organics were dried (sodium sulphate) and evaporated to give the required product (130 mg, 83%). The oxalate salt had mp>132° C. (sintered). (Found: C, 57.17; H, 6.17; N, 12.59. $C_{27}H_{34}N_6O.2(CO_2H)_2.0.75 H_2O$ requires C, 57.09; H, 6.10; N, 12.89%.) δ (360 MHz, $d_6$-DMSO) 1.64–1.86 (4H, m, 2 of $CH_2$), 1.98–2.12 (2H, m, $CH_2$), 2.31 (3H, s, CH3), 2.5 (2H, s, $CH_2$), 2.76 (2H, br t, $CH_2$), 3.0–3.17 (4H, m, 2 of $CH_2$), 3.23–3.40 (2H, m, $CH_2$), 3.68 (2H, s, $CH_2$), 7.20–7.40 (7H, m, Ar—H), 7.50 (1H, d, J=8 Hz, Ar—H), 7.80 (1H, d, J=2 Hz, Ar—H), 9.02 (2H, s, Ar—H), 11.19 (1H, s, NH). MS, m/e=459 for $(M+H)^+$.

EXAMPLE 40

3-(N-Benzyl-N-methyl)aminomethyl-1-[2-(5-(1,2,4-triazol-4-yl)-1H-indol-3-yl)ethyl]azetidine. 1.5 Hydrogen Oxalate. 1.5 Hydrate.

The title compound was prepared from Example 35 and formaldehyde using the general reductive amination procedure. The 1.5 hydrogen oxalate 1.5 hydrate salt was prepared, mp 125°–131° C. (Found: C, 56.78; H, 6.15, N, 14.13. $C_{24}H_{28}N_6.1.5(C_2H_2O_4).1.5 H_2O$ requires C, 56.48; H, 5.94; N, 14.36%, m/e 401 $(M+1)^+$. δ (360 MHz, $d_6$-DMSO) 2.13 (3H, s, Me), 2.71 (2H, d, J=7.6 Hz, C$\underline{H}_2$NMe), 2.90–3.08 (3H, m, CH and $CH_2$), 3.36–3.46 (2H, m, $CH_2$), 3.54 (2H, s, C$\underline{H}_2$Ph), 3.77 (2H, t, J=7.5 Hz, $CH_2$), 4.09 (2H, t, J=7.5 Hz, $CH_2$), 7.22–7.40 (7H, m, Ar—H), 7.53 (1H, d, J=8.7 Hz, Ar—H), 7.88 (1H, s, Ar—H), 9.03 (2H, s, Ar—H), 11.29 (1H, s, NH).

EXAMPLE 41

(3S)-3-(N-[R]-α-Methylbenzyl)aminomethyl-1-[2-(5-(1,2,4-triazol-4-yl)-1H-indol-3-yl)ethyl] pyrrolidine. 2.5 Hydrogen Oxalate. 0.5 Hydrate. 0.2 Diethyl etherate.

a) (3S)-N(H)-3-(N-[R]-α-Methylbenzyl)amino methyl pyrrolidine

Prepared from (3R)-N-tert-butyloxycarbonyl-3-(methylsulphonyloxymethyl)pyrrolidine and (R)-α-methyl benzylamine using the procedures described for Example 5, parts b and c.

b) (3S)-3-(N-[R]-α-Methylbenzyl)aminomethyl-1-[2-(5-1,2,4-triazol-4-yl)-1H-indol-3-yl)ethyl]pyrrolidine. 2.5 Hydrogen Oxalate. 0.5 Hydrate. 0.2 Diethyl etherate.

Methane sulphonyl chloride (1.44 g, 12.6 mmol) was added to a stirred suspension of Intermediate 3 (1.91 g, 8.4 mmol) in anhydrous pyridine (60 ml), at −20° C. The mixture was warmed to room temperature and stirred for 2 h. The pyridine was removed in vacuo, water (100 ml) added and the mixture extracted with $CH_2Cl_2$ (3×75 ml). The combined extracts were dried ($MgSO_4$), the solvent removed under vacuum and the residue chromatographed on silica gel eluting with $MeOH/CH_2Cl_2$ (9:1) to give the desired mesylate (1.50 g, 60%). A mixture of the preceding mesylate (0.308 g, 1.0 mmol), (3S)—N(H)-3-(N—[R]-α-methylbenzyl)aminomethyl pyrrolidine (0.35 g, 1.71 mmol) and $K_2CO_3$ (0.414 g, 3.0 mmol), in IPA (25 ml), was heated at reflux for 4 h. The solvent was removed in vacuo and the residue taken up into $CH_2Cl_2$ and washed with $H_2O$ (×3). The organic was dried ($MgSO_4$) and evaporated and the residue chromatographed on silica gel eluting with $CH_2Cl_2$/$MeOH/NH_3$ (80:8:1) to afford the title product (0.206 g, 50%). The 2.5 hydrogen oxalate 0.5 hydrate 0.2 diethyl etherate salt was prepared, mp 192°–194° C.; (Found: C, 55.61; H, 5.84; N, 12.68. $C_{25}H_{30}N_6.2.5(C_2H_2O_4).0.5 H_2O.0.2(Et_2O)$ requires C, 55.76; H, 5.77; N, 12.67%), m/e 415 $(M+1)^+$.

EXAMPLE 42

(3S)-3-(N-[S]-α-Methylbenzyl)aminomethyl-1-[2-(5-(1,2,4-triazol-4-yl)-1H-indol-3-yl)ethyl] pyrrolidine. 2.5 Hydrogen Oxalate. 0.6 Hydrate. 0.1 Diethyl etherate Prepared from Intermediate 3 as described for Example 41, mp 191°–193° C., (Found: C, 55.31; H, 5.69; N, 12.54. $C_{25} H_{30}N_6.2.5(C_2H_2O_4).0.6 H_2O.0.1(Et_2O)$ requires C, 55.65; H, 5.68; N, 12.81%), m/e 415 $(M+1)^+$.

EXAMPLE 43

(3S)-3-(N-Furan-3-ylmethyl)aminomethyl-1-[2-(5-(1,2,4-triazol-4-yl)-1H-indol-3-yl)ethyl]pyrrolidine. 2.5 Hydrogen Oxalate. 0.65 Diethyl etherate.

a) (3S)-N(H)-3-(N-Furan-3-ylmethyl)aminomethyl pyrrolidine

Prepared from (3R)-N-tert-butyloxycarbonyl-3-(methylsulphonyloxymethyl)pyrrolidine and 3-furanmethylamine using the procedures described for Example 5, parts b and c.

b) (3S)-3-(N-Furan-3-ylmethyl)aminomethyl-1-[2-(5-(1,2,4-triazol-4-yl)-1H-indol-3-yl)ethyl]pyrrolidine. 2.5 Hydrogen Oxalate. 0.65 Diethyl etherate.

Prepared from Intermediate 3 and the preceding pyrrolidine as described for Example 41, (Found: C, 53.81; H, 5.97; N, 12.69. $C_{22}H_{26}NO_6.2.5(C_2H_2O_4).0.65(Et_2O)$ requires C, 53.56; H, 5.69, N, 12.66%). δ (360 MHz, $d_6$-DMSO) 1.70–1.84 (1H, m, CH of $CH_2$), 2.14–2.26 (1H, m, CH of $CH_2$), 2.68–2.80 (1H, m, CH), 2.94–3.24 (5H, m, 2 of $CH_2$ and CH of $CH_2$), 3.26–3.58 (5H, m, 2 of $CH_2$), 4.02 (2H, s, $CH_2$), 6.65 (1H, s, Ar—H), 7.37 (1H, dd, J=2.1 and 8.7 Hz, Ar—H), 7.40 (1H, s, Ar—H), 7.53 (1H, d, J=8.7 Hz, Ar—H), 7.72 (1H, s, Ar—H), 7.81 (1H, s, Ar—H), 7.91 (1H, d, J=2.1 Hz, Ar—H), 9.05 (2H, s, Ar—H), 11.31 (1H, s, NH).

EXAMPLE 44

(3S)-3-(N-Furan-2-ylmethyl)aminomethyl-1-[2-(5-(1,2,4-triazol-4-yl)-1H-indol-3-yl)ethyl]pyrrolidine. 2.5 Hydrogen Oxalate. 0.5 Hydrate.

Prepared as described for Example 43, (Found: C, 51.92; H, 5.28; N, 13.32. $C_{22}H_{26}N_6O.2.5(C_2H_2O_4).0.5 H_2O$ requires C, 51.92; H, 5.16; N, 13.46%). δ (360 MHz, $d_6$-DMSO) 1.70–1.84 (1H, m, CH of $CH_2$), 2.12–2.24 (1H, m, CH of $CH_2$), 2.64–2.78 (1H, m, CH), 2.98 (2H, d, J=6.8 Hz, $CH_2$), 3.04–3.58 (8H, m, 4 of $CH_2$), 4.16 (2H, s, $CH_2$), 6.51 (1H, dd, J=3.2 and 1.6 Hz, Ar—H), 6.57 (1H, d, J=3.2 Hz, Ar—H), 7.36 (1H, dd, J=2.1 and 8.7 Hz, Ar—H), 7.40 (1H, s, Ar—H), 7.52 (1H, d, J=8.7 Hz, Ar—H), 7.74 (1H, d, J=1.6 Hz, Ar—H), 7.90 (1H, s, Ar—H), 9.04 (2H, s, Ar—H), 11.31 (1H, s, NH).

EXAMPLE 45

(3S)-3-[N-(R)-α-(Hydroxymethyl)benzyl] aminomethyl-1-[2-(5-(1,2,4-triazol-4-yl)-1H-indol-3-yl)ethyl]pyrrolidine. 2.4 Hydrogen Oxalate. 0.1 Hydrate.

1. (3S)-N(H)-3-[(R)-α-(Hydroxymethyl)benzyl] aminomethylpyrrolidine a) (3S)-N-tert-Butyloxycarbonyl-3-(R)-α(hydroxymethyl) benzyl]aminomethyloyrrolidine A solution of (R)-(−)-phenylglycinol (2.20 g, 16.1 mmol) and (3R)—N-tert-butyloxycarbonyl-3-methylsulphonyloxymethylpyrrolidine (1.0 g, 3.58 mmol), in toluene (20 ml), was heated at 150° C. for 6 h in sealed pressure tube (Aldrich). The solvent was then removed under vacuum and the residue taken up into ethyl acetate (200 ml) and washed with water (×4). The organic was dried (MgSO$_4$) and evaporated and the crude product chromatographed on silica gel eluting with CH$_2$Cl$_2$/MeOH (97:3) to give the title-α-(hydroxymethyl) benzylaminomethylpyrrolidine (1.0 g, 87%), δ (360 MHz, CDCl$_3$) 1.45 (9H, s, OC(Me)$_3$), 1.52–2.60 (5H, m, CH$_2$ and CH), 2.90–3.76 (7H, m, 3 of CH$_2$ and CH), 7.25–7.39 (5H, m, Ar—H).

b) (3S)-N(H)-3-[(R)-α-Hydroxymethyl)benzyl] aminomethylpyrrolidine

Prepared from the preceding N-Boc pyrrolidine using the procedure described for Example 5, part c, δ (250 MHz, CDCl$_3$) 1.25–1.45 (1H, m, CH of CH$_2$), 1.83–1.97 (1H, m, CH of CH$_2$), 2.14–2.61 (4H, m, 2 of CH$_2$), 2.80–3.09 (3H, m, CH$_2$ and CH), 3.46–3.76 (3H, m, CH$_2$ and CH), 7.25–7.38 (5H, m, Ar—H).

2. (3S)-3-[N-(R)-α-(Hydroxymethyl)benzyl]aminomethyl-1-[2-(5-(1,2,4-triazol-4-yl)-1H-indol-3-yl)ethyl]pyrrolidine. 2.4 Hydrogen Oxalate. 0.1 Hydrate Prepared from Intermediate 3 and the preceding pyrrolidine using the procedure described for Example 41, mp 158° C., (Found: C, 55.11; H, 5.58; N, 12.85. C$_{25}$H$_{30}$N$_6$O.2.4 (C$_2$H$_2$O$_4$).0.1H$_2$O requires C, 55.20; H, 5.44; N, 12.96%), m/e 431 (M+1)$^+$, δ (360 MHz, D$_6$-DMSO) 1.64–1.76 (1H, m, CH of CH$_2$), 2.12–2.24 (1H, m, CH of CH$_2$), 2.64–2.76 (2H, m, CH$_2$), 2.88–2.94 (1H, m, CH), 3.04–3.14 (3H, m, CH$_2$ and CH of CH$_2$), 3.30–3.42 (3H, m, CH$_2$ and CH of CH$_2$), 3.46–3.56 (1H, m, CH of CH$_2$), 3.73 (2H, d, J=5.7 Hz, CH$_2$), 4.12–4.16 (2H, m, CH$_2$), 7.34–7.54 (8H, m, Ar—H), 7.90 (1H, s, Ar—H), 9.04 (2H, s, Ar—H), 11.31 (1H, s, NH).

EXAMPLE 46

(3S)-3-[N-(S)-α-(Hydroxymethyl)benzyl] aminomethyl-1-[2-(5-(1,2,4-triazol-4-yl)-1H-indol-3-yl)ethyl]pyrrolidine. 2.4 Hydrogen Oxalate. 0.1 Hydrate.

a) (3S)-N(H)-3-[(S)-α-(Hydroxymethyl)benzyl] aminomethylpyrrolidine

Prepared from (S)-(+)-phenylglycinol and (3R)-N-tert-butyloxycarbonyl-3-methylsulphonyloxymethylpyrrolidine using the procedures described for Example 45, part 1a.

b) (3S)-3-[N-(S)-α-(Hydroxymethyl)benzyl]aminomethyl-1-[2-(5-(1,2,4-triazol-4-yl)-1H-indol-3-yl)ethyl]pyrrolidine. 2.4 Hydrogen Oxalate. 0.1 Hydrate.

Prepared from Intermediate 3 and the preceding pyrrolidine using the procedure described for Example 41, mp 155° C., (Found: C, 55.35; H, 5.71; N, 12.82. C$_{25}$H$_{30}$N$_6$O.2.4 (C$_2$H$_2$O$_4$).0.1 H$_2$O requires C, 55.20; H, 5.44; N, 12.96%), m/e 431 (M+1)$^+$.

EXAMPLE 47

(3S)-3-[N-Benzyl-N-(2-hydroxy)ethyl]aminomethyl-1-[2-(5-(1,2,4-triazol-4-yl)-1H-indol-3-yl)ethyl] pyrrolidine. 2.4 Hydrogen Oxalate.

a) (3S)-N(H)-3-[N-Benzyl-N-(2-hydroxy)ethyl] aminomethylpyrrolidine

Prepared from N-benzylethanolamine and (3R)-N-tert-butyloxycarbonyl-3-methylsulphonyloxymethylpyrrolidine using the procedures described for Example 5, parts b and c, δ (250 MHz, CDCl$_3$) 1.24–1.60 (2H, m, CH$_2$), 1.82–1.94 (2H, m, CH$_2$), 2.26–3.06 (9H, m, 4 of CH$_2$ and CH), 3.56–3.60 (2H, m, CH$_2$), 7.20–7.36 (5H, m, Ar—H).

b) (3S)-3-[N-Benzyl-N-(2-hydroxy)ethyl]aminomethyl-1-[2-(5-(1,2,4-triazol-4-yl)-1H-indol-3-yl)ethyl]pyrrolidine. 2.4 Hydrogen Oxalate.

Prepared from Intermediate 3 and the preceding pyrrolidine using the procedure described for Example 41, mp 117° C., (Found: C, 55.93; H, 5.39; N, 12.50. C$_{26}$H$_{32}$N$_6$O.2.4 (C$_2$H$_2$O$_4$) requires C, 55.99; H, 5.61; N, 12.72%), m/e 445 (M+1)$^+$, δ (360 MHz, D$_6$-DMSO) 1.56–1.70 (1H, m, CH of CH$_2$), 2.04–2.16 (1H, m, CH of CH$_2$), 2.52–2.68 (7H, m, 3 of CH$_2$ and CH), 3.04–3.12 (2H, m, CH$_2$), 3.28–3.52 (6H, m, 3 of CH$_2$), 3.68 (2H, ABq, J=14 Hz, CH$_2$), 7.20–7.34 (5H, m, Ar—H), 7.38 (1H, dd, J=8.6 and 1.5 Hz, Ar—H), 7.53 (1H, d, J=8.6 Hz, Ar—H), 7.89 (1H, d, J=1.5 Hz, Ar—H), 9.03 (2H, s, Ar—H), 11.31 (1H, s, NH).

EXAMPLE 48

(3S)-3-(N-Phenethyl)aminomethyl-1-[2-(5-(1,2,4-triazol-4-yl)-1H-indol-3-yl)ethyl]pyrrolidine. 2.5 Hydrogen Oxalate. Hemihydrate.

a) (3S)-N-(H)-3-(N-Phenethyl)aminomethylpyrrolidine

Prepared from phenethylamine and (3R)-N-tert-butyloxycarbonyl-3-methylsulphonyloxymethylpyrrolidine using the procedures described for Example 5, parts b and c.

b) (3S)-3-(N-Phenethyl)aminomethyl-1-[2-(5-(1,2,4-triazol-4-yl)-1H-indol-3-yl)ethyl]pyrrolidine. 2.5 Hydrogen Oxalate. Hemihydrate.

Prepared from the preceding pyrrolidine and Intermediate 3 using the procedure described for Example 41, mp 189°–190° C., (Found: C, 55.59; H, 5.55; N, 12.85. C$_{25}$H$_{30}$N$_6$.2.5(C$_2$H$_2$O$_4$).H$_2$O requires C, 55.55; H, 5.59; N, 12.96%), m/e 415 (M+1)$^+$, δ (360 MHz, D$_6$-DMSO) 1.74–1.86 (1H, m, CH of CH$_2$), 2.14–2.26 (1H, m, CH of CH$_2$), 2.68–3.60 (15H, m, CH and 7 of CH$_2$), 7.22–7.40 (7H, m, Ar—H), 7.53 (1H, d, J=8.6 Hz, Ar—H), 7.92 (1H, d, J=1.5 Hz, Ar—H), 9.05 (2H, s, Ar—H), 11.30 (1H, s, NH).

EXAMPLE 49

(3S)-3-(N-Phenethyl-N-methyl)aminomethyl-1-[2-(5-(1,2,4-triazol-4-yl)-1H-indol-3-yl)ethyl] pyrrolidine. 2.5 Hydrogen Oxalate. 0.1 Diethyl etherate.

a) (3S)-N(H)-3-(N-Phenethyl-N-methyl) aminomethylpyrrolidine

Prepared from N-phenethyl-N-methylamine and (3R)-N-tert-butyloxycarbonyl-3-methylsulphonyloxymethyl pyrrolidine using the procedures described for Example 5, parts b and c.

b) (3S)-3-(N-Phenethyl-N-methyl)aminomethyl-1-[2-(5-(1,2,4-triazol-4-yl)-1H-indol-3-yl)ethyl]pyrrolidine. 2.5 Hydrogen Oxalate. 0.1 Diethyl etherate.

Prepared from the preceding pyrrolidine and Intermediate 3 using the procedure described for Example 41, mp 168°–170° C., (Found: C, 57.02; H, 5.71; N, 12.78. C$_{26}$H$_{32}$N$_6$.2.5(C$_2$H$_2$O$_4$).0.1(Diethyl ether) requires C, 57.05; H, 5.79; N, 12.71%), m/e 429 (M+1)$^+$.

EXAMPLE 50

(3S)-3-(N-α-Dimethylbenzyl)aminomethyl-1-[2-(5-(1,2,4-triazol-4-yl)-1H-indol-3-yl)ethyl]pyrrolidine. 2.45 Hydrogen Oxalate. 0.1 Diethyl etherate.

Prepared from Intermediate 3 and (3R)-N-tert-butyloxycarbonyl-3-methylsulphonyloxymethylpyrrolidine using the general procedures, mp 172°–174° C., (Found: C, 57.15; H, 5.94; N, 13.14. $C_{26}N_{32}N_6.2.45(C_2H_2O_4).0.1$ (Diethyl ether) requires C, 57.26; H, 5.82; N, 12.80%), m/e 429 (M+1)$^+$, δ (360 MHz, D$_6$-DMSO) 1.61 (6H, s, 2 of CH$_3$), 1.61–1.70 (1H, m, CH of CH$_2$), 2.10–2.21 (1H, m, CH of CH$_2$), 2.54–2.62 (3H, m, CH$_2$ and CH), 2.96–3.48 (8H, m, 4 of CH$_2$), 7.30–7.57 (8H, m, Ar—H), 7.84 (1H, d, J=1.8 Hz, Ar—H), 8.92 (2H, s, Ar—H), 11.12 (1H, s, NH).

EXAMPLE 51

(3S)-3-(N-[S]-α-Methylbenzyl)aminomethyl-1-[2-(5-(1,2,4-triazol-1-yl)-1H-indol-3-yl)ethyl] pyrrolidine. 2.5 Hydrogen Oxalate. 0.2 Hydrate.

a) 2-[5-(1,2,4-Triazol-1-yl)-1H-indol-3-yl]ethyl alcohol

Prepared from 4-(1,2,4-triazol-1-yl)aniline (EP497512) as described for Intermediate 3, δ (250 MHz, D$_6$-DMSO) 2.89 (2H, t, J=7.2 Hz, CH$_2$), 3.64–3.74 (2H, m, CH$_2$), 4.67 (1H, t, J=5.3 Hz, OH), 7.29 (1H, d, J=2.3 Hz, Ar—H), 7.47 (1H, dd, J=8.7 and 1.5 Hz, Ar—H), 7.53 (1H, dd, J=8.7 and 2.3 Hz, Ar—H), 7.95 (1H, d, J=1.9 Hz, Ar—H), 8.19 (1H, s, Ar—H), 9.19 (1H, s, Ar—H), 11.10 (1H, s, NH).

b) (3S)-3-(N-[S]-α-Methylbenzyl)aninomethyl-1-[2-(5-(1,2,4-triazol-1-yl)-1H-indol-3-yl)ethyl]pyrrolidine. 2.5 Hydrogen Oxalate. 0.2 Hydrate Prepared from 2-[5-(1,2,4-triazol-1-yl)-1H-indol-3-yl] ethyl alcohol and (3S)-N(H)-3-(N-[S]-α-methylbenzyl) aminomethyl pyrrolidine as described for Example 41, mp 203°–204° C., (Found: C, 55.95; H, 5.51; N, 13.11. $C_{25}H_{30}N_6.2.5(C_2H_2O_4).0.2\ H_2O$ requires C, 56.02; H, 5.55; N, 13.07%), m/e 415 (M+1)$^+$, δ (360 MHz, D$_6$-DMSO) 1.54 (3H, d, J=6.7 Hz, CH$_3$), 1.60–1.74 (1H, m, CH of CH$_2$), 2.11–2.22 (1H, m, CH of CH$_2$), 2.60–3.56 (10H, m, 4 of CH$_2$ and 2 of CH of CH$_2$), 4.24–4.30 (2H, m, CH$_2$), 7.34–7.56 (8H, m, Ar—H), 8.03 (1H, s, Ar—H), 8.19 (1H, s, Ar—H), 9.19 (1H, s, Ar—H), 11.28 (1H, s, NH).

EXAMPLE 52

(3S)-3-[N-[R]-α(Hydroxymethyl)benzyl]aminomethyl-1-[2-(5-(1,2,4-triazol-1-yl)-1H-indol-3-yl)ethyl]pyrrolidine. 2.0 Hydrogen Oxalate. 0.3 Hydrate.

Prepared from 2-[5-(1,2,4-triazol-1-yl)-1H-indol-3-yl] ethyl alcohol and (3S)-N(H)-3-[(R)-α-(hydroxymethyl) benzyl]aminomethyl pyrrolidine using the procedures described for Example 41, mp 173°–174° C., (Found: C, 56.57; H, 5.77; N, 13.57. $C_{25}H_{30}N_6O.2.0(C_2H_2O_4).0.3\ H_2O$ requires C, 56.54; H, 5.66; N, 13.64%), m/e 431 (M+1)$^+$, δ (360 MHz, D$_6$-DMSO) 1.62–1.76 (1H, m, CH of CH$_2$), 2.10–2.22 (1H, m, CH of CH$_2$), 2.56–2.72 (2H, m, CH and CH of CH$_2$), 2.80–2.90 (1H, m, CH of CH$_2$), 3.02–3.52 (7H, m, 3 of CH$_2$ and CH), 3.64–3.70 (2H, m, CH$_2$), 4.02–4.06 (2H, m, CH$_2$), 7.32–7.57 (8H, m, Ar—H), 8.03 (1H, s, Ar—H), 8.20 (1H, s, Ar—H), 9.18 (1H, s, Ar—H), 11.28 (1H, s, NH).

EXAMPLE 53

(3S)-3-(N-Benzyl)aminomethyl-1-[2-(5-(1,2,4-triazol-1-ylmethyl)-1H-indol-3-yl)ethyl]pyrrolidine. 2.4 Hydrogen Oxalate.

a) 2-[5-(1,2,4-Triazol-1-ylmethyl)-1H-indol-3-yl]ethyl alcohol

Prepared from 4-(1,2,4-triazol-1-ylmethyl)aniline (EP497512) as described for Intermediate 3, δ (250 MHz, D$_4$-MeOH) 2.96 (2H, t, J=7.2 Hz, CH$_2$), 3.80 (2H, t, J=7.2 Hz, CH$_2$), 5.46 (2H, s, CH$_2$), 7.08 (1H, dd, J=1.7 and 8.6 Hz, Ar—H), 7.11 (1H, s, Ar—H), 7.33 (1H, d, J=8.6 Hz, Ar—H), 7.58–7.59 (1H, d, J=1.7 Hz, Ar—H), 7.97 (1H, s, Ar—H), 8.44 (1H, s, Ar—H).

b) (3S)-3-(N-Benzyl)aminomethyl-1-[2-(5-(1,2,4-triazol-1-ylmethyl)-1H-indol-3-yl)ethyl]pyrrolidine. 2.4 Hydrogen Oxalate.

Prepared from 2-[5-(1,2,4-triazol-1-ylmethyl)-1H-indol-3-yl]ethyl alcohol and (3S)-N(H)-3-N-(benzyl)aminomethyl pyrrolidine as described for Example 41, mp 154°–156° C., (Found: C, 56.92; H, 5.49; N, 13.40. $C_{25}H_{30}N_6.2.4(C_2H_2O_4)$ requires C, 56.76; H, 5.56; N, 13.33%), m/e 415 (M+1)$^+$, δ (360 MHz, D$_6$-DMSO) 1.72–1.86 (1H, m, CH of CH$_2$), 2.15–2.28 (1H, m, CH of CH$_2$), 2.70–2.84 (1H, m, CH), 3.00–3.62 (10H, m, 5 of CH$_2$), 4.16 (2H, s, CH$_2$), 5.44 (2H, s, CH$_2$), 7.07 (1H, d, J=8.6 Hz, Ar—H), 7.27 (1H, s, Ar—H), 7.35 (1H, d, J=8.6 Hz, Ar—H), 7.40–7.54 (5H, m, Ar—H), 7.63 (1H, s, Ar—H), 7.95 (1H, s, Ar—H), 8.64 (1H, s, Ar—H), 11.07 (1H, s, NH).

Examples 54 and 55 were prepared from 2-[5-(1,2,4-triazol-1-ylmethyl)-1H-indol-3-yl]ethyl alcohol and the appropriate pyrrolidine using the standard procedures.

EXAMPLE 54

(3S)-3-(N-[S]-α-Methylbenzyl)aminomethyl-1-[2-(5-(1,2,4-triazol-1-ylmethyl)-1H-indol-3-yl)ethyl] pyrrolidine. 2.35 Hydrogen Oxalate. 0.1 Diethyl etherate.

mp: 195°–197° C., (Found: C, 56.99; H, 5.65; N, 13.16. $C_{26}H_{32}N_6.2.35(C_2H_2O_4).0.3(H_2O).0.1$(diethyl ether) requires C, 57.21; H, 5.91; N, 12.87%), m/e 429 (M+1)$^+$.

EXAMPLE 55

(3S)-3-(N-[R]-α-(Hydroxymethyl)benzyl] aminomethyl-1-[2-(5-(1,2,4-triazol-1-ylmethyl)-1H-indol-3-yl)ethyl]pyrrolidine. 2.25 Hydrogen Oxalate.

mp: 102°–105° C., (Found: C, 56.60; H, 5.79; N, 13.02. $C_{26}H_{32}N_6O.2.25(C_2H_2O_4)$ requires C, 56.61; H, 5.69; N, 12.99%), m/e 445 (M+1)$^+$.

EXAMPLE 56

(3S)-3-(N-Benzyl-N-methyl)aminomethyl-1-[2-(5-(imidazol-1-yl)-1H-indol-3-yl)ethyl]pyrrolidine. 2.0 Hydrogen Oxalate. Hemihydrate.

a) 2-[5-(Imidazol-1-yl)-1H-indol-3-yl]ethyl alcohol

Prepared from 4-(imidazol-1-yl)aniline (EP497512) as described for Intermediate 3, δ (360 MHz, D$_6$-DMSO) 2.87 (2H, t, J=7.2 Hz, CH$_2$), 3.64–3.70 (1H, m, C$\underline{H}_2$—OH), 4.61 (1H, t, J=5.3 Hz, OH), 7.08 (1H, s, Ar—H), 7.25–7.27 (2H, m, Ar—H), 7.44 (1H, d, J=8.8 Hz, Ar—H), 7.64 (1H, d, J=2.5 Hz, Ar—H), 7.70 (1H, d, J=2.1 Hz, Ar—H), 8.11 (1H, s, Ar—H), 11.00 (1H, s, NH), m/e 228 (M+1)$^+$.

b) (3S)-3-(N-Benzyl-N-methyl)aminomethyl-1-[2-(5-(imidazol-1-yl)-1H-indol-3-yl)ethyl]pyrrolidine. 2.0 Hydrogen Oxalate. Hemihydrate.

To a solution of (3S)-N(H)-3-(N-methyl-N-benzyl) aminomethylpyrrolidine (0.21 g, 1.02 mmol) in anhydrous DMF (3 ml) was added K$_2$CO$_3$ (0.114 g, 0.83 mmol) and, dropwise, a solution of the mesylate of the preceding alcohol (0.168 g, 0.55 mmol) in DMF (7 ml). The mixture was heated at 50° C. for 1 h and then at 70° C. for 2 h. After cooling, the solvent was removed under vacuum and the residue partitioned between CH$_2$Cl$_2$ (3×25 ml) and water (25 ml). The combined organics were dried (Na$_2$SO$_4$) and evaporated and the residue chromatographed on silica gel eluting with CH$_2$Cl$_2$/MeOH/NH$_3$ (90:10:1) to give the desired product (0.134 g, 59% from the alcohol). The 2.0 hydrogen oxalate hemihydrate salt was prepared, mp 92° C. (dec.), (Found: C, 59.53; H, 6.12; N, 11.83. C$_{26}$H$_{31}$N$_5$.2 (C$_2$H$_2$O$_4$).0.5 H$_2$O requires C, 59.79; H, 6.02; N, 11.62%), m/e 414 (M+1)$^+$, δ (360 MHz, D$_6$-DMSO) 1.60–1.74 (1H, m, CH of CH$_2$), 2.09–2.20 (1H, m, CH of CH$_2$), 2.24 (3H, s, CH$_3$), 2.54–3.58 (11H, m, 5 of CH$_2$ and CH), 3.66 (2H, ABq, J=13.3 Hz, CH$_2$), 7.16 (1H, s, Ar—H), 7.26–7.39 (7H, m, Ar—H), 7.51 (1H, d, J=8.5 Hz, Ar—H), 7.73 (1H, d, J=1.2 Hz, Ar—H), 7.85 (1H, d, J=2.0 Hz, Ar—H), 8.26 (1H, s, Ar—H), 11.24 (1H, s, NH).

EXAMPLE 57

(3S)-3-(N-Benzyl-N-methyl)aminomethyl-1-[2-(5-(1,2,4-triazol-1-ylmethyl)-1H-indol-3-yl)ethyl] pyrrolidine. 2.5 Hydrogen Oxalate.

Prepared from 2-[5-(1,2,4-triazol-1-ylmethyl)-1H-indol-3-yl]ethyl alcohol and (3S)-N(H)-3-(N-methyl-N-benzyl) aminomethylpyrrolidine using the procedure described for Example 41. The 2.0 hydrogen oxalate hemihydrate salt was prepared, mp 154°–155° C., (Found: C, 57.10; H, 5.95; N, 12.66. C$_{26}$H$_{32}$N$_6$.2.5(C$_2$H$_2$O$_4$) requires C, 56.96; H, 5.70; N, 12.85%), m/e 429 (M+1)$^+$, δ (360 MHz, D$_6$-DMSO) 1.60–1.72 (1H, m, CH of CH$_2$), 2.08–2.20 (1H, m, CH of CH$_2$), 2.26 (3H, s, CH$_3$), 2.52–3.60 (11H, m, 5 of CH$_2$ and CH), 3.69 (2H, ABq, J=13.4 Hz, CH$_2$), 5.42 (2H, s, CH$_2$), 7.05 (1H, d, J=8.5 Hz, Ar—H), 7.25–7.35 (7H, m Ar—H), 7.60 (1H, s, Ar—H), 7.92 (1H, s, Ar—H), 8.58 (1H, s, Ar—H), 11.02 (1H, s NH).

EXAMPLE 58

(3R)-3-(N-Methyl-N-[S]-α-methylbenzyl) aminomethyl-1-[2-(5-(1,2,4-triazol-1-ylmethyl)-1H-indol-3-yl)ethyl]pyrrolidine. 2.0 Hydrogen Oxalate. 0.17 Diethyl etherate.

a) (3R)-N(H)-3-(N-Methyl-N-[S]-α-methylbenzyl) aminomethylpyrrolidine

Glacial acetic acid (0.9 ml, 15.7 mmol) and sodium cyanoborohydride (0.495 g, 7.88 mmol) were added successively to a stirred solution of (3S)-N-tert-butyloxycarbonyl-3-(N-[S]-α-methylbenzyl)aminomethylpyrrolidine (1.92 g, 6.31 mmol) in methanol (150 ml), at 0° C. A solution of formaldehyde (0.623 g of a 38% w/v solution, 7.88 mmol), in methanol (50 ml), was added dropwise over 0.1 h. The mixture was stirred at 0° C. for 4.5 h and then at +25° C. for 1.25 h before adding saturated K$_2$CO$_3$ solution (25 ml) and removing the solvent under vacuum. Ethyl acetate (100 ml) was added to the residue and washed with water (×1), saturated K$_2$CO$_3$ solution (×1) and brine (×1), dried (MgSO$_4$) and evaporated. The residue was chromatographed on silica gel eluting with CH$_2$Cl$_2$/MeOH (95:5) to give (3R)-N-tert-butyloxycarbonyl-3-(N-[S]-α-methylbenzyl-N-methyl)aminomethylpyrrolidine (2.02 g, 100%).

A solution of the preceding carbamate (2.01 g, 6.32 mmol) in 90% HCO$_2$H (40 ml) was stirred at 0° C. for 2.75 h and then at +25° C. for 16 h. The reaction was quenched by the addition of methanol and the solvents removed under vacuum. The residue was azeotroped with ethanol and then taken up into a small volume of water and basified with saturated K$_2$CO$_3$ solution. The aqueous was extracted with n-butanol (2×50 ml), the combined extracts evaporated in vacuo and the inorganics removed by trituration with CH$_2$Cl$_2$ and filtering. The filtrate was dried (MgSO$_4$) and evaporated and the residue chromatographed on silica gel, eluting with CH$_2$Cl$_2$/MeOH/NH$_3$ (15:8:1) to give the title pyrrolidine (1.25 g, 89%), δ (250 MHz, CDCl$_3$) 1.34 (3H, d, J=6.8 Hz, CH$_3$), 1.52–1.67 (1H, m, CH of CH$_2$), 1.96–2.10 (1H, m, CH of CH$_2$), 2.17 (3H, s, CH3), 2.25–2.52 (3H, m, CH of CH$_2$), 2.72 (1H, dd, J=11.3 and 7.3 Hz, CH of CH$_2$), 3.10 (2H, dd, J=8.0 and 6.6 Hz, CH of CH$_2$), 3.25 (1H; dd, J=11.3 and 7.3 Hz, CH of CH$_2$), 3.57 (1H, q, J=6.8 Hz, CH), 5.97 (1H, br s, NH), 7.20–7.34 (5H, m, Ar—H).

b) (3R)-3-(N-Methyl-N-[S]-α-methylbenzyl)aminomethyl-1-[2-5-(1,2,4-triazol-1-ylmethyl)-1H-indol-3-yl)ethyl] pyrrolidine. 2.0 Hydrogen Oxalate. 0.17 Diethyl etherate.

The title compound was prepared from the preceding pyrrolidine and the mesylate of 2-[5-(1,2,4-triazol-1-ylmethyl)-1H-indol-3-yl]ethyl alcohol using the standard coupling procedure. The 2.0 hydrogen oxalate 0.17 diethyl etherate salt was prepared, mp 148°–149° C., (Found: C, 59.82; H, 6.58; N, 13.32. C$_{27}$H$_{34}$N$_6$.2.0(C$_2$H$_2$O$_4$).0.17 (diethyl ether) requires C, 59.90; H, 6.30; N, 13.23%), m/e 443 (M+1)$^+$, δ (360 MHz, D$_6$-DMSO) 1.34 (3H, d, J=6.9 Hz, CH$_3$), 1.60–1.71 (1H, m, CH of CH$_2$), 2.06–2.16 (1H, m, CH of CH$_2$), 2.17 (3H, s, CH$_3$), 2.40–2.66 (3H, m, CH of CH$_2$), 2.92–3.09 (3H, m CH$_2$ and CH of CH$_2$), 3.29–3.50 (5H, m, 2 of CH$_2$ and CH of CH$_2$), 3.73 (1H, q, J=6.9 Hz, CH), 5.45 (2H, s, CH$_2$), 7.09 (1H, d, J=8.4 Hz, Ar—H), 7.22–7.38 (7H, m, Ar—H), 7.59 (1H, s, Ar—H), 7.91 (1H, s, Ar—H), 8.51 (1H, s, Ar—H), 10.87 (1H, s, NH).

EXAMPLE 59

(3R)-3-(N-Methyl-N-[R]-α-hydroxymethylbenzyl) aminomethyl-1-[2-(5-(1,2,4-triazol-1-ylmethyl)-1H-indol-3-yl)ethyl]pyrrolidine. 1.9 Hydrogen Oxalate. Hemihydrate. 0.05 Diethyl etherate.

The title compound was prepared from (3R)-N(H)-3-(N-methyl-N-[R]-α-hydroxymethylbenzyl) aminomethylpyrrolidine and the mesylate of 2-[5-(1,2,4-triazol-1-ylmethyl)-1H-indol-3-yl)ethyl alcohol using the general procedure. The 1.9 hydrogen oxalate hemihydrate 0.05 diethyl etherate salt was prepared, mp 154°–155° C., (Found: C, 57.26; H, 6.26; N, 12.75. C$_{27}$H$_{34}$N$_6$.O.1.9 (C$_2$H$_2$O$_4$).0.5 H$_2$O.0.05(diethyl ether) requires C, 57.25; H, 6.09; N, 12.92%), m/e 459 (M+1)$^+$, δ (360 MHz, D$_6$-DMSO) 1.63–1.72 (1H, m, CH of CH$_2$), 2.04–2.14 (1H, m, CH of CH$_2$), 2.19 (3H, s, CH$_3$), 2.51–2.68 (3H, m, CH and CH$_2$), 3.00–3.10 (3H, m, CH of CH$_2$ and CH$_2$), 3.30–3.50 (5H, 2 of CH$_2$ and CH of CH$_2$), 3.63–3.89 (3H, m, CH and CH$_2$), 5.43 (2H, s, CH$_2$), 7.07 (1H, d, J=8.3 Hz, Ar—H), 7.24–7.36 (7H, m, Ar—H), 7.58 (1H, s, Ar—H), 7.89 (1H, s, Ar—H), 8.50 (1H, s, Ar—H), 10.86 (1H, s, NH).

EXAMPLE 60

(3R)-3-(N-Methyl-N-[S]-α-methylcyclohexylmethyl)aminomethyl-1-[2-(5-(1,2,4-triazol-1-ylmethyl)-1H-indol-3-yl)ethyl] pyrrolidine. 2.25 Hydrogen Oxalate. 0.17 Diethyl etherate.

Prepared from 2-[5-(1,2,4-triazol-1-ylmethyl)-1H-indol-3-yl)ethyl alcohol and (3R)-N(H)-3-(N-methyl-N-[S]-α-methylcyclohexylmethyl) aminomethylpyrrolidine using previously described procedures. The 2.25 hydrogen oxalate 0.17 diethyl etherate salt was prepared, mp 191°–192° C., Found: C, 58.13; H, 7.40; N, 12.80. C$_{27}$H$_{40}$N$_6$.2.25 (C$_2$H$_2$O$_4$).0.17(diethyl ether) requires C, 58.22; H, 7.02; N, 12.66%), m/e 449 (M+1)$^+$, δ (360 MHz, D$_6$-DMSO)

0.82–0.93 (2H, m, CH$_2$), 0.91 (3H, d, J=6.6 Hz, CH$_3$), 1.09–2.40 (4H, m, 2 of CH$_2$), 1.56–1.74 (5H, m, 2 of CH$_2$ and CH of CH$_2$), 1.88–1.96 (1H, m, CH), 2.06–2.16 (1H, m, CH of CH$_2$), 2.21 (3H, s, CH$_3$), 2.36–2.44 (1H, m, CH), 2.48–2.62 (3H, m, CH$_2$ and CH of CH$_2$), 3.00–3.10 (3H, m, CH$_2$ and CH of CH$_2$), 3.28–3.48 (5H, m, 2 of CH$_2$ and CH), 5.43 (2H, s, CH$_2$), 7.07 (1H, dd, J=1.6 and 8.4 Hz, Ar—H), 7.24 (1H, d, J=1.6 Hz, Ar—H), 7.35 (1H, d, J=8.4 Hz, Ar—H), 7.58 (1H, s, Ar—H), 7.89 (1H, s, Ar—H), 8.49 (1H, s, Ar—H), 10.85 (1H, s, NH).

EXAMPLE 61

(3R)-3-(3-[R]-Hydroxy-2-[R]-phenylpiperidin-1-yl) methyl-1-[2-(5-(1,2,4-triazol-1-ylmethyl)-1H-indol-3-yl)ethyl]pyrroliodine. 2.35 Hydrogen Oxalate.

a) (3R)-N(H)-3-(3-[R]-Hydroxy-2-[R]-phenylpiperidin-1-yl) methylhyrolidine

A mixture of (3R)-N-tert-butyloxycarbonyl-3-(methylsulphonyloxymethyl)pyrrolidine (1.0 g, 3.58 mmol) and N(H)-3-[R]-hydroxy-2-[R]-phenylpiperidine (3.17 g, 17.92 mmol), in toluene (12 ml), was heated in a sealed tube at 150° C. for 8 h. The solvent was removed in vacuo and the residue partitioned between CH$_2$Cl$_2$ (2×150 ml) and water (30 ml). The extracts were dried (Na$_2$SO$_4$) and evaporated and the residue chromatographed on silica gel eluting with CH$_2$Cl$_2$/MeOH (95:5) to give the desired 3-(piperidinylmethyl)pyrrolidine (1.09 g, 85%). To this material was added formic acid (20 ml) and the solution stirred at +25° C. for 16 h. The formic acid was removed under reduced pressure and the residue basified with saturated K$_2$CO$_3$ solution. The aqueous was extracted with CH$_2$Cl$_2$ (8×100 ml), the combined extracts dried (Na$_2$SO$_4$) and evaporated. The crude product was chromatographed on silica gel eluting with CH$_2$Cl$_2$/MeOH/NH$_3$ (30:8:1) to give the title-pyrrolidine (0.79 g, 100%).

b) (3R)-3-(3-[R]-Hydroxy-2-[R]-phenylpiperidin-1-yl) methyl-1-[2-(5-(1,2,4-triazol-1-ylmethyl)-1H-indol-3-yl) ethyl]pyrrolidine. 2.35 Hydrogen Oxalate.

Prepared from the preceding pyrrolidine and the mesylate of 2-[5-(1,2,4-triazol-1-ylmethyl)-1H-indol-3-yl]ethyl alcohol using the standard coupling procedure. The 2.35 hydrogen oxalate salt was prepared, mp 118° C., (Found: C, 58.24; H, 6.22; N, 11.82. C$_{29}$H$_{36}$N$_6$O.2.35(C$_2$H$_2$O$_4$) requires C, 58.14; H, 5.89; N, 12.07%), m/e 485 (M+1)$^+$, δ (360 MHz, D$_6$-DMSO) 1.52–3.72 (21H, m, 3 of CH and 9 of CH$_2$), 5.42 (2H, s, CH$_2$), 7.06 (1H, dd, J=1.5 and 8.6 Hz, Ar—H), 7.21 (1H, d, J=1.5 Hz, Ar—H), 7.25–7.43 (6H, m, Ar—H), 7.57 (1H, s, Ar—H), 7.93 (1H, s, Ar—H), 8.58 (1H, s, Ar—H), 11.03 (1H, s, NH).

EXAMPLE 62

(3R)-3-(3-[R]-Hydroxy-2-[R]-phenylpiperidin-1-yl) methyl-1-[2-(5-(1,2,4-triazol-1-yl)-1H-indol-3-yl) ethyl]pyrrolidine. Sesquioxalate.

Prepared from (3R)-N(H)-3-(3-[R]-hydroxy-2-[R]-phenylpiperidin-1-yl)methylpyrrolidine and 2-[5-(1,2,4-triazol-1-yl)-1H-indol-3-yl]ethyl alcohol using the general procedure. The sesquioxalate salt was prepared, mp 192°–193° C., (Found: C, 64.49; H, 6.30; N, 13.83. C$_{28}$H$_{34}$N$_6$O.1.5(C$_2$H$_2$O$_4$) requires C, 61.48; H, 6.16; N, 13.87%), m/e 471 (M+1)$^+$, δ (250 MHz, D$_6$-DMSO) 1.40–3.60 (21H, 3 of CH and 9 of CH$_2$), 7.16–7.60 (8H, m, Ar—H), 7.99 (1H, s, Ar—H), 8.20 (1H, s, Ar—H), 9.17 (1H, s, Ar—H), 11.27 (1H, s, NH).

EXAMPLE 63

4-Hydroxy-4-(phenylsulfinyl)methyl-1-{3-[5-(1,2,4-triazol-4-yl)-1H-indol-3-yl]propyl}piperidine. Hydrogen Oxalate.

To a stirred solution of methyl phenyl sulphoxide (0.1268 g, 0.904 mmol), in THF (2 ml), cooled under nitrogen to −78° C., was added dropwise, over 5 minutes, a 1.0M solution of lithium bis(trimethylsilyl)amide in THF (0.90 ml, 0.900 mmol), keeping the temperature below −77° C. The mixture was then stirred at −78° C. for 30 minutes before adding by cannula, over 10 minutes, a stirred mixture of 4-keto-1-{3-[5-(1,2,4-triazol-4-yl)-1H-indol-3-yl]propyl}piperidine (0.1324 g, 0.409 mmol) in THF (2 ml), cooled under nitrogen to −78° C. The reaction mixture was stirred at <−70° C. for 2.25 h, then allowed to warm to +10° C. over 10 minutes before quenching with saturated NH$_4$Cl solution (1 ml). The mixture was then partitioned between ethyl acetate (25 ml) and saturated K$_2$CO$_3$ solution (20 ml). The aqueous layer was reextracted with more ethyl acetate (3×25 ml) and the combined organic extracts were dried (Na$_2$SO$_4$) and evaporated in vacuo. The residue was purified by flash chromatography (silica gel, CH$_2$Cl$_2$/MeOH/NH$_3$, 90:10:1), then alumina, 3–5% MeOH/CH$_2$Cl$_2$, then silica gel, CH$_2$Cl$_2$/MeOH/NH$_3$, 92:8:0.8) to give 30.9 mg (16%) of the title compound free base as a colourless oil. The oxalate salt was prepared in methanol-diethyl ether; mp 124° C. (softens). (Found: C, 57.53; H, 5.84, N, 11.92. C$_{25}$H$_{29}$N$_5$O$_2$S.(C$_2$H$_2$O$_4$).0.18(C$_4$H$_{10}$O).0.6 H$_2$O requires: C, 57.62, H, 5.93; N, 12.12%). δ$_H$ (360 MHz, DMSO-d$_6$) 1.74 (1H, m), 1.90–2.08 (5H, m), 2.77 (2H, m), 2.90–3.18 (8H, m), 7.32–7.35 (2H, m), 7.51 (1H, d, J=8.6 Hz), 7.55–7.62 (3H, m), 7.66–7.68 (2H, m), 7.81 (1H, s), 9.03 (2H, s), 11.18 (1H, s); m/e (ES) 464 (M$^+$+1).

EXAMPLE 64

(3R)-3-(2-[R,S]-Phenylpiperidin-1-yl)methyl-1-[2-(5-(1,2,4-triazol-1-ylmethyl)-1H-indol-3-yl)ethyl] pyrrolidine. 1.8 Hydrogen Oxalate. 0.75 Hydrate.

The title compound was prepared using the procedures described for Example 61. The 1.8 hydrogen oxalate 0.75 hydrate salt was prepared, mp 184°–185° C., (Found: C, 60.78; H, 6.67; N, 12.77. C$_{29}$H$_{36}$N$_6$.1.8(C$_2$H$_2$O$_4$).0.75 H$_2$O requires C, 60.78; H, 6.43; N, 13.05%); m/e 469 (M+1)$^+$.

EXAMPLE 65

4-([3,3-Dimethylpiperidin-1-yl]methyl)-4-hydroxy-1-(3-[5-(1,2,4-triazol-4-yl)-1H-indol-3-yl]propyl) piperidine. Hydrogen Oxalate.

a) 6-Aza-6-benzyl-1-oxaspirof[2.5]octane

Dimethyl sulphoxide (50 ml) was added dropwise to a stirred, cooled (10° C.) mixture of sodium hydride (1.85 g of a 55% oil dispersion, 0.0423 mol) and trimethylsulphoxonium iodide (8.0 g, 0.0423 mol) under a nitrogen atmosphere. After addition the cooling bath was removed and the mixture stirred at room temperature for 30 minutes, then cooled to 7° C. and treated with a solution of 1-benzyl-4-piperidone (8.0 g, 0.0423 mol) in dimethyl sulphoxide (50 ml). After addition the reaction mixture was stirred at room temperature for 15 minutes then at 50° C. for 1 hour. The mixture was then stirred whilst cooling to room temperature then quenched with water (20 ml). After stirring for a further 10 minutes the mixture was poured into water (250 ml) and extracted with toluene (3×100 ml). The combined organics were washed with water (200 ml), dried (sodium sulphate) then evaporated to give the title compound as a pale yellow oil (7.4 g, 86%). MS, ES$^+$, m/z=204 for (M+H)$^+$; δ (360 MHz, D$_6$-DMSO) 1.41–1.48 (2H, m) and 1.63–1.71 (2H, m, piperidine 3-CH$_2$ and 5-CH$_2$), 2.43–2.51 (4H, m, piperidine 2-CH$_2$ and 6-CH$_2$), 2.58 (2H, s, CH$_2$O), 3.51 (2H, s, CH$_2$Ph), 7.18–7.38 (5H, m, Ar—H).

b) 1-Benzyl-4-(3,3-dimethylpiperidin-1-yl)methyl-4-hydroxy piperidine

A solution of 6-aza-6-benzyl-1-oxaspiro[2.5]octane (2.0 g, 9.84 mmol) and 3,3-dimethylpiperidine (6.7 ml, 49.2 mmol) in ethanol (20 ml) was heated at reflux for 3 hours. The reaction mixture was evaporated and the residue partitioned between dichloromethane (20 ml) and water (20 ml). The organic layer was separated, washed with water (20 ml) then extracted with 2M hydrochloric acid (2×20 ml). The combined aqueous was washed with $Et_2O$ (20 ml) then basified to pH=12 with 40% sodium hydroxide solution and extracted with dichloromethane (4×20 ml). The combined organics were dried (potassium carbonate) then evaporated to give the title compound as a colourless oil (2.16 g, 69%). MS, $ES^+$, m/z=317 for $(M+H)^+$; δ (250 MHz, $D_6$-DMSO) 0.90 (6H, s, 2×$CH_3$), 1.09–1.14 (2H, m, $CH_2$), 1.34–1.62 (6H, 3×$CH_2$), 2.13 (4H, s, 2×$CH_2$N), 2.25–2.45 (6H, 3×$CH_2$N), 3.43 (2H, s, $CH_2$Ph), 3.80 (1H, s, OH), 7.19–7.34 (5H, m, Ar—H).

c) 4-(3,3-Dimethylpiperidin-1-yl)methyl-4-hydroxypiperidine

The foregoing benzyl-piperidine (2.03 g, 6.42 mmol) in methanol (60 ml) was treated with formic acid (90%, 1 ml), ammonium formate (1.21 g, 19.3 mmol) then 10% palladium on carbon (500 mg). The reaction mixture was stirred at room temperature for 18 h, then filtered and evaporated. The residue was partitioned between dichloromethane (80 ml), methanol (10 ml) and 10% potassium carbonate solution (20 ml). The organic layer was separated and the aqueous extracted with dichloromethane (2×50 ml). The combined organic layers were dried (potassium carbonate), then evaporated to give a gum which was purified using a short silica column, eluting with dichloromethane/methanol/ammonia (5:1:0.1) to give the title compound as a colourless oil which solidified on standing (1.0 g, 69%), mp 48°–52° C.; MS, $ES^+$, m/z=227 for $(M+H)^+$; δ (250 MHz, $D_6$-DMSO) 0.90 (6H, s, 2×$CH_3$), 1.10–1.14 (2H, m, $CH_2$), 1.24–1.54 (6H, m, 3×$CH_2$), 2.11 (2H, s, $CH_2$N), 2.11–2.13 (2H, m, $CH_2$N), 2.34–2.39 (2H, m, $CH_2$N), 2.52–2.60 (2H, m, $CH_2$N), 2.69–2.79 (2H, m, $CH_2$N), 3.80 (1H, br s, OH).

d) 4-([3,3-Dimethylpiperidin-1-yl]methyl)-4-hydroxy-1-(3-[5-(1,2,4-triazol-4-yl)-1H-indol-3-yl]propyl)piperidine. Hydrogen Oxalate.

3-[5-(1,2,4-Triazol-4-yl)-1H-indol-3-yl]propan-1-ol (300 mg, 1.23 mmol) was converted to the mesylate as previously described. This mesylate (343 mg) in propan-2-ol (70 ml) was treated with 4-(3,3-dimethylpiperidin-1-yl)methyl-4-hydroxypiperidine (315 mg, 1.39 mmol) and potassium carbonate (192 mg, 1.39 mmol) then heated at reflux, with stirring, for 20 h. The reaction mixture was evaporated then the residue was partitioned between dichloromethane (40 ml) and water (20 ml). The organic layer was separated then the aqueous was re-extracted with dichloromethane (40 ml). The combined organics were dried (potassium carbonate) then evaporated to give a yellow gum (512 mg) which was purified by column chromatography on silica using dichloromethane/methanol/ammonia (9:1:0.1→5:1:0.1) to give the title compound free base as a colourless gum (130 mg, 27%). The hydrogen oxalate salt had mp 125°–132° C. δ (360 MHz, $D_6$-DMSO) 0.94 (6H, s, 2×$CH_3$), 1.19–1.27 (4H, m, 2×$CH_2$), 1.55–1.59 (2H, m, $CH_2$), 1.64–1.70 (2H, m, $CH_2$), 1.80–1.92 (2H, m, $CH_2$), 2.04–2.09 (2H, m, $CH_2$ $CH_2CH_2$), 2.38–2.62 (6H, m, 3×$CH_2$N), 2.78 (2H, t, J=7 Hz, $CH_2$-indole), 3.00–3.18 (4H, m, 2×$CH_2$N), 3.34–3.40 (2H, m, $CH_2$N), 7.32–7.35 (2H, m, Ar—H), 7.51 (1H, d, J=8 Hz, Ar—H), 7.82 (1H, d, J=2 Hz, Ar—H), 9.03 (2H, s, triazole-H), 11.20 (1H, s, indole-NH). (Found: C, 54.43; H, 6.98; N, 11.25. $C_{26}H_{38}N_6O.2.8(C_2H_2O_4).0.5(C_2H_5)_2O$ requires C, 54.55; H, 6.62; N, 11.36% MS, $ES^+$, m/z=451 for $(M+H)^+$.

EXAMPLE 66

4-Hydroxy-4-([1,2,3,4-tetrahydroisoquinolin-2-yl]methyl)-1-(3-[5-(1,2,4-triazol-4-yl)-1H-indol-3-yl]propyl)piperidine. Hydrogen Oxalate.

a) 1-Benzyl-4-hydroxy-4-(1,2,3,4-tetrahydroisoquinolin-2-yl)methyl piperidine

The title compound was obtained (2.3 g, 82%) from 6-aza-6-benzyl-1-oxaspiro[2.5]octane and 1,2,3,4-tetrahydroisoquinoline, mp 57°–58° C. MS, $ES^+$, m/z=337 for $(M+H)^+$.

b) 4-Hydroxy-4-(1,2,3,4-tetrahydroisoquinolin-2-yl)methyl piperidine

The title compound was obtained (1.01 g, 69%) from the foregoing benzyl-piperidine, formic acid, ammonium formate and 10% palladium on carbon in methanol, mp 92°–93° C. MS, $ES^+$, m/z=247 for $(M+H)^+$; δ (360 MHz, $D_6$-DMSO) 1.36–1.52 (4H, m, 2×$CH_2$), 2.39 (2H, s, $CH_2$N), 2.55–2.62 (2H, m, $CH_2$N), 2.72–2.78 (2H, m, $CH_2$N), 2.80 (4H, s, $CH_2$Ph and $CH_2$N), 3.69 (2H, s, $NCH_2$Ph), 3.98 (1H, s, OH), 7.00–7.12 (4H, m, Ar—H).

c) 4-Hydroxy-4-([1,2,3,4-tetrahydroisoquinolin-2-yl]methyl)-1-(3-[5-(1,2,4-triazol-4-yl)-1H-indol-3-yl]propylpipieridine. Hydrogen Oxalate.

The title compound free base (191 mg, 38%) was obtained from 4-hydroxy-4-(1,2,3,4-tetrahydroisoquinolin-2-yl)methyl piperidine and the mesylate obtained from 3-[5-(1,2,4-triazol-4-yl)-1H-indol-3-yl]propan-1-ol. The hydrogen oxalate salt had mp 160°–165° C. δ (360 MHz, $D_6$-DMSO) 1.66–1.94 (4H, m, 2×$CH_2$), 1.98–2.10 (2H, m, $CH_2$ $CH_2CH_2$), 2.58 (2H, br s, $CH_2$N), 2.77 (2H, t, J=7 Hz, $CH_2$-indole), 2.83–2.87 (2H, m), 2.91–2.95 (2H, m), 3.00–3.18 (4H, m) and 3.30–3.40 (2H, m, 4×$CH_2$N, $CH_2$—Ph), 3.82 (2H, s, N— $CH_2$—Ph), 7.00–7.15 (4H, m, Ar—H), 7.30–7.35 (2H, m, Ar—H), 7.51 (1H, d, J=8 Hz, Ar—H), 7.80 (1H, s, Ar—H), 9.02 (2H, s, triazole-H), 11.19 (1H, s, indole-NH). (Found: C, 57.82; H, 5.81; N, 11.96. $C_{28}H_{34}N_6O.2.35(C_2H_2O_4)$ requires C, 57.57; H, 5.72; N, 12.31%). MS, $ES^+$, m/z=471 for $(M+H)^+$.

EXAMPLE 67

4-Hydroxy-4-([N-isobutyl-N-methyl]aminomethyl)-1-(3-[5-(1,2,4-triazol-4-yl)-1H-indol-3-yl]propyl) piperidine a) 6-Aza-6-t-butyloxycarbonyl-1-oxaspiro[2.5]octane Dimethyl sulphoxide (100 ml) was added dropwise to a stirred, cooled (10° C.) mixture of sodium hydride (3.70 g of a 55% oil dispersion, 0.0846 mol) and trimethylsulphoxonium iodide (18.6 g, 0.0846 mol) under a nitrogen atmosphere. After addition the cooling bath was removed and the mixture stirred at room temperature for 30 minutes, then cooled to 5° C. and was treated with a solution of N-t-butoxycarbonyl-4-piperidone (16.86 g, 0.0846 mol) in dimethylsulphoxide (50 ml). The cooling bath was removed and the reaction mixture stirred at room temperature for 15 minutes, then at 50° C. for 1 hour. The mixture was stirred whilst cooling to room temperature then quenched with water (40 ml) and stirred for a further 10 minutes. The reaction mixture was poured into water (600 ml) and extracted with toluene (4×300 ml). The combined organics were washed with water (300 ml), dried (sodium sulphate) then evaporated to give an oil which was eluted through a short silica column using ethyl acetate/n-hexane (1:1) to give a colourless solid (10.0 g, 55%), mp 49°–51° C.; δ (360 MHz, $D_6$-DMSO) 1.35–1.40 (2H, m, $CH_2$), 1.41 (9H, s, $C(CH_3)_3$), 1.60–1.67 (2H, m, $CH_2$), 2.65 (2H, s, $CH_2$O), 3.33–3.41 (2H, m, $CH_2$), 3.46–3.54 (2H, m, $CH_2$). (Found:

C, 61.88; H, 9.05; N, 6.42. $C_{11}H_{19}NO_3$ requires C, 61.95; H, 8.98; N, 6.57%). MS, ES$^+$, m/z=214 for (M+H)$^+$.

b) 1-t-Butyloxycarbonyl-4-hydroxy-4-([N-isobutyl-N-methyl]aminomethyl)piperidine A mixture of the preceding compound (3 g, 0.014 mol) and isobutylamine (7 ml, 0.0704 mol) was heated in ethanol (30 ml) at 60° C. for 2 h. The reaction mixture was evaporated to dryness and the residue eluted through a short silica column using dichloromethane/methanol/ammonia (9:1:0.1) to give 1-t-butyloxycarbonyl-4-hydroxy-4-(N-isobutylaminomethyl)piperidine (3.4 g, 85%) as a colourless viscous gum, MS, ES$^+$, m/z=287 for (M+H)$^+$. This amine (3.3 g, 0.0115 mol) in methanol (30 ml) was treated with formaldehyde (1.4 ml of a 37% aqueous solution, 0.0173 mol) and acetic acid (3.3 ml, 0.0575 mol). After 5 minutes the solution was treated portionwise with sodium cyanoborohydcride (1.09 g, 0.0173 mol) and the mixture was stirred at room temperature for 2 h then quenched with saturated aqueous potassium carbonate (50 ml). The methanol was evaporated and the aqueous extracted with dichloromethane (4×50 ml). The combined organics were dried (potassium carbonate) then evaporated to give a yellow gum which was eluted through a short silica column using dichloromethane/methanol (10:1) to give the title compound as a colourless gum (2.63 g, 76%). δ (360 MHz, D$_6$-DMSO) 0.83 (6H, d, J=7 Hz, 2×CH$_3$), 1.35–1.48 (4H, m, 2×CH$_2$) overlapped with 1.38 (9H, s, C(CH$_3$)$_3$), 1.61–1.69 (1H, m, CH), 2.11 (2H, d, J=7 Hz, CH$_2$CH), 2.22 (3H, s, NCH$_3$), 2.23 (2H, s, CH$_2$N), 3.02–3.08 (2H, m, CH$_2$N), 3.60 (2H, d, J=13 Hz, CH$_2$N), 4.09 (1H, s, OH); MS, ES$^+$, m/z=301 for (M+H)$^+$.

c) 4-Hydroxy-4-([N-isobutyl-N-methyl]aminomethyl)piperidine

The foregoing amine (2.55 g, 8.49 mmol) in dichloromethane (30 ml) was treated with trifluoroacetic acid (6.5 ml, 84.9 mmol) and the solution was left standing for 18 h, then evaporated and partitioned between saturated aqueous potassium carbonate (15 ml) and dichloromethane (40 ml) containing methanol (2 ml). The organic layer was separated and the aqueous re-extracted with dichloromethane (3×40 ml). The combined organics were dried (potassium carbonate) then evaporated to give a pale yellow gum (1.7 g) which was eluted through a short silica column using dichloromethane/methanol/ammonia (5:1:0.1) to give the title compound as a viscous colourless gum (1.44 g, 85%). δ (360 MHz, D$_6$-DMSO) 0.84 (6H, t, J=7 Hz, 2×CH$_3$), 1.31–1.47 (1H, m, CH), 2.11 (2H, d, J=7 Hz, NCH$_2$CH), 2.21 (2H, s, CH$_2$N), 2.23 (3H, s, NCH$_3$), 2.57–2.63 (2H, m, CH$_2$N), 2.73–2.80 (2H, m, CH$_2$N); MS, ES$^+$, m/z=201 for (M+H)$^+$.

d) 4-Hydroxy-4-([N-isobutyl-N-methyl]aminomethyl)-1-(3-[5-(1,2,4-triazol-4-yl)-1H-indol-3-yl]propyl)piperidine The title compound (230 mg, 65%) was obtained from 4-hydroxy-4-([N-isobutyl-N-methyl]aminomethyl)piperidine and the mesylate, obtained from 3-[5-(1,2,4-triazol-4-yl)-1H-indol-3-yl]propan-1-ol, in propan-2-ol using potassium carbonate as base, mp>60° C. δ (360 MHz, D$_6$-DMSO) 0.84 (6H, d, J=6.5 Hz), 2×CH$_3$), 1.37–1.49 (2H, m, CH$_2$), 1.49–1.60 (2H, m, CH$_2$), 1.60–1.72 (1H, m, CH), 1.75–1.86 (2H, m, CH$_2$CH$_2$CH$_2$), 2.11 (2H, d, J=7 Hz, CH$_2$CH$_2$), 2.21 (2H, s, CH$_2$N), 2.22 (3H, s, NCH$_3$), 2.20–2.35 (4H, m) and 2.37–2.52 (2H, m, 3×CH$_2$N), 2.71 (2H, t, J=7 Hz, CH$_2$-indole), 3.77 (1H, s, OH), 7.26 (1H, d, J=2 Hz, Ar—H), 7.28 (1H, dd, J$_1$=2 Hz, J$_2$=8 Hz, Ar—H), 7.47 (1H, d, J=8 Hz, Ar—H), 7.77 (1H, d, J=2 Hz, Ar—H), 9.00 (2H, s, triazole-H), 11.05 (1H, s, indole-NH); MS, ES$^+$, m/z=425 for (M+H)$^+$. (Found: C, 66.38; H, 8.71; N, 18.90. $C_{24}H_{36}N_6O$.0.65 H$_2$O requires C, 66.07; H, 8.62; N, 19.26%).

EXAMPLE 68

4-N-Benzyl-N-(2-hydroxyethyl)aminomethyl]-4-hydroxy-1-(3-[5-(1,2,4-triazol-4-yl)-1H-indol-3-yl] propyl)piperidine.

a) 1-t-Butyloxycarbonyl-4-hydoxy-4-([2-hydoxyethyl] aminomethyl)piperidine

The title compound was prepared from 6-aza-6-tert-butyloxycarbonyl-1-oxaspiro[2.5]octane and ethanolamine. MS, ES$^+$, m/z=275 for (M+H)$^+$.

b) 1-t-Butyloxycarbonyl-4-hydroxy-4-(N-benzyl-N-[2-hydroxyethyl]aminomethyl)piperidine The title compound was prepared (0.59 g, 62%) from the foregoing piperidine, benzaldehyde, sodium cyanoborohydride and acetic acid in methanol. MS, ES$^+$, m/z=365 for (M+H)$^+$, δ (360 MHz, D$_6$-DMSO) 1.30–1.45 (4H, m, 2×CH$_2$), 1.39 (9H, s, 3×CH$_3$), 2.48 (2H, s, CH$_2$N), 2.54 (2H, t, J=6 Hz, CH$_2$N), 3.06 (2H, br s, 2×CH), 3.44 (2H, q, J=6 Hz, CH$_2$O), 3.57 (2H, d, J=13 Hz, 2×CH), 3.71 (2H, s, NCH$_2$Ph), 4.32 (1H, s, OH), 4.47 (1H, t, J=6 Hz, OH), 7.22–7.36 (5H, m, Ar—H).

c) 4-(N-Benzyl-N-[2-hydroxyethyl]aminomethyl)-4-hydroxypiperidine

The title compound was obtained (0.44 g, 100%) from the foregoing piperidine and trifluoroacetic acid in dichloromethane. MS, ES$^+$, m/z=265 for (M+H)$^+$, δ (360 MHz, D$_6$-DMSO) 1.37–1.42 (4H, m, 2×CH$_2$), 2.46 (2H, s, CH$_2$N), 2.54–2.62 (2H, m, 2×CH), 2.53 (2H, t, J=6 Hz, CH$_2$N), 2.73–2.81 (2H, m 2×CH), 3.45 (2H, t, J=6 Hz, CH$_2$O), 3.71 (2H, s, NCH$_2$Ph), 4.14 (1H, br s, OH), 4.50 (1H, s, OH), 7.20–7.38 (5H, m, Ar—H).

d) 4-[N-Benzyl-N-(2-hydroxyethyl)aminomethyl]-4-hydroxy-1-(3-[5-(1,2,4-triazol-4-yl)-1H-indol-3-yl]propyl)piperidine The title compound (155 mg, 30%) was obtained from 4-(4-[N-benzyl-N-(2-hydroxyethyl)]aminomethyl)-4-hydroxypiperidine and the mesylate prepared from 3-[5-(1,2,4-triazol-4-yl)-1H-indol-3-yl]propan-1-ol in propan-2-ol using potassium carbonate as base, mp 75°–78° C. δ (360 MHz, D$_6$-DMSO) 1.41–1.46 (4H, m, 2×CH$_2$), 1.76–1.80 (2H, m, CH$_2$CH$_2$CH$_2$), 2.20–2.40 (6H, m, 3×CH$_2$N), 2.44 (2H, s, CH$_2$N), 2.53 (2H, t, J=6 Hz, CH$_2$N), 2.69 (2H, t, J=7 Hz, CH$_2$-indole), 3.43 (2H, q, J=6 Hz, CH$_2$O), 3.70 (2H, s, NCH$_2$Ph), 4.04 (1H, s, OH), 4.45 (1H, t, J=6 Hz, OH), 7.19–7.35 (7H, m), 7.46 (1H, d, J=8 Hz) and 7.77 (9H, d, J=2 Hz, 9×Ar—H), 9.01 (2H, s, triazole-H), 11.05 (1H, s, indole-NH); MS, ES$^+$, m/z=489 for (M+H)$^+$. (Found: C, 68.41; H, 7.21; N, 16.29. $C_{28}H_{36}N_6O_2$.0.2($C_4H_{10}O$) requires C, 68.71; H, 7.60; N, 16.69%).

EXAMPLE 69

4-[N-(2,2-Dimethylpropyl)-N-methylaminomethyl]-4-hydroxy-1-(3-[5-(1,2,4-triazol-4-yl)-1H-indol-3-yl]propyl)piperidine.

a) 4-[N-(2,2-Dimethylpropyl)aminomethyl]-4-hydroxy-1-(3-[5-(1,2,4-triazol-4-yl)-1H-indol-3-yl]propyl)piperidine The title compound was obtained (240 mg, 75%) from 4-aminomethyl-4-hydroxy-1-(3-[5-(1,2,4-triazol-4-yl)-1H-indol-3-yl]propyl)piperidine, sodium cyanoborohydride, trimethylacetaldehyde and acetic acid in methanol, mp>55° C. MS, ES$^+$, m/z=425 for (M+H)$^+$; δ (360 MHz, D$_{6\text{-}DMSO}$) 0.85 (9H, s, 3×CH$_3$), 1.40–1.52 (4H, m, 2×CH$_2$), 1.75–1.86 (2H, m, CH$_2$CH$_2$CH$_2$), 2.27 (2H, s, CH$_2$N), 2.20–2.35 (4H, m, 2×CH$_2$N), 2.39–2.50 (2H, m, CH$_2$N), 2.42 (2H, s, CH$_2$N), 2.71 (2H, t, J=7 Hz, CH$_2$-indole), 4.00 (1H, s, OH), 7.26 (1H, d, J=2 Hz, Ar—H), 7.29 (1H, dd, J$_1$=2 Hz, J$_2$=8 Hz, Ar—H), 7.47 (1H, d, J=8 Hz, Ar—H), 7.77 (1H, d, J=2 Hz, Ar—H), 9.00 (2H, s, triazole-H), 11.05 (1H, s, indole-NH).

b) 4-[N-(2,2-Dimethylproyl)-N-methylaminomethyl]-4-hydroxy-1-(3-[5-(1,2,4-triazol-4-yl)-1H-indol-3-yl]propyl)piperidine.

The title compound was obtained (100 mg, 74%) from the foregoing amine and formaldehyde in the presence of acetic acid and sodium cyanoborohydride in methanol as solvent, mp>70° C. MS, ES$^+$, m/z=439 for (M+H)$^+$; δ (360 MHz, D$_6$-DMSO) 0.86 (9H, s, 3×CH$_3$), 1.46–1.52 (4H, m, 2×CH$_2$), 1.76–1.86 (2H, m, CH$_2$C$\underline{H}_2$CH$_2$), 2.18 (2H, s, CH$_2$N), 2.20–2.38 (6H, m, 3×CH$_2$N), 2.37 (3H, s, NCH$_3$), 2.42–2.52 (2H, m, CH$_2$N), 2.72 (2H, t, J=7 Hz, indole-CH$_2$), 3.82 (1H, s, OH), 7.27 (1H, d, J=2 Hz, Ar—H), 7.30 (1H, dd, J$_1$=2 Hz, J$_2$=8 Hz, Ar—H), 7.47 (1H, d, J=8 Hz, Ar—H), 7.77 (1H, d, J=2 Hz, Ar—H), 9.01 (2H, s, triazole-H), 11.06 (1H, s, indole-NH). (Found: C, 67.40; H, 8.89; N, 18.62. C$_{25}$H$_{38}$N$_6$O.0.5 H$_2$O requires C, 67.08; H, 8.78; N, 18.77%).

EXAMPLE 70

4-([N-(R)-α-Hydroxymethylbenzyl-N-methyl]aminomethyl)-4-hydroxy-1-(3-[5-(1,2,4-triazol-4-yl)-1H-indol-3-yl]propyl)piperidine.

a) 1-t-Butyloxycarbonyl-4-hydroxy-4-([N-(R)-α-hydroxymethylbenzyl]aminomethyl)piperidine The title compound was obtained (2 g, 78%) from 6-aza-6-tert-butyloxycarbonyl-1-oxaspiro[2.5]octane and (R)-phenylglycinol.

b) 4-Hydroxy-4-([N-(R)-α-hydroxymethylbenzyl]aminomethyl)piperidine

The foregoing protected piperidine (1.9 g, 5.4 mmol) was stirred with trifluoroacetic acid (5 ml) in dichloromethane (10 ml) for 3 h. The solvent was evaporated and the residue azeotroped with toluene, then partitioned between water and dichloromethane and basified with saturated aqueous potassium carbonate. The organic layer was separated and the aqueous re-extracted with dichloromethane (×3). The combined organics were dried (sodium sulphate) then evaporated to give the product as a gum (600 mg, 44%), δ (360 MHz, D$_6$-DMSO) 1.32–1.52 (4H, m, 2×CH$_2$), 2.56 (2H, s, CH$_2$N), 2.47–2.52 (2H, m, CH$_2$N), 2.70–2.76 (2H, m, CH$_2$N), 3.28 (1H, dd, J$_1$=J$_2$=9 Hz, NCHPh), 3.42–3.47 (1H, m) and 3.59–3.63 (1H, m, CH$_2$OH), 4.12 (1H, br s, OH), 4.94 (1H, br s, OH), 7.20–7.35 (5H, m, Ar—H).

c) 4-([N-(R)-α-Hydroxymethylbenzyl]aminomethyl)-4-hydroxy-1-(3-[5-(1,2,4-triazol-4-yl)-1H-indol-3-yl]propyl)piperidine The title compound was prepared (290 mg, 68%) from the foregoing piperidine and the mesylate prepared from 3-[5-(1,2,4-triazol-4-yl)-1H-indol-3-yl]propan-1-ol in propan-2-ol using potassium carbonate as base, mp>55° C. MS, ES$^+$, m/z=475 for (M+H)$^+$. (Found: C, 66.73; H, 7.30; N, 16.87. C$_{27}$H$_{34}$N$_6$O$_2$.0.8 H$_2$O requires C, 66.32; H, 7.34; N, 17.19%.

d) 4-([N-(R)-α-Hydroxymethylbenzyl-N-methyl]aminomethyl)-4-hydroxy-1-(3-[5-(1,2,4-triazol-4-yl)-1H-indol-3-yl]propyl)piperidine.

The title compound was obtained (140 mg, 90%) from the foregoing benzylamine, formaldehyde, sodium cyanoborohydride and acetic acid in methanol, mp>75° C. MS, ES$^+$, m/z=489 for (M+H)$^+$; δ (360 MHz, D$_6$-DMSO) 1.40–1.56 (4H, m, 2×CH$_2$), 1.72–1.88 (2H, m, CH$_2$C$\underline{H}_2$CH$_2$), 2.23 (3H, s, NCH$_3$), 2.18–2.56 (6H, m, 3×CH$_2$N), 2.36 (2H, s, CH$_2$N), 2.72 (2H, t, J=7 Hz, indole-CH$_2$), 3.58–3.70 (2H, m, CHO and CH-phenyl), 3.80–3.88 (1H, m, CHO), 4.07 (1H, s, OH), 4.58 (1H, t, J=6 Hz, OH), 7.20–7.33 (7H, m, Ar—H), 7.48 (1H, d, J=8 Hz, Ar—H), 7.78 (1H, d, J=2 Hz, Ar—H), 9.02 (2H, s, triazole-H), 11.07 (1H, s, indole-NH). (Found: C, 67.02; H, 7.60; N, 15.89. C$_{28}$H$_{36}$N$_6$O$_2$.0.4 H$_2$O. 0.6 (C$_2$H$_6$O) requires C, 67.00; H, 7.78; N, 16.05%).

EXAMPLE 71

4-Hydroxy-4-([2-Pyridylmethyl]amino)methyl-1-(3-[5-(1,2,4-triazol-4-yl)-1H-indol-3-yl]propyl)piperidine.

The title compound was obtained using a procedure similar to 4-(benzylamino)methyl-4-hydroxy-1-(3-[5-(1,2,4-triazol-4-yl)-1H-indol-3-yl]propyl)piperidine, using 2-pyridinecarboxaldehyde in the final step. mp>55° C.; δ (360 MHz, D$_6$-DMSO) 1.40–1.53 (4H, m, 2×CH$_2$), 1.72–1.87 (2H, m, CH$_2$C$\underline{H}_2$CH$_2$), 2.20–2.37 (6H, m, 3×CH$_2$N), 2.44 (2H, s, C$\underline{H}_2$NH), 2.71 (2H, t, J=7 Hz, CH$_2$-indole), 3.80 (2H, s, NHC$\underline{H}_2$ pyridyl), 4.08 (1H, br s, OH), 7.20–7.32 (3H, m, Ar—H), 7.41 (1H, d, J=7 Hz, Ar—H), 7.46 (1H, d, J=8 Hz, Ar—H), 7.72 (1H, dd, J$_1$=2 Hz, J$_2$=8 Hz, Ar—H), 7.77 (1H, d, J=2 Hz, Ar—H), 8.46 (1H, d, J=8 Hz, Ar—H), 9.01 (2H, s, triazole-H), 11.05 (1H, s, indole-NH). MS, ES$^+$, m/z=446 for (M+H)$^+$. (Found: C, 62.07; H, 7.19; N, 19.57. C$_{25}$H$_{31}$N$_7$O.1.1 H$_2$O.0.3(CH$_2$Cl$_2$) requires C, 61.91; H, 6.94; N, 19.97%).

EXAMPLE 72

4-Hydroxy-4-([2-methylphenylmethyl]amino)methyl-1-(3-[5-(1,2,4-triazol-4-yl)-1H-indol-3-yl]propyl)piperidine. Hydrogen Oxalate.

The title compound was obtained using a procedure similar to 4-(benzylamino)methyl-4-hydroxy-1-(3-[5-(1,2,4-triazol-4-yl)-1H-indol-3-yl]propyl)piperidine. The hydrogen oxalate salt had mp>138° C.(dec); δ (360 MHz, D$_6$-DMSO) 1.70–1.90 (4H, m, 2×CH$_2$), 2.00–2.10 (2H, m, CH$_2$C$\underline{H}_2$CH$_2$), 2.34 (3H, s, CH$_3$), 2.70–2.80 (2H, m, CH$_2$-indole), 2.89 (2H, s, C$\underline{H}_2$NH), 3.00–3.10 (4H, m) and 3.20–3.30 (2H, m, 3×C$\underline{H}_2$N), 4.06 (2H, s, NHC$\underline{H}_2$Ar), 7.16–7.26 (3H, m, Ar—H), 7.30–7.35 (2H, m, Ar—H), 7.43–7.52 (2H, m, Ar—H), 7.80 (1H, d, J=2 Hz, Ar—H), 9.01 (2H, s, triazole-H), 11.19 (1H, s, indole-NH). MS, ES$^+$, m/z=459 for (M+H)$^+$. (Found: C, 55.89; H, 6.03; N, 11.50. C$_{27}$H$_{34}$N$_6$O.2.7(C$_2$H$_2$O$_4$) requires C, 55.46; H, 5.66; N, 11.98%).

EXAMPLE 73

4-Hydroxy-4-([N-2-methylphenylmethyl-N-methyl]amino)methyl-1-(3-[5-(1,2,4-triazol-4-yl)-1H-indol-3-yl]propyl)piperidine. Hydrogen Oxalate.

The title compound was prepared (45 mg, 64%) from the foregoing amine, using the procedure described for 4-([N-Benzyl-N-methyl]amino) methyl-4-hydroxy-1-(3-[5-(1,2,4-triazol-4-yl)-1H-indol-3-yl]propyl)piperidine. The hydrogen oxalate salt had mp>110° C. (dec); δ (360 MHz, D$_6$-DMSO) 1.55–1.70 (4H, m, 2×CH$_2$), 1.98–2.10 (2H, m, CH$_2$C$\underline{H}_2$CH$_2$), 2.32 (6H, s, 2×CH$_3$), 2.47 (2H, s, CH$_2$N), 2.75 (2H, t, J=7 Hz, CH$_2$-indole), 2.96–3.10 (4H, m) and 3.20–3.30 (2H, m, 3×C$\underline{H}_2$N), 3.58 (2H, s, NC$\underline{H}_2$Ar), 7.05–7.20 (3H, m, Ar—H), 7.25–7.40 (3H, m, Ar—H), 7.50 (1H, d, J=8 Hz, Ar—H), 7.80 (1H, d, J=2 Hz, Ar—H), 9.01 (2H, s, triazole-H), 11.19 (1H, s, indole-NH). MS, ES$^+$, m/z=for 473 (M+H)$^+$. (Found: C, 56.93; H, 6.42; N, 11.97. C$_{28}$H$_{36}$N$_6$O.2(C$_2$H$_2$O$_4$) requires C, 56.55; H, 6.38; N, 12.36%).

EXAMPLE 74

3-(Benzylamino)methyl-3-hydroxy-1-(3-[5-(1,2,4-triazol-4-yl)-1H-indol-3-yl]propyl)pyrrolidine.

a) 1-Benzyl-3-(t-butyloxycarbonylamino)methyl-3-hydroxypyrrolidine

3-Aminomethyl-1-benzyl-3-hydroxypyrrolidine was prepared from 1-benzyl-3-pyrrolidinone using the procedure described in *Synth. Commun.*, 1994, 24 (10), 1483. This crude amine (9.4 g, 45 mmol) in dichloromethane (200 ml) was treated with di-t-butyl dicarbonate (10 g, 45 mmol) and the reaction mixture was stirred at room temperature for 48 h. The solvent was evaporated and the crude product was purified by column chromatography on silica using methanol/dichloromethane (1:20). The title compound was obtained as a gum (2.3 g, 17%). MS, ES$^+$, m/z=307 for (M+H)$^+$; δ (250 MHz, D$_6$-DMSO) 1.37 (9H, s, 3×CH$_3$), 1.52–1.62 (1H, m, CH), 1.76–1.87 (1H, m, CH), 2.27 (1H, d, J=10 Hz, C$\underline{H}$NH), 2.42–2.64 (3H, m, C$\underline{H}$NH, CH$_2$N), 3.00–3.09 (2H, m, CH$_2$N), 3.52 (2H, s, C$\underline{H}_2$Ph), 4.67 (1H, s, OH), 6.61 (1H, t, J=6 Hz, NH), 7.18–7.33 (5H, m, Ar—H).

b) 3-(t-Butyloxycarbonylamino)methyl-3-hydroxypyrrolidine

A solution of the foregoing benzylamine (2.2 g, 7.2 mmol) in methanol (40 ml) was treated with ammonium formate (1.1 g) and 10% palladium on carbon (1.1 g). The reaction mixture was stirred at room temperature for 4 h, filtered, then evaporated. The residue was dissolved in water; basified with potassium carbonate then extracted with dichloromethane (×5). The combined organics were dried (sodium sulphate) then evaporated to give the required product as a gum (1.4 g, 91%). δ (250 MHz, D$_6$-DMSO) 1.38 (9H, s, 3×CH$_3$), 1.48–1.69 (2H, m, CH$_2$), 2.52 (1H, d, J=11 Hz, C$\underline{H}$NH), 2.62 (1H, d, J=11 Hz, C$\underline{H}$NH), 2.65–2.94 (2H, m, CH$_2$N), 3.06 (2H, d, J=6 Hz, CH$_2$N), 4.59 (1H, br s, OH), 6.66 (1H, t, J=6 Hz, N$\underline{H}$CO).

c) 3-(t-Butyloxycarbonylamino)methyl-3-hydroxy-1-(3-[5-1,2,4-triazol-4-yl)-1H-indol-3-yl]propyl)pyrrolidine The title compound was prepared (300 mg, 30%) from the foregoing amine and the mesylate prepared from 3-[5-(1,2,4-triazol-4-yl)-1H-indol-3-yl]propan-1-ol in propan-2-ol using potassium carbonate as base, δ (250 MHz, D$_6$-DMSO) 1.35 (9H, s, 3×CH$_3$), 1.50–1.60 (1H, m, CH), 1.70–1.84 (3H, m, CH and CH$_2$C$\underline{H}_2$CH$_2$), 2.26 (1H, d, J=10 Hz, C$\underline{H}$NH), 2.38 (2H, t, J=8 Hz, CH$_2$N), 2.45–2.50 (2H, m, CH$_2$N), 2.58 (1H, d, J=10 Hz, C$\underline{H}$NH), 2.73 (2H, t, J=8 Hz, CH$_2$-indole), 2.98–3.04 (2H, m, CH$_2$N), 4.64 (1H, s, OH), 6.60 (1H, t, J=6 Hz, N$\underline{H}$CO), 7.26–7.32 (2H, m, Ar—H), 7.46 (1H, d, J=8 Hz, Ar—H), 7.78 (1H, d, J=2 Hz, Ar—H), 9.02 (2H, s, triazole-H), 11.07 (1H, s, indole-NH).

d) 3-(Benzylamino)methyl-3-hydroxy-1-(3-[5-(1,2,4-triazol-4-yl)-1H-indol-3-yl]propyl)pyrrolidine The title compound was prepared from the foregoing t-butyloxycarbonyl-protected compound as described for 4-(benzylamino)methyl-4-hydroxy-1-(3-[5-(1,2,4-triazol-4-yl)-1H-indol-3-yl]propyl)piperidine. mp>61° C. MS, ES$^+$, m/z=431 for (M+H)$^+$; δ (360 MHz, D$_6$-DMSO) 1.57–1.67 (1H, m, CH), 1.72–1.86 (3H, m, CH and CH$_2$C$\underline{H}_2$CH$_2$)), 2.31–2.65 (8H, m 4×CH$_2$N), 2.72 (2H, t, J=7 Hz, CH$_2$-indole), 3.72 (2H, s, NHC$\underline{H}_2$Ph), 4.55 (1H, s, OH), 7.15–7.32 (7H, m, Ar—H), 7.47 (1H, d, J=8 Hz, Ar—H), 7.77 (1H, d, J=2 Hz, Ar—H), 9.00 (2H, s, triazole-H), 11.06 (1H, s, indole-NH). (Found: C, 68.40; H, 6.53; N, 18.73. C$_{25}$H$_{30}$N$_6$O.0.15(CH$_2$Cl$_2$) requires C, 68.14; H, 6.89; N, 18.96%).

EXAMPLE 75

3-(Benzylamino)methyl-3-hydroxy-1-(2-[5-(1,2,4-triazol-4-yl)-1H-indol-3-yl]ethyl)pyrrolidine.

The title compound was prepared from 3-(t-butyloxycarbonylamino) methyl-3-hydroxypyrrolidine and 1-chloro-2-[5-(1,2,4-triazol-4-yl)-1H-indol-3-yl]ethane (prepared from 2-[5-(1,2,4-triazol-4-yl)-1H-indol-3-yl] ethanol), followed by deprotection and functionalisation as described for 4-(benzylamino)methyl-4-hydroxy-1-(3-[5-(1,2,4-triazol-4-yl)-1H-indol-3-yl]propyl)piperidine. mp>56° C. MS, ES$^+$, m/z=417 for (M+H)$^+$; δ (360 MHz, D$_6$-DMSO) 1.60–1.68 (1H, m, CH), 1.80–1.88 (1H, m, CH), 2.40–2.76 (8H, m, 4×CH$_2$N), 2.84 (2H, t, J=7 Hz, CH$_2$-indole), 3.72 (2H, s, NHC$\underline{H}_2$Ar), 4.56 (1H, s, OH), 7.17–7.36 (7H, m, Ar—H), 7.47 (1H, d, J=8 Hz, Ar—H), 7.78 (1H, d, J=2 Hz, Ar—H), 9.01 (2H, s, triazole-H), 11.07 (1H, s, indole-NH). (Found: C, 67.40; H, 6.68; N, 19.54. C$_{24}$H$_{28}$N$_6$O.0.5 H$_2$O requires C, 67.74; H, 6.87; N, 19.75%).

EXAMPLE 76

1-{3-[5-(1,2,4-Triazol-4-yl)-1H-indol-3-yl]propyl}-4-{(R)-α-[(carbamoyl)oxymethyl] benzylamino}piperidine. 1.75 Hydrogen Oxalate.

1. (R)-α-[(carbamoyl)oxymethyl]benzylamine

To a stirred solution of N-tert-butyloxycarbonyl-(R)-2-phenylglycinol (500 mg, 2.1 mmol) in anhydrous dichloromethane (10 ml) was added dropwise, under nitrogen, trichloroacetyl isocyanate (2750μl, 2.31 mmol) over 2 minutes. The resulting clear colourless solution was stirred at room temperature for 45 minutes before neutral alumina (activity III; 12 g) was added and stirring was continued for a further 40 minutes. The mixture was filtered, and the alumina was washed with dichloromethane (1×25 ml) and with dichloromethane-ethyl acetate (1:1, 3×25 ml). The filtrate was concentrated under vacuum to leave a white solid which was dissolved in dichloromethane-trifluoroacetic acid (3:1, 40 ml) and the solution was allowed to stand at room temperature for 35 minutes. Solvents were removed under vacuum and the residue was azeotroped with methanol (2×50 ml). Flash chromatography of the residue (silica gel, dichloromethane/methanol/ammonia, 90:10:1) gave 333 mg (885) of the title compound as a white solid: δ$_H$ (360 MHz, CDCl$_3$) 4.06 (1H, dd, J=11.8 Hz and 9.5 Hz), 4.21–4.28 (2H, m), 4.68 (2H, br s), 7.24–7.40 (5H, m); m/e (ES) 181 (M$^+$+1).

2. 1-{3-[5-(1,2,4-Triazol-4-yl)-1H-indol-3-yl]propyl}-4-{(R)-α-[(carbamoyl) oxymethyl]benzylamino}piperidine. 1.75 Hydrogen Oxalate.

The title compound was prepared in 65% yield from 1-{3-[5-(1,2,4-triazol-4-yl)-1H-indol-3-yl]propyl}-4-ketopiperidine and (R)-α-[(carbamoyl) oxymethyl]benzylamine using a similar method to that described for Example 8 (step 5), mp 135°–140° C. (EtOH). (Found: C, 56.56; H, 5.89; N, 15.34. C$_{27}$H$_{33}$N$_7$O$_2$.1.75(C$_2$H$_2$O$_4$) requires: C, 56.78; H, 5.70; N, 15.20%). δ$_H$(360 MHz, DMSO-d$_6$; 353° K. 1.44–1.62 (2H, m), 1.74–1.82 (1H, m), 1.88–2.06 (3H, m), 2.55–2.68 (1H, m), 2.72–2.90 (4H, m), 2.91–3.0 (2H, m), 3.18–3.32 (2H, m), 3.92–4.06 (3H, m), 6.18 (2H, s,), 7.20–7.40 (7H, m), 7.48 (1H, d, J=8.6 Hz), 7.73 (1H, d, J=2.0 Hz), 8.87 (2H, s,), 10.97 (1H, s); m/e (ES) 488 (M$^+$+1).

EXAMPLE 77

1-{3-[5-(1,2,4-Triazol-4-yl)-1H-indol-3-yl]propyl}-4-{[(1R,2S)-2-hydroxy-1-phenyl] propylamino}piperidine. 2.45 Hydrogen Oxalate.

The title compound was prepared from 1-{3-[5-(1,2,4-triazol-4-yl)-1H-indol-3-yl]propyl}-4-ketopiperidine and (1R,2S)-1-amino-1-phenyl-2-propanol (*Helv. Chim. Acta*, 1983, 66, 2274) using a similar method to that described for Example 8 (step 5), mp 130°–135° C. (EtOH-diethyl ether).

(Found: C, 56.47; H, 5.82; N, 12.37. $C_{27}H_{34}N_6O.2.45$ $(C_2H_2O_4)$ requires: C, 56.41; H, 5.77; N, 12.37%). $\delta_H$ (360 MHz, DMSO-$d_6$) 1.85 (3H, d, J=6.1 Hz), 1.68–1.84 (2H, m), 1.90–2.16 (4H, m), 2.60–2.96 (7H, m), 3.28–3.42 (2H, m), 4.10–4.22 (2H, m), 7.26–7.42 (5H, m), 7.44–7.54 (3H, m), 7.78 (1H, d, J=1.9 Hz), 9.01 (2H, s), 11.17 (1H, s); m/e (ES) 459 ($M^+$+1).

EXAMPLE 78

1-{3-[5-(1,2,4-Triazol-4-yl)-1H-indol-3-yl]propyl}- 4-{[(1R,2R)-2-hydroxy-1-phenyl] propylamino}piperidine. 2.45 Hydrogen Oxalate.

The title compound was prepared from 1-{3-[5-(1,2,4-triazol-4-yl)-1H-indol-3-yl]propyl}-4-ketopiperidine and (1R,2R)-1-amino-1-phenyl-2-propanol (*Helv. Chim. Acta*, 1983, 66, 2274) using a similar method to that described for Example 8 (step 5), mp 124°–129° C. (EtOH-diethyl ether). (Found: C, 56.40; H, 5.60; N, 12.50. $C_{27}H_{34}N_6O.2.45$ $(C_2H_2O_4)$ requires: C, 56.41; H, 5.77; N, 12.37%). $\delta_H$ (360 MHz, DMSO-$d_6$) 1.64–2.12 (6H, m), 2.60–2.78 (5H, m,), 2.80–2.92 (2H, m), 3.24–3.28 (2H, m), 3.87 (2H, br s), 7.26–7.50 (8H, m), 7.77 (1H, d, J=2.0 Hz), 9.01 (2H, s), 11.16 (1H, s,); m/e (ES) 459 ($M^+$+1).

EXAMPLE 79

1-{3-[5-(1,2,4-Triazol-4-yl)-1H-indol-3-yl]propyl}- 4-{[(R,S)-1-hydroxy-2-phenylpropan-2-yl] amino}piperidine. 2.0 Hydrogen Oxalate.

To a stirred solution of 1-{3-[5-(1,2,4-triazol-4-yl)-1H-indol-3-yl]propyl}-4-ketopiperidine (0.133 g, 0.41 mmol) and (R,S)-2-amino-2-phenyl-1-propanol (76 mg, 0.50 mmol) in anhydrous methanol (8 ml), under nitrogen, was added glacial acetic acid (94 µl, 1.64 mmol). After a further 30 minutes, sodium cyanoborohydride (32 mg, 0.50 mmol) was added and stirring was continued at room temperature for 2 days. Saturated aqueous potassium carbonate was added and the mixture was extracted with ethyl acetate (4×25 ml). The combined organic extracts were dried ($Na_2SO_4$) and evaporated in vacuo. The residue was purified by flash chromatography (silica gel, dichloromethane/ methanol/ammonia, 92:8:0.8) and the resulting oxazolidine was dissolved in ethanol (8 ml) and glacial acetic acid (0.33 ml, 5.76 mmol) and sodium borohydride (0.58 g, 15.2 mmol) was added portionwise over 4 days whilst stirring at 20°–80° C. The reaction mixture was then partitioned between water (75 ml) and ethyl acetate (50 ml). The aqueous layer was extracted with more ethyl acetate (3×30 ml) and the combined organic extracts were dried ($Na_2SO_4$) and evaporated in vacuo. Flash chromatography of the residue (silica gel, dichloromethane/methanol/ammonia, 90:10:1 to 85:15:1.5) gave 12 mg (7%) of the title compound free base. The oxalate salt was prepared in methanol-diethyl ether, mp 123°–126° C. (Found: C, 56.47; H, 6.14; N, 12.53. $C_{27}H_{34}N_6O.2(C_2H_2O_4).1.2$ $H_2O.0.1(C_4H_{10}O)$ requires: C, 56.48; H, 6.25; N, 12.59%). $\delta_H$ (360 MHz, DMSO-$d_6$) 1.56 (3H, s), 1.62–1.82 (4H, m), 1.95 (2H, m), 2.59–2.92 (7H, m), 3.25 (2H, m), 3.63 (2H, dd), 7.30–7.32 (3H, m), 7.38 (2H, t, J=7.5 Hz), 7.49 (1H, d, J=8.6 Hz), 7.55 (2H, d, J=7.4 Hz), 7.77 (1H, d,), 9.01 (2H, s,), 11.16 (1H, s,); m/e (ES) 459 ($M^+$+1).

EXAMPLE 80

1-{3-[5-(1,2,4-Triazol-4-yl)-1H-indol-3-yl]propyl}- 4-{[(R)-2-hydroxy-1-(4-fluorophenyl)ethyl] amino}piperidine. 2.0 Hydrogen Oxalate.
1. (R)-2-Amino-2-(4-fluorophenyl)ethanol To a stirred 1.0M solution of lithium aluminium hydride in THF (23.5 ml, 23.5 mmol), cooled to 0° C. under Ar, was added portionwise over 1 h 45 min solid (−)-4-fluoro-D-α-phenylglycine (1.98 g, 11.7 mmol). The reaction mixture was then stirred at room temperature overnight before carefully adding water (0.89 ml), then 4N NaOH solution (0.89 ml) and then water (2.68 ml). The mixture was stirred for a few minutes, then filtered, and the filtrate was evaporated in vacuo. Flash chromatography of the residue (silica gel, dichloromethane/methanol/ammonia, 90:10:1) gave 1.499 g (82%) of the title compound as a white solid: $\delta_H$ (250 MHz, $CDCl_3$) 3.52 (1H, dd, J=10.7 and 8.2 Hz), 3.71 (1H, dd, J=10.7 and 4.4 Hz), 4.06 (1H, dd, J=8.1 and 4.4 Hz), 6.99–7.08 (2H, m), 7.28–7.34 (2H, m).
2. 1-{3-[5-(1,2,4-Triazol-4-yl)-1H-indol-3-yl]propyl}-4-{[(R)-2-hydroxy-1-(4-fluorophenyl)ethyl]amino}piperidine. 2.0 Hydrogen Oxalate.

This was prepared from 1-{3-[5-(1,2,4-triazol-4-yl)-1H-indol-3-yl]propyl}-4-ketopiperidine and (R)-2-amino-2-(4-fluorophenyl)ethanol using a similar method to that described in Example 8 (step 5); mp 137° C. (softens). (Found: C, 54.92; H, 5.49; N, 12.51. $C_{26}H_{31}FN_6O.2.0$ $(C_2H_2O_4).0.7$ $H_2O.0.15(CH_4O).0.12(C_4H_{10}O)$ requires C, 55.00; H, 5.76; N, 12.56%). $\delta_H$ (360 MHz, DMSO-$d_6$) 1.72 (2H, m), 1.90–2.05 (4H, m), 2.66–2.86 (5H, m), 2.94 (2H, m), 3.37 (2H, m), 3.61 (2H, m), 4.19 (1H, m), 7.23 (2H, t, J=8.8 Hz), 7.32–7.34 (2H, m), 7.49–7.55 (3H, m), 7.80 (1H, d), 9.02 (2H, s), 11.18 (1H, s); m/e (ES) 463 ($M^+$+1).

EXAMPLE 81

1-{3-[5-(1,2,4-Triazol-4-yl)-1H-indol-3-yl]propyl}- 4-{[(1R,2R)-2-hydroxyindan-1-yl]amino}piperidine. 2.0 Hydrogen Oxalate.
1. (1R,2R)-1-Amino-2-hydroxyindan Racemic trans-1-amino-2-hydroxyindan was resolved into its individual enantiomers using a similar procedure to that described in the literature: *J. Med. Chem.*, 1992, 35, 1685. The chiral purity of the individual enantiomers was assessed by HPLC analysis using a CrownPack CR(+) column (5% methanol in aqueous perchloric acid, pH 1.8; 1 ml/min; 40° C.; 210 nm); retention time for (1R,2R)-enantiomer, 3.8 min, 98.2% e.e. (retention time for (1S,2S)-enantiomer, 4.4 min).
2. 1-{3-[5-(1,2,4-Triazol-4-yl)-1H-indol-3-yl]propyl}-4-{[(1R,2R)-2-hydroxyindan-1-yl]amino}piperidine. 2.0 Hydrogen Oxalate.

The title compound was prepared from the product of the previous step and 1-{3-[5-(1,2,4-triazol-4-yl)-1H-indol-3-yl]propyl}-4-ketopiperidine using a similar method to that described for Example 8 (step 5), mp 156°–158° C. (methanol-diethyl ether). (Found: C, 58.17; H, 5.69; N, 13.19. $C_{27}H_{32}N_6O.2.0$ $(C_2H_2O_4)$ requires: C, 58.48; H, 5.70; N, 13.20%). $\delta^H$ (360 MHz, DMSO-$d_6$) 1.78–2.00 (2H, m), 2.00–2.10 (2H, m), 2.10–2.20 (1H, m), 2.20–2.40 (1H, m), 2.70–2.90 (5H, m), 2.90–3.00 (2H, m), 3.20–3.35 (1H, m), 3.35–3.50 (3H, m), 4.35–4.50 (2H, m), 7.20–7.40 (5H, m), 7.40–7.55 (2H, m), 7.81 (1H, s), 9.03 (2H, s), 11.19 (1H, s); m/e (ES) 457 ($M^+$+1).

Examples 82–84 were prepared from 1-{3-[5-(1,2,4-triazol-4-yl)-1H-indol-3-yl]propyl}-4-ketopiperidine and commercially available amines using a similar method to that described for Example 8 (step 5).

EXAMPLE 82

1-{3-[5-(1,2,4-Triazol-4-yl)-1H-indol-3-yl]propyl}- 4-{[(R,S)-indan-1-yl]amino}piperidine. 2.55 Hydrogen Oxalate.

The oxalate salt was prepared from ethanol-diethyl ether, mp 122°–128° C. (Found: C, 57.47; H, 5.55; N, 12.40.

$C_{27}H_{32}N_6.2.55(C_2H_2O_4)$ requires: C, 57.53; H, 5.58; N, 12.54%). $\delta^H$ (360 MHz, DMSO-$d_6$) 1.84–2.28 (7H, m), 2.38–2.50 (1H, m), 2.72–3.16 (8H, m), 3.30–3.52 (3H, m), 4.85 (1H, br t), 7.24–7.38 (5H, m), 7.50 (1H, d, J=8.6 Hz), 7.58 (1H, d, J=7.5 Hz), 7.82 (1H, s), 9.03 (2H, s), 11.20 (1H, s); m/e (ES) 441 (M$^+$+1).

EXAMPLE 83

1-{3-[5-(1,2,4-Triazol-4-yl)-1H-indol-3-yl]propyl}-4-{[(R,S)-1-(4-fluorophenyl)ethyl]amino}piperidine. 2.0 Hydrogen Oxalate.

The oxalate salt was prepared in methanol-diethyl ether, mp 149° C. (softens). (Found: C, 57.44; H, 5.89; N, 13.33. $C_{26}H_{31}FN_6.2(C_2H_2O_4)$. 0.17($C_4H_{10}O$) requires: C, 57.65; H, 5.79; N, 13.15%). $\delta_H$ (360 MHz, DMSO-$_6$)1.44 (3H, d, J=6.3 Hz), 1.72 (2H, m), 1.91–2.13 (4H, m), 2.58–2.90 (7H, m), 3.30 (2H, m), 4.34 (1H, m), 7.25 (2H, t, J=8.8 Hz), 7.31–7.33 (2H, m), 7.50 (1H, d, J=8.6 Hz), 7.56 (2H, m), 7.79 (1H, d), 9.02 (2H, s), 11.17 (1H, s). m/e (ES) 447 (M$^+$+1).

EXAMPLE 84

1-{3-[5-(1,2,4-Triazol-4-yl)-1H-indol-3-yl]propyl}4-{[(R)-1-phenylpropan-2-yl]amino}piperidine. 2.0 Hydrogen Oxalate.

The oxalate salt was prepared in methanol-diethyl ether; mp 145° C. (softens). (Found: C, 59.42; H, 6.69; N, 13.11. $C_{27}H_{34}N_6.2(C_2H_2O_4)$. 0.3 $H_2O.0.25(C_4H_{10}O)$ requires: C, 59.44; H, 6.41; N, 13.00%), $\delta_H$(360 MHz, DMSO-$d_6$) 1.07 (3H, d, J=6.6 Hz), 1.72 (2H, m), 1.94 (2H, m), 2.06 (2H, m), 2.42 (1H, m), 2.55–2.77 (6H, m), 3.15–3.29 (4H, m), 3.44 (1H, m), 7.26–7.34 (7H, m), 7.50 (1H, d, J=8.6 Hz), 7.80 (1H, d), 9.03 (2H, s), 11.16 (1H, s); m/e (ES) 443 (M$^+$+1).

EXAMPLE 85

1-{3-[5-(1,2,4-Triazol-4-yl)-1H-indol-3-yl]propyl}-4-{N-[(thiophen-3-yl)methyl]-N-methylamino}piperidine. 2.5 Hydrozen Oxalate. Dihydrate.

The title compound was prepared using a similar method to that described for Example 30 (step 4). The oxalate salt was prepared and recrystallised from methanol-diethyl ether, mp 135°–137° C. (Found: C, 50.57; H, 5.43; N, 12.77. $C_{24}H_{30}N_6S.2.25(C_2H_2O_4)$. 2 $H_2O$ requires C, 50.85; H, 5.76; N, 12.48%). $\delta_H$(360 MHz, DMSO-$d_6$) 1.35–1.50 (2H, m), 1.64–1.72 (2H, m), 1.72–1.84 (4H, m), 2.09 (3H, s), 2.22–2.34 (3H, m), 2.68–2.72 (2H, m), 2.86–2.90 (2H, m), 3.53 (2H, s), 6.99–7.01 (1H, m), 7.24–7.30 (3H, m), 7.43–7.47 (2H, m), 7.77–7.78 (1H, m), 9.01 (2H, s), 11.05 (1H, s); m/e (ES) 435 (M$^+$+1).

EXAMPLE 86

1-{3-[5-(1,2,4-Triazol-4-yl)-1H-indol-3-yl]propyl}-4-{N-[(furan-3-yl)methl]-N-methylamino}piperidine. 1.5 Hydrogen Oxalate. 2.25 Hydrate.

The title compound free base was prepared in a similar manner to that described in Example 30 (step 4). The oxalate salt was prepared and crystallised from methanol-diethyl ether, mp 128°–130° C. (Found: C, 55.00; H, 6.74; N, 13.53. $C_{24}H_{30}N_6O.1.5(C_2H_2O_4)$. 2.5 $H_2O.0.14(C_4H_{10}O)$ requires: C, 54.76; H, 6.49; N, 13.90%). $\delta_H$ (250 MHz, DMSO-$d_6$) 1.70–1.80 (2H, m), 1.80–2.10 (4H, m), 1.24 (3H, s), 2.60–2.80 (4H, m), 2.85–2.90 (2H, m), 3.30–3.40 (3H, m), 3.62 (2H, s), 6.46 (1H, s), 7.29–7.34 (2H, m), 7.48–7.51 (1H, m), 7.63 (2H, s), 7.80 (1H, s), 9.02 (2H, s), 11.18 (1H, s).

EXAMPLE 87

1-{3-[5-(1,2,4-Triazol-4-yl)-1H-indol-3-yl]propyl}-4-[(furan-3-yl)methylamino]piperidine. 2.0 Hydrogen Oxalate. 1.5 Hydrate.

A mixture of the product from Example 9 (free base; 765 mg), ammonium formate (349 mg) and palladium on carbon (10% w/w; 300 mg) in anhydrous methanol (10 ml) was refluxed, under nitrogen, for 3 h. After cooling, the solids were filtered off and the filtrate was concentrated under vacuum. The residue was partitioned between water and n-butanol, and the organic layer was concentrated to yield 544 mg of 1-{3-[5-(1,2,4-triazol-4-yl)-1H-indol-3-yl] propyl}-4-aminopiperidine as a white foam. $\delta_H$ (360 MHz, DMSO-$d_6$) 1.20–1.40 (2H, m), 1.70–2.04 (6H, m), 2.35–2.41 (2H, m), 2.68–2.74 (2H, m), 2.89–2.94 (3H, m), 7.27–7.32 (2H, m), 7.47 (1H, d), 7.77 (1H, d), 9.02 (2H, s), 11.12 (1H, s).

A solution of the preceding amine (150 mg, 0.46 mmol), 3-furaldehyde (47 mg, 0.49 mmol), acetic acid (160 μl, 2.77 mmol) and sodium cyanoborohydride (30 mg, 0.49 mmol) in methanol (20 ml) was stirred at room temperature, under nitrogen, for 18 h. Volatiles were removed under vacuum and the residue was partitioned between saturated aqueous potassium carbonate and ethyl acetate. The aqueous phase was extracted three times with ethyl acetate and the combined organic solutions were dried ($Na_2SO_4$) and concentrated. Flash chromatography of the residue (silica gel, dichloromethane/methanol/ammonia, 95:5:0.5 to 90:10: 1) gave 73 mg of the dialkylated amine (see Example 88) and 43 mg of the title compound free base, from which the oxalate salt was prepared, mp 150°–152° C. (methanol-diethyl ether). (Found: C, 53.13; H, 5.48; N, 13.54. $C_{23}H_{28}N_6O.2.0(C_2H_2O_4)$. 1.5 $H_2O$ requires: C, 53.02; H, 5.77; N, 13.74%). $\delta_H$ (360 MHz, DMSO-$d_6$) 1.60–1.70 (2H, m), 1.90–2.00 (2H, m), 2.05–2.10 (2H, m), 2.40–2.50 (5H, m), 2.70–2.80 (4H, m), 2.95–3.05 (1H, m), 3.15–3.20 (2H, m), 3.91 (2H, s), 6.57 (1H, s), 7.26–7.29 (2H, m), 7.47–7.49 (1H, m), 7.63 (1H, s), 7.70–7.73 (2H, m), 8.88 (2H, s), 10.95 (1H, s); m/e (ES) 405 (M$^+$+1).

EXAMPLE 88

1-{3-[5-(1,2,4-Triazol-4-yl)-1H-indol-3-yl]propyl}-4-{N,N-[di-furan-3-yl)methyl]amino}piperidine. Dihydrogen oxalate hydrate.

The title compound free base was isolated from the reaction described in Example 87. The oxalate salt was prepared and crystallised from methanol-diethyl ether, mp 119°–121° C. (Found: C, 56.18; H, 5.69: N, 12.40. $C_{28}H_{32}N_6O_2.2(C_2H_2O_4)$. $H_2O$ requires: C, 56.30; H, 5.61; N, 12.31%). $\delta_H$ (360 MHz, DMSO-$d_6$) 1.70–1.90 (4H, m), 2.02–2.10 (2H, m), 2.70–2.90 (5H, m), 2.95–3.05 (2H, m), 3.35–3.50 (2H, m), 3.49 (4H, s), 6.38 (2H, s), 7.27–7.30 (2H, m),7.47–7.53 (5H, m), 7.74–7.75 (1H, m), 8.88 (2H, s), 11.00 (1H, s); m/e (ES) 485 (M$^+$+1).

EXAMPLE 89

1-{3-[5-(1,2,4-Triazol-4-yl)-1H-indol-3-yl]propyl}-4-[N-(3,3-dimethylallyl)-N-methylaminol] piperidine. 1.25 Hydrogen Oxalate. 1.5 Hydrate.

A solution of 1-{3-[5-(1,2,4-triazol-4-yl)-1H-indol-3-yl] propyl}-4-(N-methylamino)piperidine (417 mg, 1.23 mmol), prenylbromide (149 μl, 1.29 mmol) and potassium carbonate (170 mg, 1.29 mmol) in dimethylformamide (10 ml) was heated to 80° C. for 16 h. The reaction was partitioned between water and ethyl acetate. The organic layer was dried ($Na_2SO_4$), concentrated and purified by chromatography using $CH_2Cl_2$/MeOH/$NH_4$OH (90:10:1) as eluant, to give the title compound free base. The oxalate salt was prepared and crystallised from methanoldiethyl ether, mp 128°–130° C. (Found: C, 58.64; H, 7.44; N, 14.99. $C_{24}H_{34}N_6 \cdot 1.25(C_2H_2O_4)$. 1.5 $H_2O$ requires: C, 58.28; H, 7.29; N, 15.39%). $\delta_H$ (360 MHz, DMSO-$d_6$; free base) 1.30–1.50 (2H, m), 1.59 (3H, s), 1.60–1.67 (2H, m), 1.68 (3H, s), 1.78–1.84 (4H, m), 2.09 (2H, s), 2.24–2.31 (3H, m), 2.69–2.73 (2H, m), 2.86–2.89 (2H, m), 2.95–2.97 (2H, m), 5.10–5.14 (1H, m), 7.23 (1H, s), 7.25–7.28 (1H, m), 7.45–7.47 (1H, m), 7.75–7.76 (1H, m), 8.96 (2H, s), 11.02 (1H, s); m/e (ES) 407 ($M^+$+1).

EXAMPLE 90

1-{3-[5-(1,2,4-Triazol-4-yl)-1H-indol-3-yl]propyl}-4-(N-allyl-N-methylamino)peperidine. 2.25 Hydrogen oxalate.

The title compound was prepared in a similar manner to that described in Example 89, using allyl bromide as the alkylating agent, mp 124°–126° C. (methanol-diethyl ether). (Found: C, 54.97; H, 6.24; N, 14.11. $C_{22}H_{30}N_6 \cdot 2.25 (C_2H_2O_4)$ requires: C, 54.77; H, 5.98; N, 14.46%). $\delta_H$ (360 MHz, DMSO-$d_6$; free base) 1.34–1.45 (2H, m), 1.62–1.65 (2H, m), 1.77–1.84 (4H, m), 2.11 (3H, s), 2.27–2.31 (3H, m), 2.69–2.73 (2H, m), 2.86–2.89 (2H, m), 3.02–3.03 (2H, m), 5.05–5.08 (1H, m), 5.12–5.17 (1H, m), 5.72–5.82 (1H, m), 7.26–7.31 (2H, m), 7.46–7.48 (1H, m), 7.78–7.79 (1H, m), 9.01 (2H, s), 11.06 (1H, s); m/e (ES) 379 ($M^+$+1).

EXAMPLE 91

1-{3-[5-(1,2,4-Triazol-4-yl)-1H-indol-3-yl]propyl}-4-{[(indan-1-yl)amino]methyl}peperidine. Dihydrogen Oxalate. 0.5 Hydrate.

The title compound was prepared in a similar manner to that described in Example 22 (step c), except that 1-aminoindan was used instead of (R)-α-methylbenzylamine. The oxalate was prepared and crystallised from methanol-diethyl ether, mp 140°–142° C. (Found: C, 59.57; H, 6.11; N, 13.06. $C_{28}H_{34}N_6 \cdot 2(C_2H_2O_4)$. 0.5 $H_2O$ requires: C, 59.71; H, 6.11; N, 13.06%). $\delta_H$ (360 MHz, DMSO-$d_6$; free base) 1.26–1.33 (2H, m), 1.40–1.55 (1H, m), 1.75–1.79 (4H, m), 1.83–1.95 (4H, m), 2.35–2.42 (3H, m), 2.58–2.63 (2H, m), 2.75–2.84 (3H, m), 2.94–3.02 (3H, m), 4.20–4.24 (1H, m), 7.12–7.15 (2H, m), 7.18–7.22 (3H, m), 7.30–7.35 (1H, m), 7.45–7.48 (1H, m), 7.56 (1H, s), 8.50 (2H, s), 8.60 (1H, s); m/e (ES) 455 ($M^+$+1).

EXAMPLE 92

1-{3-[5-(1,2,4-Triazol-4-yl)-1H-indol-3-yl]proply}-4-{[N-[(R)-α-(hydroxymethyl)benzyl]-N-methylamino]methyl}piperidine. 2.0 Hydrogen Oxalate. 0.5 Hydrate.

The title compound free base was prepared from the amine of Example 31 using a similar method to that described for Example 10. The oxalate salt was prepared and crystallised from methanol-diethyl ether, mp 115°–117° C. (Found: C. 57.96; H. 6.25; N, 12.66. $C_{28}H_{36}N_6O \cdot 2.0 (C_2H_2O_4) \cdot 0.5 H_2O$ requires: C, 58.08; H, 6.24; N, 12.70%).

$\delta_H$ (360 MHz, $CDCl_3$; free base) 1.19–1.28 (2H, m), 1.68–1.95 (7H, m), 2.08–2.14 (4H, m), 2.23–2.31 (1H, m), 2.38–2.44 (2H, m), 2.74–2.80 (2H, m), 2.91–2.95 (2H, m), 3.59–3.65 (1H, m), 3.71–3.77 (1H, m), 3.92–4.00 (1H, m), 7.12–7.17 (4H, m), 7.30–7.34 (3H, m), 7.45–7.48 (1H, m), 7.56–7.57 (1H, m), 8.32 (1H, s), 8.47 (2H, s); m/e (ES) 473 ($M^+$+1).

EXAMPLE 93

(3R)-3-(Benzylthio)methyl-1-{2-[5-(1,2,4-triazol-4-yl)-1H-indol-3-yl]ethyl}pyrrolidine. Hydrogen Oxalate.

1. (3R)-3-(Benzylthio)methyl-1-(tert-butoxycarbonyl)pyrrolidine

To a stirred mixture of (3R)-1-(tert-butoxycarbonyl)-3-[(methane-sulfonyloxy)methyl]pyrrolidine (0.5071 g, 1.82 mmol) and anhydrous potassium carbonate (0.3764 g, 2.72 mmol) in DMF (13 ml), under argon, was added benzyl mercaptan (0.428 ml, 3.65 mmol) and the mixture was stirred overnight at room temperature, then at 60° C. for 4 h. The mixture was then partitioned between water (50 ml) and diethyl ether (30 ml). The aqueous layer was separated and reextracted with more diethyl ether (2×30 ml). The combined organic layers were dried ($MgSO_4$) and evaporated in uacuo. The residue was purified by flash chromatography (silica gel, 20% EtOAc/pet. ether) to give 0.5186 (93%) of the title compound as a colourless oil. $\delta_H$ (360 MHz, $CDCl_3$) 1.45 (9H, s), 1.56 (1H, m), 1.99 (1H, m), 2.32 (1H, m), 2.45 (2H, t, J=6.4 Hz), 2.97 (1H, m), 3.26 (1H, m), 3.61 (2H, m), 3.72 (2H, s), 7.22–7.40 (5H, m). m/e (ES+) 330 ($M+Na$)$^+$, 308 ($M+H$)$^+$, 252 ($M-CMe_3+2H$)$^+$, 234, 213, 208 ($M-Boc+2H$)$^+$.

2. (3R)-3-[(Benzylthio)methyl]pyrrolidine

To a stirred solution of (3R)-3-(benzylthio)methyl-1-(tert-butoxycarbonyl)pyrrolidine (0.2320 g, 0.755 mmol) in dichloromethane (3 ml), under argon, was added trifluoroacetic acid (1 ml) and the mixture was stirred at room temperature for 65 minutes before quenching with anhydrous methanol (2 ml) and evaporating in vacuo. More methanol (2 ml) was added to the residue and removed in vacuo. The residual oil was then dissolved in dichloromethane (25 ml) and washed with 2N NaOH solution (10 ml). The aqueous layer was reextracted with more dichloromethane (15 ml) and the combined dichloromethane extracts were washed with saturated NaCl solution (10 ml), dried ($Na_2SO_4$) and evaporated in vacuo. The residue was purified by flash chromatography (silica gel, $CH_2Cl_2$/MeOH/$NH_3$, 85:15:1.5) to give 0.1210 g (77%) of the title compound as a colourless oil. $\delta_H$ (250 MHz,$CDCl_3$) 1.41 (1H, m), 1.90–2.00 (1H, m), 2.24 (1H, m), 2.42–2.50 (2H, m), 2.57 (1H, dd, J=6.5 and 11.0 Hz), 2.82–2.99 (2H, m), 3.07 (1H, dd, J=7.3 and 11.0 Hz), 3.72 (2H, s), 7.20–7.36 (5H, m); m/e (ES) 208 ($M^+$+1).

3. (3R)-3-(Benzylthio)methyl-1-{2-[5-(1,2,4-triazol-4-yl)-1H-indol-3-yl]ethyl}pyrrolidine. Hydrogen Oxalate.

To a stirred solution of 3-[2-(methanesulfonyloxy)ethyl]-5-(1,2,4-triazol-4-yl)-1H-indole (0.1147 g, 0.374 mmol) and sodium carbonate (59.6 mg, 0.562 mmol) in 2-propanol (8 ml), under argon, was added a solution of (3R)-3[(benzylthio)methyl]pyrrolidine (0.1165 g, 0.562 mmol) in 2-propanol (5 ml) and the mixture was heated at reflux for 2 h. After cooling, the reaction mixture was filtered and the filtrate evaporated in uacuo. The residue was purified by flash chromatography (silica gel, $CH_2Cl_2$/MeOH/$NH_3$, 92:8:0.8) to give 0.1017 g (65%) of the title compound free base as a colourless oil. The oxalate salt was prepared in methanoldiethyl ether; mp 79°–91° C. (Found: C, 61.57; H, 5.94; N, 13.40. $C_{24}H_{27}N_5C_2H_2O_4.0.25(C_4H_{10}O)$ requires: C, 61.64; H, 6.03; N, 13.31%). $\delta_H$ (360 MHz, DMSO-$d_6$) 1.63 (1H, m), 2.10 (1H, m), 2.53 (2H), 2.92 (1H, m), 3.05 (2H, m), 3.25 (4H, m), 3.38 (1H, m), 3.76 (2H, s), 7.25 (1H, m), 7.32–7.33 (5H, m), 7.37 (1H, dd, J=9.1 and 2.1 Hz), 7.52 (1H, d, J=8.7 Hz), 7.88 (1H, d, J=2.0 Hz), 9.03 (2H, s,), 11.26 (1H, s), among other signals; m/e (ES$^+$) 418 (M+H)$^+$.

EXAMPLE 94

(±)-1-{3-[5-(1,2,4-Triazol-4-yl)-1H-indol-3-yl] propyl}-4-(1-benzylamino-2-hydroxyethyl) piperidine. 2.0 Hydrogen Oxalate. 2.0 Hydrate.

1. (±)-2-[1-(tert-Butyloxycarbonyl)piperidin-4-yl]glycine methyl ester.

The title compound was prepared from 1-(tert-butyloxycarbonyl)-4-ketopiperidine and (±)-N-(benzyloxycarbonyl)-α-phosphonoglycine trimethyl ester using a similar procedure to that described by U. Schmidt et al. (*Synthesis*, 1992, 487; *Synthesis*, 1984, 53); $\delta_H$ (250 MHz, CDCl$_3$) 1.19–1.78 (5H, m), 1.45 (9H, s), 2.60–2.74 (2H, m), 3.31 (1H, d, J=5.7 Hz), 3.73 (3H, s), 4.08–4.18 (2H, m).

2. (±)-2-[1-(tert-Butyloxycarbonyl)piperidin-4-yl]glycinol.

To a cooled (−78° C.) solution of the ester from above (1.7 g, 6.24 mmol) in anhydrous tetrahydrofuran (50 ml) was added lithium aluminium hydride (1.0M in THF; 6.24 ml). The mixture was stirred at −78° C. for 3 h and at room temperature for 18 h before water was added to produce a granular precipitate, which was removed by filtration. Concentration of the filtrate followed by flash chromatography of the remaining residue (silica gel, dichloromethane/methanol/ammonia, 90:10:1) afforded the title compound as a colourless oil; m/e (ES) 245 (M$^+$+1).

3. (±)-1-(tert-Butyloxyacarbonyl)-4-(1-benzylamino-2-hydroxyethyl)peperidine.

A solution of the preceding glycinol (730 mg, 2.99 mmol), benzaldehyde (317 mg, 2.99 mmol), acetic acid (2 ml) and sodium cyanoborohydride (188 mg, 2.99 mmol) in methanol (20 ml) was stirred at room temperature for 18 h. Saturated potassium carbonate solution was added to pH>8 and the methanol was removed under vacuum. The residue was diluted with water (20 ml) and products were extracted with ethyl acetate (50 ml), dried (Na$_2$SO$_4$) and concentrated. Flash chromatography (silica gel, dichloromethane/methanol/ammonia, 90:10:1) of the residue afforded 417 mg (42%) of the title compound as a yellow oil; $\delta_H$ (360 MHz, DMSO-$d_6$) 1.00–1.10 (1H, m), 1.38 (9H, s), 1.50–1.64 (2H, m), 1.64–1.78 (1H, m), 2.50–2.70 (2H, m), 3.31–3.34 (1H, m), 3.40–3.50 (1H, m), 3.60–3.80 (2H, m), 3.90–4.00 (2H, m), 4.40–4.43 (1H, m), 7.20–7.34 (5H, m).

4. (±)-4-(1-Benzylamino-2-hydroxyethyl)piperidine

A solution of the product from step 3 (417 mg, 1.25 mmol) in a mixture of trifluoroacetic acid and dichloromethane (1:10;10 ml) was stirred for 16 h. The reaction was quenched by addition of saturated aqueous potassium carbonate and extracted with dichloromethane. The organic phase was dried (MgSO$_4$) and concentrated. Flash chromatography of the residue (silica gel, dichloromethane/methanol/ammonia, 90:9:1) gave the title compound as a colourless solid; $\delta_H$ (250 MHz, DMSO-$d_6$) 1.20–1.46 (2H, m), 1.56–1.76 (2H, m), 1.78–1.90 (1H, m), 2.20–2.30 (1H, m), 2.60–2.76 (2H, m), 3.10–3.60 (4H, m), 3.65 (1H, d, J=13.5 Hz), 3.79 (1H, d, J=13.5 Hz), 7.16–7.38 (5H, m).

5. (±)-1-{3-[5-(1,2,4-Triazol-4-yl)-1H-indol-3-yl]propyl}-4-(1-benzylamino-2-hydroxyethyl)piperidine. 2.0 Hydrogen Oxalate. 2.0 Hydrate.

The title compound was prepared from 3-[5-(1,2,4-triazol-4-yl)-1H-indol-3-yl]propan-1-ol and (±)-4-(1-benzylamino-2-hydroxyethyl)piperidine using a similar procedure to that described for Example 98 (step 3). The oxalate salt was prepared and crystallised from ethanol-diethyl ether; mp 125°–127° C. (Found: C, 55.23; H, 6.37; N, 11.66. $C_{27}H_{34}N_6O$-2($C_2H_2O_4$). 2 H$_2$O.0.3($C_4H_{10}O$) requires: C, 55.49; H, 6.51; N, 12.06%). $\delta_H$ (360 MHz, DMSO-$d_6$) 1.50–1.70 (2H, m), 1.80–1.90 (2H, m), 1.90–2.10 (3H, m), 2.70–2.95 (5H, m), 2.95–3.10 (2H, m), 3.40–3.50 (2H, m), 3.55–3.70 (1H, m), 3.70–3.74 (1H, m), 4.04–4.19 (2H, m), 7.32–7.40 (6H, m), 7.48–7.52 (3H, m), 7.82 (1H, m), 9.03 (2H, s), 11.22 (1H, s); m/e (ES) 460 (M$^+$+1).

EXAMPLE 95

1-{3-[5-(1,2,4-Triazol-1-yl)-1H-indol-3-yl]propyl}-4-[(R)-α-(hydroxymethyl)benzylamino]piperidine. 1.9 Hydrogen Oxalate.

1. 1-{3-[5-(1,2,4-Triazol-1-yl)-1H-indol-3-yl]propyl}-4-hydroxypiperidine.

The title compound was prepared from 4-(1,2,4-triazol-1-yl)-phenylhydrazine (EP497,512) and 5-(4-hydroxypiperidin-1-yl)pentanal dimethyl acetal using a similar method to that described for Example 8 (step 3). $\delta_H$ (250 MHz, DMSO-$d_6$) 1.28–1.46 (2H, m), 1.64–2.04 (6H, m), 2.30 (2H, t, J=6.8 Hz), 2.72 (4H, br t), 3.35–3.50 (1H, m), 4.53 (1H, d, J=4.2 Hz), 7.25 (1H, d, J=2.2 Hz), 7.44–7.54 (2H, m), 7.92 (1H, d, J=1.7 Hz), 8.18 (1H, s), 9.18 (1H, s), 11.06 (1H, s); m/e (ES) 326 (M$^+$+1).

2. 1-{3-[5-(1,2,4-Triazol-1-yl)-1H-indol-3-yl]propyl}-4-ketopiperidine.

The title compound was prepared from the product of the previous step following a similar procedure to that described in Example 8 (step 4); pale yellow solid, mp 158°–161° C. (ethyl acetate); $\delta_H$ (360 MHz. CDCl$_3$) 1.96 (2H, qn, J=7.3 Hz), 2.46 (4H, t, J=6.1 Hz), 2.55 (2H, t, J=7.2 Hz), 2.75 (4H, t, J=6.1 Hz), 2.86 (2H, t, J=7.5 Hz), 7.12 (1H, d, J=2.2 Hz), 7.40–7.48 (2H, m), 7.88 (1H, s), 8.12 (1H, s), 8.20 (1H, br s), 8.53 (1H, s); m/e (ES) 324 (M$^+$+1).

3. 1-{3-[5-(1,2,4-Triazol-1-yl)-1H-indol-3-yl]propyl}-4-[(R)-α-(hydroxymethyl)benzylamino]piperidine. 1.9 Hydrogen Oxalate.

The title compound was prepared from the product of the previous step and (R)-2-phenylglycinol using a similar method to that described for Example 8 (step 5), mp 155°–160° C. (ethanol). (Found: C, 58.11; H, 6.04; N, 13.44. $C_{26}H_{32}N_6O.1.9(C_2H_2O_4)$ requires: C, 58.14; H, 5.86; N, 13.65%). $\delta_H$ (360 MHz, DMSO-$d_6$) 1.56–1.76 (2H, m), 1.84–2.12 (4H, m), 2.60–2.96 (7H, m), 3.24–3.38 (2H, m), 3.50–3.64 (2H, m), 4.04–4.16 (1H, m), 7.26–7.56 (8H, m), 7.92 (1H, s), 8.18 (1H, s), 9.16 (1H, s), 11.14 (1H, s); m/e (ES) 445 (M$^+$+1).

EXAMPLE 96

1-{3-[5-(Imidazol-1-yl)-1H-indol-3-yl]propyl}-4-[(R)-α-(methyl)benzylamino]piperidine. 2.6 Hydrogen Oxalate.

1. 4-(Imidazol-1-yl)nitrobenzene.

To a stirred solution of imidazole (34.1 g, 0.50 mol) in DMF (300 ml) under Ar, was added portionwise, over 23 minutes, 60% NaH in oil (20.02 g, 0.50 mol). The mixture was then stirred at room temperature for 18 minutes before adding dropwise, over 40 minutes, a solution of 1-fluoro-4-nitrobenzene (70.62 g, 0.50 mol) in DMF (60 ml). The mixture was then stirred at room temperature overnight. Water (600 ml) was then added and the solid was filtered off, washed with water, then stirred in boiling ethyl acetate (400 ml), allowed to cool and filtered, washing the solid with more ethyl acetate (50 ml), then petroleum ether (250 ml). The filtrate, now containing more solid, was refiltered and washed with petroleum ether. The combined solids were dried in a vacuum dessicator overnight to give 90.14 g (95%) of the title compound as a yellow solid. $\delta_H$ (360 MHz, DMSO-$d_6$) 9 (1H, t, J=1.1 Hz), 7.97–8.03 (3H, m), 8.38 (2H, d, J=9.2 Hz), 8.52 (1H, t).

2. 4-(Imidazol-1-yl)aniline. Dihydrochloride.

A mixture of 4-(imidazol-1-yl)nitrobenzene (89.60 g, 0.474 mol) and 10% palladium on carbon (4.50 g) in ethanol (1200 ml) and 5N HCl (189 ml) was hydrogenated in two batches at 40 psi for 80 minutes. Water (450 ml) was then added to dissolve the product and the catalyst was removed by filtration, washing with more water, and the combined filtrates were evaporated in vacuo, using finally a freeze drier, to give 105.4 g (96%) of the title compound as a cream solid. $\delta_H$ (250 MHz, $D_2O$) 7.22 (2H, d, J=8.8 Hz), 7.35 (1H, t, J=2.1 Hz), 7.44 (2H, d, J=9.0 Hz), 7.59 (1H, t, J=1.8 Hz), 8.89 (1H, t, J=1.5 Hz).

3. 4-(Iamidazol-1-yl)phenylhydrazine. Dihydrochloride.

To a cooled (−15° C.) and stirred suspension of 4-(imidazol-1-yl)-dihydrochloride (20 g, 86.16 mmol) in concentrated hydrochloric acid (100 ml) was added dropwise, over 1 hour, a solution of sodium nitrite (6.25 g, 9.05 mmol) in water (40 ml). After a further 10 minutes of stirring at −12° C., the mixture was quickly filtered to remove a solid, and the filtrate was added portionwise to a cooled (−20° C.) and stirred solution of tin (II) chloride dihydrate (100 g) in concentrated hydrochloric acid (50 ml) at such a rate as to maintain the internal temperature below −10° C. (15 minutes). The mixture was allowed to warm to 5° C. over 30 minutes, and the solid was collected and washed with diethyl ether (4×100 ml). The above solid was suspended in water (200 ml) and basified with 4N sodium hydroxide solution and extracted with ethyl acetate (5×500 ml). The combined organic solutions were dried ($Na_2SO_4$) and filtered. The filtrate was vigorously stirred while hydrogen chloride was being bubbled through the solution until a deep red mixture was obtained. Stirring was continued for a further 20 minutes to give a cream solid which was collected by filtration and dried over phosphorous pentoxide-potassium hydroxide under high vacuum to leave 12.7 g (60%) of the title compound; $\delta_H$ (360 MHz, DMSO-$d_6$) 7.20 (2H, d, J=9.0 Hz), 7.73 (2H, d, J=9.0 Hz), 7.91 (1H, t, J=1.5 Hz), 8.23 (1H, t, J=1.7 Hz), 9.71 (1H, t, J=1.3 Hz).

4. 1-{3-[5-(Imidazol-1-yl)-1H-indol-3-yl]propyl}-4-ketopiperidine

The title compound was prepared from 4-(imidazol-1-yl)-phenylhydrazine dihydrochloride and 5-(4-hydroxypiperidin-1-yl)-pentanal dimethyl acetal using a similar method to that described for Example 8 (steps 3 and 4); $\delta_H$ (250 MHz, $CDCl_3$) 1.96 (2H, qn, d=7.5 Hz), 2.46 (4H, t, J=6.1 Hz), 2.56 (2H, t, J=7.4 Hz), 2.76 (4H, t, J=6.1 Hz), 2.84 (2H, t, J=7.5 Hz), 7.13 (1H, d, J=2.2 Hz), 7.18–7.23 (2H, m), 7.30 (1H, t, J=1.2 Hz), 7.44 (1H, d, J=8.5 Hz), 7.58 (1H, d, J=2.1 Hz), 7.84 (1H, t, J=1.0 Hz), 8.41 (1H, br s); m/e (ES) 323 ($M^+$+1).

5. 1-{3-[5-(Imidazol-1-yl)-1H-indol-3-yl]propyl}-4-[(R)-α-(methyl)benzylamino]piperidine. 2.6 Hydrogen Oxalate.

This was prepared from 1-{3-[5-(imidazol-1-yl)-1H-indol-3-yl]propyl}-4-ketopiperidine (0.201 g, 0.62 mmol) and (R)-(+)-α-methylbenzylamine (95.3 µl, 0.75 mmol) using a similar method to that described in Example 8 (step 5) to give 0.237 g (89%) of the title compound, free base. The oxalate salt was prepared in methanol-diethyl ether, mp 130° C. (softens). (Found: C, 58.63; H, 5.98; N, 10.33. $C_{27}H_{33}N_5$.2.6($C_2H_2O_4$).0.17($C_4H_{10}O$) requires: C, 58.67; H, 5.96; N, 10.39%). $\delta_H$ (360 MHz, DMSO-$d_6$) 1.50 (3H, d, J=6.6 Hz), 1.75–1.82 (2H, m), 1.92–2.06 (3H, m), 2.12–2.16 (1H, m), 2.73 (4H, m), 2.90 (3H, m), 3.38 (2H, m), 4.40 (1H, q), 7.13 (1H, s), 7.27–7.30 (2H, m), 7.37–7.47 (4H, m), 7.53 (2H, d, J=7.0 Hz), 7.68 (1H, s), 7.70 (1H, d), 8.20 (1H, s), 11.09 (1H, s); m/e (ES) 428 ($M^+$+1).

EXAMPLE 97

1-{3-[5-(Imidazol-1-yl)-1H-indol-3-yl]propyl}-4-[(R)-α-(hydroxymethyl)benzylamino]piperidine. 3.0 Hydrogen Oxalate.

The title compound was prepared from 1-{3-[5-(Imidazol-1-yl)-1H-indol-3-yl]propyl}-4-ketopiperidine (0.127 g, 0.40 mmol) and (R)-2-phenylglycinol (65 mg, 0.48 mmol) using a similar method to that described for Example 8 (step 5) to give 0.108 g (62%) of the title compound, free base. The oxalate salt was prepared in methanol-diethyl ether; mp 99°–102° C. (Found: C, 53.21; H, 5.45; N, 9.28. $C_{27}H_{33}N_5O$.3($C_2H_2O_4$).0.11($C_4H_{10}O$).1.8 $H_2O$ requires: C, 53.25; H, 5.84; N, 9.29%). $\delta_H$ (360 MHz, DMSO-$d_6$) 1.80–2.17 (6H, m), 2.72–2.96 (7H, m), 3.42 (2H, m), 3.71 (2H, d, J=5.6 Hz), 4.32 (1H, m), 7.19 (1H, s), 7.28–7.31 (2H, m), 7.40–7.48 (4H, m), 7.52 (2H, d, J=6.7 Hz), 7.72 (2H, s), 8.31 (1H, s), 11.11 (1H, s); m/e (ES) 444 ($M^+$+1).

EXAMPLE 98

1-{3-[5-(1,2,4-Triazol-1-yl)methyl-1H-indol-3-yl] propyl}-4-[(R)-α-(hydroxymethyl)benzylamino] piperidine. 2.0 Hydrogen Oxalate. 1.5 Hydrate.

1. 3-[5-(1,2,4-Triazol-1-yl)methyl-1H-indol-3-yl]propan-1-ol

A mixture of palladium acetate (0.78 g), lithium chloride (1.47 g), sodium carbonate (18.49 g), triphenylphosphine (1.8 g), 5-triethylsilyl-4-pentyn-1-ol triethylsilyl ether (16.3 g) and 2-iodo-4-[(1,2,4-triazol-1-yl)methyl]aniline (10.0 g) in degassed anhydrous dimethylformamide (400 ml) was heated at 100° C. for 10 h, under nitrogen. After cooling, the reaction was filtered, concentrated, and the residue was partitioned between water and ethyl acetate. The organic phase was dried ($MgSO_4$), concentrated and the residue was treated with 5N hydrochloric acid/methanol (1:3; 400 ml) for 3 h at room temperature. The methanol was removed under vacuum, the aqueous residue was basified with sodium carbonate solution and it was extracted with ethyl acetate. The combined organic extracts were dried ($MgSO_4$) and concentrated. Flash chromatography of the residue (silica gel, dichloromethane/methanol, 95:5) followed by trituration with petroleum ether, gave the title compound (56%) as a beige solid. $\delta_H$ (360 MHz, DMSO-$d_6$) 1.74–1.82 (2H, m), 2.66–2.70 (2H, m), 3.43–3.49 (2H, m), 4.41–4.44 (1H, m), 5.42 (2H, s), 7.01–7.04 (1H, m), 7.11–7.12 (1H, m), 7.28–7.30 (1H, m), 7.51 (1H, s), 7.93 (1H, s), 8.60 (1H, s), 10.79 (1H, s).

2. 4-[(R)-α-(Hydroxymethyl)benzyl]aminopiperidine.

To a stirred solution of N-tert-butyloxycarbonyl-4-piperidinone (2 g, 10 mmol), (R)-(−)-phenylglycinol (1.65 g, 12 mmol), and glacial acetic acid (2.29 ml, 40 mmol) in methanol (200 ml) was added sodium cyanoborohydride (754 mg, 12 mmol). After being stirred at room temperature, under nitrogen, for 16 h, the mixture was basified with 4N sodium hydroxide and the methanol was removed under vacuum. The residue was diluted with water (35 ml) and the product extracted with diethyl ether (2×200 ml), washed with brine (1×40 ml), dried ($Na_2SO_4$) and concentrated. Flash chromatography (silica gel, dichloromethane/ methanol/ammonia, 95:5:0.5) of the residue gave 2.91 g (90.9%) of 1-tert-butyloxycarbonyl-4-[(R)-α-(hydroxymethyl)benzyl]aminopiperidine.

A solution of the above BOC-protected piperidine (2.9 g) in trifluoroacetic acid (40 ml) and dichloromethane (50 ml) was allowed to stand at room temperature for 16 h. Solvents were removed under vacuum and the residue was azeotroped with toluene/ethanol (5:1, 150 ml). The residue was dissolved in 4N sodium hydroxide, extracted with dichloromethane (3×150 ml) and the combined organic solutions were washed with brine (1×50 ml), then dried ($Na_2SO_4$) and concentrated. Crystallisation from ethyl acetate/hexane (1:10, 200 ml) afforded the title compound as white crystals (1.4 g, 70.4%); $δ_H$ (360 MHz, DMSO-$d_6$) 0.96–1.12 (2H, m), 1.52 (1H, d, J=12.0 Hz), 1.78–2.06 (2H, br s and d, J=12.6 Hz), 2.17–2.32 (3H, m), 2.76–2.90 (2H, m), 3.26 (1H, t, J=8.5 Hz), 3.40 (1H, dd, J=10.5 and 4.5 Hz), 3.83 (1H, dd, J=8.5 and 4.5 Hz), 4.82 (1H, br s), 7.27–7.37 (5H, m); m/z (ES) 221 ($M^+$+1).

3. 1-{3-[5-(1,2,4-Triazol-1-yl)methyl-1H-indol-3-yl]propyl}-4-[(R)-α-(hydroxymethyl)benzylamino]piperidine. 2.0 Hydrogen Oxalate. 1.5 Hydrate.

A solution of the product from Step 1 (209 mg, 81 mmol) in THF (10 ml) was cooled to −40° C. under nitrogen. Triethylamine (146 μl) was added followed by methanesulfonyl chloride (75 μl) and the reaction allowed to attain room temperature. The reaction was filtered and solvent removed in uacuo. The residue was partitioned between water-dichloromethane and the organic phase dried ($MgSO_4$) and concentrated.

A solution of the mesylate in THF (20 ml) with diisopropylethylamine (310 μl) and the amine from step 2 (231 mg) was heated for 4 h at 40° C. and 6 h at 60° C. Sodium iodide (150 mg) was added and heating continued for 17 h in a foil covered reaction vessel. Saturated sodium chloride was added, solvent removed in vacuo and the residue extracted into n-butanol. The organic phase was concentrated, and chromatographed using methanol/dichloromethane/ammonia (15:84:1) as eluant, to give the title compound free base. The oxalate salt was prepared and crystallised from ethanol-diethyl ether. (Found: C, 58.97; H, 6.24: N, 13.56. $C_{26}H_{31}N_5O_2$.2($C_2H_2O_4$).1.5 $H_2O$ requires: C, 59.21; H, 6.11; N, 13.54%.) $δ_H$ (360 MHz, DMSO-$d_6$) 1.60–1.75 (2H, m), 1.85–2.10 (4H, m), 2.60–2.80 (4H, m), 2.80–2.95 (2H, m). 3.20–3.30 (2H, m), 3.50–3.60 (2H, m), 4.05–4.15 (1H, m), 5.42 (2H, s), 7.02–7.05 (1H, m), 7.16 (1H, m), 7.29–7.39 (4H, m), 7.44–7.50 (3H, m), 7.93 (1H, s), 8.60 (1H, s), 10.90 (1H, s); m/e 459 ($M^+$+1).

EXAMPLE 99

1-{3-[5-(1,2,4-Triazol-4-yl)-1H-indol-3-yl]propyl}-4-[(R)-α-(methoxymethyl)benzylamino]piperidine. Dihydrogen Oxalate. Hydrate.

The title compound was prepared in a similar manner to that described in Example 8 (step 5) using (R)-(−)-1-amino-1-phenyl-2-methoxyethane (A. I. Meyers et al., *J. Org. Chem.*, 1978, 43, 892); mp 138°–140° C. (methanol-diethyl ether). (Found: C, 56.65; H, 6.03; N, 12.86. $C_{27}H_{34}N_6O$.2($C_2H_2O_4$).1.0 $H_2O$ requires: C, 56.70; H, 6.14; N, 12.80%.) $δ_H$ (360 MHz, DMSO-$d_6$) 1.60–1.80 (2H, m), 1.90–2.20 (4H, m), 2.65–2.90 (5H, m), 2.90–3.05 (2H, m), 3.27 (3H, m), 3.27–3.40 (2H, m), 3.50–3.56 (2H, m), 4.20–4.30 (1H, m), 7.31–7.33 (5H, m), 7.46–7.51 (3H, m), 7.79 (1H, m), 9.02 (2H, s), 11.19 (1H, s); m/e (ES) 459 ($M^+$+1).

EXAMPLE 100

1-{3-[5-(1,2,4-Triazol-4-yl)-1H-indol-3-yl]propyl}-4-{N-[(R)-α-(methoxymethyl)benzyl]-N-methylamino}piperidine. 2.0 Hydrogen Oxalate. 0.6 Hydrate.

The title compound was prepared from the product of Example 99 following a similar method to that described for Example 10, mp 119°–121° C. (Found: C, 57.65; H, 6.33; N, 13.02. $C_{28}H_{36}N_6O$.2.0($C_2H_2O_4$).0.6 $H_2O$ requires: C, 57.93; H, 6.26; N, 12.67%). $δ_H$ (360 MHz, $CDCl_3$; free base) 1.60–1.91 (10H, m), 2.25 (3H, s), 2.33–2.37 (2H, m), 2.45–2.48 (1H, m), 2.72–2.77 (2H, m), 2.90–2.93 (2H, m), 3.29 (3H, s), 3.59–3.63 (2H, m), 3.69–3.73 (2H, m), 3.84–3.87 (2H, m), 7.11–7.14 (2H, m), 7.23–7.31 (6H, m), 7.44–7.47 (1H, m), 7.53–7.54 (1H, m), 8.40 (1H, s), 8.45 (2H, s); m/e (ES) 473 ($M^+$+1).

EXAMPLE 101

1-{3-[5-(Imidazol-1-yl)-1H-indol-3-yl]propyl}-4-[(R)-α-(methoxymethyl)benzylamino]piperidine. 2.0 Hydrogen Oxalate. 1.5 Hydrate.

The title compound was prepared from 1-{3-[5-(imidazol-1-yl)-1H-indol-3-yl]propyl}-4-ketopiperidine and (R)-α-(methoxymethyl)benzylamine using a similar procedure to that described for Example 8 (step 5); mp 128°–130° C. (Found: C, 57.72; H, 6.19; N, 10.35. $C_{28}H_{35}N_5O$.2.0($C_2H_2O_4$).1.5 $H_2O$ requires: C, 57.82; H, 6.37; N, 10.54%). $δ_H$ (250 MHz, DMSO-$d_6$) 1.55–1.80 (2H, m), 1.80–2.20 (4H, m), 2.60–2.85 (6H, m), 2.85–3.00 (2H, m), 3.23 (3H, s), 3.20–3.40 (2H, m), 3.40–3.60 (2H, m), 7.10 (1H, s), 7.24–7.46 (8H, m), 7.65–7.68 (2H, m), 8.18 (1H, s), 11.07 (1H, s); m/e (ES) 458 ($M^+$+1).

EXAMPLE 102

1-{3-[5-(1,2,4-Triazol-1-yl)methyl-1H-indol-3-yl]propyl}-4-{[(R)-1-(4-fluorophenyl)-2-methoxyethyl]amino}piperidine. 2.0 Hydrogen Oxalate Hydrate.

1. (R)-2-Amino-2-(4-fluorophenyl)-1-methoxy ethane. Hydrochloride.

A solution of (R)-2-amino-2-(4-fluorophenyl)ethanol (Example 80, step 1) (600 mg, 3.9 mmol) in anhydrous THF (5 ml) was added dropwise to a stirred suspension of sodium hydride (0.46 g of 35% wt suspension in oil, washed with anhydrous pentane) in anhydrous THF (5 ml). The reaction was stirred for 2 h, treated with iodomethane (237 μl) and allowed to stand for 18 h. The reaction was partitioned between diethyl-ether and saturated aqueous sodium chloride. The organic phase was dried ($MgSO_4$), concentrated, and redissolved in diethyl ether. The solution was treated with hydrogen chloride-diethyl ether (10 ml) and concentrated to a yellow solid. Recrystallisation from ethyl acetate gave colourless needles (551 mg). $δ_H$ (250 MHz, DMSO-$d_6$) 3.32 (3H, s), 3.57–3.72 (2H, m), 4.48–4.53 (1H, m), 7.24–7.32 (2H, m), 7.56–7.61 (2H, m), 8.6 (3H, br s).

2. 1-tert-Butyloxycarbonyl-4-[(R)-1-(4-fluorophenyl)-2-methoxyethyl]aminopiperidine The product from above (250 mg) and N-tert-butyloxycarbonyl-4-ketopiperidine were reacted as described in Example 98 (step 2). The crude product was reacted as described below (step 3).

3. 4-[(R)-1-(4-Fluorophenyl)-2-methoxyethyl]aminopiperidine hydrogen chloride

To a solution of the product from above (0.67 g) in methanol (5 ml) was added 1N hydrogen chloride-diethyl ether (5 ml). The reaction was concentrated and recrystallised from methanol-ethyl acetate to give a colourless solid (367 mg). $δ_H$ (250 MHz, $d_4$-methanol) 2.08–2.44 (4H, m), 2.84–3.08 (2H, m), 3.43 (2H, br s), 3.47 (3H, s), 3.76–3.96 (2H, m), 7.15–7.22 (2H, m), 7.61–7.66 (2H, m).

4. 1-{3-[5-(1,2,4-Triazol-1-yl)methyl-1H-indol-3-yl]propyl}-4-{[(R)-1-(4-fluorophenyl)-2-methoxyethyl]amino}piperidine. 2.0 Hydrogen Oxalate Hydrate.

The product from above (367 mg) was reacted as described in Example 98 with the mesylate described in Example 98 (step 3) to give the title compound. (Found: C, 55.68; H, 6.12; N, 11.92. $C_{28}H_{35}FN_6O.2(C_2H_2O_4).H_2O$ requires: C, 55.81; H, 6.00; N, 12.20%.) $\delta_H$ (360 MHz, DMSO-$d_6$) 1.52–1.70 (2H, m), 1.80–1.90 (1H, m), 1.90–2.12 (3H, m), 2.56–2.74 (4H, m), 2.74–3.04 (4H, m), 3.24 (3H, s), 3.28–3.54 (3H, m), 4.20 (1H, br s), 5.43 (2H, s), 7.04–7.06 (1H, m), 7.17–7.22 (3H, m), 7.30–7.33 (1H, m), 7.47–7.51 (3H, m), 7.94 (1H, s), 8.60 (1H, s), 10.92 (1H, s); m/e (ES) 491 (M$^+$+1).

EXAMPLE 103

1-{3-[5-(1,2,4-Triazol-1-yl)methyl-1H-indol-3-yl] propyl}-4-[N-(4-fluorobenzyl)-N-methylamino] piperidine. 2 Hydrogen Oxalate. Hydrate.

1. 1-tert-Butyloxycarbonyl-4-(4-fluorobenzyl) aminopiperidine

4-Fluorobenzylamine (2.5 g) and N-tert-butoxycarbonyl-4-piperidone (4 g) were reacted as described in Example 98 (step 2), to give the title product as a yellow oil which crystallised (6.2 g). $\delta_H$ (250 MHz, CDCl$_3$) 1.22–1.37 (2H, m), 1.43 (9H, s), 1.82–1.94 (2H, m), 2.60–2.72 (1H, m), 2.74–2.84 (2H, m), 3.80 (2H, s), 3.94–4.10 (2H, m), 6.97 (2H, m), 7.26–7.31 (2H, m).

2. 1-tert-Butyloxycarbonyl-4-[N-(4-fluorobenzyl)-N-methylamino]piperidine

The product from above (6.2 g) was reacted using a similar procedure to that described in Example 10 to give the title product as a colourless oil (5.66 g). $\delta_H$ (250 MHz, CDCl$_3$) 1.46 (9H, s), 1.46–1.57 (2H, m), 1.71–1.81 (2H, m), 2.17 (3H, s), 2.50–2.74 (3H, m), 3.53 (3H, s), 4.06–4.26 (2H, m), 6.95–7.02 (2H, m), 7.24–7.30 (2H, m).

3. 4-[N-(4-fluorobenzyl)-N-methylamino]piperidine

The product from above (2.73 g) was deprotected using a similar procedure to that described in Example 98 (step 2). The amine was obtained as a yellow oil (1.81 g). $\delta_H$ (360 MHz, CDCl$_3$) 1.48–1.59 (2H, m), 1.81–1.85 (2H, m), 2.18 (3H, s), 2.30–2.44 (2H, br s), 2.48–2.64 (3H, m), 3.16–3.20 (2H, m), 3.53 (2H, s), 6.96–7.00 (2H, m), 7.24–7.28 (2H, m).

4. 1-{3-[5-(1,2,4-Triazol-1-yl)methyl-1H-indol-3-yl]propyl}4-[N-(4-fluorobenzyl)-N-methylamino]piperidine. 2.0 Hydrogen Oxalate Hydrate.

The title compound was prepared using a similar method to that described in Example 98 (step 3) using the product from above (642 mg) and the mesylate from Example 98 (step 3). The oxalate salt was prepared and crystallised from methanol-diethyl ether; mp 180°–181° C. (Found: C, 56.83; H, 5.79, N, 12.78. $C_{27}H_{33}N_6F.2(C_2H_2O_4)$. $H_2O$ requires C, 56.53; H, 5.97; N, 12.76%). $\delta_H$ (360 MHz, DMSO-$d_6$) 1.80–1.95 (2H, m), 1.95–2.08 (4H, m), 2.24 (3H, s), 2.68–2.78 (2H, m), 2.80–2.98 (3H, s), 3.00–3.10 (2H, m), 3.40–3.54 (2H, m), 3.77 (2H, s), 5.44 (2H, s), 7.05–7.07 (1H, m), 7.16–7.21 (3H, m), 7.32–7.34 (1H, m), 7.40–7.44 (2H, m), 7.54 (1H, s), 7.95 (1H, s), 8.6 (1H, s), 10.93 (1H, s); m/e (ES) 461 (M$^+$+1).

EXAMPLE 104

1-{3-[5-(1,2,4-Triazol-4-yl)-1H-indol-3-yl]propyl}-4-(2-phenylpiperidin-1-yl)piperidine. 2.5 Hydrogen Oxalate. 1.5 Hydrate.

1. 1-tert-Butyloxycarbonyl-4-[2-phenylpiperidin-1-yl]piperidine

N-tert-Butyloxycarbonyl-4-piperidone (5 g), 2-phenylpiperidine (4.03 g) and titanium isopropoxide (8.9 ml) were stirred at room temperature under a nitrogen atmosphere for 3 h. The resulting orange solution was diluted with methanol (40 ml), treated with sodium cyanoborohydride (1.6 g), and stirred for 20 h. Water (50 ml) was added to give a granular precipitate which was removed by filtration through celite. The filtrate was partitioned between water-ethyl acetate, the organic phase separated, dried (MgSO$_4$) and concentrated. The residue was dissolved in ethyl acetate and washed with a saturated aqueous solution of citric acid. The aqueous phase was basified to pH10 using 4N sodium hydroxide, and extracted into ethyl acetate. The organic phase was dried (MgSO$_4$) and concentrated. The residue was chromatographed using ethyl acetate-petroleum ether (20:80 to 50:50) to afford a partially purified mixture, which was dissolved in ethyl acetate. The organic phase was washed with a saturated aqueous solution of citric acid. The aqueous phase was separated, basified to pH10 using 4N sodium hydroxide and extracted with ethyl acetate. The organic phase was dried (MgSO$_4$) and concentrated to give the product in 3% yield. $\delta_H$ (250 MHz, CDCl$_3$) 1.16–1.79 (19H, m), 2.21–2.29 (2H, m), 2.41–2.50 (2H, m), 2.90–3.04 (1H, m), 3.36–3.44 (1H, m), 3.92–4.10 (2H, m), 7.16–7.40 (5H, m).

2. 4-(2-Phenylpiperidin-1-yl)piperidine

The product from above (245 mg) was deprotected as described in Example 98 (step 2). The product was obtained as a yellow solid (170 mg). $\delta_H$ (360 MHz, CDCl$_3$) 1.29–1.83 (10H, m), 2.10–2.18 (1H, m), 2.25–2.45 (3H, m), 2.97–3.06 (3H, m), 3.39–3.42 (1H, m), 7.21–7.30 (5H, m).

3. 1-{3-[5-(1,2,4-Triazol-4-yl)-1H-indol-3-yl]propyl}-4-(2-phenylpiperidin-1-yl)piperidine. 2.5 Hydrogen Oxalate. 1.5 Hydrate.

The title compound was prepared from 3-[5-(1,2,4-triazol-4-yl)-1H-indol-3-yl]propan-1-ol and 4-(2-phenylpiperidin-1-yl)piperidine using a similar method to that described for Example 36 (step b). The oxalate salt was prepared and crystallised from methanol-diethyl ether; mp 126°–128° C. (Found: C, 56.42; H, 6.17; N, 11.56. $C_{29}H_{36}N_6.2.5(C_2H_2O_4)$. 1.5 H$_2$O requires: C, 56.66; H, 6.15; N, 11.66%).$\delta_H$ (360 MHz, DMSO-$d_6$, 353° K) 1.30–1.50 (1H, m), 1.52–2.06 (12H, m), 2.30–2.70 (4H, m), 2.71–2.75 (2H, m), 2.80–2.88 (2H, m), 3.00–3.14 (1H, m), 3.24–3.40 (2H, m), 3.60–3.70 (1H, m), 7.25–7.38 (7H, m), 7.47–7.50 (1H, m), 7.71–7.72 (1H, m), 8.86 (2H, m), 10.93 (1H, m); m/e (ES) 469 (M+1)$^+$.

EXAMPLE 105

1-{3-[5-(1,2,4-Triazol-4-yl)-1H-indol-3-yl]propyl}-4-{[(R)-1-(4-fluorophenyl)-2-methoxyethyl] aminol}piperidine. Hydrogen Oxalate.

(R)-2-Amino-2-(4-fluorophenyl)-1-methoxy ethane (Example 102, step 1) (310 mg) and 1-{3-[5-(1,2,4-triazol-4-yl)-1H-indol-3-yl]propyl}-4-ketopiperidine (487 mg) were reacted as described in Example 8 (step 5) to give the title compound. The oxalate salt was prepared and crystallised from methanol-diethyl ether. (Found: C, 54.75; H, 5.94; N, 12.47. $C_{27}H_{33}FN_6.2(C_2H_2O_4).1.2$ H$_2$O requires: C, 54.89; H, 5.86; N, 12.39%). $\delta_H$ (360 MHz, DMSO-$d_6$) 1.56–1.70 (2H, m), 1.82–1.94 (1H, s), 1.94–2.20 (3H, m), 2.54–2.68 (1H, m), 1.68–1.90 (4H, m) 1.90–3.06 (2H, m), 3.25 (3H, s), 3.28–3.42 (2H, m), 3.42–3.56 (2H, m), 4.20–4.30 (1H, m), 7.17–7.22 (2H, m), 7.31–7.34 (2H, m), 7.48–7.51 (3H, m) 7.79–7.80 (1H, m), 9.01 (2H, s), 11.17 (1H, s).

EXAMPLE 106

(3R)-3-(Benzylsulfinyl)methyl-1-{2-[5-(1,2,4-triazol-4-yl)-1H-indol-3-yl]ethyl}pyrrolidine. Hydrogen Oxalate.

1. (3R)-3-(Benzylsulfinyl)methyl-1-(tert-butoxycarbonyl) pyrrolidine

To a stirred solution of (3R)-3-(benzylthio)methyl-1-(tert-butoxycarbonyl)pyrrolidine (0.2553 g, 0.830 mmol) in ethyl acetate (15 ml), under argon, cooled in a bath at ca. −40° C., was added portionwise 57–86% 3-chloroperoxybenzoic acid (0.2094 g). The mixture was then allowed to warm to 0° C. over 1.5 h, before pouring into 5% NaHCO$_3$ solution (15 ml). The organic layer was separated and washed with more 5% NaHCO$_3$ solution (15 ml), then saturated NaCl solution (10 ml), dried (MgSO$_4$) and evaporated in vacuo. The residue was purified by flash chromatography (silica gel, 3% MeOH/CH$_2$Cl$_2$) to give 0.2381 g (89%) of the title compound as a colourless oil. $\delta_H$ (250 MHz, CDCl$_3$) 1.44 (9H, s), 1.61 (1H, m), 2.15 (1H, m), 2.52 (1H, m), 2.66 (2H, m), 3.00 (1H, m), 3.29 (1H, m), 3.43 (1H, m), 3.63 (1H, m), 3.96 (1H, d, J=12.9 Hz), 4.07 (1H, d, J=12.9 Hz), 7.28–7.30 (2H, m), 7.35–7.39 (3H, m). m/e (ES+) 324 (M+H)$^+$.

2. (3R)-3-[(Benzylsulfinyl)methyl]pyrrolidine

Using a similar method to that described in Example 93, step 2, (3R)-3-(benzylsulfinyl)methyl-1-(tert-butoxycarbonyl)pyrrolidine (0.2376 g, 0.735 mmol) was reacted with trifluoroacetic acid (1 ml) in dichloromethane (3 ml) to give, after work up, 0.1543 g (94%) of the title compound as a white solid, which was used without further purification. $\delta_H$ (250 MHz, CDCl$_3$) 1.47 (1H, m), 2.09 (1H, m), 2.52–2.72 (4H, m), 2.94 (2H, m), 3.19 (1H, m), 3.96 (1H, d, J=12.9 Hz), 4.06 (1H, dd, J=12.9 and 3.6 Hz), 7.27–7.43 (5H, m).

3. (3R)-3-(Benzylsulfinyl)methyl-1-{2-[5-(1,2,4-triazol-4-yl)-1H-indol-3-yl]ethyl}pyrrolidine. Hydrogen Oxalate.

Using a similar method to that described in Example 93, step 3, (3R)-3-[(benzylsulfinyl)methyl]pyrrolidine (0.1500 g, 0.672 mmol) was reacted with 3-[2-(methanesulfonyloxy)ethyl]-5-(1,2,4-triazol-4-yl)-1H-indole (0.1375 g, 0.449 mmol) and sodium carbonate (71.3 mg, 0.673 mmol) in 2-propanol (15 ml) to give 93.8 mg (48%) of the title compound free base as a colourless solid. The oxalate salt was prepared in methanol-diethyl ether: mp 100°–108° C. (Found: C, 57.77; H, 5.90; N, 12.36. C$_{24}$H$_{27}$N$_5$SO.C$_2$H$_2$O$_4$.0.18(C$_4$H$_{10}$O).H$_2$O requires: C, 57.83; H, 5.96; N, 12.62%). $\delta_H$ (360 MHz, DMSO-d$_6$) 1.80 (1H, m), 2.06 (1H, m), 2.79–2.86 (2H, m), 2.94 (1H, m), 3.09 (3H, m), 3.38 (4H, m), 3.62 (1H, m), 4.01 (1H, dd, J=3.4 and 12.7 Hz), 4.18 (1H, dd, J=6.1 and 12.8 Hz), 7.32–7.40 (7H, m), 7.52 (1H, d, J=8.6 Hz), 7.89 (1H, s), 9.03 (2H, s), 11.29 (1H, s). m/e (ES+) 434 (M+H)$^+$.

EXAMPLE 107

(3R)-3-[(4-Fluorobenzylthio)methyl]-1-{2-(5-[(1,2,4-triazol-1-yl)methyl]-1H-indol-3-yl)ethyl}pyrrolidine. Hydrogen Oxalate.

1. (3R)-1-(tert-Butoxycarbonyl)-3-[(4-fluorobenzylthio)methyl]pyrrolidine

Using a similar method to that described in Example 93, step 1, (3R)-1-(tert-butoxycarbonyl)-3-[(methanesulfonyloxy)methyl]pyrrolidine (1.5000 g, 5.37 mmol) was reacted with 4-fluorobenzyl mercaptan (1.5511 g, 10.91 mmol) and potassium carbonate (1.1132 g, 8.05 mmol) in DMF (30 ml) at room temperature for 24 h to give 1.7507 g (100%) of the title compound as a colourless oil. $\delta_H$ (360 MHz, CDCl$_3$) 1.45 (9H, s), 1.60 (1H, m), 2.00 (1H, m), 2.44 (2H, m), 2.97 (1H, m), 3.28 (1H, m), 3.46 (2H, m), 3.69 (2H, s), 7.00 (2H, t, J=8.6 Hz), 7.25–7.29 (2H, m). m/e (ES+) 348 (M+Na)$^+$, 326 M+H)$^+$, 270 (M−CMe$_3$+2H)$^+$.

2. (3R)-3-[(4-Fluorobenzylthio)methyl]pyrrolidine

A solution of (3R)-1-(tert-butoxycarbonyl)-3-[(4-fluorobenzylthio)methyl]pyrrolidine (0.5422 g, 1.67 mmol) in 90% formic acid (5 ml) was stirred at room temperature for 23 h. The solvents were removed in vacuo and the residue was dissolved in dichloromethane (25 ml) and washed with 2N NaOH solution (10 ml). The aqueous layer was reextracted with more dichloromethane (25 ml) and the combined organic extracts were washed with saturated NaCl solution (10 ml), dried (Na$_2$SO$_4$) and evaporated in vacuo to leave 0.3903 g of the title compound as an oil. $\delta_H$ (360 MHz, CDCl$_3$) 1.42 (1H, m), 1.94 (1H, m), 2.24 (1H, m), 2.45 (2H, m), 2.59 (1H, m), 2.92 (2H, m), 3.08 (1H, m), 3.69 (2H, s), 7.00 (2H, t, J=8.6 Hz), 7.25–7.29 (2H, m).

3. (3R)-3-[(4-Fluorobenzylthio)methyl]-1-{2-(5-[(1,2,4-triazol-1-yl)methyl]-1H-indol-3-yl)ethyl}pyrrolidine. Hydrogen Oxalate.

To a stirred solution of 3-(2-hydroxyethyl)-5[(1,2,4-triazol-1-yl)methyl]-1H-indole (0.1425 g, 0.588 mmol) and triethylamine (0.107 ml, 0.768 mmol) in THF (10 ml), cooled under argon in a bath at −40° C., was added dropwise methanesulfonyl chloride (56.0 μl, 0.709 mmol). The mixture was then stirred at room temperature for 1.5 h before diluting with ethyl acetate (40 ml) and washing with brine (20 ml). The organic layer was dried (MgSO$_4$) and evaporated in vacuo. The residue was immediately dissolved in anhydrous 2-propanol (10 ml) to which was added anhydrous potassium carbonate (0.1626 g, 1.176 mmol) followed by a solution of (3R)-3-[(4-fluorobenzylthio)methyl]pyrrolidine (0.1978 g, 0.878 mmol) in anhydrous 2-propanol (8 ml). The mixture was then heated at reflux for 4 h. After cooling, the solvents were removed in vacuo and the residue was partitioned between dichloromethane (25 ml) and water (15 ml). The aqueous layer was separated and reextracted with more dichloromethane (2×25 ml). The combined organic layers were washed with saturated NaCl solution (20 ml), dried (Na$_2$SO$_4$) and evaporated in vacuo. The residue was purified by flash chromatography (silica gel, CH$_2$Cl$_2$/MeOH/NH$_3$, 94:6:0.6), then by preparative t.l.c. (silica gel, CH$_2$Cl$_2$/MeOH/NH$_3$, 92:8:0.8) to give 0.147 g (56%) of the title compound, free base. The oxalate salt was prepared in methanol-diethyl ether; mp 68°–71° C. (Found: C, 61.02; H, 5.65; N, 13.70. C$_{25}$H$_{28}$FN$_5$S.0.8(C$_2$H$_2$O$_4$) requires: C, 61.25; H, 5.72; N, 13.43%). $\delta_H$ (360 MHz, DMSO-d$_6$) 1.60 (1H, m), 2.07 (1H, m), 2.81 (1H, m), 2.96 (2H, m), 3.13 (4H, m), 3.27 (1H, m), 3.76 (2H, s), 5.43 (2H, s), 7.05 (1H, d, J=9.7 Hz), 7.15 (2H, t, J=8.9 Hz), 7.23 (1H, s), 7.32–7.39 (3H, m), 7.58 (1H, s), 7.94 (1H, s), 8.81 (1H, s), 10.97 (1H, s) among other signals. m/e (ES+) 450 (M+H)$^+$.

EXAMPLE 108

(3R)-3-[(4-Fluorobenzylsulfinyl)methyl)-1-{2-(5[(1,2,4-triazol-1-yl)methyl]-1H-indol-3-yl) ethyl}pyrrolidine. Hydrogen Oxalate.

1. (3R)-1-(tert-Butoxycarbonyl)-3-[(4-fluorobenzylsulfinyl)methyl]pyrrolidine

Using a similar procedure to that described in Example 107, step 1, (3R)-1-(tert-butoxycarbonyl)-3-[(4-fluorobenzylthio)methyl]pyrrolidine (0.5818 g, 1.79 mmol) was reacted with 57–86% 3-chloroperoxybenzoic acid (0.4477 g) in ethyl acetate (35ml) to give 0.5233 g (86%) of the title compound as a colourless oil. $\delta_H$ (360 MHz, CDCl$_3$) 1.45 (9H, s), 1.66 (1H, m), 2.15 (1H, m), 2.54(1H, m), 2.63–2.71 (2H, m), 3.03 (1H, m), 3.31 (1H, m), 3.44 (1H, m), 3.65 (1H, m), 3.96 (2H, s), 7.08 (2H, t, J=8.6 Hz), 7.25–7.29 (2H, m). m/e (ES+) 342 (M+H)$^+$.

2. (3R)-3-[(4-Fluorobenzylsulfinyl)methyl]pyrrolidine

Using a similar procedure to that described in Example 93, step 2, (3R)-1-(tert-butoxycarbonyl)-3-[(4-fluorobenzylsulfinyl)methyl}pyrrolidine (0.5149 g, 1.51 mmol) was reacted with trifluoroacetic acid (2ml) in dichloromethane (6ml) to give, after work up, 0.3447 g (95%) of the title compound as a white solid, which was used without further purification. $\delta_H$ (360 MHz, CDCl$_3$) 1.57 (1H, m), 2.13 (1H, m), 2.54–2.72 (4H, m), 3.05 (2H, m), 3.27 (1H, m), 3.96 (2H, m), 708 (2H, t, J=8.6 Hz), 7.26–7.30 (2H, m).

3. (3R)-3-[(4-Fluorobenzylsulfinyl)methyl]-1-{2-(5[(1,2,4-triazol-1-yl)methyl]-1H-indol-3-yl)ethyl}pyrrolidine. Hydrogen Oxalate.

Using a similar method to that described in Example 108, step 3, 3-(2-hydroxyethyl)-5-[(1,2,4-triazol-1-yl)methyl)-1H-indole (0.1200 g, 0.495 mmol) was reacted with methanesulfonyl chloride (58.7 μl, 0.743 mmol) and triethylamine (0.138ml, 0.990 mmol) in THF (3ml), then with (3R)-3-[(4-fluorobenzylsulfinyl)methyl]pyrrolidine (0.1793 g, 0.743 mmol) and sodium carbonate (0.1048 g, 0.989 mmol) in 2-propanol (12ml) to give, after purification by flash chromatography (silica gel, CH$_2$Cl$_2$/MeOH/NH$_3$, 92:8:0.8), then by preparative t.l.c. (silica gel, CH$_2$Cl$_2$/MeOH/NH$_3$, 3,90:10:1), 70.1 mg (30%), of the title compound, free base. The oxalate salt was prepared in methanol-diethyl ether (softens). (Found: C, 57.68; H, 5.85; N, 11.82. C$_{25}$H$_{28}$FN$_5$OS.C$_2$H$_2$O$_4$.0.23 (C$_4$H$_{10}$O).0.5 H$_2$O requires: C, 57.65; H, 5.77; N, 12.04%). $\delta_H$ (360 MHz, DMSO-d$_6$) 1.79 (1H, m), 2.25 (1H, m), 2.80 (2H, m), 2.92 (1H, m), 3.04 (3H, m), 3.35 (4H, m), 4.01 (1H, dd, J=2.9 and 12.9 Hz), 4.21 (1H, dd, J=5.8 and 13.0 Hz), 5.44 (2H, s), 7.07 (1H, d, J=8.4 Hz), 7.23 (1H, t, J=8.8 Hz), 7.26 (1H, s), 7.34–7.41 (3H, m), 7.61 (1H, s), 7.95 (1H, s), 8.81 (1H, s), 11.03 (1H, s) among other signals. m/e (ES+) 466 (M+H)$^+$.

EXAMPLE 109

(3R)-3-[(4-Fluorobenzylsulfonyl)methyl]-1-{2-(5[(1,2,4-triazol-1-yl)methyl]-1H-indol-3-yl)ethyl}pyrrolidine. Hydrogen Oxalate.

1. (3R)-1-(tert-Butoxycarbonyl)-3-[(fluorobenzylsulfonyl)methyl]pyrrolidine

To a stirred solution of (3R)-1-(tert-butoxycarbonyl)-3-[(4-fluorobenzylthio)methyl]pyrrolidine (0.5671 g, 1.74 mmol) in ethyl acetate (35ml), cooled under argon in a bath at −40° C., was added portionwise 57–86% 3-chloroperoxybenzoic acid (0.8780 g). The mixture was allowed to warm to +8° C. over 1.5 h, then stirred at this temperature for 1 h. The mixture was then poured into 5% NaHCO$_3$ solution (30ml). The organic layer was separated and washed with more 5% NaHCO$_3$ solution (30ml), then brine (20ml), dried (MgSO$_4$) and evaporated in vacuo. The residue was purified by flash chromatography (silica gel, 1% MeOH/CH$_2$Cl$_2$ and silica gel, Et$_2$O) to give 0.612 g (98%) of the title compound as a colourless oil. $\delta_H$ (360 MHz, CDCl$_3$) 1.45 (9H, s), 1.68 (1H, m), 2.19 (1H, m), 2.73 (1H, m), 2.90 (2H, m), 3.01 (1H, dd, J=8.2 and 11.0 Hz), 3.29 (1H, m), 3.45 (1H, m), 3.69 (1H, dd, J=7.2 and 10.9 Hz), 4.21 (2H, s), 7.11 (2H, t, J=8.6 Hz), 7.39 (2H, m). m/e (ES+) 358 (M+H)$^+$.

2. (3R)-3-[(4-Fluorobenzylsulfonyl)methyl)pyrrolidine

Using a similar method to that described in Example 93, step 2, (3R)-1-(tert-butoxycarbonyl)-3-[(4-fluorobenzylsulphonyl)-methyl]pyrrolidine (0.6465 g, 1.81 mmol) was reacted with trifluoroacetic acid (2ml) in dichloromethane (6 ml) to give, after work up, 0.4755 g of the title compound as a white solid, which was used without further purification. $\delta_H$ (360 MHz, CDCl$_3$) 1.55 (1H, m), 2.15 (1H, m), 2.60–2.73 (2H, m), 2.90–3.00 (4H, m), 3.30 (1H, m), 4.21 (2H, s), 7.11 (2H, t, J=8.6 Hz), 7.37–7.41 (2H, m).

3. (3R)-3-[(4-Fluorobenzylsulfonyl)methyl]-1-{2-(5[(1,2,4-triazol-1-yl)methyl]-1H-indol-3-yl)ethyl}pyrrolidine. Hydrogen Oxalate.

Using a similar method to that described in Example 108, step 3, 3-(2-hydroxyethyl)-5-[(1,2,4-triazol-1-yl)methyl]-1H-indole (0.1480 g, 0.611 mmol) was reacted with methanesulfonyl chloride (72.4 μl, 0.916 mmol) and triethylamine (0.170 ml, 1.22 mmol) in THF (5ml), then with (3R)-3-[(4-fluorobenzylsulfonyl)methyl]pyrrolidine (0.2360 g, 0.917 mmol) and sodium carbonate (0.1295 g, 1.22 mmol) in 2-propanol (14ml) to give, after purification by flash chromatography (silica gel, CH$_2$Cl$_2$/MeOH/NH$_3$, 94:6:0.6), 48.7mg (17%) of the title compound, free base. The oxalate salt was prepared in methanol-diethyl ether: mp 79° C. (softens). (Found: C, 53.86; H, 5.49; N, 10.64. C$_{25}$H$_{28}$FN$_5$O$_2$S.1.5(C$_2$H$_2$O$_4$).0.2(C$_4$H$_{10}$O).0.6 H$_2$O requires: C, 53.86; H, 5.37; N, 10.90%). $\delta_H$ (360 MHz, DMSO-d$_6$) 1.81 (1H, m), 2.16 (1H, m), 2.87 (1H, m), 3.05 (2H, m), 3.30–3.42 (4H, m), 4.56 (2H, s), 5.44 (2H, s), 7.07 (1H, d, J=8.6 Hz), 7.25–7.29 (3H, m), 7.35 (1H, d, J=8.3 Hz), 7.45–7.49 (2H, m), 7.62 (1H, s), 7.95 (1H, s), 8.81 (1H, s), 11.04 (1H, s) among other signals. m/e (ES+) 482 (M+H)$^+$.

EXAMPLE 110

4-(4-Fluorobenzylsulfinyl)-1-{3-[5-(1,2,4-triazol-4-yl)-1H-indol-3-yl]propyl}piperidine. Hydrogen Oxalate.

1. 1-(tert-Butoxycarbonyl)-4-(4-fluorobenzylthio)piperidine

To a stirred solution of 4-fluorobenzyl mercaptan (23.34 g, 164 mmol) in DMF (150ml) under argon, cooled in a bath at −2° C. as added portionwise 60% NaH in oil (6.57 g, 164 mmol) over 12 minutes. The mixture was then stirred at room temperature for 15 minutes before recooling in bath at −2° C. and adding by cannular, over 13 minutes, a solution of 4-bromo-1(tert-butoxycarbonyl)piperidine (10.84 g, 41.0 mmol) in DMF (50ml). The mixture was then stirred at room temperature for 24 h before partitioning between water (500ml) and diethyl ether (500ml). The aqueous layer was reextracted with more diethyl ether (500ml) and the combined organic extracts were dried (MgSO$_4$) and evaporated in vacuo. The residue was purified by flash chromatography (silica gel, 10–15% EtOAc/hexane) to give 4.58 g (34%) of the title compound as a colourless oil. $\delta_H$ (360 MHz, CDCl$_3$) 1.45 (9H, s), 1.49 (2H, m), 1.86 (2H, m), 2.67 (1H, m), 2.88 (2H, m), 3.73 (2H, s), 3.92 (2H, m), 6.99 (2H, t, J=8.6 Hz), 7.28 (2H, m). m/e (ES+) 326 (M+H)$^+$.

2. 1-(tert-Butoxycarbonyl)-4-(4-fluorobenzylsulfinyl)piperidine

Using a similar method to that described in Example 107, step 1, 1-(tert-butoxycarbonyl)-4-(4-fluorobenzylthio)piperidine (1.5065 g, 4.63 mmol) was reacted with 57–86% 3-chloroperoxybenzoic acid (1.0190 g) in dichloromethane (100ml) to give 1.5287 g (97%) of the title compound as a white solid. $\delta_H$ (250 MHz, CDCl$_3$) 1.46 (9H, s), 1.64–1.82 (3H, m), 2.02 (1H, m), 2.63 (1H, m), 2.81 (2H, m), 3.88 (1H, d, J=13.2 Hz), 3.98 (1H, d, J=13.2 Hz), 4.21 (2H, m), 7.08 (2H, t, J=8.6 Hz), 7.29 (2H, m); m/e (ES+) 683 (2M+H)$^+$, 342 (M+H)$^+$.

3. 4-(4-Fluorobenzylsulfinyl)piperidine

Using a similar method to that described in Example 108, step 2, 1-(tert-butoxycarbonyl)-4-(4-fluorobenzylsulfinyl) piperidine (1.524 g, 4.46 mmol) was reacted with 90% formic acid (15ml) to give 1.0276 g (95%) of the title compound as a white solid. $\delta_H$ (250 MHz, CDCl$_3$) 1.47 (2H, m), 1.82 (2H, m), 2.49 (2H, m), 2.69 (1H, tt, J=4.0 and 11.8 Hz), 3.03 (2H, m), 3.88 (1H, d, J=13.0 Hz), 4.11 (1H, d, J=13.0 Hz), 7.20 (2H, t, J=8.9 Hz), 7.37 (2H, m). m/e (ES+) 242 (M+H)$^+$.

4. 4-(4-Fluorobenzylsulfinyl)-1-{3-[5-(1,2,4-triazol-4-yl)-1H-indol-3-yl)propyl}piperidine. Hydrogen Oxalate.

Using a similar procedure to that described in Example 108, step 3, 3-(3-hydroxypropyl)-5-(1,2,4-triazol-4-yl)-1H- indole (0.1499 g, 0.619 mmol) was reacted with methanesulfonyl chloride (0.103ml, 1.30 mmol) and triethylamine (0.183ml, 1.31 mmol) in THF (20ml) at room temperature and then with 4-(4-fluorobenzylsulfinyl)piperidine (0.2376 g, 0.985 mmol) and anhydrous potassium carbonate (0.1822 g, 1.32 mmol) in anhydrous 2-propanol (20ml) at reflux overnight to give, after purification by flash chromatography (silica gel, $CH_2Cl_2$/MeOH/$NH_3$, 92:8:0.8) and preparative t.l.c. (silica gel, $CH_2Cl_2$/MeOH/$NH_3$, 90:10:1), 0.1159 g (40%) of the title compound free base. The oxalate salt was prepared in ethanol-diethyl ether; mp 100° C. (softens). (Found: C, 55.09, H, 5.35, N, 11.30. $C_{25}H_{28}FN_5OS.1.5$ $(C_2H_2O_4).0.6H_2O$ requires: C, 55.00, H, 5.31, N, 11.45%) $\delta_H$ (360 MHz, DMSO-$d_6$) 1.90 (2H, m), 2.00–2.16 (4H, m), 2.77 (2H, t, J=7.2 Hz), 2.85 (1H, m), 2.90–3.06 (4H, m), 3.96 (1H, d, J=13.1 Hz), 4.17 (1H, d, J=13.1 Hz), 7.21 (2H, t, J=8.8 Hz), 7.31–7.34 (2H, m), 7.39 (2H, m), 7.50 (1H, d, J=8.6 Hz), 7.81 (1H, d, J=1.9 Hz), 9.01 (2H, s), 11.18 (1H, s) among other signals. m/e (ES+) 466 (M+H)$^+$.

EXAMPLE 111

2S-2-(N-Benzyl-N-methylaminomethyl)-1-[2-(5-(1, 2,4-triazol-1-yl)-1H-pyrrolo[2,3-c]pyridin-3-yl)ethy] pyrrolidine oxalate 1. Intermediate 5: 2-(5-(1,2,4-Triazol-1-yl)-1H-pyrrolo[2,3-c]pyridin-3-yl)acetonitrile a) 4-Methyl-5-nitro-2-(1 2,4-triazol-1-yl)pyridine To a solution of 1,2,4-triazole (4.0 g, 58 mmol) in dry dimethyl formamide (20ml) was added potassium carbonate (12.0 g, 87 mmol) and 2-chloro-4-methyl-5-nitropyridine (10 g, 58 mmol) and the mixture stirred at ambient temperature under nitrogen for 24 h. Ethyl acetate (500ml) and water (250ml) were added to the mixture and the resulting precipitate was collected by filtration to give the title compound (5.08 g, 43%) as a pale brown solid. The filtrate was separated and the organic phase was washed with water (250ml) and brine (250ml), dried ($MgSO_4$) and evaporated. The residue was triturated with ethyl acetate and the precipitate collected by filtration to give the title compound as a brown solid (4.11 g, 35%, overall yield 78%); mp 198°–200° C. $^1$H NMR (360 MHz, $CDCl_3$) δ 2.72 (3H, s), 7.86 (1H, s), 8.07 (1H, s), 9.03 (1H, s), 9.15 (1H, s).

b) N,N-Dimethyl-2-(5-nitro-2-(1,2,4-triazol-1-yl)-pyridin-4-yl)ethenamine

To a suspension of 4-methyl-5-nitro-2-(1,2,4-triazol-1-yl) pyridine (4.1 g, 20 mmol) in dry dimethylformamide (30ml) was added dimethylformamide dimethyl acetal (5.9ml, 44 mmol) and the mixture heated at 90° C. for 20 min. The solvent was evaporated in vacuo using toluene as an azeotrope to give the title compound (5.2 g, 100%) as a dark red solid; mp 225°–228° C. $^1$H NMR (360 MHz, $CDCl_3$) δ 3.10 (6H, s), 6.13 (1H, J=13.1 Hz), 7.54 (1H, J=13.1 Hz), 7.81 (1H, s), 8.04 (1H, s), 8.92 (1H, s), 9.17 (1H, s).

c) 5-(1,2,4-Triazol-1-yl)-1H-pyrrolo[2,3-c]pyridine

N,N-Dimethyl-2-(5-nitro-2-(1,2,4-triazol-1-yl)pyridin-4-yl)ethenamine (8 g, 31 mmol) was hydrogenated over platinum oxide (1.6 g) in ethanol (150ml) at 30 psi of hydrogen for 1 h. The catalyst was removed by filtration and the solvent evaporated in uacuo. The residue was chromatographed on silica eluting with ethyl acetate to afford an orange/brown solid. This was triturated with ether and the precipitate collected by filtration to give the title compound (2.89 g, 51%) as a pink solid; mp 203°–205° C., $^1$H NMR (360 MHz, $d_6$-DMSO) δ 6.67 (1H, d, J=3.0 Hz), 7.76 (1H, d, J=2.9 Hz), 8.01 (1H, s), 8.23 (1H, s), 8.70 (1H, s), 9.25 (1H, s), 11.86 (1H, br s).

d) N,N-Dimethyl-[5-(1,2,4-triazol-1-yl)-1H-pyrrolo[2,3-c] pyrridin-3-yl]methylamine To aqueous dimethylamine (40%, 0.35ml, 2.8 mmol), was added acetic acid (1.46ml, 26 mmol) at 0° C. Aqueous formaldehyde solution (38%, 0.21ml, 2.8 mmol) was added and the mixture was stirred at 0° C. for 5 min. 5-(1,2,4-Triazol-1-yl)-1H-pyrrolo[2,3-c]pyridine (0.5 g, 2.7 mmol) was added in one portion and then the mixture was allowed to warm to room temperature and then heated at 60° C. for 18 h. The reaction was cooled to 0° C. and treated with NaOH (4M, 8ml) to basify. Water (20ml) was added, followed by dichloromethane (50ml). The solid generated was removed by filtration and the two layers of the filtrate were separated. The aqueous phase was extracted with dichloromethane (5×50ml) and the combined organics were dried ($Na_2SO_4$) and the solvent evaporated in vacuo. The residue was chromatographed on silica eluting with 10% MeOH in DCM followed by a gradient of 90:10:1 to 80:20:1, DCM/MeOH/$NH_3$ to afford the title compound (0.58 g, 87%) as a colourless solid; mp 172°–175° C. $^1$H NMR (360 MHz, $d_6$-DMSO) δ 2.16 (6H, s), 3.59 (2H, s), 7.65 (1H, s), 8.04 (1H, s), 8.22 (1H, s), 8.64 (1H, s), 9.25 (1H, s) 11.69 (1H, br s).

e) N-([5-(1,2,4-Triazol-1-yl)-1H-pyrrolo[2,3-c]pyridin-3-yl]methyl)-N,N,N-trimethylammonium methyl sulphate A mixture of dimethylsulphate (0.13ml, 1.4 mmol) and dry THF (5ml) was cooled to 0° C. under nitrogen and N,N-dimethyl-[5-(1,2,4-triazol-1-yl)-1H-pyrrolo[2,3-c] pyridin-3-yl]methylamine (0.15 g, 0.62 mmol) was added portionwise over a period of 5 min. The mixture was stirred at 0° C. for 90 min. The resulting precipitate was collected by filtration and washed with THF to afford the title compound (0.23 g, 100%) as a colourless solid; mp 182°–185° C. $^1$H NMR (250 MHz, $d_6$-DMSO) δ 3.06 (9H, s), 3.38 (3H, s), 4.77 (2H, s), 8.08 (1H, s), 8.30 (1H, s), 8.38 (1H, s), 8.78 (1H, s), 9.31 (1H, s), 12.40 (1H, br s).

f) 2-(5-(1,2,4-Triazol-1-yl)-1H-pyrrolo[2,3-c]pyridin-3-yl) acetonitrile

To a solution of N-([5-(1,2,4-triazol-1-yl)-1H-pyrrolo[2, 3-c]pyridin-3-yl]methyl-N,N,N-trimethylammonium methylsulphate (0.56 g, 1.5 mmol) in water (4ml) was added a solution of potassium cyanide (0.239 g, 3.7 mmol) in water (2ml). This mixture was heated at 70° C. for 1 h. Further potassium cyanide (80mg, 1.2 mmol) was added and the mixture heated for another hour at 70° C. Further potassium cyanide (80mg, 1.2 mmol) was added and the mixture heated at 70° C. for 1 hour and then at 100° C. for 20 min. The mixture was then cooled in ice for 30 min. The precipitate was collected by filtration and washed with water. The solid was chromatographed on silica eluting with 5% MeOH in DCM to afford the title compound (0.215 g, 63%) as a colourless solid; mp 218°–220° C. $^1$H NMR (250 MHz, $d_6$-DMSO) δ 4.19 (2H, s), 7.78 (1H, s), 8.12 (1H, s), 8.26 (1H, s), 8.71 (1H, s), 9.29 (1H, s), 11.93 (1H, br s).

2. Intermediate 6: 2S-2-(N-Benzyl-N-methyl) aminomethylpyrrolidine a) 2S-N-tert-Butyloxycarbonyl-2-hydroxymethylpyrrolidine To a solution of L-prolinol (15 g, 0.15mol) in DCM (250ml) was added di-tert-butyl dicarbonate (36.5 g, 0.163mol). The solution was stirred at ambient temperature for 18 h. The solvents were evaporated in vacuo to give the title compound (30 g, 100%) as a colourless oil. δ (250 MHz, $CDCl_3$) 1.47 (9H, s), 1.57–2.10 (4H, m), 3.26–3.52 (2H, m), 3.55–3.78 (3H, m), 3.86–4.00 (1H, m).

b) 2S-N-tert-Butyloxycarbonyl-2-methylsulphonylmethylpyrrolidine

A solution of methanesulphonyl chloride (6.3 g, 55 mmol) in dichloromethane (25ml) was added dropwise to a solution of 2S-N-tert-butyloxycarbonyl-2-hydroxymethylpyrrolidine (10 g, 50 mmol) and triethylanmine (5.53 g, 55 mmol) in dichloromethane (160ml) at −5° C. The solution was stirred at 0° C. for 1 h and then at ambient temperature for 17 h. The mixture was diluted with dichloromethane (100ml) and washed with water (100ml) and brine (100ml). The organic layer was dried ($Na_2SO_4$) and evaporated in vacuo to give the title compound (13.43 g, 97%) as a pale yellow gum. δ (250 MHz, $CDCl_3$) 1.47 (9H, s), 1.71–2.10 (4H, m), 3.01 (3H, s), 3.28–3.46 (2H, m), 3.90–4.36 (3H, m).

c) 2S-N-tert-Butyloxycarbonyl-2-(-benzyl-N-methyl) aminomethylpyrrplidine

A solution of 2S-N-tert-butyloxycarbonyl-2-methylsulphonylmethyl pyrrolidine (2 g, 7.2 mmol) and N-benzylmethylamine (4.6ml, 36 mmol) in dry DMF (5ml) was stirred at ambient temperature for 2 h and then heated at 100° C. for 8 h. The reaction mixture was partitioned between ether (50ml) and water (50ml). The organic phase was washed with brine (30ml), dried ($Na_2SO_4$) an evaporated in vacuo. The residue was chromatographed on silica eluting with EtOAc:Petrol (60/80) (1:1) to give the title compound (1.07 g, 49%) as an orange oil. δ (250 MHz, $CDCl_3$) 1.46 (9H, s), 1.55–2.04 (5H, m), 2.10–2.60 (4H, m), 3.19–3.42 (3H, m), 3.52–4.09 (2H, m), 7.18–7.40 (5H, m).

d) 2S-2-(N-Benzyl-N-methyl)aminomethyl)pyrrolidine

A solution of 2S-N-tert-butyloxycarbonyl-2-(N-benzyl-N-methyl)aminomethylpyrrolidine (1.07 g, 3.5 mmol) and trifluoroacetic acid (2ml) in dichloromethane (20ml) was stirred at room temperature for 16 h, heated at reflux for 8 h and then stirred at room temperature for a further 16 h. The solvents were evaporated in uacuo and the residue was partitioned between ethyl acetate (50ml) and $K_2CO_3$ (saturated, 50ml). The aqueous was extracted with ethyl acetate (3×25ml), dichloromethane (2×25ml) and butanol (2×25ml). The EtOAc and DCM layers were dried ($Na_2SO_4$) and combined with the butanol phases and evaporated. The residue was chromatographed on silica with DCM/MeOH (98:2) followed by DCM/MeOH/$NH_3$ (90:10:1) to afford the title compound (0.62 g, 86%) as a pale yellow oil. δ (250 MHz, $CDCl_3$) 1.38–1.50 (1H, m), 1.60–2.08 (3H, m), 2.27 (3H, s), 2.30–2.50 (2H, m), 2.77–2.87 (1H, m), 2.95–3.05 (1H, m), 3.36–3.65 (3H, m), 4.85 (1H, br s), 7.23–7.36 (5H, m).

3. 2-(5-(1,2,4-Triazol-1-yl)-1H-pyrrolo[2,3-c]pyridin-3-yl) acetic acid (2S-2-(N-benzyl-N-methylaminomethyl) pyrrolidinyl)amide To a suspension of Intermediate 5 (0.89 g, 4.0 mmol) in methanol (10ml) was added sodium hydroxide (2M, 25ml). This mixture was heated at 80° C. for 16 h. After cooling the mixture was neutralised (2M HCl) and the solvents evaporated. The residue was chromatographed on silica eluting with a gradient of 90:10:1 to 80:20:2, DCM/MeOH/Acetic acid followed by MeOH to afford 2-(5-(1,2,4-triazol-1-yl)-1H-pyrrolo[2,3-c]pyridin-3-yl)acetic acid (3 g) as a pale yellow solid. $^1$H NMR (360 MHz, $d_6$-DMSO) δ 3.53 (2H, s), 7.58 (1H, s), 7.98 (1H, s), 8.20 (1H, s), 8.60 (1H, s), 9.22 (1H, s), 11.68 (1H, br s). This was used without further purification in the next step.

To a suspension of 2-(5-(1,2,4-triazol-1-yl)-1H-pyrrolo[2, 3-c]pyridin-3-yl)acetic acid (0.84 g) in dry DMF (5ml) was added Intermediate 6 (0.262 g, 1.3 mmol), 1-hydroxybenzotriazole (0.174 g, 1.3 mmol), 1-ethyl-3-[3-(dimethylamino)propyl]carbodiimide hydrochloride (0.247 g, 1.3 mmol) and triethylamine (0.18ml, 1.3 mmol), and this mixture was stirred at room temperature under nitrogen for 64 h. The mixture was neutralised (2M HCl) and the solvent evaporated in vacuo. The residue was triturated with DCM and the solid removed by filtration. The filtrate was evaporated in vacuo and the residue chromatographed on silica with 5% MeOH in DCM followed by a gradient of 95:5:1 to 90:10:1 DCM/MeOH/$NH_3$ to afford the title compound (87mg) as a yellow gum. $^1$H NMR (360 MHz, $CDCl_3$)δ 1.54–2.70 (10H, m), 3.28–3.92 (5H, m), 4.09–4.16 and 4.34–4.44 (1H, 2×m), 7.16–7.41 (6H, m), 7.98 and 8.00 (1H, 2×s), 8.07 and 8.09 (1H, 2×s), 8.42 and 8.45 (1H, 2×s), 9.08 and 9.10 (1H, 2×s), 9.12–9.30 (1H, m).

4. 2S-2-(N-Benzyl-N-methylaminomethyl)-1-[2-(5-(1,2,4-triazol-1-yl)-1H-pyrrolo[2,3-c]pyridin-3-yl)ethyl] pyrrolidine oxalate To a solution of $LiAlH_4$ in ether (1.0M, 0.6ml, 0.6 mmol) and dry THF (2ml) was added a solution of 2-(5-(1,2,4-triazol-1-yl)-1H-pyrrolo[2,3-c]pyridin-3-yl)acetic acid (2S-2-(N-benzyl-N-methyl-aminomethyl)pyrrolidinyl)amide (87mg, 0.2 mmol) in dry THF (3ml) dropwise at ambient temperature under nitrogen. The mixture was heated at 50° C. for 1 h. After cooling, water (24 μL) was added, followed by sodium hydroxide (4M, 24 μL), followed by water (72 μL). The solid was removed by filtration and the solvent evaporated in vacuo. The residue was chromatographed on silica eluting with a gradient of 5 to 10% MeOH in DCM followed by 90:10:1, DCM/MeOH/$NH_3$ to afford a yellow gum. This was rechromatographed on silica eluting with a gradient of 98:2:1 to 95:5:1 DCM/MeOH/$NH_3$ to afford the free base (53mg, 63%) as a yellow gum. The free base (40mg, 0.1 mmol) was dissolved in ether/MeOH (4:1, 5ml) and treated dropwise with a solution of oxalic acid (8.7mg, 0.1 mmol) in ether (1ml). The precipitate formed was collected by filtration to afford the title compound (30mg) as a beige solid. mp 100° C. (dec.). Found: C, 56.90; H, 6.22; N, 16.44. $C_{24}H_{29}N_7$. 1.75($CO_2H$)$_2$.0.6($H_2O$) requires C, 56.57; H, 5.82; N, 16.79%. $^1$H NMR (360 MHz, $d_6$-DMSO) δ 1.60–1.74 (1H, m), 1.83–2.23 (6H, m), 2.50–2.60 (1H, m), 2.88–2.98 (1H, m), 3.12–3.42 (4H, m), 3.48–3.84 (5H, m), 7.16–7.38 (5H, m), 7.65 (1H, d, J=2.3 Hz), 8.08 (1H, s), 8.23 (1H, s), 8.68 (1H, s), 9.25 (1H, s), 11.85 (1H, br s).

We claim:

1. A compound of formula I, or a pharmaceutically acceptable salt thereof:

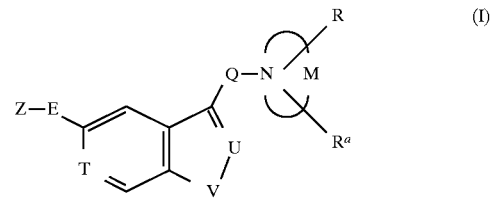

wherein

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

E represents a chemical bond or a straight or branched alkylene chain containing from 1 to 4 carbon atoms;

Q represents a straight or branched alkylene chain containing from 1 to 4 carbon atoms, optionally substituted in any position by a hydroxy group;

T represents CH;

U represents C—$R^2$;

V represents N—$R^3$;

$R^2$ and $R^3$ independently represent hydrogen or $C_{1-6}$ alkyl;

M represents the residue of an azetidine, pyrrolidine or piperidine ring;

R represents a group of formula —W—$R^1$;

W represents a chemical bond or a straight or branched alkylene chain containing from 1 to 4 carbon atoms, optionally substituted in any position by a hydroxy group;

$R^1$ represents —$OR^x$, —$SR^x$, —$SOR^x$, —$SO_2R^x$ or —$NR^xR^y$;

$R^x$ and $R^y$ independently represent hydrogen or a hydrocarbon group; wherein hydrocarbon is selected from the group consisting of: $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, indanyl, aryl and aryl($C_{1-6}$)alkyl;

aryl is phenyl or naphthyl;

aryl($C_{1-6}$)alkyl is benzyl, phenylethyl, phenylpropyl or naphthylmethyl;

and wherein the hydrocarbon group may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, aminocarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —$NR^vR^w$, —$NR^vCOR^w$, —$NR^vCO_2R^w$, —$NR^vSO_2R^w$, —$CH_2NR^vSO_2R^w$, —$NHCONR^vR^w$, —$CONR^vR^w$, —$SO_2NR^vR^w$ and —$CH_2SO_2NR^vR^w$, in which $R^v$ and $R^w$ independently represent hydrogen, $C_{1-6}$ alkyl, aryl or aryl($C_{1-6}$)alkyl, or $R^v$ and $R^w$ together represent a $C_{2-6}$ alkylene group; or $R^x$ and $R^y$ together represent a $C_{2-6}$ alkylene group, which alkylene group may be optionally substituted by one or more substituents selected from $C_{1-6}$ alkyl, aryl and hydroxy, or fused with a phenyl ring; and $R^a$ represents hydrogen, hydroxy, or a hydrocarbon group, as defined above.

2. A compound as claimed in claim 1 represented by formula IIA, and salts thereof:

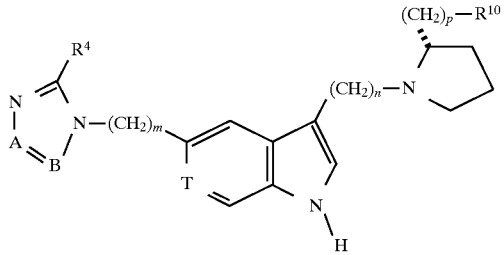

(IIA)

wherein m is zero, 1, 2 or 3;

n is 2, 3 or 4;

p is zero, 1 or 2;

T represents CH;

A represents nitrogen or CH;

B represents nitrogen or C—$R^5$;

$R^4$ and $R^5$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl; and $R^{10}$ represents —X—$R^{11}$ or a group of formula (a) or (b):

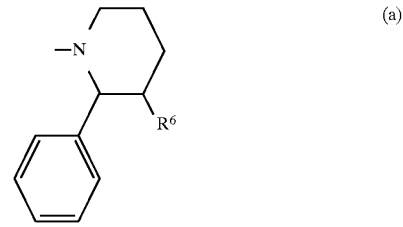

(a)

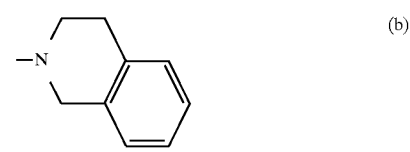

(b)

in which $R^6$ represents hydrogen or hydroxy;

X represents oxygen, sulphur, —SO—, —$SO_2$— or N—$R^{12}$; and $R^{11}$ and $R^{12}$ independently represent hydrogen, $C_{1-6}$ alkyl, $C_{2-6}$ alkenyl, $C_{3-7}$ cycloalkyl($C_{1-6}$)alkyl, indanyl, aryl, aryl($C_{1-6}$)alkyl, any of which groups may be optionally substituted by a substituent selected from the group consisting of: $C_{1-6}$ alkyl, halogen, cyano, trifluoromethyl, hydroxy, $C_{1-6}$ alkoxy, aminocarbonyloxy, $C_{2-6}$ alkylcarbonyl, amino, $C_{1-6}$ alkylamino, di($C_{1-6}$)alkylamino, $C_{2-6}$ alkylcarbonylamino, $C_{1-6}$ alkylsulphonylamino and $C_{1-6}$ alkylaminosulphonylmethyl.

3. A compound as claimed in claim 1 represented by formula IIB, and pharmaceutically acceptable salts thereof:

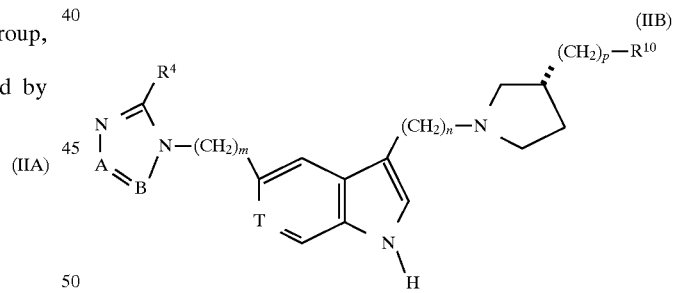

(IIB)

wherein m is zero, 1,2 or 3;

n is 2, 3 or 4;

p is zero, 1 or 2;

T represents CH;

A represents nitrogen or CH;

B represents nitrogen or C—$R^5$;

$R^4$ and $R^5$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl; and $R^{10}$ represents —X—$R^{11}$ or a group of formula (a) or (b):

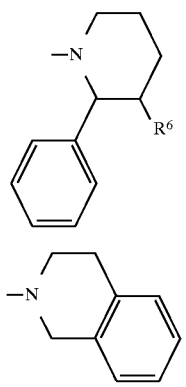

(a)

(b)

in which
$R^6$ represents hydrogen or hydroxy;
X represents oxygen, sulphur, —SO—, —SO$_2$— or N—$R^{12}$; and
$R^{11}$ and $R^{12}$ independently represent hydrogen, $C_{1-6}$ alkyl, $C_{2-6}$ alkenyl, $C_{3-7}$ cycloalkyl($C_{1-6}$)alkyl, indanyl, aryl, aryl($C_{1-6}$)alkyl, any of which groups may be optionally substituted by a substituent selected from the group consisting of: $C_{1-6}$ alkyl, halogen, cyano, trifluoromethyl, hydroxy, $C_{1-6}$ alkoxy, aminocarbonyloxy, $C_{2-6}$ alkylcarbonyl, amino, $C_{1-6}$ alkylamino, di($C_{1-6}$)alkylamino, $C_{2-6}$ alkylcarbonylamino, $C_{1-6}$ alkylsulphonylamino and $C_{1-6}$ alkylaminosulphonylmethyl.

4. A compound as claimed in claim 1 represented by formula IIC, and pharmaceutically acceptable salts thereof:

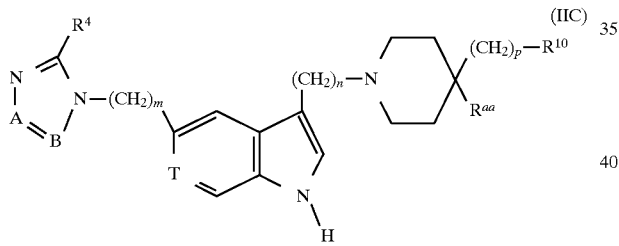

(IIC)

wherein
$R^{aa}$ represents hydrogen, hydroxy or aryl($C_{1-6}$)alkyl; and $C_{1-6}$ alkoxy, $C_{1-6}$ alkylthio, amino, $C_{1-6}$ alkylamino, di($C_{1-6}$)alkylamino, halogen, cyano or trifluoromethyl; and $R^{10}$ represents —X—$R^{11}$ or a group of formula (a) or (b):

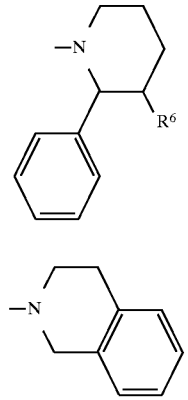

(a)

(b)

in which
$R^6$ represents hydrogen or hydroxy;
X represents oxygen, sulphur, —SO—, —SO$_2$— or N—$R^{12}$; and
$R^{11}$ and $R^{12}$ independently represent hydrogen, $C_{1-6}$ alkyl, $C_{2-6}$ alkenyl, $C_{3-7}$ cycloalkyl($C_{1-6}$)alkyl, indanyl, aryl, aryl($C_{1-6}$)alkyl, any of which groups may be optionally substituted by a substituent selected from the group consisting of: $C_{1-6}$ alkyl, halogen, cyano, trifluoromethyl, hydroxy, $C_{1-6}$ alkoxy, aminocarbonyloxy, $C_{2-6}$ alkylcarbonyl, amino, $C_{1-6}$ alkylamino, di($C_{1-6}$)alkylamino, $C_{2-6}$ alkylcarbonylamino, $C_{1-6}$ alkylsulphonylamino and $C_{1-6}$ alkylaminosulphonylmethyl.

5. A compound as claimed in claim 1 represented by formula IID, and pharmaceutically acceptable salts thereof:

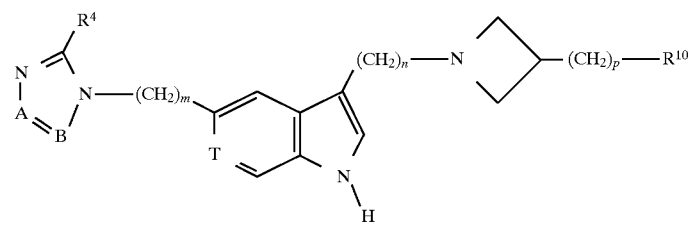

(IID)

wherein
m is zero, 1, 2 or 3;
n is 2, 3 or 4;
p is zero, 1 or 2;
T represents CH;
A represents nitrogen or CH;
B represents nitrogen or C—$R^5$;
$R^4$ and $R^5$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, wherein
m is zero, 1, 2 or 3;
n is 2, 3 or 4;
p is zero, 1 or 2;
T represents CH;
A represents nitrogen or CH;
B represents nitrogen or C—$R^5$;
$R^4$ and $R^5$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl,

91

$C_{1-6}$ alkoxy, $C_{1-6}$ alkylthio, amino, $C_{1-6}$ alkylamino, di($C_{1-6}$)alkylamino, halogen, cyano or trifluoromethyl; and $R^{10}$ represents —X—$R^{11}$ or a group of formula (a) or (b):

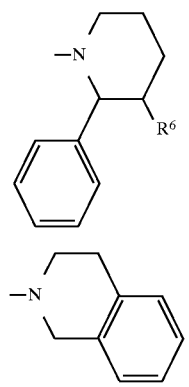

in which $R^6$ represents hydrogen or hydroxy;

X represents oxygen, sulphur, —SO—, —$SO_2$— or N—$R^{12}$; and $R^{11}$ and $R^{12}$ independently represent hydrogen, $C_{1-6}$ alkyl, $C_{2-6}$ alkenyl, $C_{3-7}$ cycloalkyl($C_{1-6}$)alkyl, indanyl, aryl, aryl($C_{1-6}$)alkyl, any of which groups may be optionally substituted by a substituent selected from the group consisting of: $C_{1-6}$ alkyl, halogen, cyano, trifluoromethyl, hydroxy, $C_{1-6}$ alkoxy, aminocarbonyloxy, $C_{2-6}$ alkylcarbonyl, amino, $C_{1-6}$ alkylamino, di($C_{1-6}$)alkylamino, $C_{2-6}$ alkylcarbonylamino, $C_{1-6}$ alkylsulphonylamino and $C_{1-6}$ alkylaminosulphonylmethyl.

6. A compound selected from:
(3R)-3-benzyloxy-1-[2-(5-(1,2,4-triazol-4-yl)-1-H-indol-3-yl)ethyl]pyrrolidine;
(3R)-3-(4-methoxyphenyl)methoxy-1-[2-(5-(1,2,4-triazol-4-yl)-1H-indol-3-yl)ethyl]pyrrolidine;
(3R)-3-benzyloxymethyl-1-[2-(5-(1,2,4-triazol-4-yl)-1H-indol-3-yl)ethyl]pyrrolidine;
(3S)-3-(N-benzyl-N-methyl)aminomethyl-1-[2-(5-(1,2,4-triazol-4-yl)-1H-indol-3-yl)ethyl]pyrrolidine;
(2S)-2-(N-benzyl-N-methyl)aminomethyl-1-[2-(5-(1,2,4-triazol-4-yl)-1H-indol-3-yl)ethyl]pyrrolidine;
(3S)-3-(N-benzyl)aminomethyl-1-[2-(5-(1,2,4-triazol-4-yl)-1H-indol-3-yl)ethyl]pyrrolidine;
4-(4-acetylaminophenyl)methylamino-1-[3-(5-(1,2,4-triazol-4-yl)-1H-indol-3-yl)propyl]piperidine;
4-benzylamino-1-[3-(5-(1,2,4-triazol-4-yl)-1H-indol-3-yl)propyl]piperidine;
4-(N-benzyl-N-methyl)amino-1-[3-(5-(1,2,4-triazol-4-yl)-1H-indol-3-yl)propyl]piperidine;
4-(N-benzyl)aminomethyl-1-[3-(5-(1,2,4-triazol-4-yl)-1H-indol-3-yl)propyl]piperidine;
(2S)-2-(N-benzyl-N-methylaminomethyl)-1-[2-(5-(1,2,4-triazol-1-yl)-1H-pyrrolo[2,3-c]pyridin-3-yl)ethyl]pyrrolidine; and pharmaceutically acceptable salts and prodrugs thereof.

7. A compound selected from:
4-(N-benzyl-N-methyl)aminomethyl-1-[3-(5-(1,2,4-triazol-4-yl)-1H-indol-3-yl)propyl]piperidine;
1-[3-(5-(1,2,4-triazol-4-yl)-1H-indol-3-yl)propyl]-4-[(R)-α-(methyl)benzylamino]piperidine;
1-[3-(5-(1,2,4-triazol-4-yl)-1H-indol-3-yl)propyl]-4-[(S)-α-(methyl)benzylamino]piperidine;

92

1-[3-(5-(1,2,4-triazol-4-yl)-1H-indol-3-yl)propyl]-4-[(S)-α-(hydroxymethyl)benzylamino]piperidine;
1-[3-(5-(1,2,4-triazol-4-yl)-1H-indol-3-yl)propyl]-4-[(R)-α-(hydroxymethyl)benzylamino]piperidine;
1-[3-(5-(1,2,4-triazol-4-yl)-1H-indol-3-yl)propyl]-4-[(S)-(1-hydroxymethyl-2-phenyl)ethylamino]piperidine;
1-[3-(5-(1,2,4-triazol-4-yl)-1H-indol-3-yl)propyl]-4-[(1R,2S)-(2-hydroxy-1-methyl-2-phenyl)ethylamino]piperidine;
1-[3-(5-(1,2,4-triazol-4-yl)-1H-indol-3-yl)propyl]-4-[(1S,2R)-(2-hydroxy-1-methyl-2-phenyl)ethylamino]piperidine;
1-[3-(5-(1,2,4-triazol-4-yl)-1H-indol-3-yl)propyl]-4-[(1R,2R)-(2-hydroxy-1-methyl-2-phenyl)ethylamino]piperidine;
1-[3-(5-(1,2,4-triazol-4-yl)-1H-indol-3-yl)propyl]-4-[2-(4-acetylaminophenyl)ethylamino]piperidine;
1-[3-(5-(1,2,4-triazol-4-yl)-1H-indol-3-yl)propyl]-4-[(R)-α-(methyl)benzylamino]methylpiperidine;
1-[3-(5-(1,2,4-triazol-4-yl)-1H-indol-3-yl)propyl]-4-[(S)-α-(methyl)benzylamino]methylpiperidine;
1-[3-(5-(1,2,4-triazol-4-yl)-1H-indol-3-yl)propyl]-4-[(S)-1-(4-acetylaminophenyl)ethylamino]methylpiperidine;
1-[3-(5-(1,2,4-triazol-4-yl)-1H-indol-3-yl)propyl]-4-[(R)-1-(4-acetylaminophenyl)ethylamino]methylpiperidine;
1-[3-(5-(1,2,4-triazol-4-yl)-1H-indol-3-yl)propyl]-4-[N-[(R)-α-(hydroxymethyl)benzyl]-N-methylamino]piperidine;
1-[3-(5-(1,2,4-triazol-4-yl)-1H-indol-3-yl)propyl]-4-[N-[(S)-α-(hydroxymethyl)benzyl]-N-methylamino]piperidine;
1-[3-(5-(1,2,4-triazol-4-yl)-1H-indol-3-yl)propyl]-4-[N-(2-(4-acetylaminophenyl)ethyl)-N-methylamino]piperidine;
1-[3-(5-(1,2,4-triazol-4-yl)-1H-indol-3-yl)propyl]-4-[N-(4-acetylaminobenzyl)-N-methylamino]methylpiperidine;
1-[3-(5-(1,2,4-triazol-4-yl)-1H-indol-3-yl)propyl]-4-[(R)-α-(hydroxymethyl)benzylamino]methylpiperidine;
(3S)-3-(4-acetylaminobenzyl)aminomethyl-1-[2-(5-(1,2,4-triazol-4-yl)-1H-indol-3-yl)ethyl]pyrrolidine;
(3R)-3-(N-benzyl)aminomethyl-1-[2-(5-(1,2,4-triazol-4-yl)-1H-indol-3-yl)ethyl]pyrrolidine;
3-(N-benzyl)aminomethyl-1-[2-(5-(1,2,4-triazol-4-yl)-1H-indol-3-yl)ethyl]azetidine;
4-benzyl-4-hydroxy-1-[3-(5-(1,2,4-triazol-4-yl)-1H-indol-3-yl)propyl]piperidine;
3-(N-benzyl)aminomethyl-1-[3-(5-(1,2,4-triazol-4-yl)-1H-indol-3-yl)propyl]azetidine;
4-(N-benzyl)aminomethyl-4-hydroxy-1-[3-(5-(1,2,4-triazol-4-yl)-1H-indol-3-yl)propyl]piperidine;
4-(N-benzyl-N-methyl)aminomethyl-4-hydroxy-1-[3-(5-(1,2,4-triazol-4-yl)-1H-indol-3-yl)propyl]piperidine;
3-(N-benzyl-N-methyl)aminomethyl-1-[2-(5-(1,2,4-triazol-4-yl)-1H-indol-3-yl)ethyl]azetidine;
(3S)-3-[N-(R)-α-(methyl)benzyl]aminomethyl-1-[2-(5-(1,2,4-triazol-4-yl)-1H-indol-3-yl)ethyl]pyrrolidine;
(3S)-3-[N-(S)-α-(methyl)benzyl]aminomethyl-1-[2-(5-(1,2,4-triazol-4-yl)-1H-indol-3-yl)ethyl]pyrrolidine;
(3S)-3-[N-(furan-2-ylmethyl)amino]methyl-1-[2-(5-(1,2,4-triazol-4-yl)-1H-indol-3-yl)ethyl]pyrrolidine;
and pharmaceutically acceptable salts and prodrugs thereof.

8. A compound selected from:

(3S)-3-[N-(R)-α-(hydroxymethyl)benzyl]aminomethyl-1-[2-(5-(1,2,4-triazol-4-yl)-1H-indol-3-yl)ethyl]pyrrolidine;

(3S)-3-[N-(S)-α-(hydroxymethyl)benzyl]aminomethyl-1-[2-(5-(1,2,4-triazol-4-yl)-1H-indol-3-yl)ethyl]pyrrolidine;

(3S)-3-[N-benzyl-N-(2-hydroxy)ethyl]aminomethyl-1-[2-(5-(1,2,4-triazol-4-yl)-1H-indol-3-yl)ethyl]pyrrolidine;

(3S)-3-[N-(2-phenylethyl)amino]methyl-1-[2-(5-(1,2,4-triazol-4-yl)-1H-indol-3-yl)ethyl]pyrrolidine;

(3S)-3-[N-(2-phenylethyl)-N-methylamino]methyl-1-[2-(5-(1,2,4-triazol-4-yl)-1H-indol-3-yl)ethyl]pyrrolidine;

(3S)-3-(N-α-dimethylbenzyl)aminomethyl-1-[2-(5-(1,2,4-triazol-4-yl)-1H-indol-3-yl)ethyl]pyrrolidine;

(3S)-3-[N-(S)-α-methylbenzyl]aminomethyl-1-[2-(5-(1,2,4-triazol-1-yl)-1H-indol-3-yl)ethyl]pyrrolidine;

(3S)-3-[N-(R)-α-(hydroxymethyl)benzyl]aminomethyl-1-[2-(5-(1,2,4-triazol-1-yl)-1H-indol-3-yl)ethyl]pyrrolidine;

(3S)-3-(N-benzyl)aminomethyl-1-[2-(5-(1,2,4-triazol-1-ylmethyl)-1H-indol-3-yl)ethyl]pyrrolidine;

(3S)-3-[N-(S)-α-methylbenzyl]aminomethyl-1-[2-(5-(1,2,4-triazol-1-ylmethyl)-1H-indol-3-yl)ethyl]pyrrolidine;

(3S)-3-[N-(R)-α-(hydroxymethyl)benzyl]aminomethyl-1-[2-(5-(1,2,4-triazol-1-ylmethyl)-1H-indol-3-yl)ethyl]pyrrolidine;

(3S)-3-(N-benzyl-N-methyl)aminomethyl-1-[2-(5-(imidazol-1-yl)-1H-indol-3-yl)ethyl]pyrrolidine;

(3S)-3-(N-benzyl-N-methyl)aminomethyl-1-[2-(5-(1,2,4-triazol-1-ylmethyl)-1H-indol-3-yl)ethyl]pyrrolidine;

(3R)-3-[N-methyl-N-(S)-α-methylbenzyl]aminomethyl-1-[2-(5-(1,2,4-triazol-1-ylmethyl)-1H-indol-3-yl)ethyl]pyrrolidine;

(3R)-3-[N-methyl-N-(R)-α-hydroxymethylbenzyl]aminomethyl-1-[2-(5-(1,2,4-triazol-1-ylmethyl)-1H-indol-3-yl)ethyl]pyrrolidine;

(3R)-3-[N-methyl-N-(S)-α-methylcyclohexylmethyl]aminomethyl-1-[2-(5-(1,2,4-triazol-1-ylmethyl)-1H-indol-3-yl)ethyl]pyrrolidine;

(3R)-3-[3-(R)-hydroxy-2-(R)-phenylpiperidin-1-yl]methyl-1-[2-(5-(1,2,4-triazol-1-ylmethyl)-1H-indol-3-yl)ethyl]pyrrolidine;

(3R)-3-[3-(R)-hydroxy-2-(R)-phenylpiperidin-1-yl]methyl-1-[2-(5-(1,2,4-triazol-1-yl)-1H-indol-3-yl)ethyl]pyrrolidine;

4-hydroxy-4-(phenylsulfinyl)methyl-1-[3-(5-(1,2,4-triazol-4-yl)-1H-indol-3-yl)propyl]piperidine;

(3R)-3-[2-(R,S)-phenylpiperidin-1-yl]methyl-1-[2-(5-(1,2,4-triazol-1-ylmethyl)-1H-indol-3-yl)ethyl]pyrrolidine;

4-(3,3-dimethylpiperidin-1-yl)methyl-4-hydroxy-1-[3-(5-(1,2,4-triazol-4-yl)-1H-indol-3-yl)propyl]piperidine;

4-hydroxy-4-(1,2,3,4-tetrahydroisoquinolin-2-yl)methyl-1-[3-(5-(1,2,4-triazol-4-yl)-1H-indol-3-yl)propyl]piperidine;

4-hydroxy-4-(N-isobutyl-N-methyl)aminomethyl-1-[3-(5-(1,2,4-triazol-4-yl)-1H-indol-3-yl)propyl]piperidine;

4-[N-benzyl-N-(2-hydroxyethyl)amino]methyl-4-hydroxy-1-[3-(5-(1,2,4-triazol-4-yl)-1H-indol-3-yl)propyl]piperidine;

4-[N-(2,2-dimethylpropyl)-N-methylamino]methyl-4-hydroxy-1-[3-(5-(1,2,4-triazol-4-yl)-1H-indol-3-yl)propyl]piperidine;

4-[N-(R)-α-hydroxymethylbenzyl-N-methylamino]methyl-4-hydroxy-1-[3-(5-(1,2,4-triazol-4-yl)-1H-indol-3-yl)propyl]piperidine;

4-hydroxy-4-(2-methylphenylmethyl)aminomethyl-1-[3-(5-(1,2,4-triazol-4-yl)-1H-indol-3-yl)propyl]piperidine;

4-hydroxy-4-[N-(2-methylphenylmethyl)-N-methylamino]methyl-1-[3-(5-(1,2,4-triazol-4-yl)-1H-indol-3-yl)propyl]piperidine;

3-(benzylamino)methyl-3-hydroxy-1-[3-(5-(1,2,4-triazol-4-yl)-1H-indol-3-yl)propyl]pyrrolidine;

3-(benzylamino)methyl-3-hydroxy-1-[2-(5-(1,2,4-triazol-4-yl)-1H-indol-3-yl)ethyl]pyrrolidine;

1-[3-(5-(1,2,4-triazol-4-yl)-1H-indol-3-yl)propyl]-4-[(R)-α-(carbamoyl-oxymethyl)benzylamino]piperidine;

1-[3-(5-(1,2,4-triazol-4-yl)-1H-indol-3-yl)propyl]-4-[(1R,2S)-2-hydroxy-1-phenylpropylamino]piperidine;

1-[3-(5-(1,2,4-triazol-4-yl)-1H-indol-3-yl)propyl]-4-[(1R,2R)-2-hydroxy-1-phenylpropylamino]piperidine;

1-[3-(5-(1,2,4-triazol-4-yl)-1H-indol-3-yl)propyl]-4-[(R,S)-1-hydroxy-2-phenylprop-2-ylamino]piperidine;

1-[3-(5-(1,2,4-triazol-4-yl)-1H-indol-3-yl)propyl]-4-[(R)-2-hydroxy-1-(4-fluorophenyl)ethylamino]piperidine;

1-[3-(5-(1,2,4-triazol-4-yl)-1H-indol-3-yl)propyl]-4-[(1R,2R)-2-hydroxyindan-1-ylamino)piperidine;

1-[3-(5-(1,2,4-triazol-4-yl)-1H-indol-3-yl)propyl]-4-[(R,S)-indan-1-ylamino]piperidine;

1-[3-(5-(1,2,4-triazol-4-yl)-1H-indol-3-yl)propyl]-4-[(R,S)-1-(4-fluorophenyl)ethylamino]piperidine;

1-[3-(5-(1,2,4-triazol-4-yl)-1H-indol-3-yl)propyl]-4-[(R)-1-phenylprop-2-ylamino]piperidine;

1-[3-(5-(1,2,4-triazol-4-yl)-1H-indol-3-yl)propyl]-4-[N-(3,3-dimethylallyl)-N-methylamino]piperidine;

1-[3-(5-(1,2,4-triazol-4-yl)-1H-indol-3-yl)propyl]-4-(N-allyl-N-methylamino)piperidine;

1-[3-(5-(1,2,4-triazol-4-yl)-1H-indol-3-yl)propyl]-4-(indan-1-ylaminomethyl)piperidine;

1-[3-(5-(1,2,4-triazol-4-yl)-1H-indol-3-yl)propyl]-4-[N-(R)-α-(hydroxymethyl)benzyl-N-methylaminomethyl]piperidine;

(3R)-3-(benzylthio)methyl-1-[2-(5-(1,2,4-triazol-4-yl)-1H-indol-3-yl)ethyl]pyrrolidine;

(±)-1-[3-(5-(1,2,4-triazol-4-yl)-1H-indol-3-yl)propyl]-4-(1-benzylamino-2-hydroxyethyl)piperidine;

1-[3-(5-(1,2,4-triazol-1-yl)-1H-indol-3-yl)propyl]-4-[(R)-α-(hydroxymethyl)benzylamino]piperidine;

1-[3-(5-(imidazol-1-yl)-1H-indol-3-yl)propyl]-4-[(R)-α-(methyl)benzylamino]piperidine;

1-[3-(5-(imidazol-1-yl)-1H-indol-3-yl)propyl]-4-[(R)-α-(hydroxymethyl)benzylamino]piperidine;

1-[3-(5-(1,2,4-triazol-1-ylmethyl)-1H-indol-3-yl)propyl]-4-[(R)-α-(hydroxymethyl)benzylamino]piperidine;

1-[3-(5-(1,2,4-triazol-4-yl)-1H-indol-3-yl)propyl]-4-[(R)-α-(methoxymethyl)benzylamino]piperidine;

1-[3-(5-(1,2,4-triazol-4-yl)-1H-indol-3-yl)propyl]-4-[N-(R)-α-(methoxymethyl)benzyl-N-methylamino]piperidine;

1-[3-(5-(imidazol-1-yl)-1H-indol-3-yl)propyl]-4-[(R)-α-(methoxymethyl)benzylamino]piperidine;

1-[3-(5-(1,2,4-triazol-1-ylmethyl)-1H-indol-3-yl)propyl]-4-[(R)-1-(4-fluorophenyl)-2-methoxyethylamino]piperidine;

1-[3-(5-(1,2,4-triazol-1-ylmethyl)-1H-indol-3-yl)propyl]-4-[N-(4-fluorobenzyl)-N-methylamino]piperidine;

1-[3-(5-(1,2,4-triazol-4-yl)-1H-indol-3-yl)propyl]-4-(2-phenylpiperidin-1-yl)piperidine;

1-[3-(5-(1,2,4-triazol-4-yl)-1H-indol-3-yl)propyl]-4-[(R)-1-(4-fluorophenyl)-2-methoxyethylamino]piperidine;

(3R)-3-(benzylsulfinyl)methyl-1-[2-(5-(1,2,4-triazol-4-yl)-1H-indol-3-yl)ethyl]pyrrolidine;

(3R)-3-(4-fluorobenzylthio)methyl-1-[2-(5-(1,2,4-triazol-1-ylmethyl)-1H-indol-3-yl)ethyl]pyrrolidine;

(3R)-3-(4-fluorobenzylsulfinyl)methyl-1-[2-(5-(1,2,4-triazol-1-ylmethyl)-1H-indol-3-yl)ethyl]pyrrolidine;

(3R)-3-(4-fluorobenzylsulfonyl)methyl-1-[2-(5-(1,2,4-triazol-1-ylmethyl)-1H-indol-3-yl)ethyl]pyrrolidine;

4-(4-fluorobenzylsulfinyl)-1-[3-(5-(1,2,4-triazol-4-yl)-1H-indol-3-yl)propyl]piperidine;

and pharmaceutically acceptable salts and prodrugs thereof.

9. A pharmaceutical composition comprising a compound as claimed in claim 1 in association with a pharmaceutically acceptable carrier.

10. A method for the treatment and/or prevention of clinical conditions for which a subtype-selective agonist of 5-HT$_{1D}$ receptors is indicated, which method comprises administering to a patient in need of such treatment an effective amount of a compound as claimed in claim 1.

* * * * *